(12) United States Patent
Huang et al.

(10) Patent No.: US 11,576,957 B2
(45) Date of Patent: Feb. 14, 2023

(54) VACCINE AND THERAPEUTIC COMPOSITIONS COMPRISING ANTIGEN-CONJUGATED VIRAL CAPSIDS

(71) Applicant: Board of Trustees of Michigan State University, East Lansing, MI (US)

(72) Inventors: Xuefei Huang, Okemos, MI (US); Suttipun Sungsuwan, Bangkok (TH)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 16/642,690

(22) PCT Filed: Apr. 23, 2018

(86) PCT No.: PCT/US2018/028887
§ 371 (c)(1),
(2) Date: Feb. 27, 2020

(87) PCT Pub. No.: WO2019/045791
PCT Pub. Date: Mar. 7, 2019

(65) Prior Publication Data
US 2020/0261559 A1    Aug. 20, 2020

Related U.S. Application Data

(60) Provisional application No. 62/551,045, filed on Aug. 28, 2017.

(51) Int. Cl.
| | |
|---|---|
| *A61K 39/00* | (2006.01) |
| *A61K 47/64* | (2017.01) |
| *A61P 35/04* | (2006.01) |
| *C12N 7/00* | (2006.01) |
| *A61K 39/112* | (2006.01) |
| *A61K 39/12* | (2006.01) |
| *C07K 14/005* | (2006.01) |

(52) U.S. Cl.
CPC .... *A61K 39/00117* (2018.08); *A61K 39/0275* (2013.01); *A61K 39/12* (2013.01); *A61K 47/646* (2017.08); *A61P 35/04* (2018.01); *C07K 14/005* (2013.01); *C12N 7/00* (2013.01); A61K 2039/572 (2013.01); A61K 2039/6075 (2013.01); A61K 2039/812 (2018.08); A61K 2039/86 (2018.08); C12N 2795/18122 (2013.01); C12N 2795/18134 (2013.01); C12N 2795/18171 (2013.01)

(58) Field of Classification Search
None
See application file for complete search history.

(56) References Cited

U.S. PATENT DOCUMENTS

| | | |
|---|---|---|
| 2013/0209413 A1 | 8/2013 | Rommelaere et al. |
| 2014/0023647 A1 | 1/2014 | Slawin et al. |
| 2017/0080069 A1 | 3/2017 | Cerullo et al. |

FOREIGN PATENT DOCUMENTS

| | | | | |
|---|---|---|---|---|
| CA | 2597878 A1 | * | 3/2009 | ........... C07K 14/005 |
| EP | 1524994 B1 | | 4/2011 | |
| WO | WO-2002/000251 A1 | | 4/2002 | |
| WO | WO-2009035494 A2 | * | 3/2009 | ........... C12Q 1/6886 |
| WO | WO-2019/045791 A1 | | 3/2019 | |

OTHER PUBLICATIONS

Frietze et al., Curr Opin Virol, Jun. 2016, 18:44-49. (Year: 2016).*
International Search Report and Written Opinion for International Application No. PCT/US18/28887 dated Oct. 4, 2018.
Michigan State University Department of Chemistry: Huang Group, <https://www2.chemistry.msu.edu/faculty/huang/> (May 19, 2017).
Pejawar-Gaddy et al., "Generation of a tumor vaccine candidate based on conjugation of a MUC1 peptide to polyionic papillomavirus-like particles (VLPs)," Cancer Immunol Immunother, 59(11):1-19 (2010).
Sungsuwan, "Lipopeptide-coated iron oxide nanoparticles and engineered QB virus like particles as potential glycoconjugate-based synthetic anticancer vaccines," https://d.lib.msu.edu/etd/4663, (2017).

* cited by examiner

*Primary Examiner* — Nicole Kinsey White
(74) *Attorney, Agent, or Firm* — Foley Hoag LLP; DeAnn F. Smith

(57) ABSTRACT

Provided herein are vaccine composition comprising an antigen conjugated to a capsid, wherein the capsid comprises wild type or native sequence. Provided herein are also vaccine composition comprising an antigen conjugated to a capsid, wherein said capsid comprises at least one mutation, such as a non-natural mutation. Such compositions are useful in the treatment and prevention of pathogenic infections, inflammatory diseases, and neurodegenerative disease, and cancer, among others.

13 Claims, 120 Drawing Sheets
Specification includes a Sequence Listing.

Qβ(WT) and Qβ(WT)-Tn1

Qβ(T7K) and Qβ(T7K)-Tn1

Qβ(N10K) and Qβ(N10K)-Tn1

Qβ(A38K) and Qβ(A38K)-Tn1

Qβ(A38K/A40C/D102C) and Qβ(A38K/A40C/D102C)-Tn1

Qβ(A40C/D102C) and Qβ(A40C/D102C)-Tn1

Qβ(T75K) and Qβ(T75K)-Tn1

Qβ(A117K) and Qβ(A117K)-Tn1

Qβ(P119K) and Qβ(P119K)-Tn1

*In vitro* CTL Assay

*In vivo* CTL Assay

1. Marker
2. Qb-A40CD102C-(MUC1-Tn)
3. Qb-A38KA40CD102C-(MUC1-Tn)

5 MUC1 Tg. mice : Qb-A40CD102C-(MUC1-Tn)
5 MUC1 Tg. mice : Qb-A38KA40CD102C-(MUC1-Tn)

MUC1-STA 1: ESI ($C_{88}H_{140}N_{28}O_{32}$): calculated ($[M+2H^+]/2$): 1052.0156, found: 1052.0145.
MUC1-STA-Tn 2: ESI ($C_{96}H_{153}N_{29}O_{37}$): calculated ($[M+2H^+]/2$): 1153.5547, found: 1153.5508.
MUC1-DTR 3: ESI ($C_{96}H_{152}N_{30}O_{34}$): calculated (($[M+Na+2H^+]/3$): 765.0406, found: 765.0400.
MUC1-DTR-Tn 4: ESI ($C_{104}H_{165}N_{31}O_{39}$): calculated ($[M+2H^+]/2$): 1237.6016, found: 1237.5977.

N₃-AHGVTSAPDTRPAPGSTnAPP

MUC1-STA-Tn 2

N₃-APGSTAPPAHGVTSAPDTRPAP
MUC1-DTR 3

N₃-APGSTAPPAHGVTSAPDTnRPAP
MUC1-DTR-Tn 4

Conjugate 10

Conjugate 11

Conjugate 12

Conjugate 13

Conjugate 14 carbohydrates from Salmonella bacteria

FIG. 83

| Sera concentration | PBS | Normal rabbit serum (control) | Q-beta glycan serum |
|---|---|---|---|
| neat | 0% (0/5) | 100% (5/5) | 80% (4/5) |
| 1:10 | | 20% (1/5) | 100% (5/5) |
| 1:100 | | 20% (1/5) | 80% (4/5) |
| 1:1,000 | | 0% (0/5) | 80% (4/5) |
| 1:10,000 | | 20% (1/5) | 0% (0/5) |

VACCINE AND THERAPEUTIC COMPOSITIONS COMPRISING ANTIGEN-CONJUGATED VIRAL CAPSIDS

RELATED APPLICATIONS

This application is a national-stage application based on PCT/US18/28887, filed Apr. 23, 2018, which claims the benefit of priority to U.S. Provisional Patent Application Ser. No. 62/551,045 filed Aug. 28, 2017, each of which is hereby incorporated herein by reference in its entirety.

GOVERNMENT SUPPORT

This invention was made with government support under CA149451 and under CA225105 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 25, 2018, is named MSS-019_25 (31742-01925)_SL.txt and is 64,498 bytes in size.

BACKGROUND OF THE INVENTION

The development of effective vaccines for cancer treatment and prevention is a grand scientific challenge. While tumor cells can be antigenic, a significant roadblock is the low immune responses to the tumor associated antigens due to their low inherent immunogenicities as well as the immune suppression by tumor cells. As a result, innovative strategies are needed to activate the immune system and generate tumor specific immunity.

One important class of tumor antigens is the tumor associated carbohydrate antigens (TACAs). Due to genetic and/or epigenetic alterations, the structures and expression levels of carbohydrates on tumor cells are significantly different from those on normal cells, thus presenting appealing targets for anticancer vaccine development.

A carrier system is essential to deliver TACAs to the immune system and elicit strong anti-TACA antibody responses. This is because TACAs typically are B cell antigens only. Administration of TACA alone generally cannot engage T cells, which results in weak B cell activation producing only low IgM antibody titers. Many carrier systems for TACAs have been investigated, which include immunogenic proteins, polysaccharides, self-assembled peptides macromolecules, nanoparticles and liposomes. Among these, protein carriers exemplified by KLH is the most advanced, as multiple KLH-TACA conjugates have been evaluated in late stage clinical trials. Anti-TACA antibodies can be generated via KLH-TACA conjugates. Multiple studies have shown that cancer patients capable of producing high levels of anti-TACA antibodies are associated with better prognosis and survival. However, with the full patient cohort, vaccination failed to exhibit statistically significant protection as the antibody titers elicited overall were not sufficient highlighting the critical need for further development.

A potential drawback of protein carrier is that high anti-carrier antibody responses can be induced by the glycoconjugate. As an example, GD3-KLH generated an-antiGD3 IgG titer of 300, while that for KLH were 1,800,000. The high anti-carrier antibodies can significantly suppress the generation of anti-glycan antibodies. This phenomenon has been reported for carbohydrate based anti-microbial disease vaccines. It has been suggested that an ideal carrier should induce high levels of anti-glycan antibodies without strong anti-self antibodies.

Accordingly, there is a great need in the art to identify potential therapeutic strategies and compositions that activate immune responses in the treatment and prevention of cancer.

Recently, virus like particles have emerged as a new class of immunogenic carriers for carbohydrate based anti-cancer vaccine design. VLP Qb is capable of eliciting strong IgG antibodies against multiple TACAs. However, as a protein carrier, Qb can also induce significant anti-carrier antibodies. Herein, we report structure guided rational design of Qb mutants. When conjugated with a TACA, the novel mutants are associated with significantly reduced anti-Qb antibody responses and at the same time elicit super high levels of anti-TACA IgG antibodies. Evaluation in a highly aggressive tumor model showed that while all mice died within 14 days without treatment, vaccination with an mQb-TACA conjugate combined with chemotherapy provided 100% protection to all mice against repeated tumor challenges.

SUMMARY OF THE INVENTION

Provided herein are vaccine compositions comprising an antigen conjugated to a capsid. In some embodiments, the vaccine composition comprises an antigen conjugated to a wild type capsid. In some embodiments, the vaccine composition comprises an antigen conjugated to a wild type bacteriophage Qβ capsid. In some embodiments, the vaccine composition comprises an antigen conjugated to a bacteriophage Qβ capsid having a wild type or native sequence. In some embodiments, the vaccine composition comprises an antigen conjugated to a bacteriophage Qβ capsid having a wild type or natural sequence set forth in SEQ ID NO: 1 or SEQ ID NO: 3. In some embodiments, the vaccine composition comprises an antigen conjugated to a capsid having at least one mutation from the wild type capsid. In some embodiments, the vaccine composition comprises an antigen conjugated to a bacteriophage Qβ capsid having at least one mutation from the wild type bacteriophage Qβ capsid. In some embodiments, the at least one mutation comprises a non-natural mutation. In some embodiments, the non-natural mutation comprises a non-natural amino acid mutation.

In certain embodiments of the vaccine composition, the capsid comprises at least one, two, three, four, five, six, seven, eight, nine, ten, eleven, twelve, thirteen, fourteen, fifteen, sixteen, seventeen, eighteen, nineteen, or twenty mutations.

In certain embodiments of the vaccine composition, the at least one non-natural mutation is a disulfide bond mutation.

In certain embodiments of the vaccine composition, the antigen is selected from the group consisting of carbohydrate antigen, peptide, protein, nucleic acid, and organic molecular antigen.

In certain embodiments of the vaccine composition, the antigen is a carbohydrate antigen.

In certain embodiments of the vaccine composition, the carbohydrate antigen is selected from the group consisting of (a) Mucin1 (MUC1), (b) Mucin4 (MUC4), (c) Ganglioside GD2 (GD2), (d) Fucosyl Ganglioside GM1 (GM1), (e) acetylated GD2, (f) Ganglioside GD3 (GD3), (g) acetylated GD3, (h) Fucosyl Ganglioside GM2 (GM2), (i) Globo-H, (j)

Lewis A, (k) Lewis Y, (1) polysialic acid, (m) sialyl-Lewis A, (n) Tf, (o) Tn, (p) sTn, Tn1, and Tn2.

In certain embodiments of the vaccine composition, the carbohydrate antigen is MUC1.

In certain embodiments of the vaccine composition, the carbohydrate antigen is GD2 or 9-NHAc-GD2.

In certain embodiments of the vaccine composition, the capsid is a bacteriophage capsid.

In certain embodiments of the vaccine composition, the bacteriophage is selected from the group consisting of (a): bacteriophage Qβ; (b) bacteriophage R17; (c) bacteriophage fr; (d) bacteriophage GA; (e) bacteriophage SP; (f) bacteriophage MS2; (g) bacteriophage M11; (h) bacteriophage MX1; (i) bacteriophage NL95; (j) bacteriophage f2; (k) bacteriophage PP7; (1) bacteriophage AP205; and (m) bacteriophage P22.

In certain embodiments of the vaccine composition, the bacteriophage is bacteriophage Qβ.

In certain embodiments of the vaccine composition, the mutation comprises at least one mutation selected from N10K, A38K, A40C, A40S, T75K, D102C, D102S, or A117K, or combination thereof.

In certain embodiments of the vaccine composition, the capsid comprises at least two mutations selected from A40C/D102C, A40S/D102S, or A43C/Q98C.

In certain embodiments of the vaccine composition, the capsid comprises at least three mutations selected from A40C/D102C/K13R or A38K/A40C/D102C.

Also provided herein is a method for preventing or treating cancer in a subject, the method comprising administering to the subject a vaccine composition as described herein.

In another aspect, a method of preventing or treating a pathogenic infection in a subject, the method comprising administering to the subject a vaccine composition as described herein, is provided.

In yet another aspect, a method of preventing or treating an inflammatory disease, the method comprising administering to the subject a vaccine composition as described herein, is provided.

In yet another aspect, a method of preventing or treating a neurodenerative disease, the method comprising administering to the subject a vaccine composition as described herein, is provided.

Numerous embodiments are further provided that can be applied to any aspect of the present invention described herein.

For example, in some embodiments, the pathogenic infection is a bacterial, fungal, or viral infection.

In some embodiments, the vaccine composition is administered systematically.

In some embodiments, the systematic administration is selected from the group consisting of oral, intravenous, intradermal, intraperitoneal, subcutaneous, and intramuscular administration.

In some embodiments, the composition is administered intratumorally or peritumorally.

In some embodiments, the cancer is a solid tumor.

In some embodiments, the cancer is selected from the group consisting of oral cancer, breast cancer, brain cancer, childhood cancer, ovarian cancer, prostate cancer, pancreatic cancer, lung cancer, liver cancer, throat cancer, stomach cancer, and kidney cancer.

In some embodiments, the cancer is lung cancer.

In some embodiments, the cancer is breast cancer.

In some embodiments, the childhood cancer is neuroblastoma.

In some embodiments, the subject is a mammal.

In some embodiments, the mammal is human.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF FIGURES

FIGS. 11A and 11B show Anti-Tn1 titers of the post-immunized sera presented in linear and log scale, respectively. The statistical significance of differences between a mQβ and wtQβ was determined by the Student t test (p<0.01; *p<0.001; ****p<0.0001). FIG. 11C shows $OD_{450}$ from ELISA result at 1/819200 sera dilution of IgG subtypes antibodies (IgG1, IgG2b, IgG2c and IgG3) elicited by wtQβ-Tn1, mQβ(A38K/A40C/D102C)-Tn1 and mQβ(A40C/D102C)-Tn1 immunization against BSA-Tn1.

FIG. 14A shows $OD_{450}$ from the ELISA result of the post-immunized sera at 1/819200 dilution against BSA-Tn1. FIG. 14B shows $OD_{450}$ from the ELISA result of the post-immunized sera at 1/1638400 against the corresponding carrier capsids. The statistical significance of differences between mQβ and wtQβ was determined by the Student t test.

FIGS. 15A and 15B are graphs of median fluorescent intensities of the binding recognition of the elicited antibodies towards Jurkat cells and TA3Ha cells, respectively.

FIG. 16B and FIG. 16C depict MFI of cellular binding against Jurkat cells of the serum from mice immunized with wtQβ-Tn2 and mQβ(A38K/A40C/D102C)-Tn2 compared with those from wtQβ-Tn1 and mQβ(A38K/A40C/D102C)-Tn1.

FIG. 17A depicts a histogram showing binding recognition of the elicited antibodies against TA3Ha cells, respectively. FIG. 17B is a graph comparing median fluorescent intensities of the binding recognition of the elicited antibodies towards TA3Ha cells.

FIG. 19A depicts the survival after $1^{st}$ tumor challenge with treatment of CP (n=10). FIG. 19B depicts the survival after $2^{nd}$ tumor challenge without any further treatment (n=5). Statistical analysis of survival is determined by using the log-rank test in GraphPad Prism software. Note: Control experiments have been done in reference (Yin, Z et al. *ACS Chemical Biology* 2015, 10 (10), 2364-2372).

FIGS. 21A and 21B depict histograms showing binding recognition of the elicited antibodies against Jurkat cells and TA3Ha cells, respectively, c and d) Graph of median fluorescent intensities of the binding recognition of the elicited antibodies towards Jurkat cells and TA3Ha cells, respectively.

FIG. 22A corresponds to Qβ_WT_Tn1. FIG. 22B corresponds to Qβ_T7K_Tn1. FIG. 22C corresponds to Qβ_N10K_Tn1. FIG. 22D corresponds to Qβ_K13R/A40C/D102C_Tn1. FIG. 22E corresponds to Qβ_A38K_Tn1. FIG. 22F corresponds to QR_A38K/A40C/D102C_Tn1. FIG. 22G corresponds to QR_A38K/A40C/D102C_Tn2. FIG. 22H corresponds to QR_A40C/D102C_Tn1. FIG. 22I corresponds to QR_A40C/D102C_Tn2. FIG. 22J corresponds to QR_A40S/D102S_Tn1. FIG. 22K corresponds to Qβ_T75K_Tn1. FIG. 22L corresponds to Qβ_A117K_Tn1. FIG. 22M corresponds to Qβ_P119K_Tn1.

FIG. 23A corresponds to Qβ(WT) and Qβ(WT)-Tn1. FIG. 23B corresponds to Qβ(T7K) and Qβ(T7K)-Tn1. FIG. 23C corresponds to Qβ(N10K) and Qβ(N10K)-Tn1. FIG. 23D corresponds to Qβ(A38K) and Qβ(A38K)-Tn1. FIG. 23E corresponds to Qβ(A38K/A40C/D102C) and Qβ(A38K/A40C/D102C)-Tn1. FIG. 23F corresponds to Qβ(A40C/D102C) and Qβ(A40C/D102C)-Tn1. FIG. 23G corresponds to Qβ(T75K) and Qβ(T75K)-Tn1. FIG. 23H corresponds to Qβ(A117K) and Qβ(A117K)-Tn1. FIG. 23I corresponds to Qβ(P119K) and Qβ(P119K)-Tn1.

FIG. 42 contains three panels FIGS. 42A-42C.

FIG. 44 contains three panels FIGS. 44A-44C depicting flow cytometry analysis of the specific recognition of tumor cells by anti-MUC1 IgG antibodies.

FIG. 49 contains two panels, FIG. 49A and FIG. 49B.

FIG. 58 contains three panels. FIG. 58A shows solid phase synthesis of MUC1 (glyco)peptides 38 and 39. FIG. 58B shows synthesis of Qβ-MUC1 conjugates 42, 43. FIG. 58C shows KLH-MUC1 conjugate 44 (Scheme 5).

FIG. 59 contains three panels. (FIG. 59B) MCF-7 cells; and (FIG. 59C) MCF-10A cells. The binding was tested with 1:20 dilution of the sera. *p<0.05, p<0.01, *p<0.001. The p values were determined through a two tailed t test using GraphPad Prism.

FIG. 76 contains three panels, FIG. 76A-76C, showing complement dependent cytotoxicity of post-immune sera.

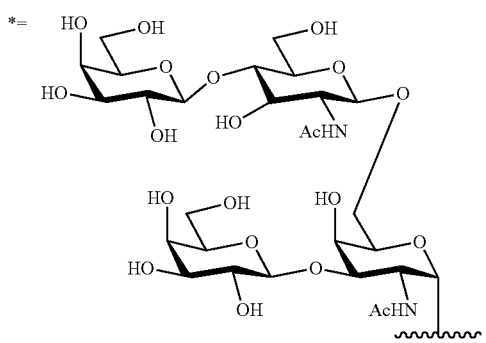

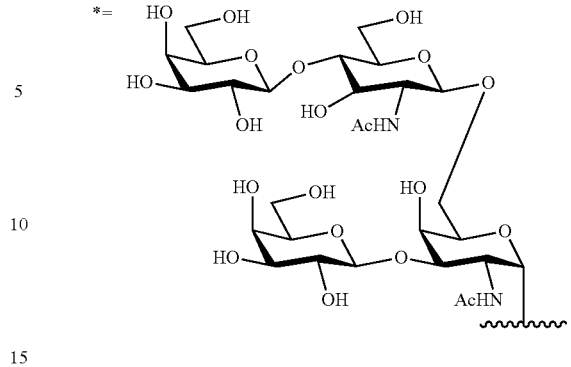

Analytical HPLC $R_t$=19.07 min (A/B: (95:5)→(95:5), 200 µL/min, 5 min, (95:5)→(40:60), 200 µL/min, 55 min); Preparative HPLC $R_t$=12.73 min (A/B: (95:5)→(55:45), 20 mL/min, 40 min); HR-ESI-MS, m/z: 729.9993 ([M+3H]$^{3+}$, calc. 729.9974), 1094.5014 ([M+2H]$^{2+}$, calc. 1094.4923); Yield: 47% (13.3 mg, 6.08 µmol). FIG. 79B shows MUC5B (13mer) core 2 type-2: H2N-(TEG)-ATPSSTPGT*THTP-OH (Pep 89)_(SEQ ID NO: 17) Analytical HPLC $R_t$=19.90 min (A/B: (95:5)→(95:5), 200 µL/min, 5 min, (95:5)→(40:60), 200 µL/min, 55 min); Preparative HPLC $R_t$=12.75 min (A/B: (95:5)→(55:45), 20 mL/min, 40 min); HR-ESI-MS, m/z: 729.9983 ([M+3H]3+, calc. 729.9974), 1094.4977 ([M+2H]2+, calc. 1094.4923); Yield: 38% (11.0 mg, 5.03 µmol).

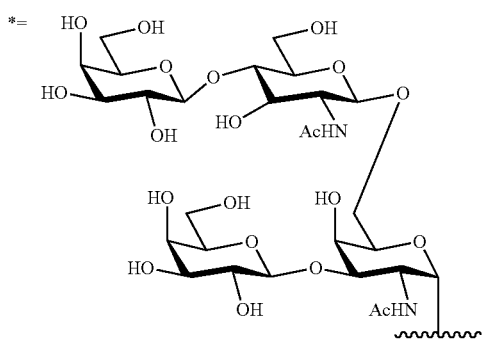

Figure 79A:
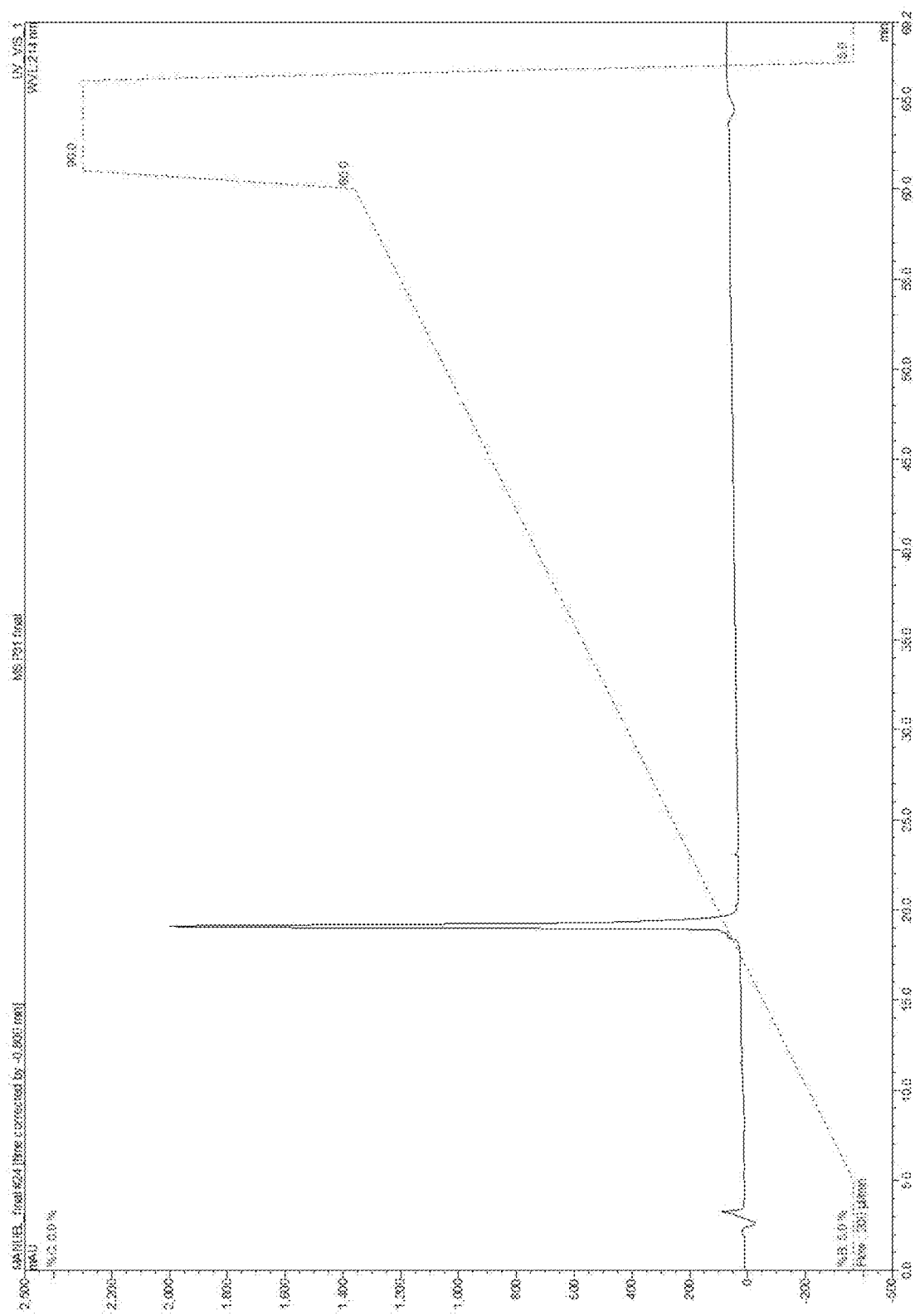
FIG. 79A shows the MUC5B (13mer) core 2 type-2: H$_2$N-(TEG)-ATPSST*PGTTHTP-OH (Pep 88) (SEQ ID NO: 16)
Figure 79B:
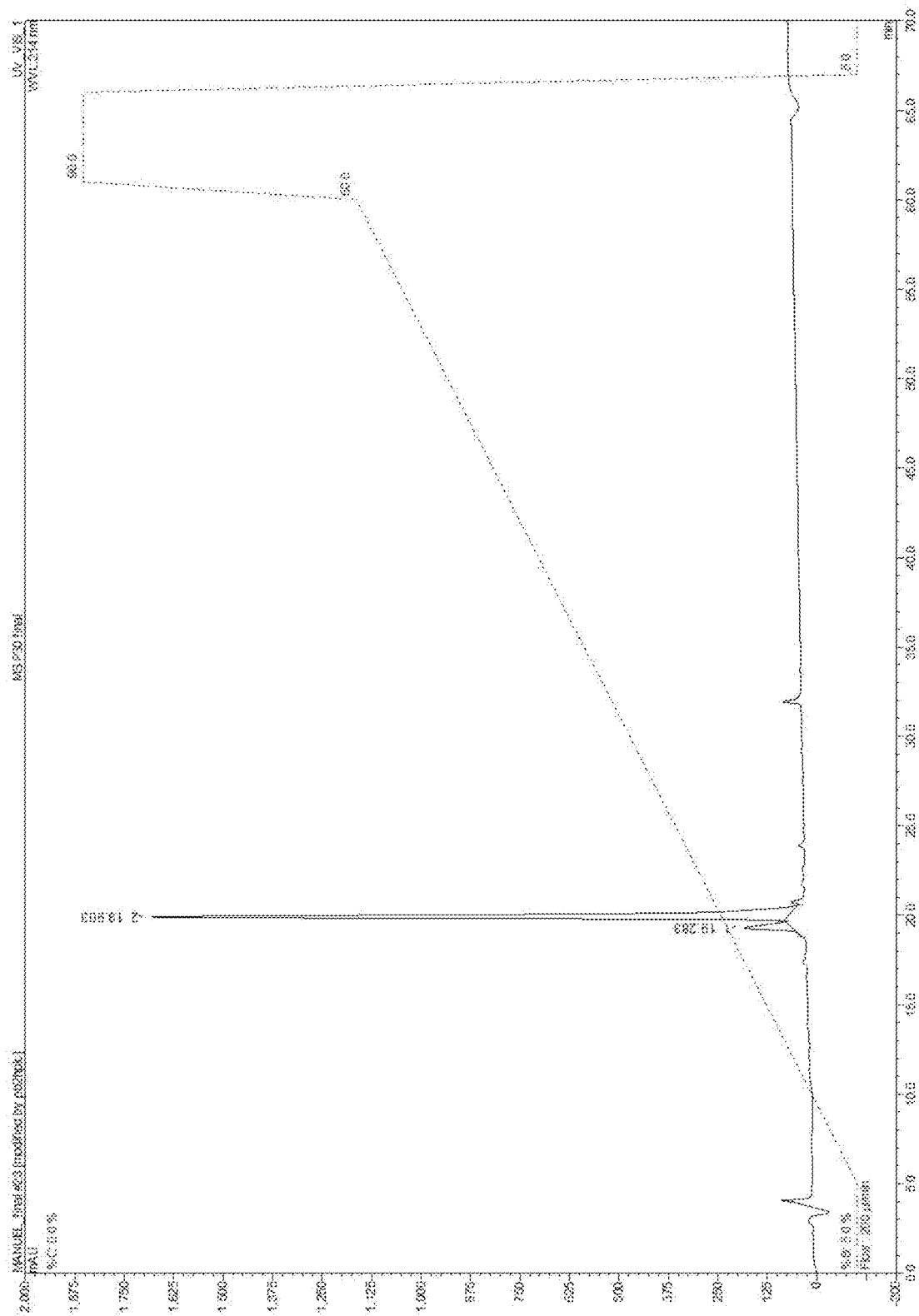
FIG. 79 contains three panels, FIGS. 79A-79C, showing purification and characterization data of MUC5b glycopeptides.
Figure 79C:
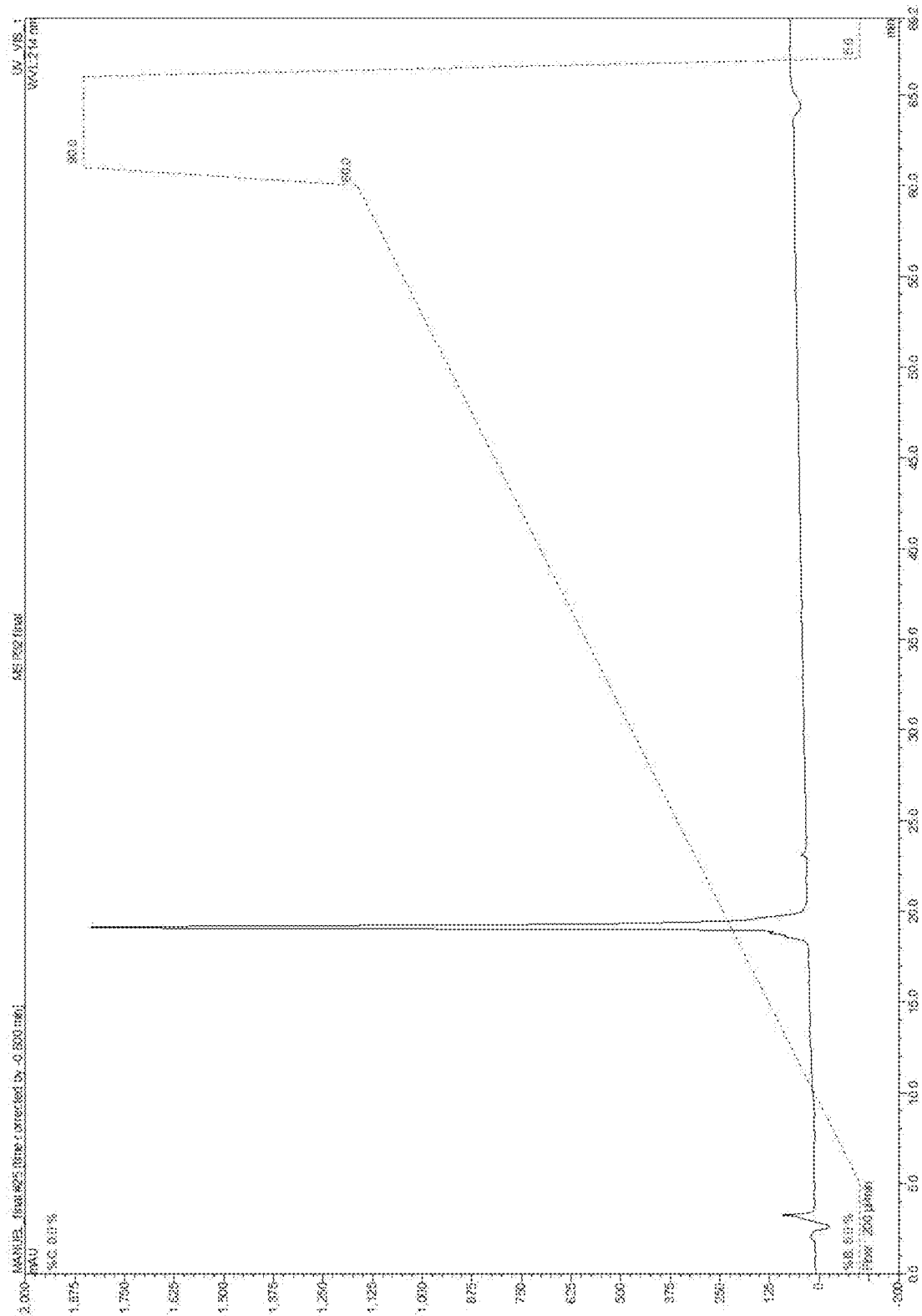

FIG. 79C shows MUC5B (13mer) core 2 type-2: H₂N-(TEG)-AT*PSSTPGTTHTP-OH (Pep 90) (SEQ ID NO: 18) Analytical HPLC $R_t$=19.11 min (A/B: (95:5)→(95:5), 200 µL/min, 5 min, (95:5)→(40:60), 200 L/min, 55 min); Preparative HPLC $R_t$=12.72 min (A/B: (95:5)→(55:45), 20 mL/min, 40 min); HR-ESI-MS, m/z: 729.9985 ([M+3H]3+, calc. 729.9974), 1094.4963 ([M+2H]$^{2+}$, calc. 1094.4923); Yield: 45% (12.8 mg, 5.85 µmol).

Figure 80:
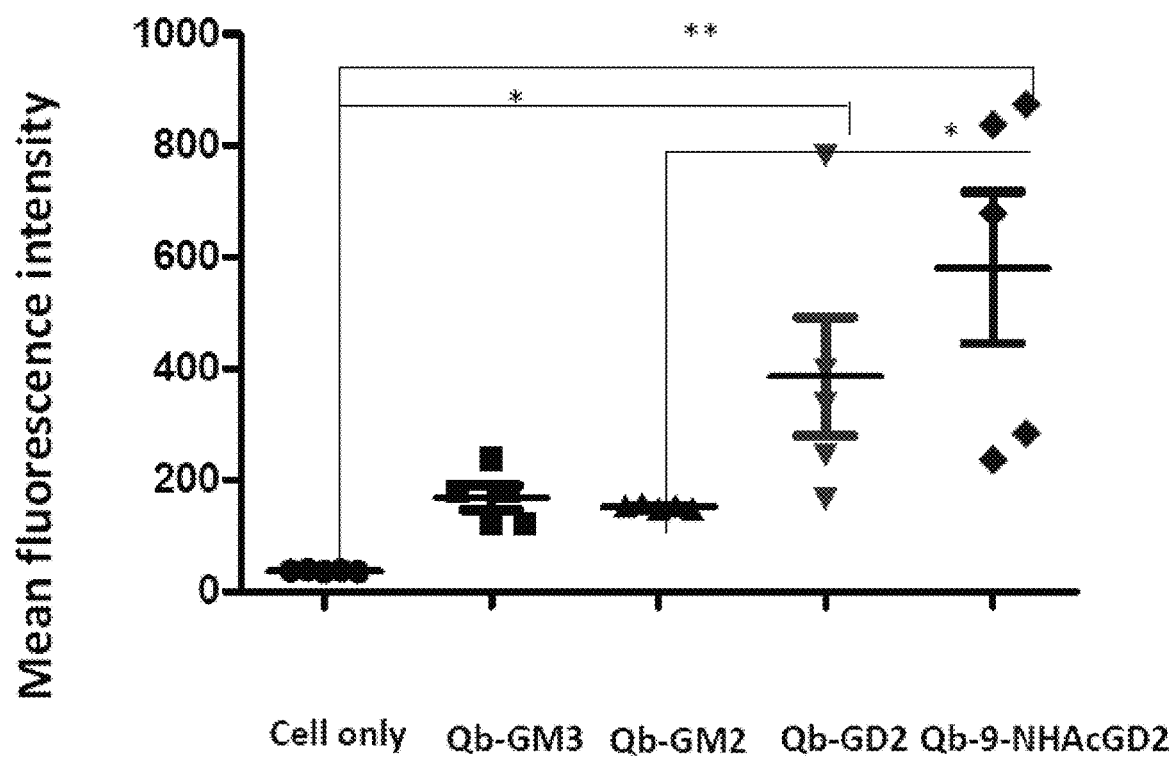

FIG. 80 depicts FACS binding to EL4 lymphoma cells. Post immune sera exhibited strong binding to lymphoma cells. The binding was stronger than post-immune sera from Qβ-GM3 and Qβ-GM2 vaccines.

Figure 81:
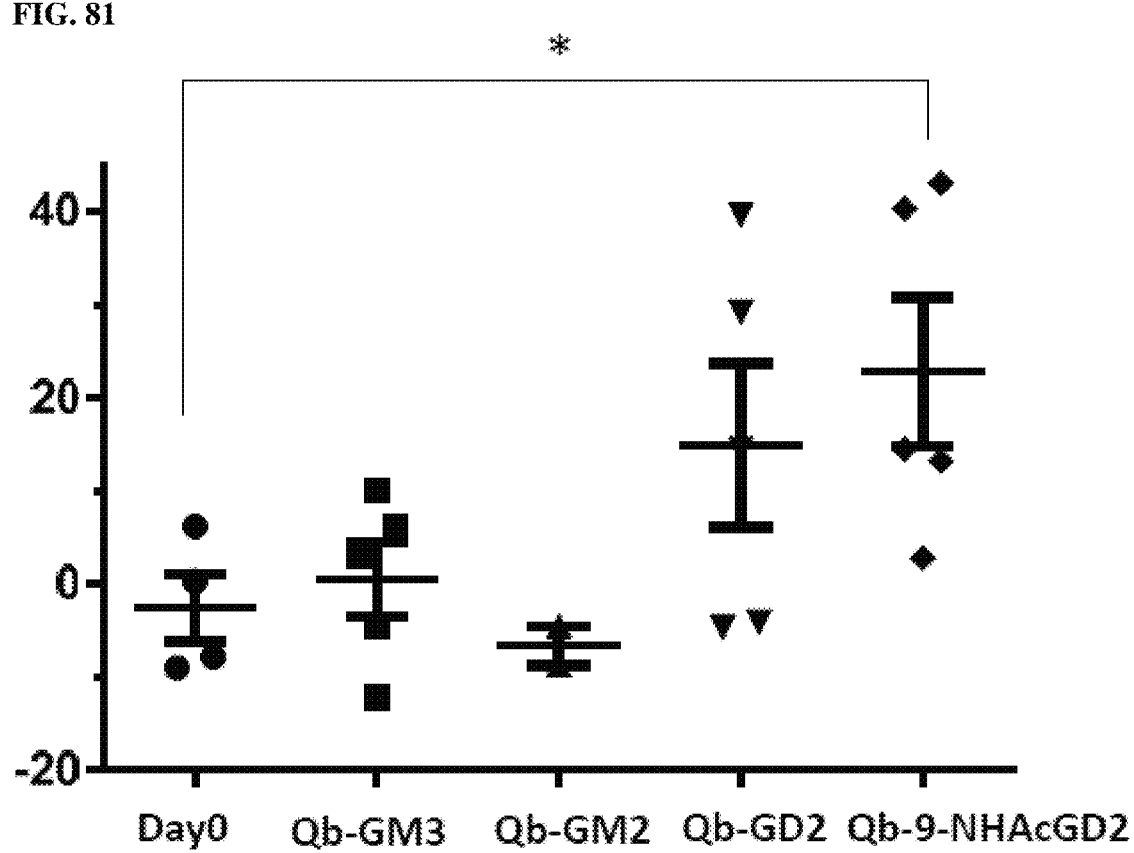

FIG. 81 shows that anti-GD2 sera exhibited strong killing of lymphoma cells EL4 via complement mediated cytotoxicities. Complement dependent cytotoxicity of EL4 was determined by MTS assay. EL4 cells (7000 cells/well) were cultured in DMEM (10% horse serum, 100 µl) for 24 h, incubated with a 1/40 dilution of antisera at 37° C. for 30 min from different groups of immunized mice, then rabbit sera complement at a 1/15 dilution in 50 µl of culture medium were added and then incubated at 37° C. for 4 h. MTS (20 µl) was added into each well and further incubated at 37° C. for 3 h. Cells cultured in Triton X-100 (0.5%) were used as a positive control.

Figure 82A:
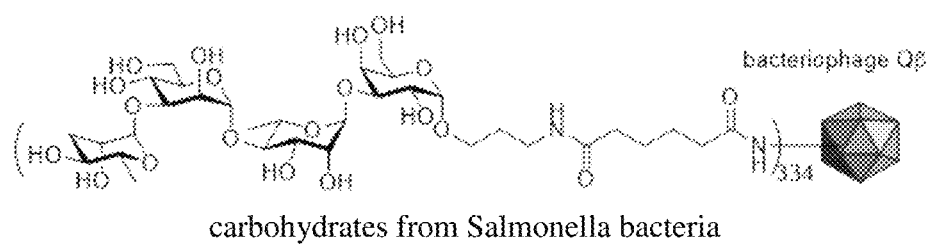
Figure 82B:
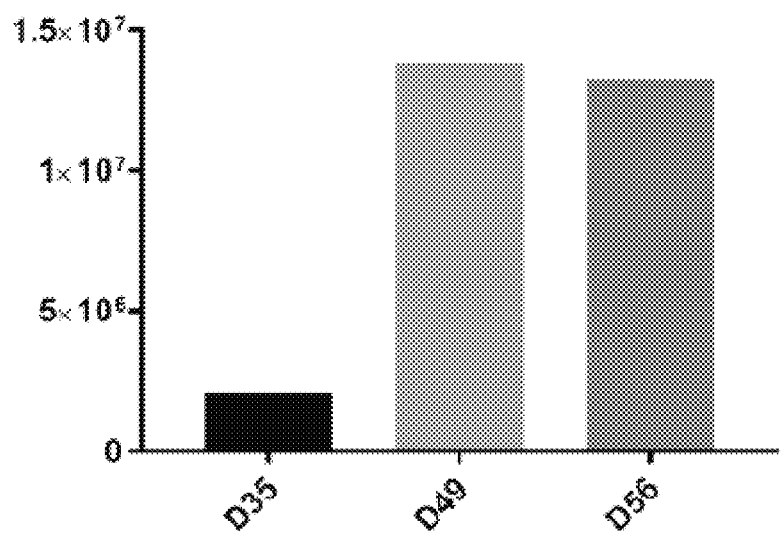

FIG. 82 contains 2 panels, FIGS. 82A and 82B, showing Qβ as carriers for anti-microbial vaccines. FIG. 82A is an example of carbohydrates from Salmonella bacteria that were synthesized and linked with bacteriophage Qβ. FIG. 82B shows that after rabbit immunization, very high IgG titers (>10,000,000) were obtained.

FIG. 83 shows that post-immune sera provided significant protection to mice against lethal salmonella infection. 5 mice per group. 0/5 means 0 mice survived bacterial challenge.

Figure 84A:
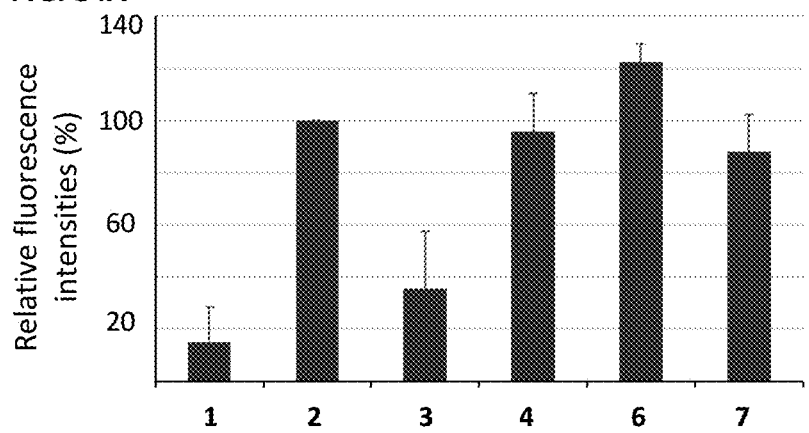
Figure 84B:
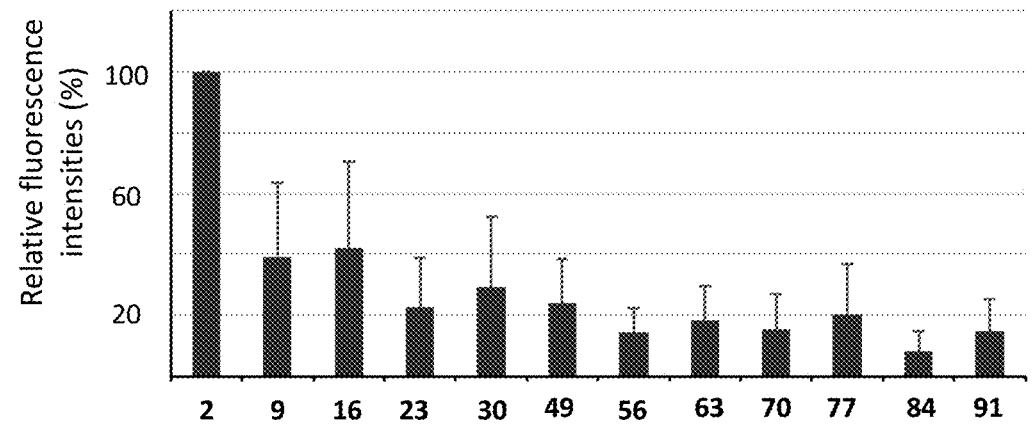

FIG. 84 contains 2 panels, FIGS. 84A and 84B. FIG. 84A shows comparison of fluorescence intensities of MUC1 glycopeptides bearing Tn antigen at various locations showed that glycosylation at PDT*R region (SEQ ID NO: 19) led to strongest recognition by post-immune sera. Glycopeptide 1: PAHGVT*SAPDTRPAPGSTA (SEQ ID NO: 20); 2: PAHGVTSAPDT*RPAPGSTA (SEQ ID NO: 21); 3: PAHGVTSAPDTRPAPGS*A (SEQ ID NO: 22); 4: PAHGVT*SAPDT*RPAPGSTA (SEQ ID NO: 23); 6: PAHGVTSAPDT*RPAPGST*A (SEQ ID NO: 24); 7: PAHGVT*SAPDT*RPAPGST*A (SEQ ID NO: 25). FIG. 84B shows comparison of fluorescence intensities of MUC1 glycopeptides bearing various glycans at PAHGVT*SAPDT*RPAPGSTA (SEQ ID NO: 21) showed that while Tn gave the strongest recognition, other glycans can be recognized as well. Glycan structures: glycopeptide 2: Tn; 9: C3T1 (for abbreviations and structures, see FIG. 78); 16: C3T2; 23: C4T1; 30: C4T2; 49: T; 56: C1T1; 63: C1T2; 70: C2T1he; 77: C2T1te; 84: C2T2he; 91: C2T2te.

Note that for every figure containing a histogram, the bars from left to right for each discreet measurement correspond to the figure boxes from top to bottom in the figure legend as indicated.

DETAILED DESCRIPTION OF THE INVENTION

A. Definitions

The articles "a" and "an" are used herein to refer to one or to more than one (i.e., to at least one) of the grammatical object of the article. By way of example, "an element" means one element or more than one element.

The term "administering" means providing a pharmaceutical agent or composition to a subject, and includes, but is not limited to, administering by a medical professional and self-administering.

As used herein, "bacteriophage" refers to viruses that infect and replicate within bacterium. In certain embodiments, the bacteriophage is selected from, but not limited to, the group consisting of bacteriophage Qβ; (b) bacteriophage R17; (c) bacteriophage fr; (d) bacteriophage GA; (e) bacteriophage SP; (f) bacteriophage MS2; (g) bacteriophage M11; (h) bacteriophage MX1; (i) bacteriophage NL95; (j) bacteriophage f2; (k) bacteriophage PP7; (1) bacteriophage AP205; and (m) bacteriophage P22. As used herein, "bacteriophage Qβ" (also referred to as "bacteriophage Qb", "Qβ" and "Qb") is one of many small RNA bacteriophages infecting *Escherichia coli*.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, hepatocellular carcinoma (HCC), acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, Wilms tumor. In certain embodiments, any of the vaccine described herein may target the cancer stem cells of any of the aforementioned cancers.

As used herein, the "carbohydrate antigen" refers to classes of antigens that elicit elicit strong antibody responses. In certain embodiments, carbohydrate antigens are selected from, but not limited to, Mucins ("MUC1"), Ganglioside GD2 (Ahmed M. et al. FEBS Letters 588:288-297 (2014), Fucosyl GM1, GD2 (including acetylated GD2), GD3 (including acetylated GD3), GM2, Globo-H, Lewis A, Lewis Y, mucins (e.g., MUC1, MUC4), polysialic acid, sialyl-Lewis A, carbohydrates from *Salmonella* bacteria (or any of the bacterial, virial, or pathogenic diseases provided herein), Tf, Tn, or sTn (Tn, Tf and STn are commonly found on glycoproteins such as MUC1).

The term "inhibit" or "inhibits" means to decrease, suppress, attenuate, diminish, arrest, or stabilize the development or progression of a disease, disorder, or condition, the activity of a biological pathway, or a biological activity, such as the growth of a solid malignancy, e.g., by at least 10%, 20%, 30%, 40%, 50%, 60%, 70%, 80%, 90%, 95%, 98%, 99%, or even 100% compared to an untreated control subject, cell, biological pathway, or biological activity or compared to the target, such as a growth of a solid malignancy, in a subject before the subject is treated. By the term "decrease" is meant to inhibit, suppress, attenuate, diminish, arrest, or stabilize a symptom of a cancer disease, disorder, or condition. It will be appreciated that, although not precluded, treating a disease, disorder or condition does not require that the disease, disorder, condition or symptoms associated therewith be completely eliminated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Pharmaceutically-acceptable salts" refers to the relatively non-toxic, inorganic and organic acid addition salts of compounds.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

A "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, and the like).

The term "subject in need thereof" means a subject identified as in need of a therapy or treatment.

The terms "systemic administration," "administered systemically," "peripheral administration," and "administered peripherally" mean the administration of a compound, drug or other material other than directly into the central nervous system, such that it enters the patient's system and, thus, is subject to metabolism and other like processes, for example, subcutaneous administration.

The term "therapeutic agent" or "pharmaceutical agent" refers to an agent capable of having a desired biological effect on a host.

The term "therapeutic effect" refers to a local or systemic effect in animals, particularly mammals, and more particularly humans, caused by a pharmacologically active substance.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The term "treating" a disease in a subject or "treating" a subject having a disease refers to subjecting the subject to a pharmaceutical treatment, e.g., the administration of a vaccine composition as described herein, such that at least one symptom of the disease is decreased, prevented from worsening, or delayed from worsening.

The terms "tumor," "solid malignancy," or "neoplasm" refer to a lesion that is formed by an abnormal or unregulated growth of cells. Preferably, the tumor is malignant, such as that formed by a cancer.

B. Capsids

Provided herein are vaccine compositions comprising an antigen conjugated to a capsid. In some embodiments, the vaccine composition comprises an antigen conjugated to a wild type capsid. In some embodiments, the vaccine composition comprises an antigen conjugated to a wild type bacteriophage Qβ capsid. In some embodiments, the vaccine composition comprises an antigen conjugated to a bacteriophage Qβ capsid having a wild type or native sequence. In some embodiments, the vaccine composition comprises an antigen conjugated to a bacteriophage Qβ capsid having a wild type or natural sequence set forth in SEQ ID NO: 1 or SEQ ID NO: 3. In some embodiments, the vaccine composition comprises an antigen conjugated to a capsid having at least one mutation from the wild type capsid. In some embodiments, the vaccine composition comprises an antigen conjugated to a bacteriophage Qβ capsid having at least one mutation from the wild type bacteriophage Qβ capsid. In some embodiments, the at least one mutation comprises a non-natural mutation. In some embodiments, the non-natural mutation comprises a non-natural amino acid mutation. In some embodiments, the vaccine compositions provided herein comprises an antigen (e.g., carbohydrate antigen, polypeptides, peptides, proteins and small molecules) conjugated to a capsid (e.g., bacteriophage Qb), wherein said capsid comprises at least one mutation (e.g., at least one point mutation, or at least one non-natural disulfide bond). In some embodiments, the capsid are fragments or a portion of the capsid amino acid sequence of sufficient length, that when conjugated to the antigen, can elicit an enhanced and strong immune response. In certain embodiments, the capsid polypeptide also includes amino acids that do not correspond to the naturally occurring capsid amino acid sequence (e.g., comprising at least one point mutation, or at least one non-natural disulfide bond mutation, or a fusion protein comprising a capsid amino acid sequence and an amino acid sequence corresponding to a non-capsid protein or polypeptide).

In some embodiments, the capsid is derived from bacteriophage. In certain embodiments, the bacteriophage is selected from the group consisting of bacteriophage Qβ; (b) bacteriophage R17; (c) bacteriophage fr; (d) bacteriophage GA; (e) bacteriophage SP; (f) bacteriophage MS2; (g) bacteriophage M11; (h) bacteriophage MX1; (i) bacteriophage NL95; (j) bacteriophage f2; (k) bacteriophage PP7; (l) bacteriophage AP205; and (m) bacteriophage P22.

In some embodiments, the capsid has a sequence set forth in coat protein Table A.

TABLE A

Listing of capsid and associated GenBank numbers

[*Escherichia* virus Qbeta] (GenBankAEQ25550.1)
coat protein [Enterobacteria phage M11] (GenBank AAC06250.1)
coat protein [Enterobacteria phage SP] (GenBank AEQ25562.1)
coat protein [Enterobacteria phage FI sensu lato] (Genbank NP_695027.1)
capsid protein [*Escherichia* virus FI] (Genbank ACT66758.1)
coat protein [*Escherichia* virus Qbeta] (Genbank ACY07224.1)
Chain A, Bacteriophage Q Beta Capsid (Genbank 1QBE_A)
capsid protein [*Escherichia* virus Qbeta] (ACT66734.1)
capsid protein [*Escherichia* virus Qbeta] (ACT66730.1)
capsid protein [*Escherichia* virus Qbeta] (ACT66742.1)
read-through protein [*Escherichia* virus Qbeta] (ACY07231.1)
A1 protein [*Escherichia* virus Qbeta] (AAA16663.1)
read-through protein [*Escherichia* virus Qbeta] (AEQ25545.1)
Minor capsid protein A1 (Q8LTE1.2)
read-through protein [*Escherichia* virus Qbeta] (ACY07227.1)
read-through protein [*Escherichia* virus Qbeta] (ACY07235.1)
capsid protein [*Escherichia* virus Qbeta] (ACT66738.1)
read-through protein [*Escherichia* virus Qbeta] (AEQ25549.1)
read-through protein [*Escherichia* virus Qbeta] (AEQ25541.1)
read-through protein [*Escherichia* virus Qbeta] (ACY07223.1)
read-through protein [*Escherichia* virus Qbeta] (ACT66735.1)
Chain A, Bacteriophage Qbeta Coat Protein In Complex With Rna Operator Hairpin (4L8H_A)
read-through protein [*Escherichia* virus Qbeta] (ACT66731.1)
read-through protein [*Escherichia* virus Qbeta] (ACT66743.1)
read-through protein [*Escherichia* virus Qbeta] (ACT66739.1)
capsid protein [*Escherichia* virus Qbeta] (ACT66746.1)
major coat protein [*Escherichia* virus Qbeta] (NP_046751.1)
read-through protein [*Escherichia* virus Qbeta] (ACT66747.1)
minor coat protein [*Escherichia* virus Qbeta] (NP_046750.1)
coat protein [Enterobacteria phage SP] (ACY07244.1)
coat protein [Enterobacteria phage SP] (ACY07240.1)
A1-protein [Enterobacteria phage M11] (AAC06251.1)
coat protein [Enterobacteria phage SP] (AEQ25558.1)
capsid protein [*Escherichia* virus FI] (ACT66762.1)
major coat protein [*Escherichia* virus FI] (YP_009208147.1)
capsid protein [*Escherichia* virus FI] (ACT66750.1)
coat protein [Enterobacteria phage SP] (ACY07248.1)
read-through protein [Enterobacteria phage SP] (ACY07251.1)
read-through protein [Enterobacteria phage SP] (AEQ25561.1)
read-through protein [Enterobacteria phage SP] (ACY07243.1)
Minor capsid protein A1 (P09677.1)
readthrough protein [Enterobacteria phage FI sensu lato] (NP_695026.1)
capsid protein [*Escherichia* virus FI] (ACT66754.1)
read-through protein [Enterobacteria phage SP] (AEQ25553.1)
read-through protein [Enterobacteria phage SP] (ACY07239.1)
read-through protein [Enterobacteria phage SP] (AEQ25557.1)
read-through protein [*Escherichia* virus FI] (ACT66759.1)
major coat protein [Enterobacteria phage NL95] (AAC14703.1)
read-through protein [*Escherichia* virus FI] (ACT66763.1)
read-through protein [Enterobacteria phage SP] (ACY07247.1)
A1-protein [*Escherichia* virus FI] (YP_009208146.1)
read-through protein [*Escherichia* virus FI] (ACT66751.1)
read-through protein [*Escherichia* virus FI] (ACT66755.1)
A1-protein [Enterobacteria phage NL95] (AAC14704.1)

In some embodiments, the bacteriophage Qβ capsid comprises a sequence set forth in SEQ ID NO: 1.

(SEQ ID NO: 1)
(M)AKLETVTLGNIGKDGKQTLVLNPRGVNPTNGVASLSQAGAVPALEKR
VTVSVSQPSRNRKNYKVQVKIQNPTACTANGSCDPSVTRQAYADVTFSFT
QYSTDEERAFVRTELAALLASPLLIDAIDQLNPAY

In some embodiments, the bacteriophage Qβ3 capsid comprises at least one mutation set forth in Table B.

TABLE B

Qβ mutants reported that assemble to form the capsid.

| entry | Mutation(s) | category | Yield (mg/L) | $T_m$ (° C.) |
|---|---|---|---|---|
| 1 | WT | — | ++ | 83.3 |
| 2[42a] | K16M | exterior charge/reactive site | na | na |
| 3[42a] | T93M | internal reactive site | na | na |
| 3[42b] | D14R | exterior charge | − | na |
| 4[42b] | N10R | exterior charge | ++ | na |
| 5[42b] | T18R | exterior charge | ++ | na |
| 6[42b] | D14R/T18R | exterior charge | − | unstable |
| 7[7a] | C74S | Remove disulfide | + | 61.7 |
| 8[7a] | C74S/C80S | Remove disulfide | ++ | 61 |
| 9[7a] | | Interdimer | | |
| 10[7a] | | Interdimer salt bridge | | |
| 11[7a] | Q65H | RNA binding | ++ | 78.6 |
| 12[7a] | D91N | RNA binding | + | 79.4 |
| 13[7a] | Q65H/D91N | RNA binding | + | 81.6 |
| 14[7a] | Y62F/C74S/C80S | combination | ++ | 60.4 |
| 15[7a] | D81N/C74S/C80S | combination | ++ | 62 |
| 16[7a] | Q65H/C74S | combination | + | 60.7 |
| 17[7a] | D91N/C74S | combination | + | 62.1 |
| 18[7a] | Q65H/D91N/C74S | combination | ++ | 61.4 |
| 19[7a] | | interdimer H-bond | | |
| 20[7a] | Y62W | Trp replace | + | 77.0 |
| 21[7a] | Y99W | Trp replace | + | 74.8 |
| 22[7a] | Y132W | C-term. Trp replace | + | 80.9 |
| 23[7a] | L35W | Trp replace | ++ | 72.2 |
| 24[7a] | P23A | structure | − | 73.8 |
| 25[7a] | K2Q | exterior charge | ++ | 74.5 |
| 26[7a] | K13Q/K16Q | exterior charge | ++ | 75.6 |
| 27[7a] | A1S | conjugation handle | + | 73.9 |
| 28[43] | K13E | exterior charge | na | na |
| 29[43] | K13Q | exterior charge | na | na |
| 30[43] | K16E | exterior charge | na | na |
| 31[43] | K16Q | exterior charge | na | na |
| 32[43] | K16F | exterior charge | na | na |
| 33[43] | K16Y | exterior charge | na | na |
| 34[43] | K46Q | exterior charge | na | na |
| 35[43] | K13Q/K16Q | exterior charge | na | na |

Note:
Yield ++: >80 mg/L,
+: >20-80 mg/L,
−: <20 mg/L,
na: not applicable
[7a] corresponds to Fiedler, J et al. *Biomacromolecules* 2012, 13 (8), 2339-2348;
[42a] corresponds to Prasuhn, D et al. *JACS* 2008, 130 (4), 1328-1334;
[42b] corresponds to Udit, A et al. *ChemBioChem* 2009, 10 (3), 503-510.
[43] corresponds to Hovlid, M. L et al. *The Scripps Research Institute*, La Jolla, 2014.

In certain embodiments, the capsid comprises at least two, three, four, five, six, seven, eight, nine, ten, eleven, twelve, thirteen, fourteen, fifteen, sixteen, seventeen, eighteen, nineteen, or twenty mutations. In some embodiments, the mutation is a non-natural disulfide bond mutation. In some embodiments, the capsid comprises, but not limited to, the following mutations (Table C).

TABLE C

Listing of bacteriophage Qβ capsid

N10K (Asparagine at position 10 of SEQ ID NO: 1 mutated to Lysine)
K13R (Lysine at position 13 of SEQ ID NO: 1 mutated to Arginine)
A38K (Alanine at position 38 of SEQ ID NO: 1 mutated to Lysine)
A40C (Alanine at position 40 of SEQ ID NO: 1 mutated to Cysteine)
A40S (Alanine at position 40 of SEQ ID NO: 1 mutated to Serine)
T75K (Threonine at position 75 of SEQ ID NO: 1 mutated to Lysine)
D102C (Aspartic acid at position 102 of SEQ ID NO: 1 mutated to Cysteine)

TABLE C-continued

Listing of bacteriophage Qβ capsid

D102S (Aspartic acid at position 102 of SEQ ID NO: 1 mutated to Serine)
A117K (Alanine at position 117 of SEQ ID NO: 1 mutated to Lysine)
A40C/D102C (double mutant wherein the Alanine at position 40 of SEQ ID NO: 1 mutated to Cysteine and the Aspartic acid at position 102 of SEQ ID NO: 1 mutated to Cysteine)
A40S/D102S (double mutant wherein the Alanine at position 40 of SEQ ID NO: 1 mutated to Serine and the Aspartic acid at position 102 of SEQ ID NO: 1 mutated to Serine).
A43C/N98C (double mutant wherein the Alanine at position 43 of SEQ ID NO: 1 mutated to Cysteine and the Glutamine at position 98 of SEQ ID NO: 1 mutated to Cysteine).
A40C/D102C/K13R (triple mutant wherein the Alanine at position 40 of SEQ ID NO: 1 mutated to Cysteine, the Aspartic acid at position 102 of SEQ ID NO: 1 mutated to Cysteine, and the Lysine at position 13 of SEQ ID NO: 1 mutated to Arginine)
A38K/A40C/D102C (triple mutant wherein Alanine at position 38 of SEQ ID NO: 1 mutated to Lysine, the Alanine at position 40 of SEQ ID NO: 1 mutated to Cysteine, and the Aspartic acid at position 102 of SEQ ID NO: 1 mutated to Cysteine).

Additional single point mutations may comprise, but not limited to, point mutations at K2, L4, V7, N10, K13, D14, K16, Q18, L20, A38, G40, E46, V67, T75, V85, Q99, E103, A117, P119, L122, or D127 of SEQ ID NO: 3, or combinations thereof.

N10K
(SEQ ID NO: 2)
(M) AKLETVTLGKIGKDGKQTLVLNPRGVNPTNGVASLSQAGAVPALEKR
VTVSVSQPSRNRKNYKVQVKIQNPTACTANGSCDPSVTRQAYADVTFSFT
QYSTDEERAFVRTELAALLASPLLIDAIDQLNPAY

A38K
(SEQ ID NO: 4)
(M) AKLETVTLGNIGKDGKQTLVLNPRGVNPTNGVASLSQKGAVPAL
EKRVTVSVSQPSRNRKNYKVQVKIQNPTACTANGSCDPSVTRQAYADVTF
SFTQYSTDEERAFVRTELAALLASPLLIDAIDQLNPAY

A40C
(SEQ ID NO: 5)
(M) AKLETVTLGNIGKDGKQTLVLNPRGVNPTNGVASLSQAGCVPAL
EKRVTVSVSQPSRNRKNYKVQVKIQNPTACTANGSCDPSVTRQAYADVTF
SFTQYSTDEERAFVRTELAALLASPLLIDAIDQLNPAY

A40S
(SEQ ID NO: 6)
(M) AKLETVTLGNIGKDGKQTLVLNPRGVNPTNGVASLSQAGSVPAL
EKRVTVSVSQPSRNRKNYKVQVKIQNPTACTANGSCDPSVTRQAYADVTF
SFTQYSTDEERAFVRTELAALLASPLLIDAIDQLNPAY

T75K
(SEQ ID NO: 7)
(M) AKLETVTLGNIGKDGKQTLVLNPRGVNPTNGVASLSQAGAVPAL
EKRVTVSVSQPSRNRKNYKVQVKIQNPTACKANGSCDPSVTRQAYADVTF
SFTQYSTDEERAFVRTELAALLASPLLIDAIDQLNPAY

D102C
(SEQ ID NO: 8)
(M) AKLETVTLGNIGKDGKQTLVLNPRGVNPTNGVASLSQAGAVPAL
EKRVTVSVSQPSRNRKNYKVQVKIQNPTACTANGSCDPSVTRQAYADVTF
SFTQYSTCEERAFVRTELAALLASPLLIDAIDQLNPAY

D102S
(SEQ ID NO: 9)
(M) AKLETVTLGNIGKDGKQTLVLNPRGVNPTNGVASLSQAGAVPAL
EKRVTVSVSQPSRNRKNYKVQVKIQNPTACTANGSCDPSVTRQAYADVTF
SFTQYSTSEERAFVRTELAALLASPLLIDAIDQLNPAY

A117K
(SEQ ID NO: 10)
(M) AKLETVTLGNIGKDGKQTLVLNPRGVNPTNGVASLSQAGAVPAL
EKRVTVSVSQPSRNRKNYKVQVKIQNPTACTANGSCDPSVTRQAYADVTF
SFTQYSTDEERAFVRTELAALLKSPLLIDAIDQLNPAY

A40C/D102C
(SEQ ID NO: 11)
(M) AKLETVTLGNIGKDGKQTLVLNPRGVNPTNGVASLSQAGCVPAL
EKRVTVSVSQPSRNRKNYKVQVKIQNPTACTANGSCDPSVTRQAYADVTF
SFTQYSTCEERAFVRTELAALLASPLLIDAIDQLNPAY

A40S/D102S
(SEQ ID NO: 12)
(M) AKLETVTLGNIGKDGKQTLVLNPRGVNPTNGVASLSQAGCVPAL
EKRVTVSVSQPSRNRKNYKVQVKIQNPTACTANGSCDPSVTRQAYADVTF
SFTQYSTSEERAFVRTELAALLASPLLIDAIDQLNPAY

A40C/D102C/K13R
(SEQ ID NO: 13)
(M) AKLETVTLGNIGRDGKQTLVLNPRGVNPTNGVASLSQAGCVPAL
EKRVTVSVSQPSRNRKNYKVQVKIQNPTACTANGSCDPSVTRQAYADVTF
SFTQYSTCEERAFVRTELAALLASPLLIDAIDQLNPAY

A43C/Q98C
(SEQ ID NO: 14)
(M) AKLETVTLGNIGKDGKQTLVLNPRGVNPTNGVASLSQAGAVPCL
EKRVTVSVSQPSRNRKNYKVQVKIQNPTACTANGSCDPSVTRQAYADVTF
SFTCYSTDEERAFVRTELAALLASPLLIDAIDQLNPAY

A38K/A40C/D102C
(SEQ ID NO: 15)
(M) AKLETVTLGNIGKDGKQTLVLNPRGVNPTNGVASLSQKGCVPAL
EKRVTVSVSQPSRNRKNYKVQVKIQNPTACTANGSCDPSVTRQAYADVTF
SFTQYSTCEERAFVRTELAALLASPLLIDAIDQLNPAY

In certain embodiments, bacteriophage Qb mutants may possess the following physical characteristics.

TABLE D

Physical characteristics of Qβ mutants.

| Qβ Mutants | Yield (mg/L) | SEC rv. (mL) | Z-Ave (d · nm) | PDI | Zeta potential |
|---|---|---|---|---|---|
| WT | 60 | 11.7 | 28.79 | 0.046 | −2.89 |
| T7K | 10 | 11.8 | 29.00 | 0.278 | −1.08 |
| N10K | 12 | 11.7 | 28.72 | 0.192 | −1.90 |
| A38K | 16 | 12.7 | 26.58 | 0.083 | −1.43 |
| T75K | 25 | 12.0 | 29.02 | 0.096 | −1.64 |
| A117K | 31 | 12.1 | 29.73 | 0.187 | −1.54 |
| P119K | 22 | 12.1 | 29.72 | 0.070 | −2.00 |
| A40C/D102C | 38 | 11.8 | 29.06 | 0.031 | −1.67 |
| A38K/A40C/D102C | 26 | 12.6 | 27.55 | 0.028 | −1.55 |
| A40S/D102S | 20 | 12.0 | 27.82 | 0.028 | −1.37 |
| A40C/D102C/K13R | 15 | 11.9 | 28.86 | 0.119 | −1.97 |

Figure 27:
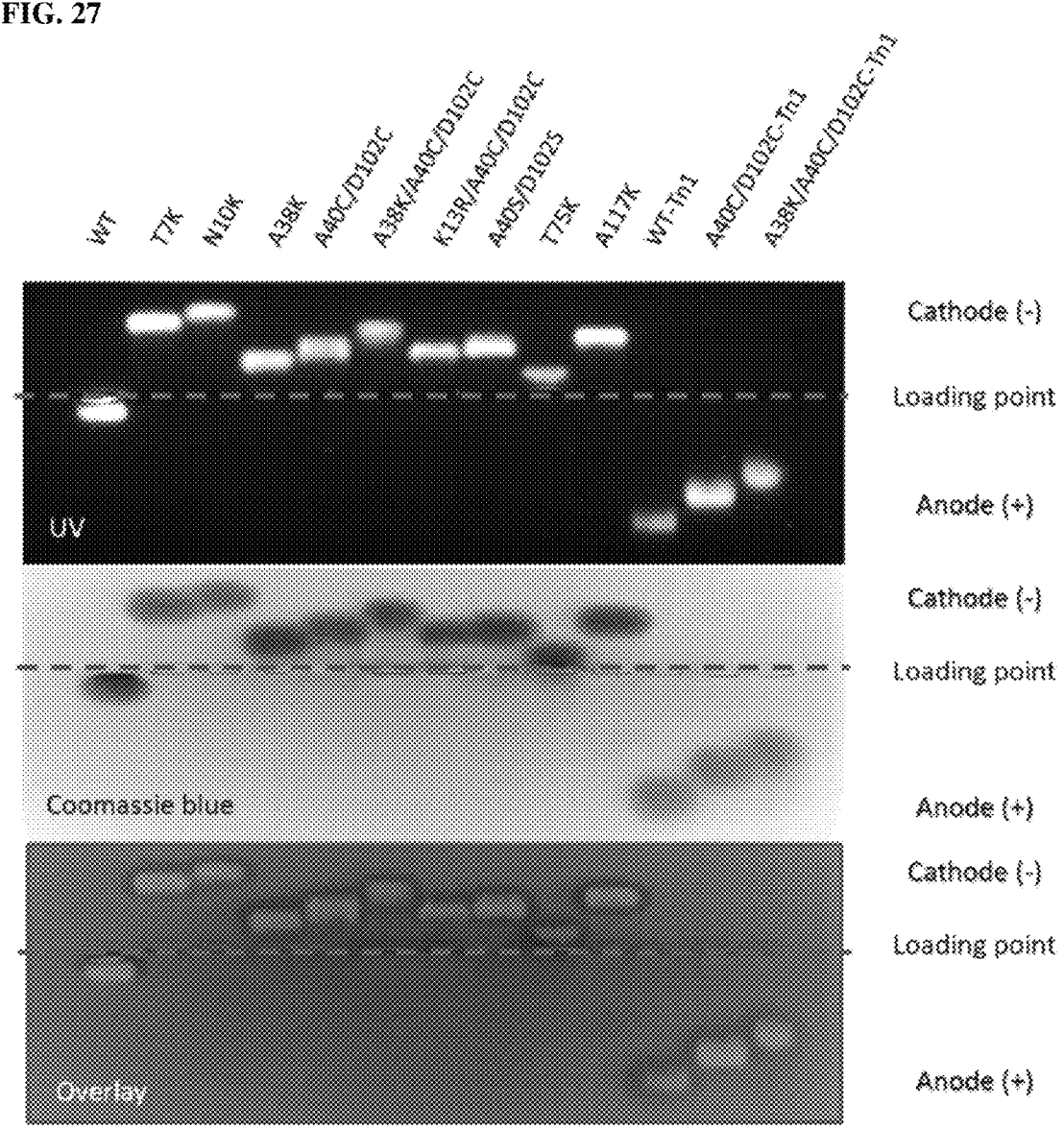
FIG. 27 shows electrophoretic mobility of Qβ whole capsids by native agarose gel. The samples (~30 μg of each capsid protein) were loaded into 0.7% agarose gel in PBS with SYBR Safe DNA gel strain as a straining reagent for the encapsulated RNA. The electrophoresis was performed in TEA buffer at 4° C. for 4 hours. The top panel shows the encapsulated RNA strain in the capsids as detected by UV light. The middle panel shows that capsid proteins were detected by Coomassie staining. The bottom panel shows an overlay of the two panels confirming the presence of the encapsulated RNA in the mQβs.

See also FIG. 27 for non-denaturing agarose gel showing that mutation of the native amino acids to lysine in all Qb mutants makes the surface charge of the mutant capsids more positive.

In some embodiments, the bacteriophage Qb capsid comprises a polypeptide comprising amino acid sequences at least 50%, 55%, 60%, 65%, 70%, 75%, 80%, 85%, 90%, 91%, 92%, 93%, 94%, 95%, 96%, 97%, 98% or 99% identical to the amino acid sequence set forth in SEQ ID NOs: 1-15. In some embodiments of the methods, compositions, and kits provided herein, the Qb mutant has at least one mutation set forth in Table C. In some embodiments, the bacteriophage Qβ capsid comprises a wild type or native sequence. In some embodiments, the bacteriophage Qβ capsid comprises a sequence consisting essentially of the sequence set forth in SEQ ID NO: 1 or SEQ ID NO: 3. In some embodiments, the Qb mutant has an amino acid sequence that consists essentially of the mutations set forth in SEQ ID NOs: 2-15. In some embodiments, the capsid comprises a polypeptide comprising amino acid sequences at least 50%, 55%, 60%, 65%, 70%, 75%, 80%, 85%, 90%, 91%, 92%, 93%, 94%, 95%, 96%, 97%, 98% or 99% identical to the amino acid sequence set forth in the GenBank numbers set forth in Table A.

In some embodiments of the methods, compositions and kits provided herein, the vaccine composition comprises a capsid having an amino acid sequence that consists of 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130 of SEQ ID Nos: 1-15, or biologically active variant thereof, or combinations thereof, or consecutive amino acids that are at least 70%, 75%, 80%, 85%, 90%, 91%, 92%, 93%, 94%, 95%, 96%, 97%, 98% or 99% identical to an amino acid sequence for a capsid (e.g., SEQ ID NOs: 1-15, or any of the GenBank numbers set forth in Table A). In some embodiments, the bacteriophage Qβ capsid comprises a wild type or native sequence. In some embodiments, the bacteriophage Qβ capsid comprises a sequence consisting essentially of the sequence set forth in SEQ ID NO: 1 or SEQ ID NO: 3.

As is well-known to those skilled in the art, polypeptides having substantial sequence similarities can cause identical or very similar immune reaction in a host animal. Accordingly, in some embodiments, a derivative, equivalent, variant, fragment, or mutant of the Qb capsid, or fragment thereof, can also suitable for the methods, compositions and kits provided herein.

In some embodiments, the altered polypeptide may have an altered amino acid sequence, for example by conservative substitution, yet still elicits an enhanced immune response, and are considered functional equivalents. As used herein, the term "conservative substitution" denotes the replacement of an amino acid residue by another, biologically similar residue. It is well known in the art that the amino acids within the same conservative group can typically substitute for one another without substantially affecting the function of a protein. According to certain embodiments, the derivative, equivalents, variants, or mutants of the Qb are at least 85% homologous to a sequence set forth in SEQ ID NOs: 1-15, or biologically active variant thereof, or combinations thereof. In some embodiments, the homology is at least 90%, at least 91%, at least 92%, at least 93%, at least 94%, at least 95%, at least 96%, at least 97%, at least 98%, or at least 99%. In some embodiments, the bacteriophage Qβ capsid comprises a wild type or native sequence. In some embodiments, the bacteriophage Qβ capsid comprises a sequence consisting essentially of the sequence set forth in SEQ ID NO: 1 or SEQ ID NO: 3.

C. Vaccine Compositions and Pharmaceutical Compositions/Formulations of Same Provided herein are vaccine compositions comprising an antigen conjugated to a capsid. In some embodiments, the vaccine composition comprises an antigen conjugated to a wild type capsid. In some embodiments, the vaccine composition comprises an antigen conjugated to a wild type bacteriophage Qβ capsid. In some embodiments, the vaccine composition comprises an antigen conjugated to a bacteriophage Qβ capsid having a wild type or native sequence. In some embodiments, the vaccine composition comprises an antigen conjugated to a bacteriophage Qβ capsid having a wild type or natural sequence set forth in SEQ ID NO: 1 or SEQ ID NO: 3. In some embodiments, the vaccine composition comprises an antigen conjugated to a capsid having at least one mutation from the wild type capsid. In some embodiments, the vaccine composition comprises an antigen conjugated to a bacteriophage Qβ capsid having at least one mutation from the wild type bacteriophage Qβ capsid. In some embodiments, the at least one mutation comprises a non-natural mutation. In some embodiments, the non-natural mutation comprises a non-natural amino acid mutation. In some embodiments, the vaccine compositions provided herein comprises an antigen (e.g., carbohydrate antigen, polypeptides, peptides, proteins, and small molecules) conjugated to a capsid (e.g., bacteriophage Qb), wherein said capsid comprises at least one mutation (e.g., at least one point mutation, at least one non-natural amino acid mutation, or at least one non-natural disulfide bond mutation). The capsid is described in Section B, supra. In some embodiments, the antigens are fragments or a portion of the carbohydrate antigen of sufficient length, that when conjugated to the capsid, can elicit an enhanced and strong immune response. The capsid may be conjugated to a plurality of multiple antigens that are the same or different antigen. In certain embodiments, the antigen is a protein and peptide is selected from, but not limited to, TNFalpha, IL1α, IL1β, tau protein, PCSK9, or amyloid β. In some embodiments, the antigen is a small molecule selected from, but not limited to, nicotine, cocaine, or advanced glycation product.

In certain embodiments, the antigen polypeptide also includes amino acids that do not correspond to the naturally occurring antigen amino acid sequence (e.g., comprising at least one non-natural mutation). In some embodiments, the carbohydrate antigen is selected from the group consisting of (a) Mucin1 (MUC1), (b) Mucin4 (MUC4), (c) Ganglioside GD2 (GD2), (d) Fucosyl Ganglioside GM1 (GM1), (e) acetylated GD2, (f) Ganglioside GD3 (GD3), (g) acetylated GD3, (h) Fucosyl Ganglioside GM2 (GM2), (i) Globo-H, (j) Lewis A, (k) Lewis Y, (l) polysialic acid, (m) sialyl-Lewis A, (n) Tf, (o) Tn, (p) sTn, Tn1, and Tn2.

Figure 10:
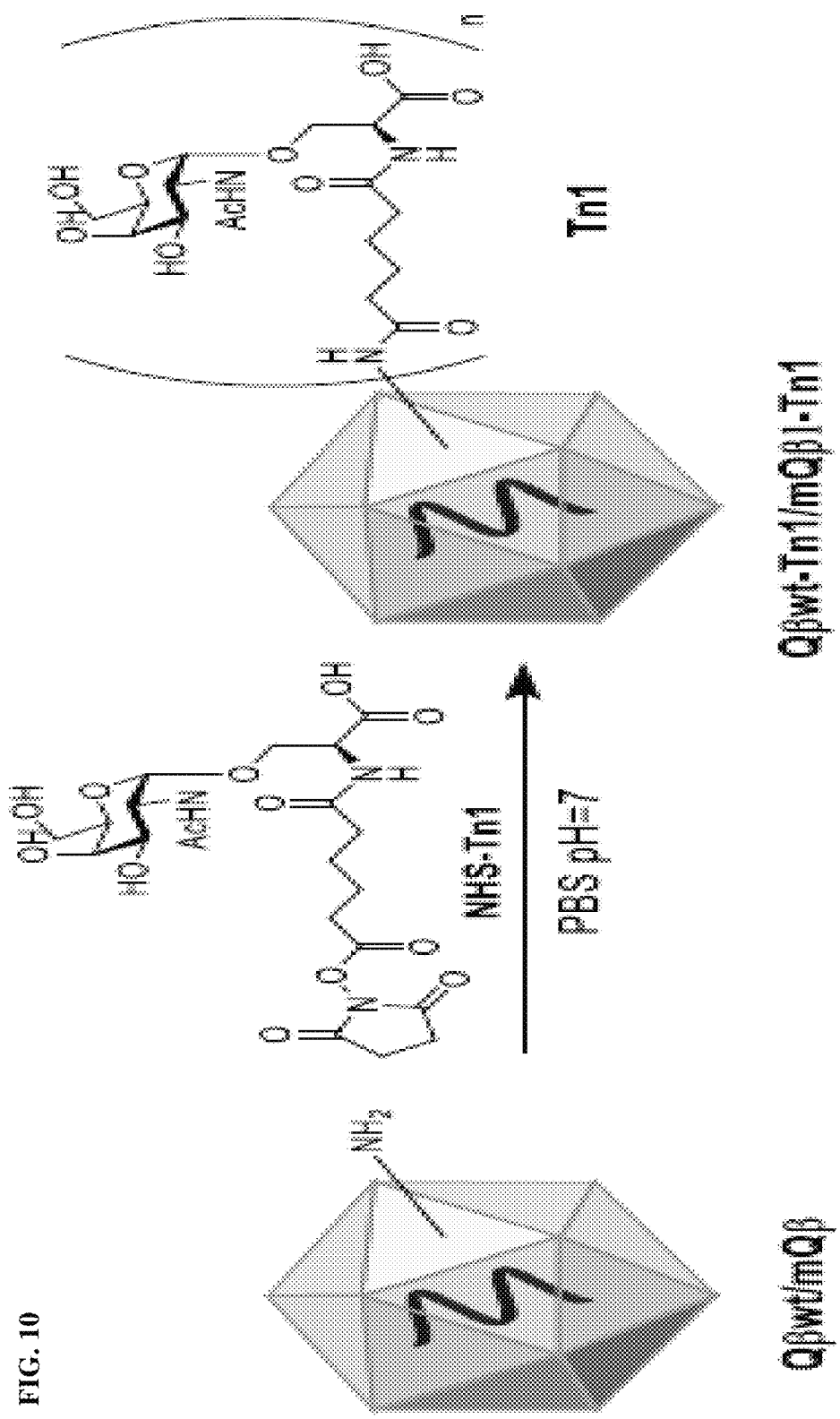
FIG. 10 shows immobilization of prototypical TACA, Tn1, on Qb and Qb mutants.
Figure 16A:
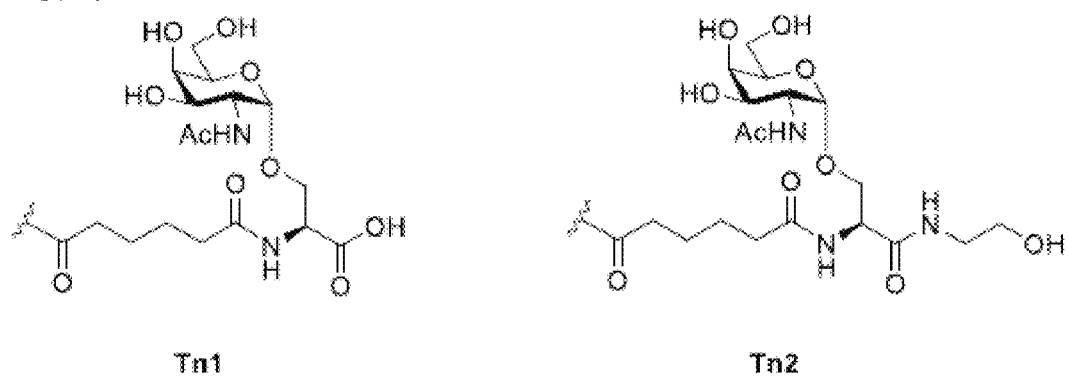
FIG. 16A-16C show the chemical structures of Tn1 and Tn2.
Figure 28:
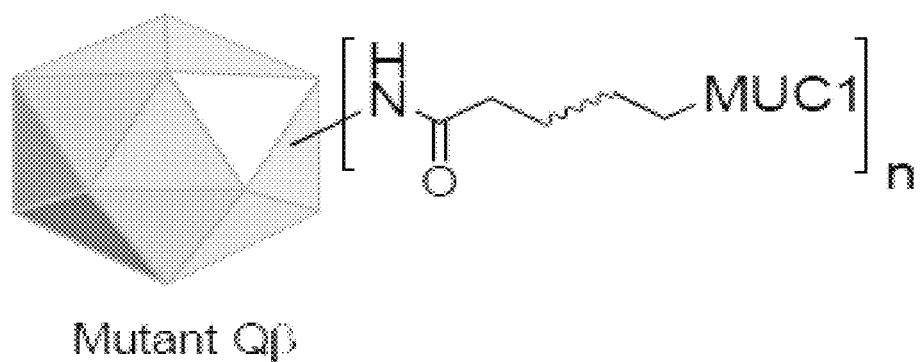
FIG. 28 shows a graphical depiction of a Qβ mucin conjugate.

In some embodiments, the antigen is conjugated to the capsid as set forth in Examples 6 and 9, infra. In some embodiments, the vaccine composition is a Qb mutant conjugated to MUC1 (e.g., FIG. 28). In some embodiments, the vaccine composition is a Qb mutant conjugated to GD2. In some embodiments, the vaccine composition is a Qb mutant conjugated to Tn1 or Tn2 (e.g., FIGS. 10 and 16A).

In some embodiments, the present invention provides pharmaceutically acceptable compositions which comprise a therapeutically-effective amount of one or more vaccine compositions (e.g., one or more Qb wild type, or Qβ mutant, antigen conjugate as described above), formulated together with one or more pharmaceutically acceptable carriers (additives) and/or diluents. In another aspect, the compositions can be administered as such or in admixtures with pharmaceutically acceptable carriers and can also be administered in conjunction with other anti-cancer therapies, such as chemotherapeutic agents, scavenger compounds, radiation therapy, biologic therapy, and the like. Conjunctive therapy thus includes sequential, simultaneous and separate, or co-administration of the composition, wherein the therapeutic effects of the first administered has not entirely disappeared when the subsequent compound is administered. In some embodiments, at least one vaccine compositions (e.g., one or more Qβ wild type, or Qβ mutant, antigen conjugate as described above) may be provided to the subject alone or in combination with at least one anti-cancer therapeutic drug, chemotherapeutic agents, scavenger compounds, antibiotics, anti-virals, anti-fungals, anti-inflammatories, vasoconstrictors and anticoagulants, antigens useful for cancer vaccine applications or corresponding pro-drugs.

Anti-cancer therapeutic drugs and chemotherapeutic agents for use with the compositions and methods of treatment described herein include, but are not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylomithine (DMFO); retinoids such as retinoic acid; capecitabine; and pharmaceutically acceptable salts, acids or derivatives of any of the above.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

As set out above, certain embodiments of the one or more vaccine compositions (e.g., one or more Qβ wild type, or Qβ mutant, antigen conjugate as described above) may contain a basic functional group, such as amino or alkylamino, and are, thus, capable of forming pharmaceutically-acceptable salts with pharmaceutically-acceptable acids. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", J. Pharm. Sci. 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the one or more vaccine compositions (e.g., one or more Qβ wild type, or Qβ mutant, antigen conjugate as described above) may contain one or more acidic functional groups and, thus, are capable of forming pharmaceutically-acceptable salts with pharmaceutically-acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The one or more vaccine compositions (e.g., one or more Qβ wild type, or Qβ mutant, antigen conjugate as described above) may be formulations suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, a formulation of one or more vaccine compositions (e.g., one or more Qβ wild type, or Qβ mutant, antigen conjugate as described above) can comprise other carriers to allow more stability, to allow more stability, different releasing properties in vivo, targeting to a specific site, or any other desired characteristic that will allow more effective delivery of the one or more vaccine compositions (e.g., one or more Qβ wild type, or Qβ mutant, antigen conjugate as described above) to a subject or a target in a subject, such as, without limitation, liposomes, microspheres, nanospheres, nanoparticles, bubbles, micelle forming agents, e.g., bile acids, and polymeric carriers, e.g., polyesters and polyanhydrides. In certain embodiments, an aforementioned formulation renders orally bioavailable a compound of the present invention.

Liquid dosage formulations of one or more vaccine compositions (e.g., one or more Qβ wild type, or Qβ mutant, antigen conjugate as described above) include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an active ingredient. One or more vaccine compositions (e.g., one or more Qβ wild type, or Qβ mutant, antigen conjugate as described above) may also be administered as a bolus, electuary or paste.

In solid dosage forms (e.g., capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. Compositions may also be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations which are suitable for vaginal administration also include pessaries, tampons, creams, gels, pastes, foams or spray formulations containing such carriers as are known in the art to be appropriate.

Dosage forms for the topical or transdermal administration of one or more vaccine compositions (e.g., one or more Qβ wild type, or Qβ mutant, antigen conjugate as described above) include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions suitable for parenteral administration can comprise sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In certain embodiments, the above-described pharmaceutical compositions can be combined with other pharmacologically active compounds ("second active agents") known in the art according to the methods and compositions provided herein. Second active agents can be large molecules (e.g., proteins) or small molecules (e.g., synthetic inorganic, organometallic, or organic molecules). In one embodiment, second active agents independently or synergistically help to treat cancer.

In another embodiment, the composition of the invention may comprise other biologically active substances, including therapeutic drugs or pro-drugs, for example, other chemotherapeutic agents, scavenger compounds, antibiotics, anti-virals, anti-fungals, anti-inflammatories, vasoconstrictors and anticoagulants, antigens useful for cancer vaccine applications or corresponding pro-drugs.

Exemplary scavenger compounds include, but are not limited to thiol-containing compounds such as glutathione, thiourea, and cysteine; alcohols such as mannitol, substituted phenols; quinones, substituted phenols, aryl amines and nitro compounds.

Various forms of the chemotherapeutic agents and/or other biologically active agents may be used. These include, without limitation, such forms as uncharged molecules, molecular complexes, salts, ethers, esters, amides, and the like, which are biologically active.

D. Therapeutic Methods

Provided herein are vaccine compositions for the treatment of and/or prevention of diseases and conditions for which an enhanced immune response may be beneficial. Such diseases include, but not limited to, pathogenic infections (e.g., bacterial, viral, or fungal infections) and cancer. In some embodiments, the vaccine compositions described herein may be use as an immunotherapy.

In some embodiments, the vaccine compositions (e.g., one or more Qβ wild type, or Qβ mutant, antigen conjugate as described above) are useful in the treatment of diseases including, but not limited to, persistent infectious disease, proliferative diseases, neurodegenerative diseases, inflammatory diseases, cancers, psychological diseases, metabolic diseases, autoimmune diseases, sexually transmitted diseases, gastro-intestinal diseases, pulmonary diseases, cardiovascular diseases, stress- and fatigue-related disorders, fungal diseases, pathogenic diseases, obesity-related disorders, viral infections, bacterial infections, or substance addiction (e.g., cocaine and nicotine).

Viral infectious diseases including human papilloma virus (HPV), hepatitis A Virus (HAV), hepatitis B Virus (HBV), hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, influenza virus, Hepatitis A and B, FIV, lentiviruses, pestiviruses, West Nile Virus, measles, smallpox, cowpox, ebola, coronavirus, retrovirus, herpesvirus, potato S virus, simian Virus 40 (SV40), Mouse Mammary Tumor Virus (MMTV) promoter, Moloney virus, ALV, Cytomegalovirus (CMV), Epstein Barr Virus (EBV), Zika, or Rous Sarcoma Virus (RSV).

In addition, bacterial, fungal and other pathogenic diseases are included, such as *Aspergillus, Brugia, Candida, Chikungunya, Chlamydia, Coccidia, Cryptococcus, Dengue, Dirofilaria, Gonococcus, Histoplasma, Leishmania, Myco-* bacterium, *Mycoplasma*, Paramecium, Pertussis, *Plasmodium*, Pneumococcus, Pneumocystis, *P. vivax* in *Anopheles* mosquito vectors, *Rickettsia, Salmonella, Shigella, Staphylococcus*, Streptococcus, *Toxoplasma* and Vibriocholerae. Exemplary species include *Neisseria* gonorrhea, *Mycobacterium tuberculosis, Candida albicans, Candida tropicalis, Trichomonas vaginalis, Haemophilus vaginalis*, Group B *Streptococcus* sp., Microplasma *hominis, Hemophilus ducreyi*, Granuloma inguinale, Lymphopathia venereum, *Treponema pallidum, Brucella abortus. Brucella melitensis, Brucella suis, Brucella canis, Campylobacter fetus, Campylobacter fetus* intestinalis, Leptospira pomona, *Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus* equi, *Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Clostridium tetani, Clostridium botulinum*; or, a fungus, such as, e.g., *Paracoccidioides brasiliensis*; or other pathogen, e.g., *Plasmodium falciparum*.

Also included are National Institute of Allergy and Infectious Diseases (NIAID) priority pathogens. These include Category A agents, such as variola major (smallpox), *Bacillus anthracis* (anthrax), *Yersinia pestis* (plague), *Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever) and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphylococcus* enterotoxin B, *Salmonella* species, *Shigella dysenteriae, Escherichia coli* strain O157:H7, *Vibrio cholerae, Cryptosporidium parvum*; Category C agents, such as nipah virus, hantaviruses, yellow fever in *Aedes* mosquitoes, and multidrug-resistant tuberculosis; helminths, such as *Schistosoma* and *Taenia*; and protozoa, such as *Leishmania* (e.g., *L. mexicana*) in sand flies, *Plasmodium*, Chagas disease in assassin bugs.

Bacterial pathogens include, but are not limited to, such as bacterial pathogenic gram-positive cocci, which include but are not limited to: pneumococci; staphylococci; and streptococci. Pathogenic gram-negative cocci include: meningococci; and gonococci. Pathogenic enteric gram-negative bacilli include: enterobacteriaceae; *pseudomonas*, acinetobacteria and eikenella; melioidosis; *salmonella*; shigellosis; hemophilus; chancroid; brucellosis; tularemia; *yersinia (pasteurella)*; *Streptobacillus moniliformis* and spirilum; *Listeria monocytogenes*; erysipelothrix rhusiopathiae; diphtheria; cholera; anthrax; and donovanosis (granuloma inguinale). Pathogenic anaerobic bacteria include; tetanus; botulism; other clostridia; tuberculosis; leprosy; and other mycobacteria. Pathogenic spirochetal diseases include: syphilis; treponematoses: yaws, pinta and endemic syphilis; and leptospirosis. Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include rickettsial and rickettsioses. Examples of *mycoplasma* and chlamydial infections include: *Mycoplasma pneumoniae*; lymphogranuloma venereum; psittacosis; and perinatal chlamydial infections. Pathogenic protozoans and helminths and infections eukaryotes thereby include: amebiasis; malaria; leishmaniasis; trypanosomiasis; toxoplasmosis; *Pneumocystis carinii*; giardiasis; trichinosis; filariasis; schistosomiasis; nematodes; trematodes or flukes; and cestode (tapeworm) infections.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, Wilms tumor. In certain embodiments, any of the vaccine described herein may target the cancer stem cells of any of the aforementioned cancers.

The present invention further provides novel therapeutic methods of preventing, delaying, reducing, and/or treating a cancer, including a cancerous tumor. In one embodiment, a method for preventing or treating cancer in a subject, the method comprising administering one or more vaccine compositions (e.g., one or more Qβ wild type, or Qβ mutant, antigen conjugate as described above). In one embodiment, a method of treatment comprises administering to a subject (e.g., a subject in need thereof), an effective amount of one or more vaccine compositions (e.g., one or more Qβ wild type, or Qβ mutant, antigen conjugate as described above). A subject in need thereof may include, for example, a subject who has been diagnosed with a tumor, including a precancerous tumor, a cancer, or a subject who has been treated, including subjects that have been refractory to the previous treatment.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

The methods of the present invention may be used to treat any cancerous or pre-cancerous tumor. In certain embodiments, the cancerous tumor has a highly glycolytic phenotype. For example, highly glycolytic tumors may be located in a tissue selected from brain, colon, urogenital, lung, renal, prostate, pancreas, liver, esophagus, stomach, hematopoietic, breast, thymus, testis, ovarian, skin, bone marrow and/or uterine tissue. In some embodiments, methods and compositions of the present invention may be used to treat any cancer. Cancers that may treated by methods and compositions of the invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain embodiments, any of the vaccine described herein may target the cancer stem cells of any of the aforementioned cancers.

The compositions described herein may be delivered by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The terms "systemic administration," "administered systemically," "peripheral administration," and "administered peripherally" as used herein mean the administration of the vaccine compositions described herein such that it enters the patient's system and, thus, is subject to metabolism and other like processes.

The terms "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

In certain embodiments the pharmaceutical compositions are delivered generally (e.g., via oral or parenteral administration). In certain other embodiments the pharmaceutical compositions are delivered locally through direct injection into a tumor or direct injection into the tumor's blood supply (e.g., arterial or venous blood supply). In some embodiments, the pharmaceutical compositions are delivered by both a general and a local administration. For example, a subject with a tumor may be treated through direct injection of a composition containing a composition described herein into the tumor or the tumor's blood supply in combination with oral administration of a pharmaceutical composition of the present invention. If both local and general administration is used, local administration can occur before, concurrently with and/or after general administration.

In some embodiments, the subject pharmaceutical compositions of the present invention will incorporate the substance or substances to be delivered in an amount sufficient to deliver to a patient a therapeutically effective amount of an incorporated therapeutic agent or other material as part of a prophylactic or therapeutic treatment. The desired concentration of the active compound in the particle will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Dosage may be based on the amount of the one or more vaccine compositions (e.g., one or more Qβ wild type, or Qβ mutant, antigen conjugate as described above) per kg body weight of the patient. For example, a range of amounts of compositions or compound encapsulated therein are contemplated, including about 0.001, 0.01, 0.1, 0.5, 1, 10, 15, 20, 25, 50, 75, 100, 150, 200 or 250 mg or more of such compositions per kg body weight of the patient. Other amounts will be known to those of skill in the art and readily determined.

In certain embodiments, the dosage of the one or more vaccine compositions (e.g., one or more Qβ wild type, or Qβ mutant, antigen conjugate as described above) will generally be in the range of about 0.001 mg to about 250 mg per kg body weight, specifically in the range of about 50 mg to about 200 mg per kg, and more specifically in the range of about 100 mg to about 200 mg per kg. In one embodiment, the dosage is in the range of about 150 mg to about 250 mg per kg. In another embodiment, the dosage is about 200 mg per kg.

In some embodiments the molar concentration of the one or more vaccine compositions (e.g., one or more Qβ wild type, or Qβ mutant, antigen conjugate as described above) in a pharmaceutical composition will be less than or equal to about 2.5 M, 2.4 M, 2.3 M, 2.2 M, 2.1 M, 2 M, 1.9 M, 1.8 M, 1.7 M, 1.6 M, 1.5 M, 1.4 M, 1.3 M, 1.2 M, 1.1 M, 1 M, 0.9 M, 0.8 M, 0.7 M, 0.6 M, 0.5 M, 0.4 M, 0.3 M or 0.2 M. In some embodiments the concentration of the one or more vaccine compositions (e.g., one or more Qβ wild type, or Qβ mutant, antigen conjugate as described above) will be less than or equal to about 0.10 mg/ml, 0.09 mg/ml, 0.08 mg/ml, 0.07 mg/ml, 0.06 mg/ml, 0.05 mg/ml, 0.04 mg/ml, 0.03 mg/ml or 0.02 mg/ml.

Actual dosage levels of the active ingredients in the compositions of the present invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular therapeutic agent in the formulation employed, or the ester, salt or amide thereof, the route of administration, the time of administration, the rate of excretion or metabolism of the particular therapeutic agent being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. All aspects of the treatment, including supplements, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments, for example, to the amount(s) of agent administered and to the time of administration may be made based on these reevaluations.

Treatment may be initiated with smaller dosages which are less than the optimum dose of the compound. Thereafter, the dosage may be increased by small increments until the optimum therapeutic effect is attained.

As described above, the one or more vaccine compositions (e.g., one or more Qβ wild type, or Qβ mutant, antigen conjugate as described above) may be administered in combination with radiation therapy. An optimized dose of radiation therapy may be given to a subject as a daily dose. Optimized daily doses of radiation therapy may be, for example, from about 0.25 to 0.5 Gy, about 0.5 to 1.0 Gy, about 1.0 to 1.5 Gy, about 1.5 to 2.0 Gy, about 2.0 to 2.5 Gy, and about 2.5 to 3.0 Gy. An exemplary daily dose may be, for example, from about 2.0 to 3.0 Gy. A higher dose of radiation may be administered, for example, if a tumor is resistant to lower doses of radiation. High doses of radiation may reach, for example, 4 Gy. Further, the total dose of radiation administered over the course of treatment may, for example, range from about 50 to 200 Gy. In an exemplary embodiment, the total dose of radiation administered over the course of treatment ranges, for example, from about 50 to 80 Gy. In certain embodiments, a dose of radiation may be given over a time interval of, for example, 1, 2, 3, 4, or 5 mins., wherein the amount of time is dependent on the dose rate of the radiation source.

In certain embodiments, a daily dose of optimized radiation may be administered, for example, 4 or 5 days a week, for approximately 4 to 8 weeks. In an alternate embodiment, a daily dose of optimized radiation may be administered daily seven days a week, for approximately 4 to 8 weeks. In certain embodiments, a daily dose of radiation may be given a single dose. Alternately, a daily dose of radiation may be given as a plurality of doses. In a further embodiment, the optimized dose of radiation may be a higher dose of radiation than can be tolerated by the patient on a daily base. As such, high doses of radiation may be administered to a patient, but in a less frequent dosing regimen.

The types of radiation that may be used in cancer treatment are well known in the art and include electron beams, high-energy photons from a linear accelerator or from radioactive sources such as cobalt or cesium, protons, and neutrons. An exemplary ionizing radiation is an x-ray radiation.

Methods of administering radiation are well known in the art. Exemplary methods include, but are not limited to, external beam radiation, internal beam radiation, and radiopharmaceuticals. In external beam radiation, a linear accelerator is used to deliver high-energy x-rays to the area of the body affected by cancer. Since the source of radiation originates outside of the body, external beam radiation can be used to treat large areas of the body with a uniform dose of radiation. Internal radiation therapy, also known as brachytherapy, involves delivery of a high dose of radiation to a specific site in the body. The two main types of internal radiation therapy include interstitial radiation, wherein a source of radiation is placed in the effected tissue, and intracavity radiation, wherein the source of radiation is placed in an internal body cavity a short distance from the affected area. Radioactive material may also be delivered to tumor cells by attachment to tumor-specific antibodies. The radioactive material used in internal radiation therapy is typically contained in a small capsule, pellet, wire, tube, or implant. In contrast, radiopharmaceuticals are unsealed sources of radiation that may be given orally, intravenously or directly into a body cavity.

Radiation therapy may also include stereotactic surgery or stereotactic radiation therapy, wherein a precise amount of radiation can be delivered to a small tumor area using a linear accelerator or gamma knife and three dimensional conformal radiation therapy (3DCRT), which is a computer assisted therapy to map the location of the tumor prior to radiation treatment.

Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the one or more vaccine compositions (e.g., one or more Qβ wild type, or Qβ mutant, antigen conjugate as described above) described herein relative to the control. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the one or more vaccine compositions (e.g., one or more Qβ wild type, Qβ mutant, antigen conjugate as described above) described herein relative to control. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the one or more vaccine compositions (e.g., one or more Qβ wild type, or Qβ mutant, antigen conjugate as described above) described herein relative to control. Although compounds that exhibit toxic side effects may be used, care should be taken to design a delivery system that targets the compounds to the desired site in order to reduce side effects.

In some embodiments, the presently disclosed methods produce at least about a 10%, 15%, 20%, 25%, 30%, 35%, 40%, 45%, 50%, 55%, 60%, 65%, 70%, 75%, 80%, 85%, 90%, 95%, or even 100% inhibition of cancer cell growth in an assay.

In any of the above-described methods, the administering of the one or more vaccine compositions (e.g., one or more Qβ wild type, or Qβ mutant, antigen conjugate as described above) can result in at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy in a subject, compared to the solid malignancy before administration of the vaccine compositions.

In some embodiments, the therapeutically effective amount of one or more vaccine compositions (e.g., one or more Qβ wild type, or Qβ mutant, antigen conjugate as described above) is administered prophylactically to prevent a solid malignancy from forming in the subject.

In some embodiments, the subject is human. In other embodiments, the subject is non-human, such as a mammal.

The data obtained from the cell culture assays and animal studies may be used in formulating a range of dosage for use in humans. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the $IC_{50}$ as determined in cell culture. Such information may be used to more accurately determine useful doses in humans. Levels in plasma may be measured, for example, by high performance liquid chromatography.

Exemplification

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1: Materials and Methods i. Site-Directed Mutagenesis of Qβ VLPs

Primers were designed following a guildline in the manual of QuikChange® Site-Directed Mutagenesis Kit Online based software PrimerX (http://www.bioinformatics.org/primerx/) was used to generate the primer sequence, or the sequence can be designed manually in some cases. The designed primers were further analyzed for proper % GC and Tm again by Oligoanalyzer 3.1 from IDT Inc. All primers were commercially synthesized by IDT Inc. For PCR reaction, the reagent mixture and cycling setting are prepared by adding reagents, respectively, as the following:

TABLE 1

PCR reagents

| Reagents | µl |
|---|---|
| 10X buffer | 5 |
| 20 ng plasmid template (from 20 ng/µl) | 1 |
| 125 ng Forward primer (from 100 ng/µl) | 1.25 |
| 125 ng Reverse primer (from 100 ng/µl) | 1.25 |
| dNTP mix | 1 |
| BP561-1 water | 39.5 |
| Pfu turbo | 1 |

TABLE 2

PCR thermocycler setting

| Number of cycles | Temperature | Time |
|---|---|---|
| 1X | 95 C.° | 30 Sec |
| 17X | 95 C.° | 30 Sec |
|  | 5 C.° less than $T_m$ of the primers, or using gradian | 1 Min |
|  | 68 C.° | 6 Min |
| Finish | 4 C.° | till done |

After PCR reaction, the resulting reaction was added 1 µl DpnI and incubated at 37° C. for 1 hour to digest the template plasmid DNA. The reaction's products were verified by 0.8% agarose gel electrophoresis with ethidium bromide as a staining reagent. The reactions were then used without purification to transform DH5a E. coli. The transformed DH5αE. coli cultures were plated onto SOB agar plate with 20 g/mL Kanamycin sulfate and incubated at 37° C. overnight. 4-6 colonies were selected to inoculate 6 mL SOB with 20 ug/mL Kanamycin and incubated at 37° C. overnight to amplify the E. coli. Mutated DNA plasmid from the bacteria cultures were extracted with QIAprep Spin Miniprep Kit (QIAGEN). The extracted plasmids were submitted to GENEWIZ for sequencing. Plasmid of the mutated plasmids that provide correct DNA sequences with highest scores of sequencing quality were used for transformation into BL21(DE3) pLysS E. coli by the heat shock method, then plated on SOB agar plate as DH5a E. coli. A single colony was selected for protein expression.

TABLE 3

Primers used in the construction of mutant β VLPs

| Primer# | Name | Sequence | SEQ ID NO: |
|---|---|---|---|
| 1 | CP_T7K_F1 | 5'-ATTAGAGACTGTTAAGTTAGGTAACATCGGG-3' | 26 |
| 2 | CP_T7K_R1 | 5'-CCCGATGTTACCTAACTTAACAGTCTCTAAT-3' | 27 |
| 3 | CP_N10K_F1 | 5'-CTGTTACTTTAGGTAAGATCGGGAAAGATGG-3' | 28 |
| 4 | CP_N10K_R1 | 5'-CCATCTTTCCCGATCTTACCTAAAGTAACAG-3' | 29 |
| 5 | CP_K13R_F1 | 5'-GGTAACATCGGGAGAGATGGAAAACAA-3' | 30 |
| 6 | CP_K13R_R1 | 5'-TTGTTTTCCATCTCTCCCGATGTTACC-3' | 31 |
| 7 | CP_A38K_F1 | 5'-GCCTCGCTTTCACAAAAGGGTGCAGTTCCTGCG-3' | 32 |

TABLE 3-continued

Primers used in the construction of mutant β VLPs

| | | | |
|---|---|---|---|
| 8 | CP_A38K_R1 | 5'-CGCAGGAACTGCACCCTTTTGTGAAAGCGAGG C-3' | 33 |
| 9 | CP_A38K_[A40C]_F1 | 5'-CCTCGCTTTCACAAAAGGGTTGTGTTCCTGC-3' | 34 |
| 10 | CP_A38K_[A40C]_R1 | 5'-GCAGGAACACAACCCTTTTGTGAAAGCGAGG-3' | 35 |
| 11 | CP_A40C_F1 | 5'-CACAAGCGGGTGTGTTCCTGCGCTGG-3' | 36 |
| 12 | CP_A40C_R1 | 5'-CCAGCGCAGGAACACACCCGCTTGTG-3' | 37 |

| Primer# | Name | Sequence | |
|---|---|---|---|
| 13 | CP_A40S_F1 | 5'-CACAAGCGGGTTCAGTTCCTGCGCTGG-3' | 38 |
| 14 | CP_A40S_R1 | 5'-CCAGCGCAGGAACTGAACCCGCTTGTG-3' | 39 |
| 15 | CP_T75K_F1 | 5'-CCGACCGCTTGCAAGGCAAACGGTTC-3' | 40 |
| 16 | CP_T75K_R1 | 5'-GAACCGTTTGCCTTGCAAGCGGTCGG-3' | 41 |
| 17 | CP_D102C_F1 | 5'-GCAGTATAGTACCTGTGAGGAACGAGC-3' | 42 |
| 18 | CP_D102C_R1 | 5'-GCTCGTTCCTCACAGGTACTATACTGC-3' | 43 |
| 19 | CP_D102S_F1 | 5'-GCAGTATAGTACCTCTGAGGAACGAGC-3' | 44 |
| 20 | CP_D102S_R1 | 5'-GCTCGTTCCTCAGAGGTACTATACTGC-3' | 45 |
| 21 | CP_E103K_F1 | 5'-GTATAGTACCGATAAGGAACGAGCTTTTG-3' | 46 |
| 22 | CP_E103K_R1 | 5'-CAAAAGCTCGTTCCTTATCGGTACTATAC-3' | 47 |
| 23 | CP_A117K_F1 | 5'-GCTTGCTGCTCTGCTCAAGAGTCCTCTGCTGAT CG-3' | 48 |
| 24 | CP_A117K_R1 | 5'-CGATCAGCAGAGGACTCTTGAGCAGAGCAGCA AGC-3' | 49 |
| 25 | CP_P119K_F1 | 5'-GCTCTGCTCGCTAGTAAGCTGCTGATCGATGC-3' | 50 |
| 26 | CP_P119K_R1 | 5'-GCATCGATCAGCAGCTTACTAGCGAGCAGAGC-3' | 51 | ii. Qβ Viral Capsid Protein Expression and Purification

A single colony of BL21(DE3) pLysS *E. coli* with mutated plasmid was selected to be inoculated into starting culture of 50 mL SOC containing 20 ug/mL Kanamycin. The starting culture was grown overnight at 37° C., 230 rpm. After overnight, the resulting cloudy culture was then transferred into 1 L culture medium with the antibiotic selection. The culture was continued at the same condition until the $OD_{600}$ was between 0.7-1.0, 1 mL of 1M isopropyl β-D-1-thiogalactopyranoside (IPTG) was then added into the culture to induce protein expression (final concentration=1 mM). The culture was continued 4-5 hours. After 4-5 hours, the bacteria were pelleted at 6,000 rpm for 30 min. The culture medium was discarded. The pellets were re-suspended in 0.1M PBS pH 7. The bacteria in the suspension were then lysed with a probe sonicator in an ice bath. The sonication generator was set at power of 30% for 10 min, with interval of 5 second pulses and 5 second stops. The lysis was centrifuged at 14,000 rpm for 20 min. The supernatant containing the capsid protein was added PEG 8000 to final concentration of 10% (w/v) and put on a nutating mixer at 4° C. overnight to allow complete protein precipitation. The precipitate was pelleted down at 14,000 rpm for 20 min. The pellet was resuspended in 0.1M PBS pH=7. The re-suspended solution was 1:1 (v/v) mixed with 1:1 (v/v) chloroform/n-butanol till the mixture turns colloid. The colloidal mixture was centrifuged at 7,000 rpm for 1 hour to separate layer. The top (aqueous) layer was collected. Viral capsid protein in the collected aqueous layer was further purified by sucrose density gradients 10-40% (w/v). The linear (continuous) sucrose gradients was prepared following freezing-thawing method (Luthe, D. S. et al. *Analytical Biochemistry* 1983, 135 (1), 230-232). The loaded sucrose gradients were centrifuged with swing bucket rotor SW32 rotor at 28,000 rpm for 5 hours. The viral capsid band can be visualized by LED light shining through the top of the tube. The bright blue band from scattered light was collected as fractions of 1 mL. The collected fraction was analyzed for purity of the capsid by size-exclusion chromatography using column Superose 6 resin 10/300 (void volume=9 mL). The fraction that shows a single peak at elution around 11-15 mL was determined as a fraction containing pure VLP. The remaining sucrose in the collected fraction was removed by filtration through Millipore 100 k MWCO centrifugal filter tube, and washed thoroughly with the PBS buffer. Total protein concentration in the final solution was quantified by Pierce BCA Protein Assay Kit, using bovine serum albumin as the standard. The purified VLP was characterized by size-exclusion chromatography, Dynamic light scattering (DLS), and transmission electron microscopy (TEM) for particles' size, homogeneity, shape, and purity. The change of the amino acid(s) as a result of mutation was determined by the molecular weight difference compared with widetype Qβ. The molecular weight of the protein was determined by LCMS QTOF ESI mass spectroscopy and the multiple charge mass spectra were transformed to single charge by Maximum Entropy deconvolution algorithm (MaxEnt™ 1) (Da Ren, H et al. *Mass spectrometry quantification of protein mixtures*; Wright, T et al. Science 354(6312) pii: aag1465 2016).

iii. Synthesis and Characterization of Qβ or mQ3 Conjugates (Yin, Z et al. *ACS Chemical Biology* 2015, 10 (10), 2364-2372)

13.2 mg of VLP Qβ or mQβ (5.1 nmol particle, 0.9 μmol subunit, 3.6 mol reactive amines) suspended in potassium phosphate buffer (0.1 M, pH=7, 5.5 mL) was added into a 15-mL falcon tube. DMSO 0.35 mL was slowly dropped into the solution. Tn1-NHS or Tn2-NHS (20 mg/mL in 0.35 mL, 0.017 mmol, 4.7 eq. to the reactive amine) was added into the reaction tube. The reaction mixture was rotated on a rotating mixer at room temperature overnight. The reaction was diluted with 0.1 M PBS pH=7 to total volume 50 mL. The VLP conjugates were purified by filtration through Millipore 100 k MWCO centrifugal filter tube, and washed thoroughly with the PBS buffer. The purified VLP conjugates were characterized as described above. The average number of conjugated Tn1 or Tn2 on each viral capsid subunit was estimated from the intensity of peaks in the deconvoluted mass spectra from LCMS analysis. Results are shown in FIG. 22A-22M.

iv. Size Exclusion Chromatography (SEC)

SEC analysis and purification were performed on an AKTApure 25 L system, equipped with Superose 6 Increase 10/300 GL column. 0.1 M potassium phosphate buffer pH=7 was used as the eluent with a flow rate of 0.5 mL/min at 4° C. The capsid protein was detected with a UV detector at wavelength 280 nm. 0.5 mL of sample was injected. The sample was eluted with 1.5 column volume and the fractions were collected every 1 mL. Results are shown in FIG. 23A-23I.

v. Non-Denaturing Agarose Gel

Figure 24:
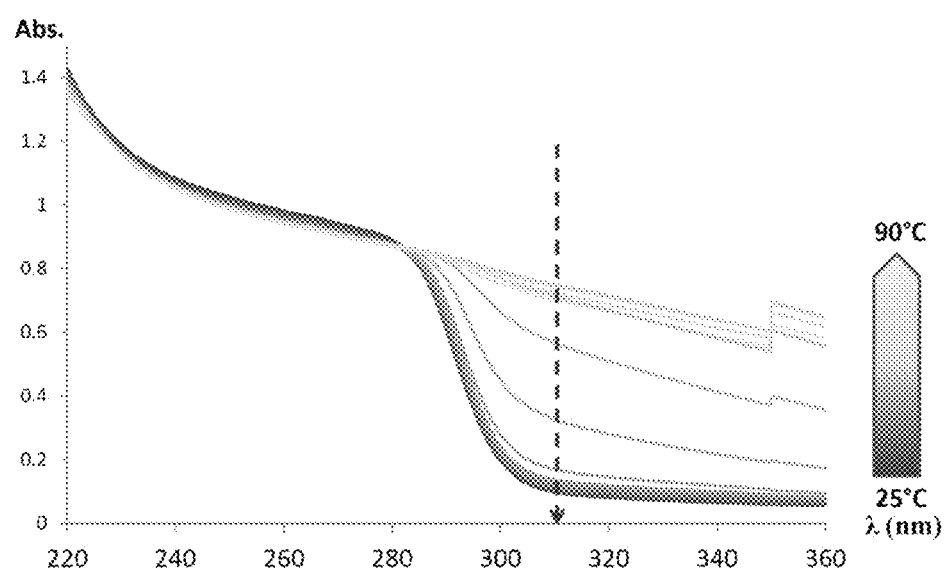
FIG. 24 depicts UV-visible absorption of wtQβ at varied temperature from 25 to 90° C. The estimated wavelength that provides the most different absorption is 310 nm (dashed line).

The viral capsid samples (30 μg of each capsid protein) were loaded into 0.7% agarose gel in PBS with SYBR Safe DNA gel stain as a staining reagent for the encapsulated RNA. The electrophoresis was performed in TEA (Trisacetate-EDTA) buffer at 4° C. for 4 hours. After visualizing the encapsulated RNA bands by UV light, the gel was later stained with Coomassie blue stain to detect the capsid protein.

vi. Thermal Stability Measurement of Viral Capsid by Temperature Varied UV-Vis Spectroscopy 1 mg/mL of VLPs in potassium phosphate buffer (0.1 M, pH=7) was measured against the buffer as a standard solution. 1 cm quartz cuvettes with caps were used as cells for the sample and standard buffer. The measurement was done with Varian Cary 1 Bio UV-Vis spectroscopy equipped with Cary temperature variable controller (Agilent Technologies). The wavelength was set at 310 nm as this wavelength gives the most sensitivity for detecting the denatured protein (FIG. 24). The absorbances were measured every 1° C. with temperature change at a rate 5° C./min from 25° C. to 60° C., then the absorbances were measured every 0.5° C. with temperature change at a rate 1° C./min from 60° C. to 90° C.

vii. Dynamic Light Scattering (DLS) and Transmission Electron Microscopy (TEM)

Figure 25:
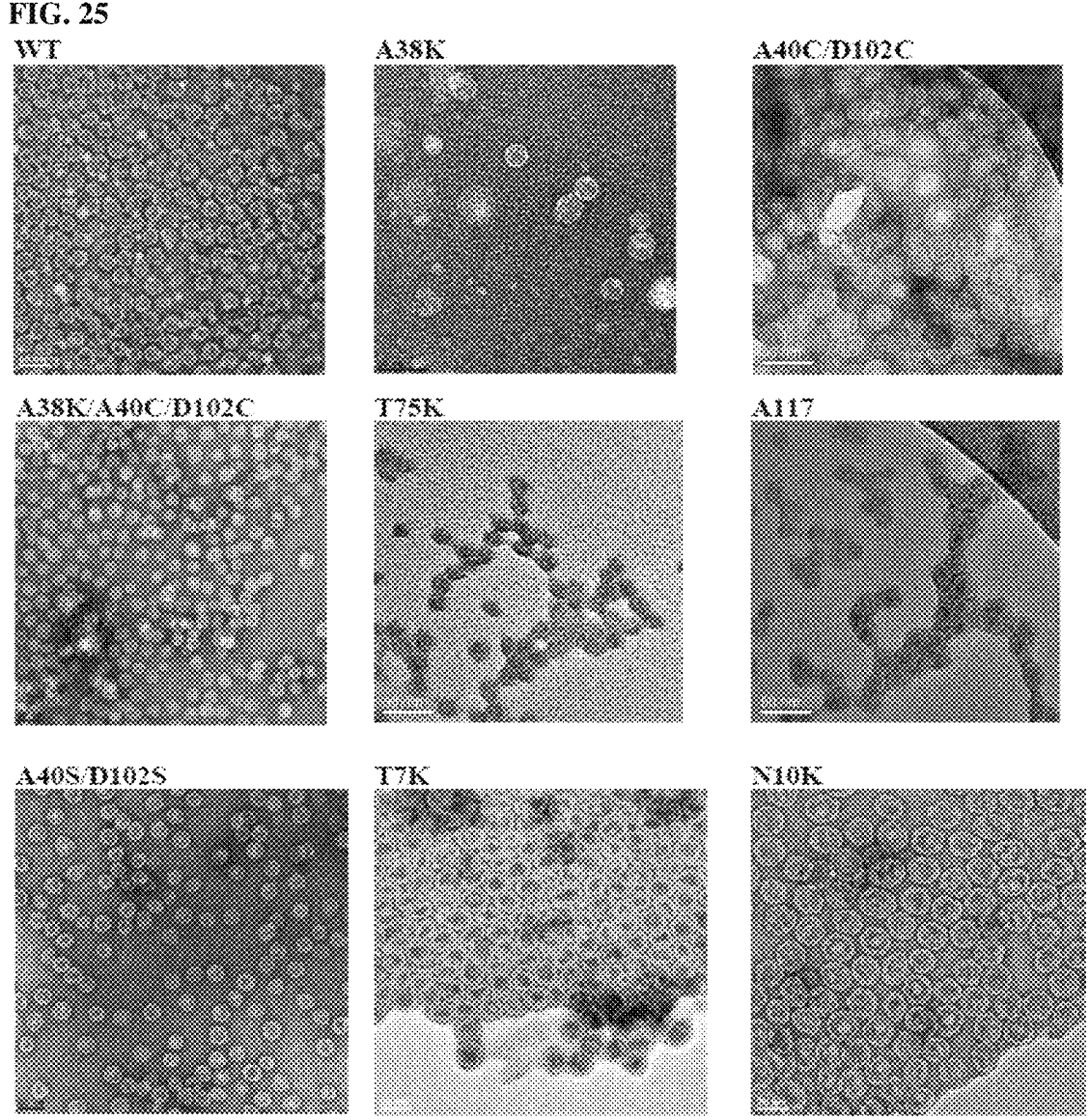
FIG. 25 depicts TEM images of wild-type Qβ and various Qβ mutants.

The hydrodynamic diameter and zeta potential were assessed on a Malvern Zetasizer Nano zs instrument. TEM images were collected on a JEM-2200FS operating at 200 kV using Gatan multiscan CCD camera with Digital Micrograph imaging software. Samples were prepared on ultrathin-carbon type A, 400 mesh copper grids, or ultrathin C film on holey carbon support film, 400 mesh, Cu for high resolution TEM (Ted Pella, Inc.). The viral capsids were strained by aqueous 2% uranyl acetate. Results are shown in FIG. 25.

viii. Immunization Studies (Yin, Z et al. *ACS Chemical Biology* 2015, 10 (10), 2364-2372)

Pathogen-free C57BL/6 female mice age 6-10 weeks were obtained from the Jackson Laboratory and maintained in the University Laboratory Animal Resources facility of Michigan State University. All animal care procedures and experimental protocols have been approved by the Institutional Animal Care and Use Committee (IACUC) of Michigan State University. Groups of 5 mice were injected subcutaneously under the scruff on day 0 with 0.1 mL of various Qβ constructs as emulsions in complete Freund's adjuvant (Sigma-Aldrich, F5881), and boosters were given subcutaneously under the scruff on days 14 and 28 with 0.1 mL of various Qβ constructs as emulsions in incomplete Freund's adjuvant (Sigma-Aldrich, F5506). All Tn vaccine constructs administered have the same amounts of Tn antigen (1.93 μg). Serum samples were collected on day 0 (before immunization), 7, and 35. The final bleeding was done by cardiac bleed.

ix. Enzyme-Linked Immunosorbent Assay (ELISA)

A Nunc MaxiSorp® flat-bottom 96 well plate was coated with BSA-Tn (10 ug/mL) or corresponding Qβ capsids (1 ug/mL) in PBS pH=7.4, overnight at 4° C. The coated plate was then washed 4 times with PBS/0.5% Tween-20 (PBST), followed by the addition of 1% (w/v) BSA in PBS to each well and incubation at room temperature for one hour. The plate was washed again 4 times with PBST. 100 μl of the dilution of mouse sera in 0.1% BSA/PBS were added in each well. (For competitive ELISA, the diluted sera were incubated with 50 μg of the viral capsids at 37° C. for 1 hour before adding into the plate.) The plate was incubated for two hours at 37° C. and washed. A 1:2000 diluted horseradish peroxidase (HRP)-conjugated goat anti-mouse IgG, IgG1, IgG2b, IgG2c, IgG3 or IgM antibody (Jackson ImmunoResearch Laboratory IgG #115-035-071, IgM #115-035-075) in 0.1% BSA/PBS was added to each well, respectively. The plate was incubated for one hour at 37° C., washed, and a solution of 3,3',5,5'-tetramethylbenzidine (TMB) was added. Color was allowed to develop for 15 min, and then a solution of 0.5 M $H_2SO_4$ (50 μl) was added to stop the reaction. The optical density was measured at 450 nm using a microplate autoreader (BioRad). Each experiment was repeated at least four times, and the average of the quadruplicate was used to calculate the titer. The titer was determined by regression analysis with log 10 dilution plotted with optical density. The titer was calculated as the highest dilution that gave OD=0.3.

x. Cell Cultures

Human lymphoma Jurkat cells (kindly provided by Profs. Barbara Kaplan and Norbert Kaminski, Michigan State University) were cultured in RPMI 1640 supplemented with 10% FBS, 2 mM L-glutamine, 1 mM sodium pyruvate, minimal essential medium nonessential amino acid, 100 U/mL each of penicillin G, and streptomycin.

Murine mammary adenocarcinoma cell line TA3Ha (kindly provided by Prof. John Hilkens, The Netherlands Cancer Institute) were isolated from ascites collected from passage growing on A/J mice. The cells were cultured using RPMI 1640, 10% FBS, 100 U/mL penicillin and 100 U/mL streptomycin.

xi. Flow Cytometry Experiment

Cells were harvested from the culture. The cells suspended in FACS buffer (5% FBS, 0.1% $NaN_3$ in PBS) were incubated with 1:20 diluted mice sera on ice for 30 min. The cell suspension was centrifuged at 1600 rpm, 5 min at 4° C. to remove the unbound antibodies. The cell-bound IgG antibodies were then labeled with goat anti-mouse IgG conjugated with FITC (BioLegend, 405305) for 30 min. The excess secondary antibody was washed out and the cells were suspended in FACS buffer. Acquisition of cells was performed with LSR II (BD), and data was analyzed with FlowJo® software (Tree Star Inc.).

xii. Anti-Tumor Immunoprotection (Tumor Challenge)

After day 35 of the immunization, 5,000 cells of TA3Ha were intraperitoneally injected into groups of C57BL/6 mice (n=10) on day 36. Mice were injected cyclophosphamide (50 mg/kg) intraperitoneally on day 37. Survival of mice was monitored for 30 days. Statistical analysis of survival was performed with GraphPad Prism using log-rank test.

xiii. Liquid Chromatography-Mass Spectrometry (LCMS)

The samples for LCMS were prepared with the following procedure: 1:1 v/v of 40 g/mL of VLP stock solution and 100 mM DTT was mixed and incubated in a water bath at 37° C. for 30 min. One drop of 50% formic acid was added into the mixture. The samples are ready for the LCMS. LCMS was performed on Waters Xevo G2-XS quadrupole/time-of-flight UPLC/MS/MS. The liquid chromatography was done on ACQUITY UPLC® Peptide BEH C18 column, 130 Å, 1.7 μm, 2.1 mm×150 mm, using gradient eluent from 95% 0.1% formic acid in water to 95% 0.1% formic acid in ACN (0.3 mL/min flowrate) at column temperature 40° C. The multiple charge mass spectra were transformed to single charge by using algorithm MaxEnd1 (Da Ren, H et al. Mass spectrometry quantification ofprotein mixtures). The average numbers of Tn/subunit were analyzed by signal intensity of mass spectrum. Results are shown in FIG. 22A-22M.

xiv. Transmission Electron Microscopy (TEM) Images

Refer to FIG. 25 and section vii supra.

xv. Synthesis of Tn1 and Tn2

Figure 26:
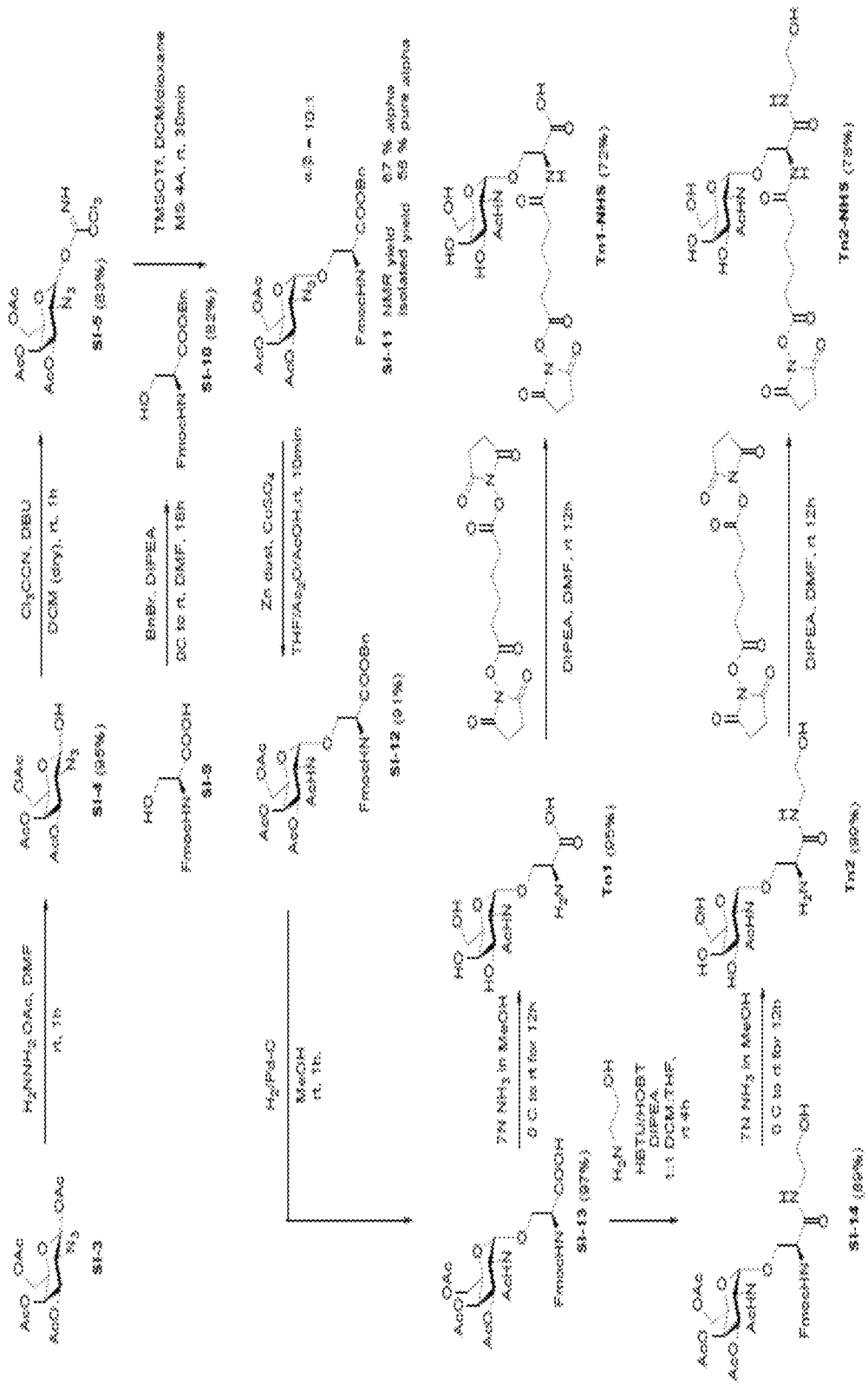
FIG. 26 depicts synthesis of Tn1-NHS and Tn2-NHS.

See FIG. 26 for scheme of synthesis.

All chemicals were reagent grade and used as received from the manufacturer, otherwise noted. $^1$H NMR spectra were recorded on an Agilent-500M spectrometer and processed by MestReNova version 10.0.2.

Synthesis Procedure

N-(Fluoren-9-ylmethoxycarbonyl)-O-(3,4,6-tri-O-acetyl-2-azido-2-deoxy-α-D-galactopyranosyl-L-serine benzyl ester (SI-11) (Ludek, O et al. *Carbohydrate Research* 2010, 345 (14), 2074-2078)

Trichloroacetimidate SI-5 (49) (3.01 g, 6.33 mmol) and N-Fmoc-O-Bn-Serine SI-10 (Mukai, S et al. *Amino Acids* 2012, 43 (2), 857-874) (2.2 g, 5.28 mmol) were mixed in the reaction flask with freshly activated molecular sieves 4A (10 g) under nitrogen gas. Anhydrous DCM:Dioxane (1:1, 60 mL) was added to dissolve the mixture, and the solution was left stirred at rt. for 30 min. TMSOTf (0.297 mL, 1.925 mmol) was added dropwise into the reaction. The reaction was left stirred at rt. for an hour. Upon monitoring the reaction, if there was some starting material SI-5 left, 0.1 more eq. of TMSOTf was further added and the reaction was allowed to proceed for another hour. Upon completion, diisopropylethylamine (DIPEA) was added to quench the reaction. The reaction was diluted with DCM and washed with 0.1 M HCl and then water. The organic layer was dried over $Na_2SO_4$ and then concentrated. The crude product was purified by column chromatography (silica gel; 3:1 EtOAc:Hexane) to yield SI-11(alpha) (2.23 g, 58%). Spectral analysis of the product compared with reported literature (Ludek, O et al. *Carbohydrate Research* 2010, 345 (14), 2074-2078) confirmed the identity of the product. $^1$H NMR (500 MHz, Chloroform-d) δ 7.76 (dt, J=7.7, 0.9 Hz, 2H), 7.66-7.59 (m, 2H), 7.44-7.28 (m, 9H), 6.00 (d, J=8.1 Hz, 1H), 5.40 (dd, J=3.4, 1.2 Hz, 1H), 5.31-5.19 (m, 3H), 4.87 (d, J=3.6 Hz, 1H), 4.62 (dt, J=8.2, 3.1 Hz, 1H), 4.45-4.36 (m, 2H), 4.24 (t, J=7.2 Hz, 1H), 4.17 (dd, J=10.9, 3.2 Hz, 1H), 4.10-3.94 (m, 4H), 3.59 (dd, J=11.2, 3.6 Hz, 1H), 2.15 (s, 3H), 2.07 (s, 3H), 1.96 (s, 3H).

N-(Fluoren-9-ylmethoxycarbonyl)-O-(3,4,6-tri-O-acetyl-2-acetamido-2-deoxy-α-D-galactopyranosyl-L-serine benzyl ester (SI-12) (Miermont, A et al. *Chemistry—A European Journal* 2008, 14 (16), 4939-4947)

The synthesis procedure was modified from reported literature (Miermont, A et al. *Chemistry—A European Journal* 2008, 14 (16), 4939-4947). Compound SI-11 (2.41 g, 3.30 mmol) was dissolved in 3:2:1 of THF:Ac20:AcOH (60 mL). Zinc dust (2.72 g, 41.23 mmol) was added and then 5 mL of saturated aq. $CuSO_4$ was added to activate zinc. The reaction was stirred at rt. for about half an hour. After completion as monitored by TLC, the zinc dust was removed by filtering the reaction mixture through Celite®. The filtrate was coevaporated with toluene to concentrate the crude product. The crude product was purified by column chromatography (silica gel; 1:1 EtOAc:Hexanes) to yield SI-12 (2.24 g, 91%). Spectral analysis of the product compared with reported literature confirmed the identity of the product. $^1$H NMR (500 MHz, Chloroform-d) δ 7.77 (d, J=7.5 Hz, 2H), 7.61 (d, J=7.5 Hz, 2H), 7.43-7.28 (m, 9H), 5.88 (d, J=8.3 Hz, 1H), 5.58 (d, J=9.5 Hz, 1H), 5.31 (d, J=3.2 Hz, 1H), 5.20 (q, J=12.1 Hz, 2H), 5.04 (dd, J=11.4, 3.2 Hz, 1H), 4.78 (d, J=3.7 Hz, 1H), 4.66-4.48 (m, 2H), 4.43 (d, J=7.1 Hz, 2H), 4.23 (t, J=7.1 Hz, 1H), 4.16-3.89 (m, 5H), 2.16 (s, 3H), 2.01 (s, 3H), 1.97 (s, 3H), 1.91 (s, 3H).

N-(Fluoren-9-ylmethoxycarbonyl)-O-(3,4,6-tri-O-acetyl-2-acetamido-2-deoxy-α-D-galactopyranosyl-L-serine (SI-13) (Miermont, A et al. *Chemistry—A European Journal* 2008, 14 (16), 4939-4947)

The synthesis procedure was as reported (Miermont, A et al. *Chemistry—A European Journal* 2008, 14 (16), 4939-4947). The reaction yielded the product SI-13 (0.88 g, 98%). Spectral analysis of the product compared with reported literature (Miermont, A et al. *Chemistry—A European Journal* 2008, 14 (16), 4939-4947) confirmed the identity of the product.

N-(Fluoren-9-ylmethoxycarbonyl)-O-(3,4,6-tri-O-acetyl-2-acetamido-2-deoxy-α-D-galactopyranosyl-L-serine 2-ethanolyl amide (SI-14)

Compound SI-13 (1.90 g, 2.89 mmol) in 1:1 anhydrous THF:DCM was activated using HBTU (1.2 g, 3.18 mmol), HOBt (0.43 g, 3.18 mmol) and DIPEA (1.1 mL, 6.37 mmol) at rt. For 20 min. Ethanolamine (0.22 mL, 3.62 mmol) was added into the reaction mixture. Upon completion, the precipitate was filtered out and the crude mixture in filtrate was dried and purified by column chromatography (silica gel; 2-10% Methanol in Hexanes) to yield 1.8 g. (89%). Spectral analysis of the product compared with reported literature confirmed the identity of the product (Miermont, A et al. *Chemistry—A European Journal* 2008, 14 (16), 4939-4947)$^1$H NMR (500 MHz, Chloroform-d) δ 7.75 (d, J=7.6 Hz, 2H), 7.57 (d, J=7.5 Hz, 2H), 7.39 (t, J=7.5 Hz, 2H), 7.30 (t, J=7.5 Hz, 2H), 6.87 (t, J=5.7 Hz, 1H), 6.37 (d, J=9.5 Hz, 1H), 5.92 (d, J=7.4 Hz, 1H), 5.35-5.28 (m, 1H), 5.11 (dd, J=11.4, 3.2 Hz, 1H), 4.89 (d, J=3.3 Hz, 1H), 4.57 (ddd, J=11.4, 9.5, 3.6 Hz, 1H), 4.50-4.31 (m, 3H), 4.17 (dt, J=24.6, 6.5 Hz, 2H), 4.08-3.98 (m, 2H), 3.92 (d, J=8.8 Hz, 1H), 3.73 (d, J=17.4 Hz, 3H), 3.44 (s, 2H), 3.08 (s, 1H), 2.15 (s, 3H), 2.00 (s, 3H), 1.97 (s, 3H), 1.95 (s, 3H).

O-2-acetamido-2-deoxy-α-D-galactopyranosyl-L-serine or O-2-acetamido-2-deoxy-α-D-galactopyranosyl-L-serine 2-ethanolyl amide (Tn1 or Tn2)

The synthesis procedure was as from reported literature (Miermont, A et al. *Chemistry—A European Journal* 2008, 14 (16), 4939-4947). Compound SI 13 (100 mg, 0.152 mmol) or SI-14 (660 mg, 0.94 mmol) under N2 at 0° C. was added 5 mL of 7N ammonia in methanol. The reaction was warm up to rt. overnight. Upon completion, the solvent was evaporated by flowing N2 gas. The crude reaction mixture was dissolved in MeOH and then precipitated in EtOAc. The filtrate was dried to yield Tn1 (43.4 mg, 92%) or Tn2 (330 mg, 99%), respectively. Tn1: $^1$H NMR (500 MHz, Methanol-d4) δ 4.81 (d, J=3.7 Hz, 1H), 4.31 (dd, J=10.9, 3.6 Hz, 1H), 4.06 (d, J=17.2 Hz, 1H), 3.92-3.65 (m, 7H), 2.01 (s, 3H). Tn2: $^1$H NMR (500 MHz, Methanol-d4) δ 4.78 (d, J=3.7 Hz, 1H), 4.28 (dd, J=11.0, 3.7 Hz, 1H), 3.92-3.65 (m, 7H), 3.65-3.49 (m, 3H), 3.37-3.28 (m, 3H), 2.00 (s, 3H).

N—(N-Hydroxysuccinimidyl adipoyl)-O-2-acetamido-2-deoxy-α-D-galactopyranosyl-L-serine or N—(N-Hydroxysuccinimidyl adipatyl)-O-2-acetamido-2-deoxy-α-D-galactopyranosyl-L-serine 2-ethanolyl amide (Tn1-NHS or Tn2-NHS)

Disuccinimidyl adipate (5 eq.) in anhydrous DMF (0.5 mL) was added to Tn (40 mg, 0.13 mmol) or Tn2 (66 mg, 0.18 mmol) dissolved in DMF (0.5 mL). DIPEA (1 eq.) was added in the reaction mixture. The reaction was left stirred for 2-3 h. Upon completion, DMF was evaporated under vacuum until dryness. The crude product was precipitated in EtOAc twice and then washed with 10% MeOH in EtOAc 3-5 times to remove the excess diNHS-linker. The final precipitate was dried under vacuum to yield Tn1-NHS (50 mg, 72%). Tn1-NHS: $^1$H NMR (500 MHz, Methanol-$d_4$) δ 4.83 (d, J=3.7 Hz, 1H), 4.65 (t, J=4.0 Hz, 1H), 4.25 (dd, J=11.0, 3.7 Hz, 1H), 3.99-3.62 (m, 5H), 2.83 (s, 4H), 2.73-2.62 (m, 2H), 2.35 (t, J=6.8 Hz, 2H), 2.00 (d, J=7.7 Hz, 4H), 1.77 (dt, J=6.9, 3.5 Hz, 4H); Tn2-NHS (84.5 mg, 78%). Tn2-NHS: $^1$H NMR (500 MHz, Methanol-d4) δ 4.82 (d, J=3.8 Hz, 1H), 4.59 (t, J=5.2 Hz, 1H), 4.26 (dd, J=11.0, 3.7 Hz, 1H), 3.92-3.65 (m, 8H), 3.60 (td, J=5.8, 1.8 Hz, 2H), 3.37-3.26 (m, 6H), 2.83 (s, 4H), 2.73-2.63 (m, 2H), 2.42-2.27 (m, 2H), 2.01 (d, J=2.0 Hz, 4H), 1.82-1.70 (m, 3H).

Example 2: Qb can Elicit High Levels of Anti-Qb IgG Antibodies and Heterologous Prime and Boost Strategy is not Effective in Reducing Anti-Qb Antibody Responses without Influencing Anti-TACA Antibodies To test antibody responses to Qb capsid, mice were immunized with Qb subcutaneously following the typical protocol for TACA based vaccine with one prime and two boost vaccinations. Qb was administered as an emulsion in complete Freund's adjuvant (CFA) for prime injection on day 0 and in incomplete Freund's adjuvant (IFA) for boost injections on days 14 and 28. Sera were collected from these mice on day 35 after the first immunization. ELISA analysis showed that very strong anti-Qb IgG levels were produced (average IgG titer 3,100,000), which confirms Qb can generate high levels of antibodies against the capsid itself.

One potential approach to reduce anti-Qb responses is the heterologous prime and boost strategy by preparing multiple types of VLP-TACA conjugates. One TACA conjugate would be used to prime the immune system and a second VLP-TACA conjugate for boost injections. In this strategy, as B-cell epitopes from various carriers are different, TACA antigen is the only component common to all injections. Thus, anti-TACA immunity should benefit the most from boost injections. However, when TACA conjugates with Qb and another VLP CPMV were tested in a heterologous prime and boost protocol, anti-Qb titers remained at a high level while the anti-TACA titers were actually lower than when wtQb-TACA was used for both prime and boost. This is presumably due to the powerful immune potentiation by Qb and lower ability of CPMV to generate anti-Tn antibodies. This consideration prompted us to focus on Qb engineering.

Figure 1:
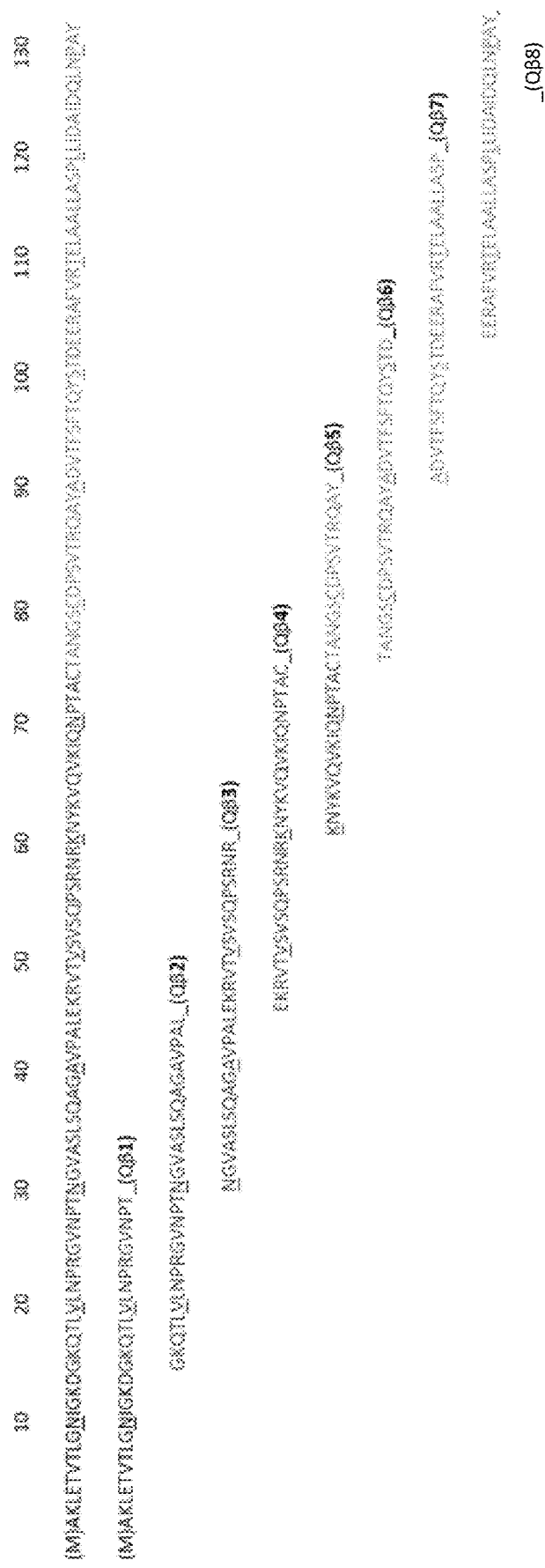
FIG. 1 depicts eight of synthetic 30-amino-acid peptides that overlapped sequence by 15 amino acids covering the entire amino acid sequence of Qβ capsid protein. Figure discloses SEQ ID NOS 1, 3, and 61-68, respectively, in order of appearance.
Figure 2:
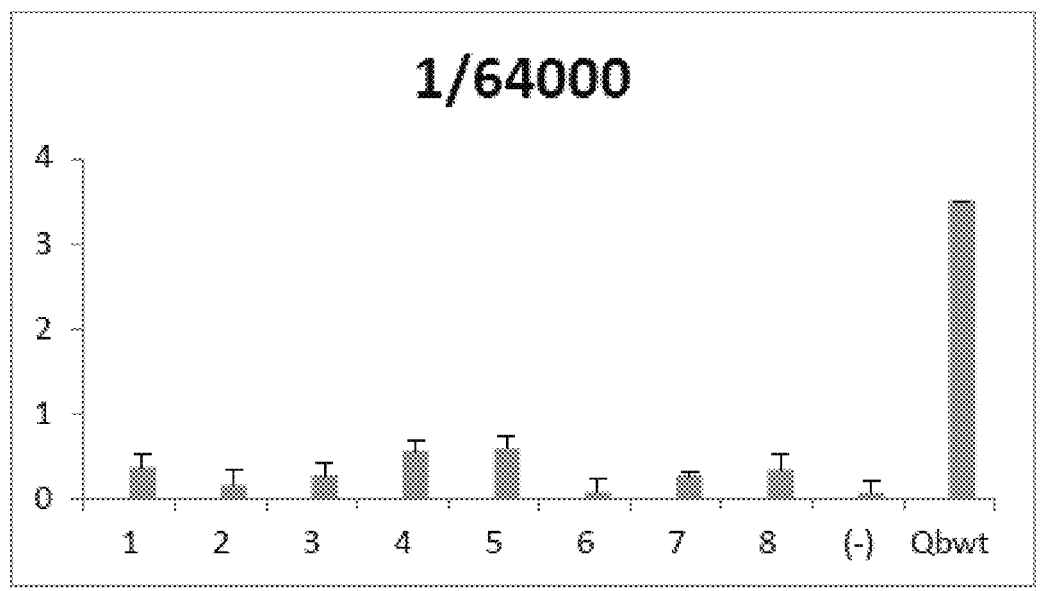
FIG. 2 depicts ELISA result of peptide scanning experiment showing the binding of the peptides fragments with the anti-wtQβ IgG antibodies. The synthetic peptides were coated on the ELISA plate. The dilution of serum (1/64000 dilution) from wtQβ-immunized mice was added to test recognition towards each peptide fragments. Group (−) is a negative control group where only PBS was used in coating process.

Example 3: The Major B Cell Epitopes of Qb do not Reside within a Linear Sequence Anti-Qb antibodies originate from the recognition of B cell epitopes on the Qβ capsid by B cells, which leads to the activation and proliferation of anti-Qb B cells and subsequent antibody production. To identify these B cell epitopes, we first performed peptide screening (FIG. 1). The Qb capsid is made up of 180 copies of a monomeric coat protein containing 132 amino acid residues. We synthesized eight 30 amino acid peptides with sequences overlapping by 15 amino acids, which covered the full sequence of Qb coat protein. Peptides were immobilized into ELISA wells individually and sera from Qb immunized mice were added to each well to test the recognition of the peptides by the polyclonal antibodies. As shown in FIG. 2, none of the synthetic peptides showed strong binding to anti-Qb IgG antibodies in the post-immune sera as compared to the intact capsid. These results suggest that the B cell epitopes of Qb do not reside within a linear sequence. Rather, they are most likely conformational (i.e., residues are far apart in primary sequence but close to each other in tertiary structure).

Example 4: Design of Qb Mutants to Reduce Anti-Qb Antibody Levels

To identify the epitopes of Qb, one possible approach is to mutate all 132 amino acid residues and screen for proteins with reduced binding to anti-Qb antibodies. However, this would require the tedious and labor intensive process of generating and screening a large number of mutants. To better understand the structure, we have obtained crystal structure of Qb. The near atomic resolution crystal structure provides valuable guidance to our mutant design.

Figure 3:
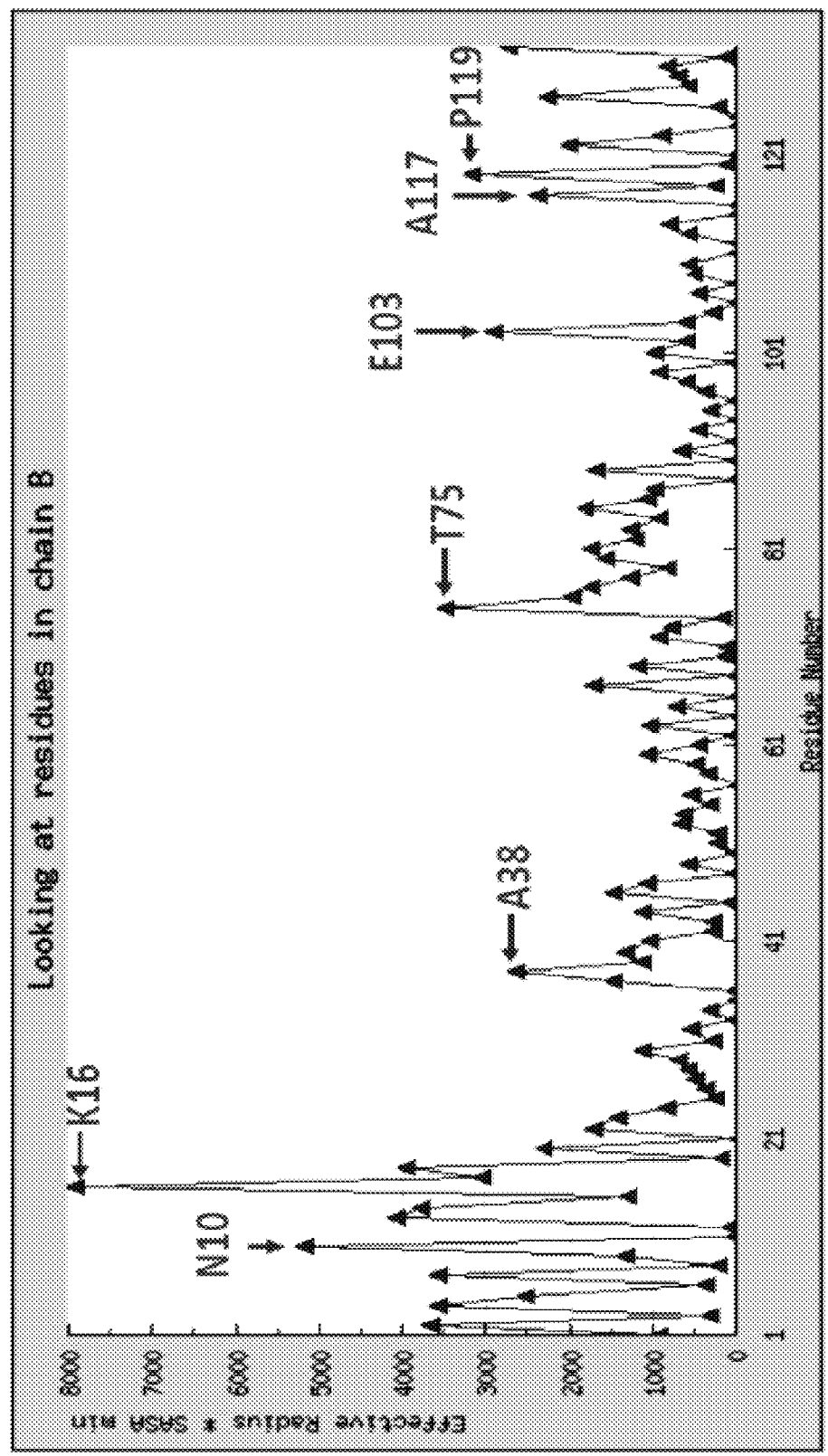
FIG. 3 depicts representative solvent accessible surface area on each residue on Qb capsid protein from chain B.

We envision that due to the large sizes of B cell receptors (similar to those of antibodies), B cell epitopes most likely reside on the external surface of Qb capsid and are well exposed to solvents so that they can bind with the bulky B cell receptors. Qb was screened in VIPERdb, a database for icosahedral virus capsid structures, to determine its accessible surface profile. As shown in FIG. 3, asparagine 10 (N10), lysine 16 (K16), alanine 38 (A38), threonine 75 (T75), glutamic acid 103 (E103) are among the residues with high accessibilities to external solvents. Besides VIPERdb, another search was performed using DiscoTope 2.0 (Haste Andersen, P. et al. *Protein Science* 2006, 15 (11), 2558-2567) (http://www.cbs.dtu.dk/services/DiscoTope/), a program for predicting discontinuous B cell epitopes, which suggests K2, K13, K16, A38 and T75 reside in areas of high potential B cell epitopes. These predictions correlate well with accessible surface profile predicted from VIPERdb database (http://viperdb.scripps.edu/) (FIG. 4), suggesting mutations of these residues can possibly disrupt the inherent B cell epitopes of Qb.

Another factor for mutant design was based on a serendipitous discovery. When a Qb-carbohydrate conjugate was treated with a di-activated adipic ester #, which crosslinked subunits of Qb, significantly higher anti-carbohydrate antibody responses were obtained. As it was difficult to control the location of crosslinking with the bifunctional linker #, we hypothesize that cysteines can be introduced close to interfaces between subunits of Qb, which can potentially form disulfide bonds to crosslink the subunits and enhance anti-TACA antibody responses. However, mutations of residues directly involved in inter-subunit interactions should be avoided to prevent obstructions of viral capsid assembly.

Figure 4:
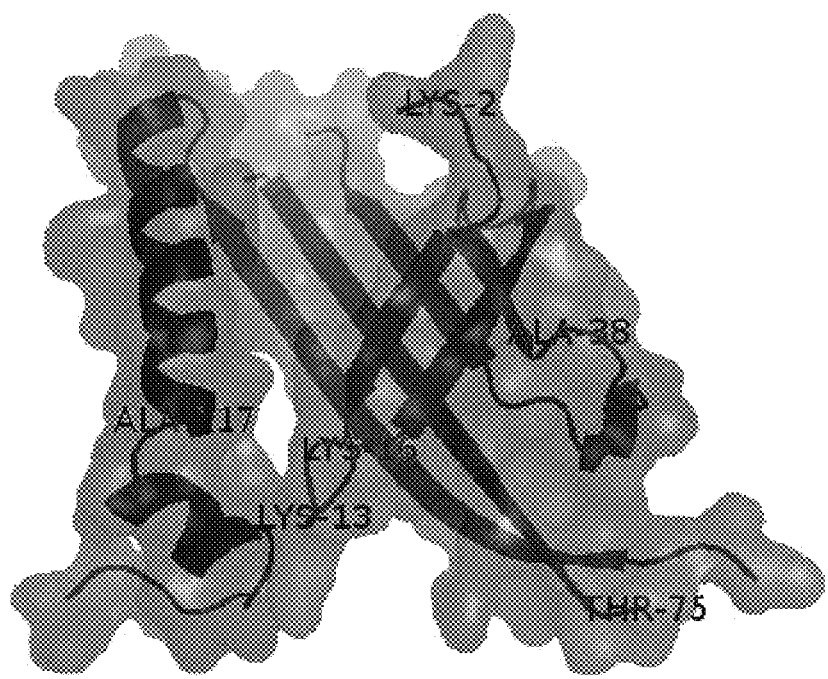
FIG. 4 depicts B cell epitope prediction from DiscoTope 2.0 server8 (http://www.cbs.dtu.dk/services/DiscoTope/). Blue area indicates low potential B cell epitope, Red area indicates high potential B cell epitope.
Figure 5:
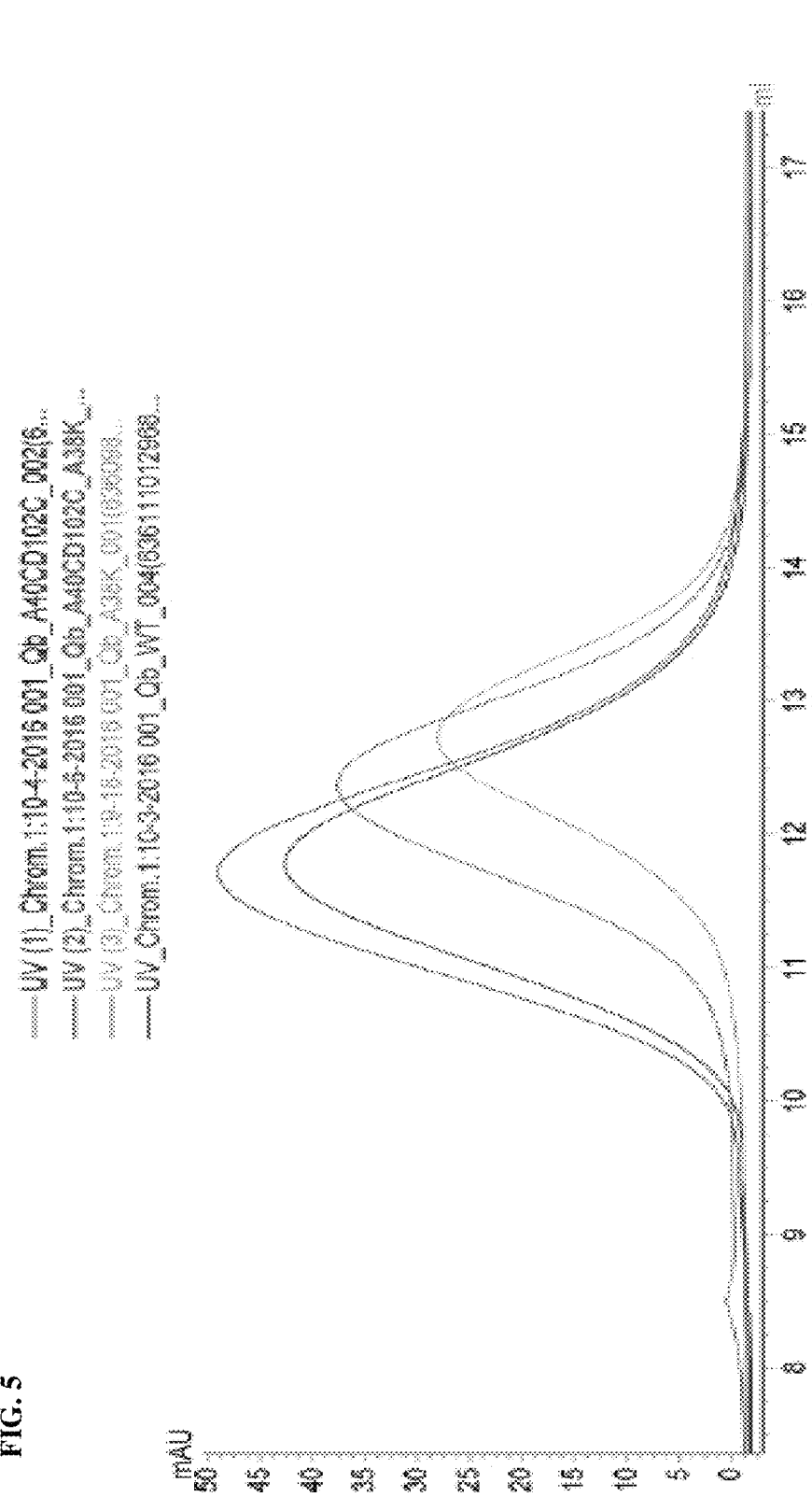
FIG. 5 depicts fast protein liquid chromatography of Qbwt, mQb A38K, A38K/A40C/D102C and A40C/D102C.
Figure 6:
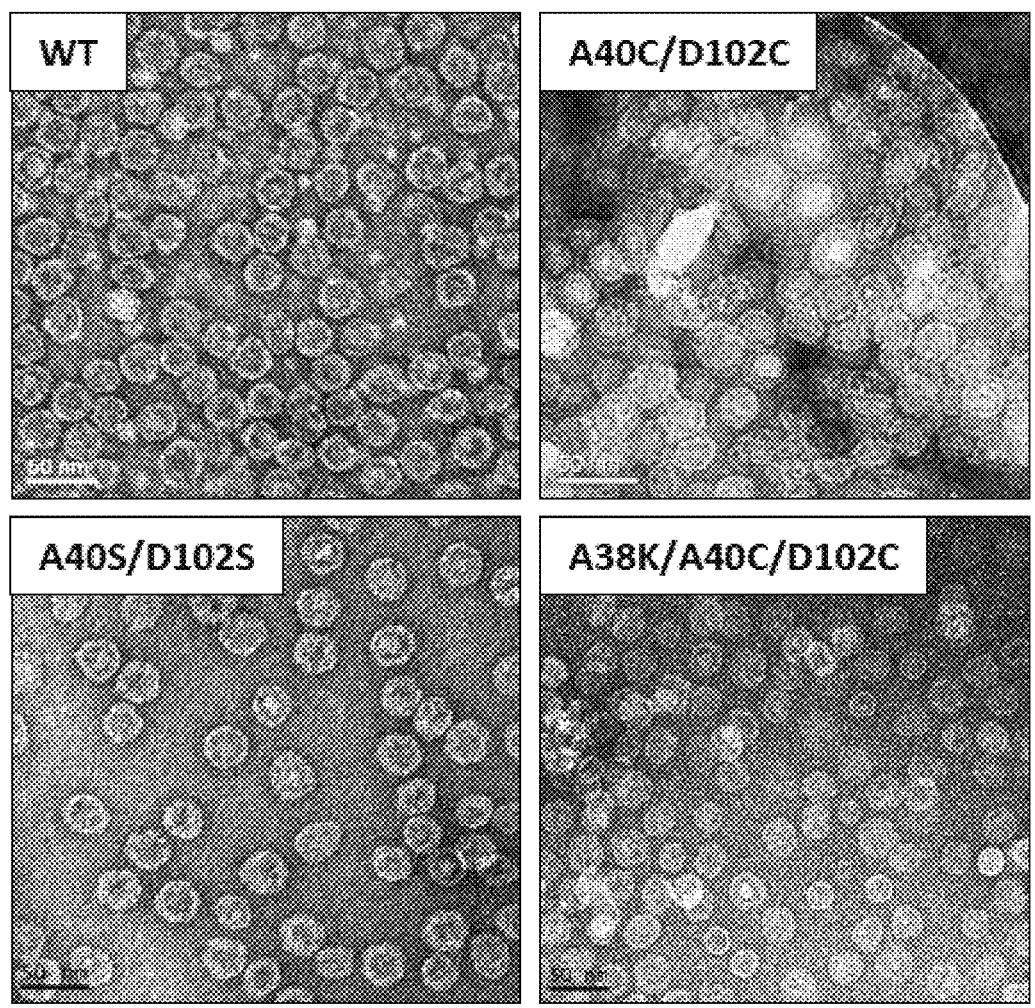
FIG. 6 depicts TEM images of mutant capsids.
Figure 7:
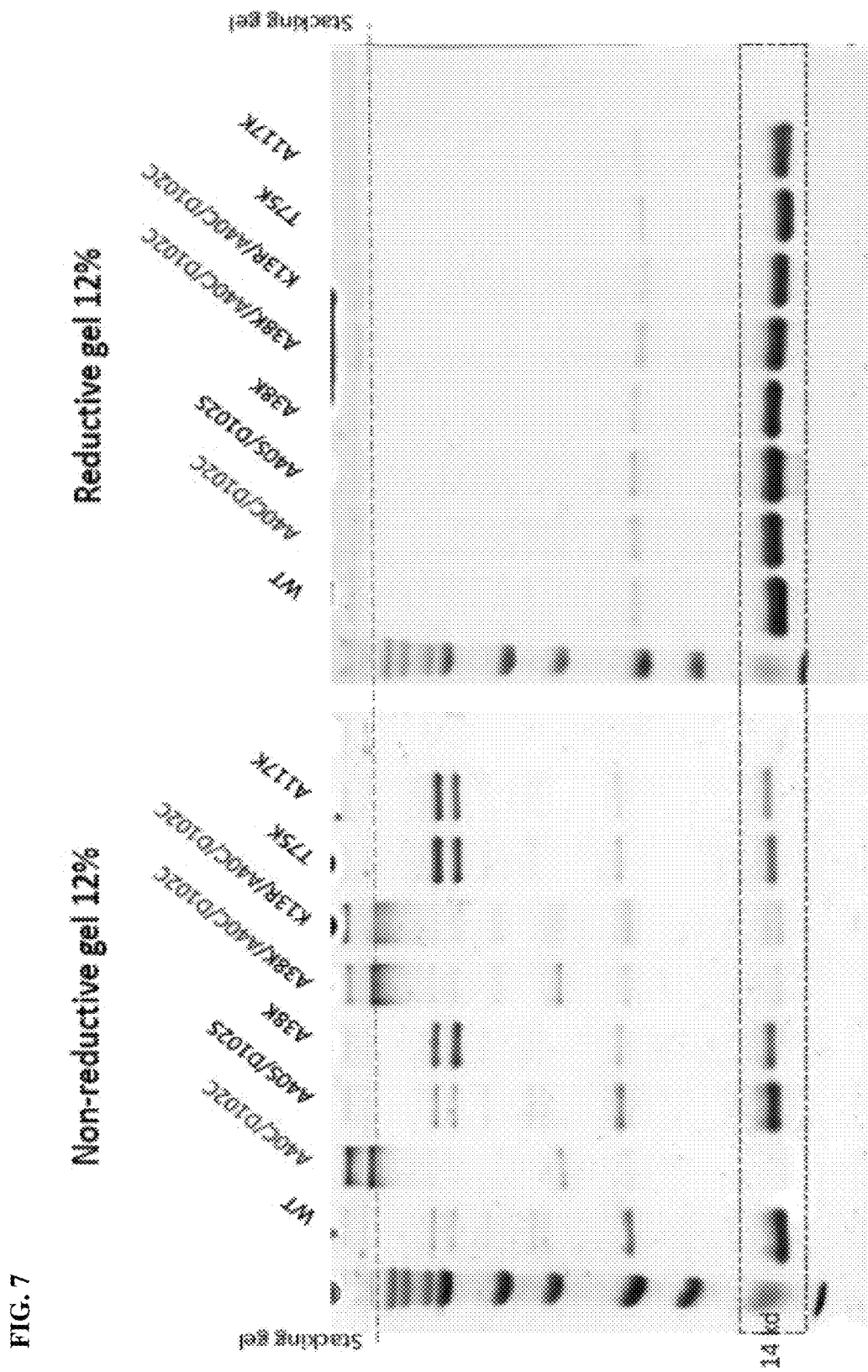
FIG. 7 depicts SDS-PAGE of the viral capsids in non-reductive (oxidative) condition (Left) and reductive condition (right).
Figure 8A:
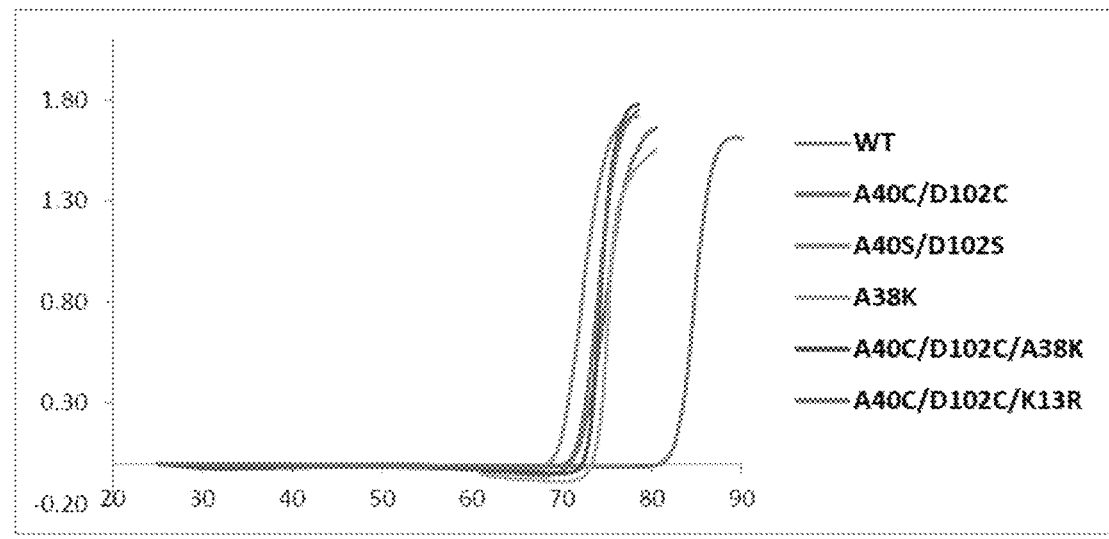
FIGS. 8A and 8B show thermal stability of mQbs determined by UV absorption at λ=310 nm at increasing temperature.
Figure 8B:
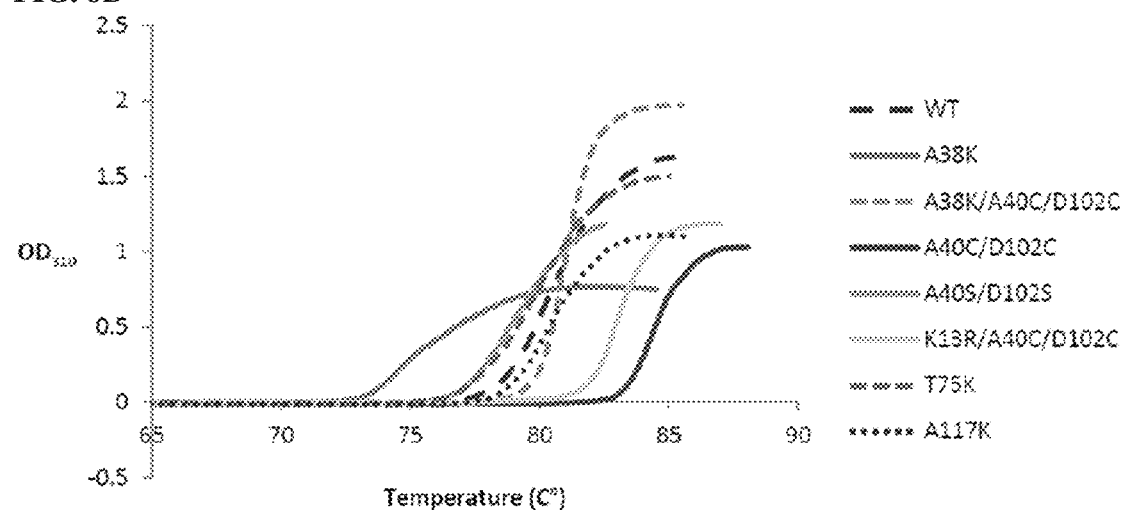
Figure 9A:
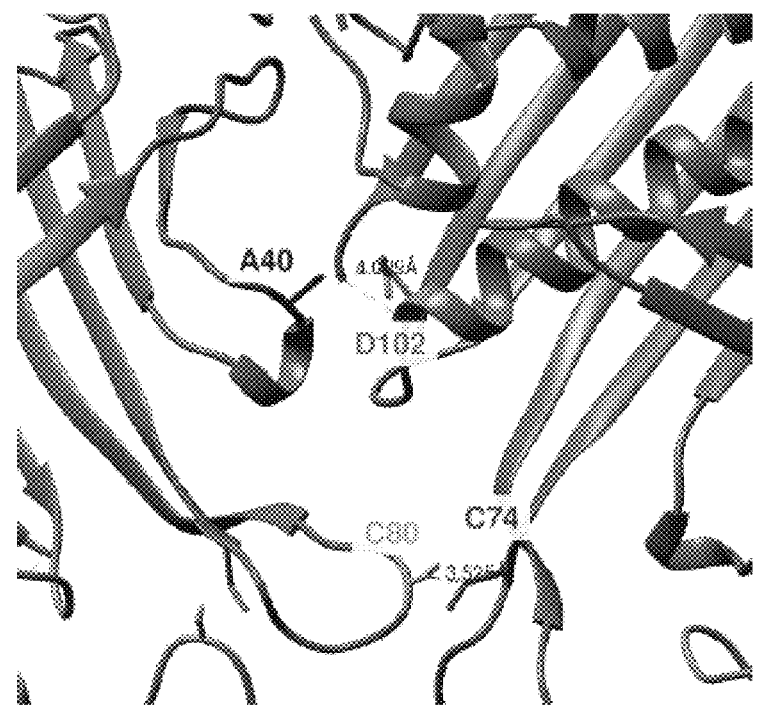
FIGS. 9A and 9B show X-ray crystal structure of Qb showing a) distance between β-carbon of residues involving disulfide formation; b) disulfide bond networks from native disulfide bonds between C74 and C80 (green residues) and non-native disulfide bonds in mQb A40C/D102C (yellow residues).
Figure 9B:
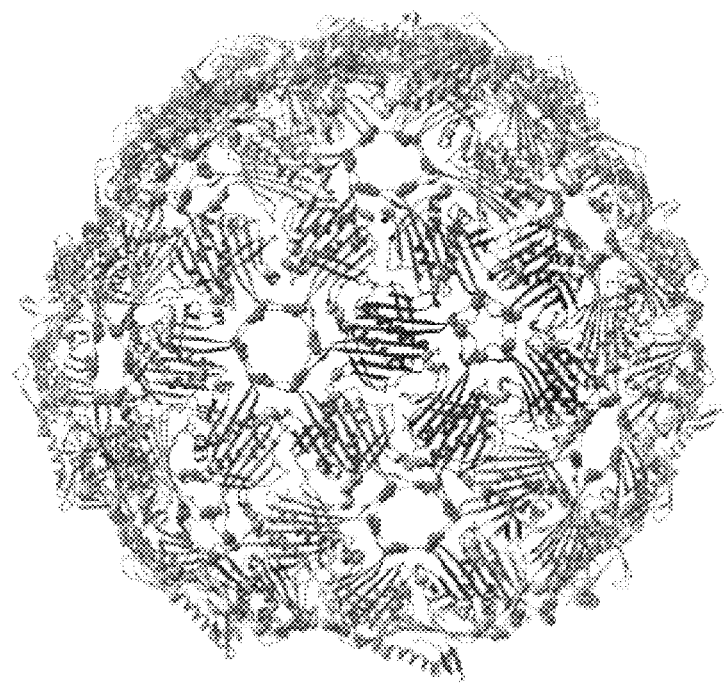

Based on the aforementioned considerations, alanine 38 (A38), threonine 75 (T75), and glutamic acid 103 (E103) were selected for mutation to lysine (K) (FIGS. 3 and 4). Lysine is chosen as the mutation target since it can be additional site for future TACA functionalization. Alanine 40 (A40) and aspartic acid 102 (D102) were selected as sites for mutation to cysteines. Analysis of crystal structure of Qb capsid (PDB code: 1QBE) revealed that A40 and D102 on adjacent coat protein monomers are close to each other in space for possible disulfide bond formation. K2 and K16 are not mutated as they are the most likely derivatization sites when wtQb is functionalized through amide formation.

The designed mutants were cloned and then expressed recombinantly in *E. coli*. Although E103K failed to assemble into nanoparticles, the A38K, T75K, A40C/D102C, and A38K/A40C/D102C mutants formed nanoparticle capsids in good yields. It is interesting to note that while most of the mQb particles have hydrodynamic diameters similar to that of the wildtype capsid (28.8 nm), the A38K mutant is noticeably smaller with a mean diameter of 26.6 nm. The characteristic properties of all mQb capsids are summarized as in Table 4.

TABLE 4

Physical characterization of Qb mutants.

| Qb Mutants | Yield (mg/L) | SEC rv. (mL) | Z-Ave (d · nm) | PDI | Zeta potential |
|---|---|---|---|---|---|
| WT | 60 | 11.7 | 28.8 | 0.046 | −2.89 |
| N10K | 12 | 11.7 | 28.7 | 0.192 | −1.90 |
| A38K | 16 | 12.7 | 26.6 | 0.083 | −1.43 |
| T75K | 25 | 12.0 | 29.0 | 0.096 | −1.64 |
| A117K | 31 | 12.1 | 29.7 | 0.187 | −1.54 |
| A40C/D102C | 38 | 11.8 | 29.1 | 0.031 | −1.67 |
| A38K/A40C/D102C | 26 | 12.6 | 27.6 | 0.028 | −1.55 |
| A40S/D102S | 20 | 12.0 | 27.8 | 0.028 | −1.37 |
| A40C/D102C/K13R | 15 | 11.9 | 28.9 | 0.119 | nd |

Example 5: mQb Capsids with A40C/D102C Mutations have Higher Thermal Stabilities To test the possibility of A40C/D102C forming an additional disulfide bond, mutants were subjected to non-reducing SDS-PAGE gel electrophoresis analysis (Figure X). All Qb mutants containing A40C/D102C mutations showed high molecular weight protein bands in the stacking gel presumably due to multimerization of the subunits. Mutants lacking A40C/D102C showed similar gel patterns as wild type Qb. On a SDS-PAGE gel under a reducing condition, all capsids appeared similar with the majority of proteins appearing at positions corresponding to monomers and dimers, indicating the A40C/D102C disulfide bond was formed in mQbs containing A40C/D102C.

The effect of the additional disulfide bond on capsid stability was evaluated next by measuring the melting temperature of the capsid by gradually heating a solution of the capsid. The wtQb has a melting temperature of 78° C. when it starts to denature upon heating. The mQb A40C/D102C capsid has significantly higher stability with its melting temperature increasing to 83° C. The melting temperature of the double mutant A40S/D102S, which is chemically similar to A40C/D102C but unable to form the disulfide bonds, dropped back to wild type level (76° C.), supporting the importance of disulfide bond for stabilizing the capsid. Similar stabilizing effects were observed when mQb A38K (melting T: 73° C.) was compared to mQb A38K/A40C/D102C (melting T: 79° C.). Higher thermal stability of the capsid may contribute to better antibody responses as the vaccine constructs can potentially provide longer stimulation to the immune system.

Example 6: The New mQβs can Reduce Anti-Carrier Immune Responses, Yet Significantly Enhance Levels of Antibodies Against a TACA Antigen To assess the potency of mQb in inducing immunity against TACA and the carrier itself, a prototypical TACA, Tn1, was conjugated with wtQb as well as Qb mutants under identical reaction conditions via amide formation between amino groups of surface exposed lysines and NHS-Tn1. Tn is an attractive TACA, which was detected in 90% of human carcinomas (Springer G. Science 1984; 224: 1198-206), and regarded as one of the most specific human cancer associated structures (Hakomori S. Aberrant glycosylation in tumors and tumor-associated carbohydrate antigens. Adv Cancer Res 1989; 52: 257-31.) A LC-MS method was developed to quantify the average number of Tn immobilized per capsid by dissociating the subunits under a reducing condition. The molecular weight of modified protein subunits was determined by LC-ESI MS and the multiple charge mass spectra were transformed to single charge by Maximum Entropy deconvolution algorithm. LC-MS analysis showed that the wild type Qb (wtQb)-Tn1 conjugate contained an average of 332 Tn1 per capsid. The numbers of Tn1 on A38K, T75K, A117K, A40C/D102C and A38K/A40C/D102C ranged from 390 to 498. The quantification results obtained from LC-MS are comparable to those from microfluidic capillary gel electrophoresis analysis method utilized before for Qb-TACA characterization (Yin Z et al. *ACS Chem. Biol.* 2013, 8, 1253-1262). LC-MS method was more quantitative, which also confirmed amino acid sequences of all mutants.

TABLE 5

The average number of Tn1 conjugated on each capsid of Qb particle and yield of Qb- Tn1 conjugate.

| Qb | Tn1/Qb | #Tn1/ subunit | Yield (mg) | % |
|---|---|---|---|---|
| WT | 332 | 1.84 | 9.6 | 73 |
| A40C/D102C | 436 | 2.42 | 7.55 | 57 |
| A38K | 410 | 2.27 | 9.6 | 73 |
| A117K | 390 | 2.16 | 10.15 | 77 |
| T75K | 447 | 2.48 | 9.53 | 72 |
| A38K/A40C/D102C | 498 | 2.77 | 8.45 | 64 |

| Qb Mutants | SEC rv. (mL) | Z-Ave (d · nm) | PDI | Zeta potential |
|---|---|---|---|---|
| WT-Tn1 | 11.7 | | | |
| A38K-Tn1 | 12.6 | 26.82 | 0.028 | |
| T75K-Tn1 | 11.8 | 31.66 | 0.110 | |
| A117K-Tn1 | 11.9 | 30.77 | 0.105 | |
| A40C/D102C-Tn1 | 11.6 | | | |
| A38K/A40C/D102C-Tn1 | 12.4 | 27.61 | 0.024 | |

The abilities of mQb-Tn1 conjugates in eliciting antibody responses were evaluated in vivo. Mice (n=5) were vaccinated with various mQβ-Tn1 conjugates (all at equivalent doses of 1.9 μg of Tn) following the aforementioned protocol of Qb immunization. The sera from immunized mice were collected on day 35.

The first analysis was performed to determine the titers of anti-Tn antibodies assayed against BSA-Tn1 conjugate by ELISA. wtQb was a powerful platform generating anti-Tn IgG antibodies with an average titer of 3,300,000. The immune potentiation effect of Qb-Tn is specific to Tn as mice receiving wtQb without Tn only gave an anti-Tn titer of 1,000. The monomeric Tn conjugate with KLH failed to induce significant anti-Tn titer, highlighting the power of Qb as the vaccine carrier.

Figure 11A:
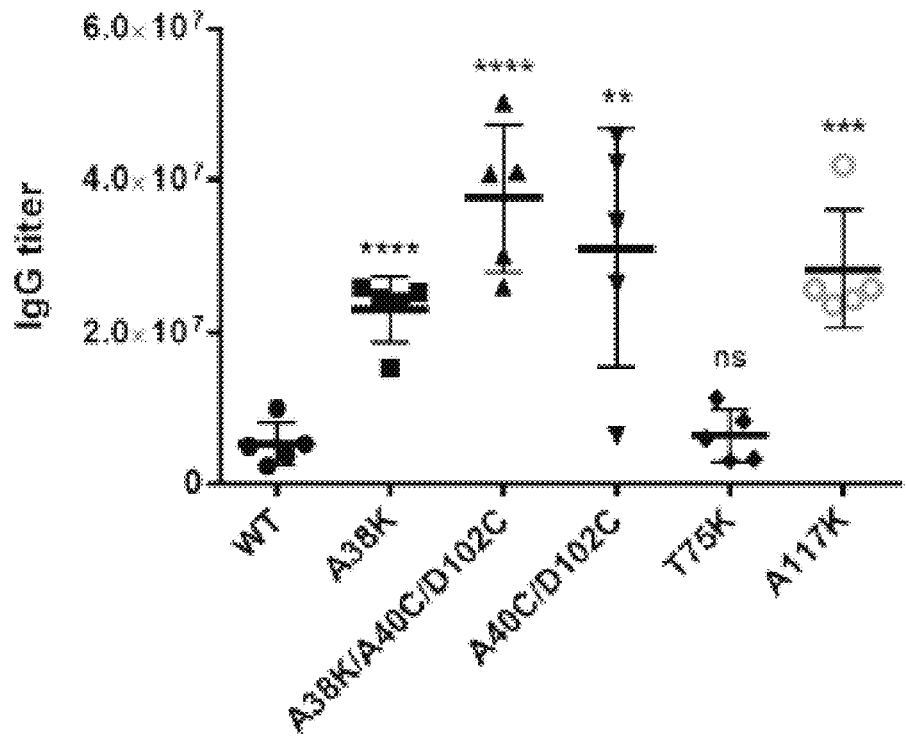
FIG. 11A-11C show ELISA results of post-immunized sera (day 35) from groups of mice (n=5) vaccinated with variant mQβ-Tn1.
Figure 11B:
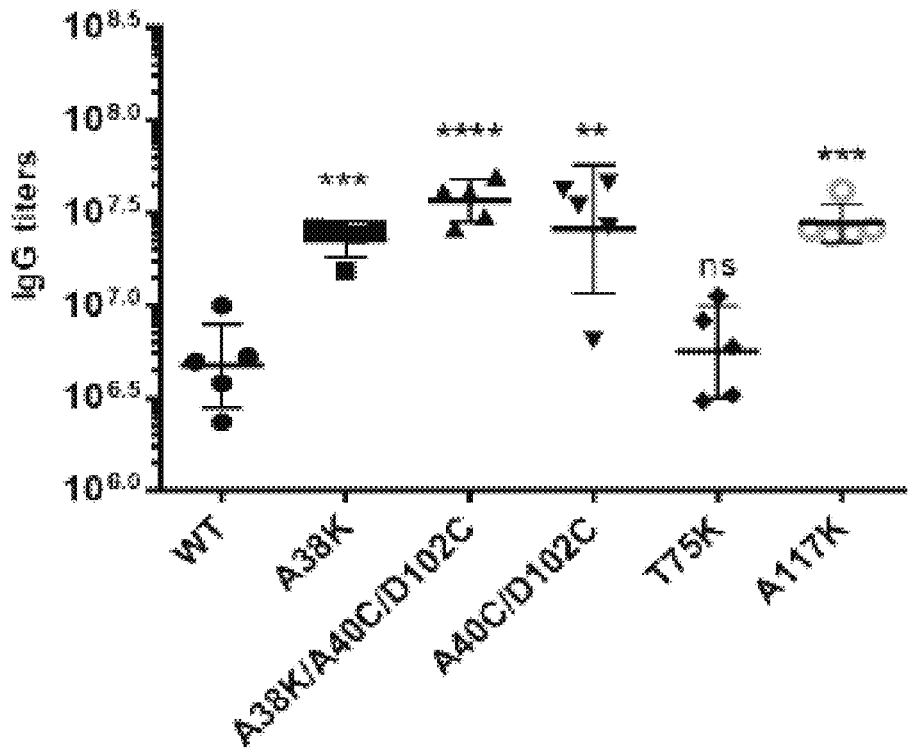
Figure 11C:
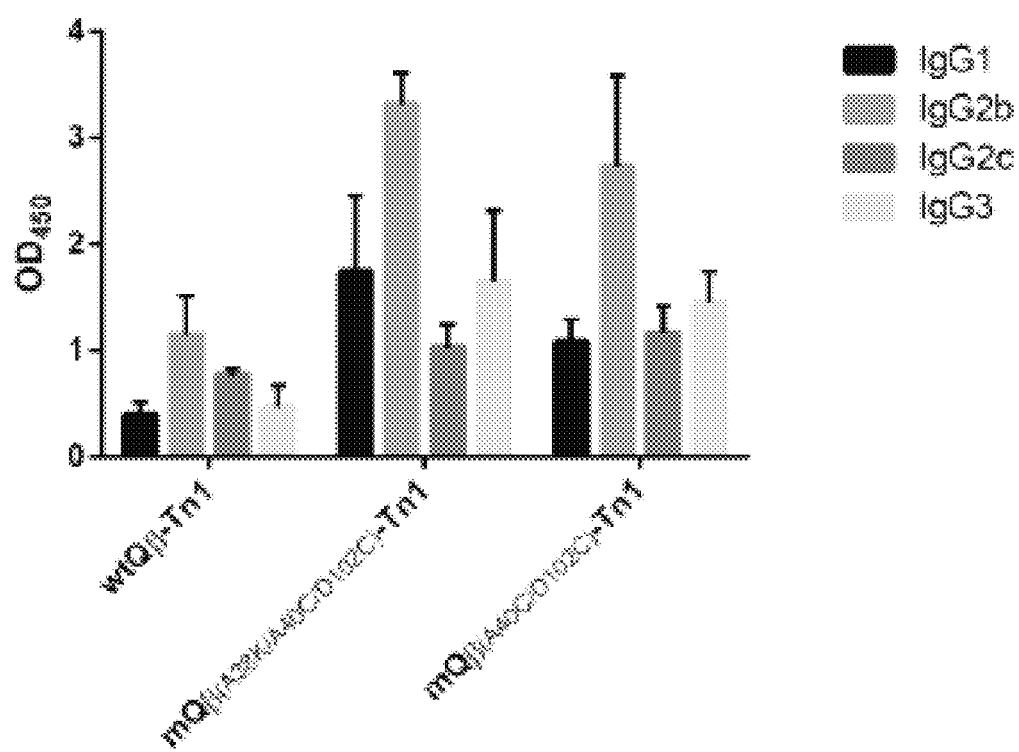

For mQbs, T75K mutant led to comparable anti-Tn IgG titers as wtQb. The three mutants of A38K, A40C/D102C, and A38K/A40C/D102C induced more superior anti-Tn IgG responses. The mean anti-Tn IgG titers with these mutants were close to one order of magnitude higher, reaching 30,000,000. To the best of our knowledge, this is the highest anti-Tn titers reported to date. Antibody subtype analysis showed similar IgG subtype patterns induced by mQb vs wtQb. All major IgG subtypes were induced with a preference of IgG2 over IgG1 indicating a T-cell dependent immune response bias towards Th1 response (FIG. 11A-11C).

ELISA results of post-immunized sera (day 35) from groups of mice (n=5) vaccinated with variant mQβ-Tn1. a and b) Anti-Tn1 titers of the post-immunized sera presented in linear and log scale, respectively. The statistical significance of differences between a mQβ and wtQβ was determined by the Student t test (p<0.01; *p<0.001; ****p<0.0001)

$OD_{450}$ from ELISA result at 1/819200 sera dilution of IgG subtypes antibodies (IgG1, IgG2b, IgG2c and IgG3) elicited by wtQβ-Tn1, mQβ(A38K/A40C/D102C)-Tn1 and mQβ (A40C/D102C)-Tn1 immunization against BSA-Tn1.

Figure 12:
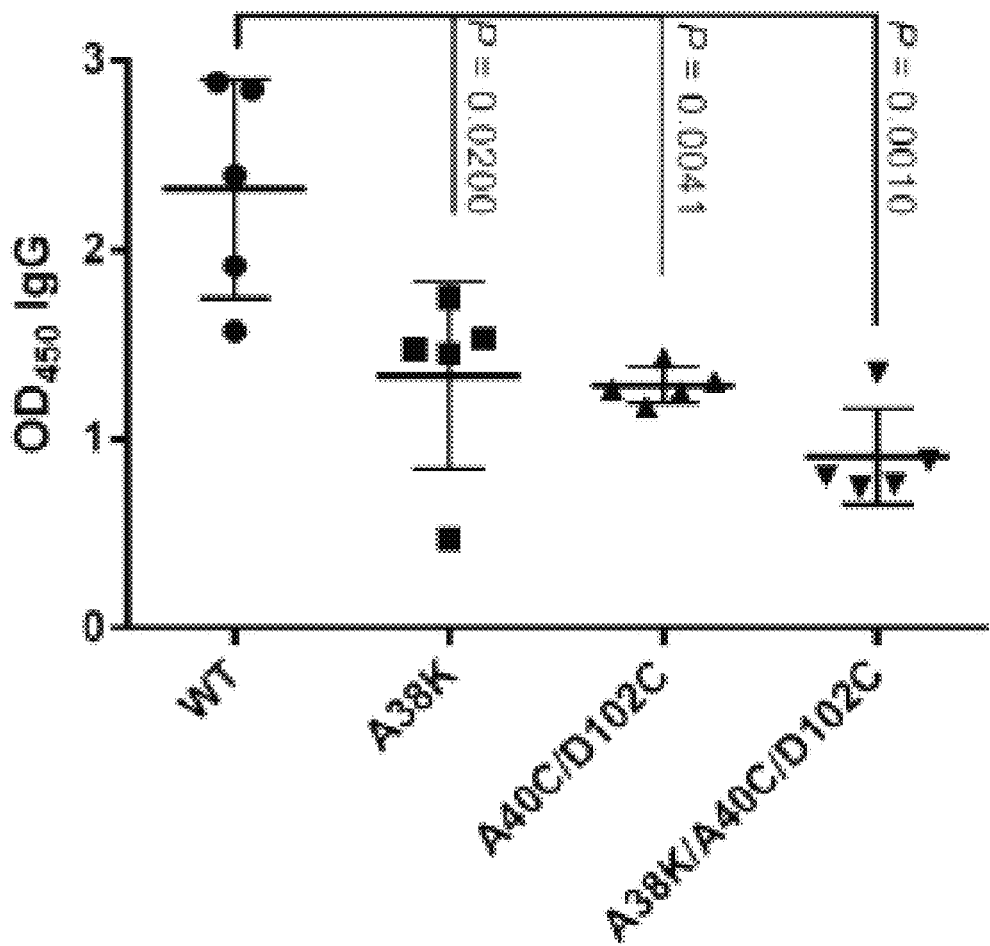
FIG. 12 shows the reduced antibody levels against wtQβ generated by the mutants.

We tested next whether mutations of the Qb capsids can reduce their recognition by anti-wtQb antibodies. The abilities of IgG antibodies elicited by wtQb-Tn, A38K-Tn, A40C/D102C-Tn and A38K/A40C/D102C-Tn to recognize wtQb were measured against wtQb immobilized in ELISA wells. As shown in FIG. 12, all mQb-Tn conjugates elicited significantly less anti-wtQb antibodies compared to wtQb-Tn.

Figure 13:
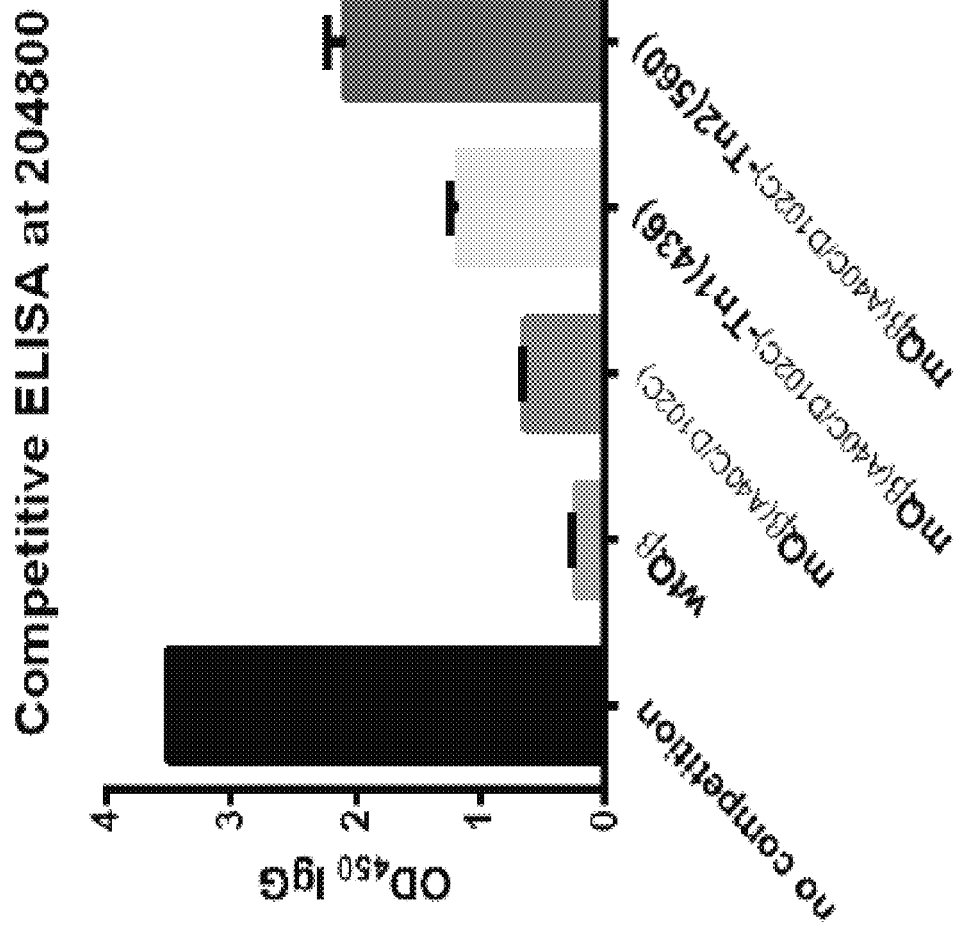
FIG. 13 shows competitive ELISA showing reduced anti-wtQβ antibody recognition of mQβ-Tn conjugates.
Figure 14A:
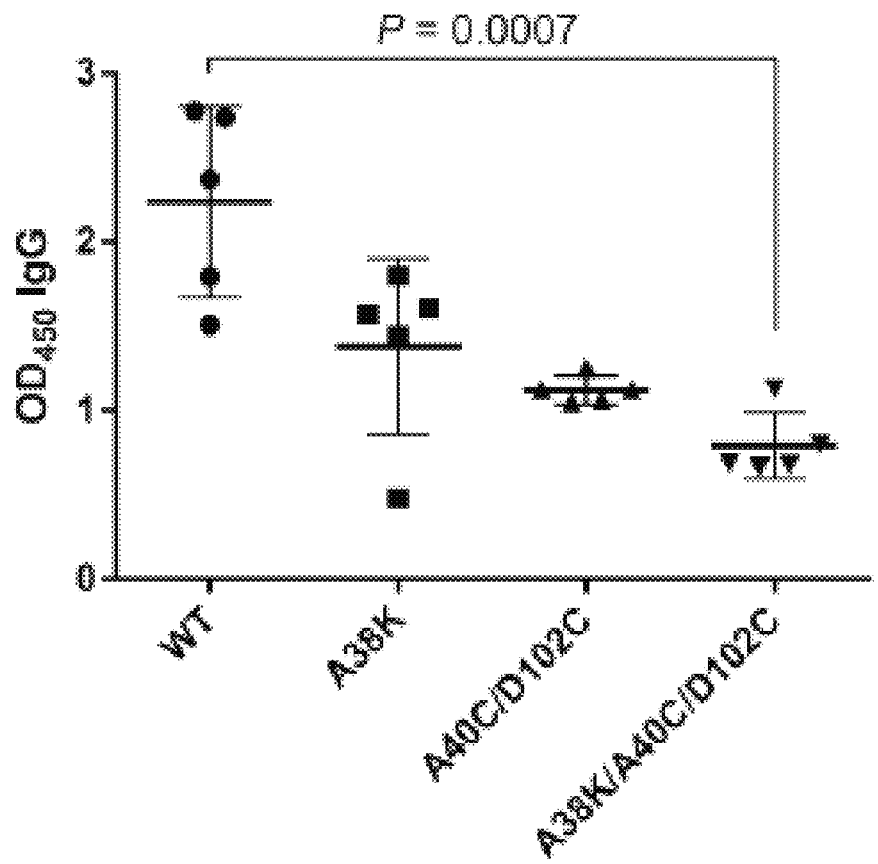
FIGS. 14A and 14B show ELISA results of post-immunized sera (day 35) from groups of mice (n=5) vaccinated with variant mQβ-Tn1.
Figure 14B:
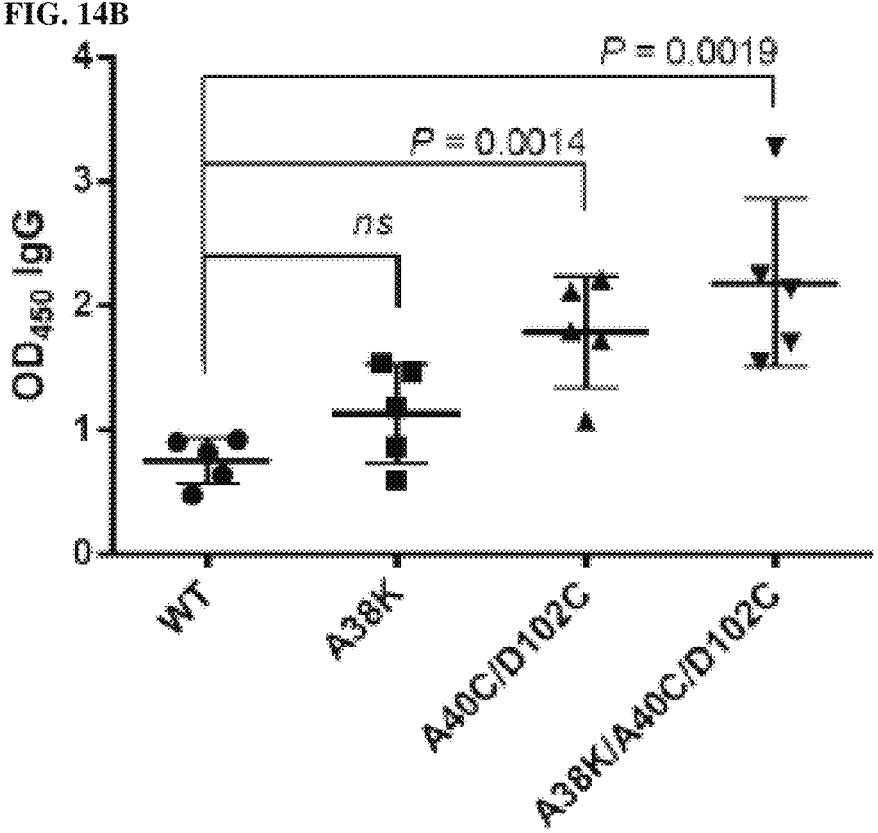
Figure 15A:
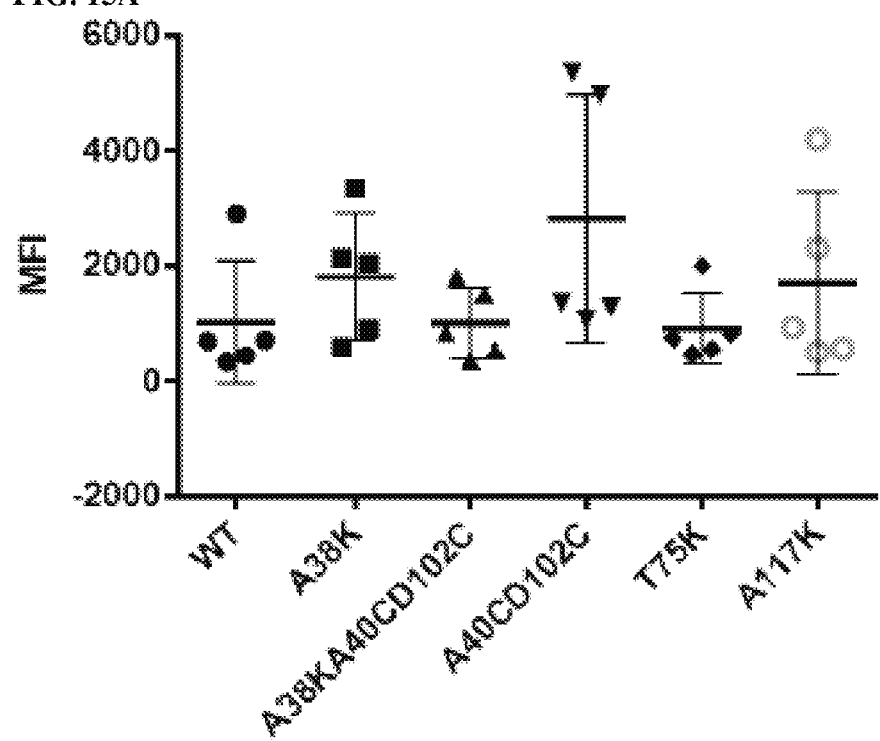
FIGS. 15A and 15B binding of elicited IgG antibodies by Qβ conjugates.
Figure 15B:
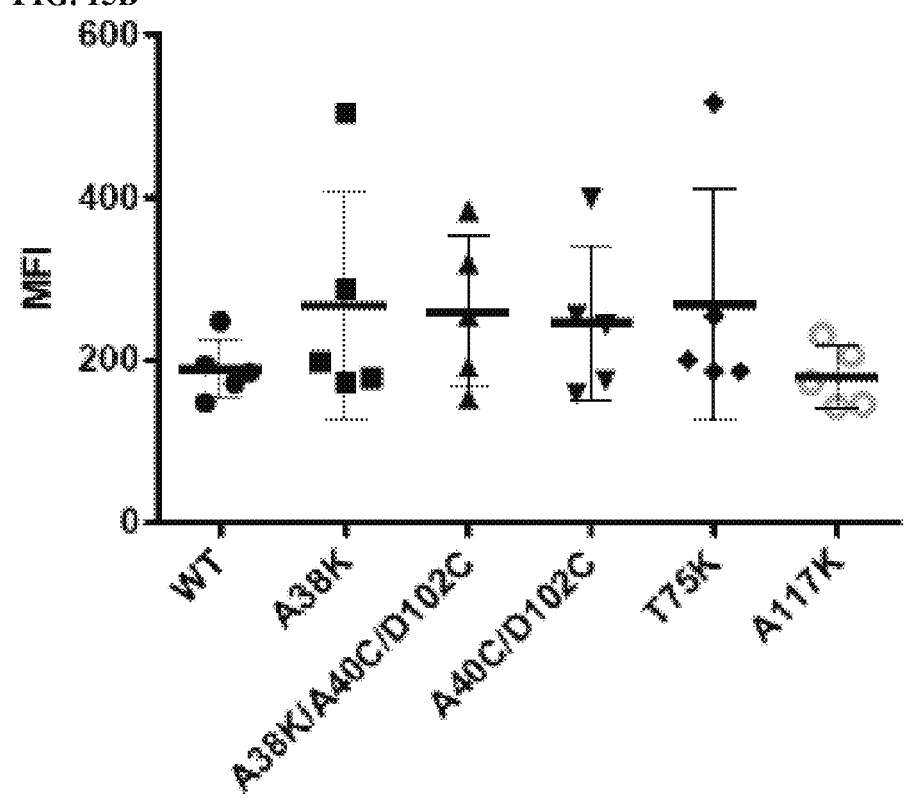

To further confirm the reduction of wtQb recognition, a competitive ELISA assay was set up. Sera from wtQβ-immunized mice were incubated with the wtQβ, mQβ (e.g. A38K and A40C/D102C) or mQβ-Tn conjugate respectively. These pre-incubated sera were then added into individual ELISA wells coated with wtQβ. Any viral capsids that can be recognized by anti-wtQβ antibodies will compete with the immobilized wtQβ for binding with antibodies in sera resulting in reduction of absorbance in the wells. As expected, free wtQb efficiently competed with immobilized wtQb lowering the absorbance level in the wells to only 5% of wells with no competition. All mutants exhibited reduced recognition by anti-wtQb antibodies. For example, the wells with sera pre-incubated with mQb (A40C/D102C) showed 2.5 times the absorbance compared to those with wtQb (FIG. 13). This effect became more pronounced with mQβ(A40C/D102C)-Tn conjugate, where the Tn immobilized could further shield the B cell epitopes of Qb for immune recognition. These results suggest mutations have successfully removed some epitopes of wtQb Antibody responses elicited by mQb against the mutant carrier itself were analyzed next, as it is possible that the mutations can create new B cell epitopes that compete with the generation of anti-TACA antibodies. All mQb-Tn induced less IgG antibodies against the respective carrier as compared to the level of anti-wtQb antibodies elicited by wtQb. Correlation with anti-Tn antibody responses from Tn conjugates of A38K, A40C/D102C and A38K/A40C/D102C exhibited an interesting reverse trend of anti-carrier vs anti-Tn antibodies. The vaccine construct producing lower anti-carrier antibody responses elicited higher levels of anti-Tn IgG (FIG. 14A, 14B).

Figure 21A:
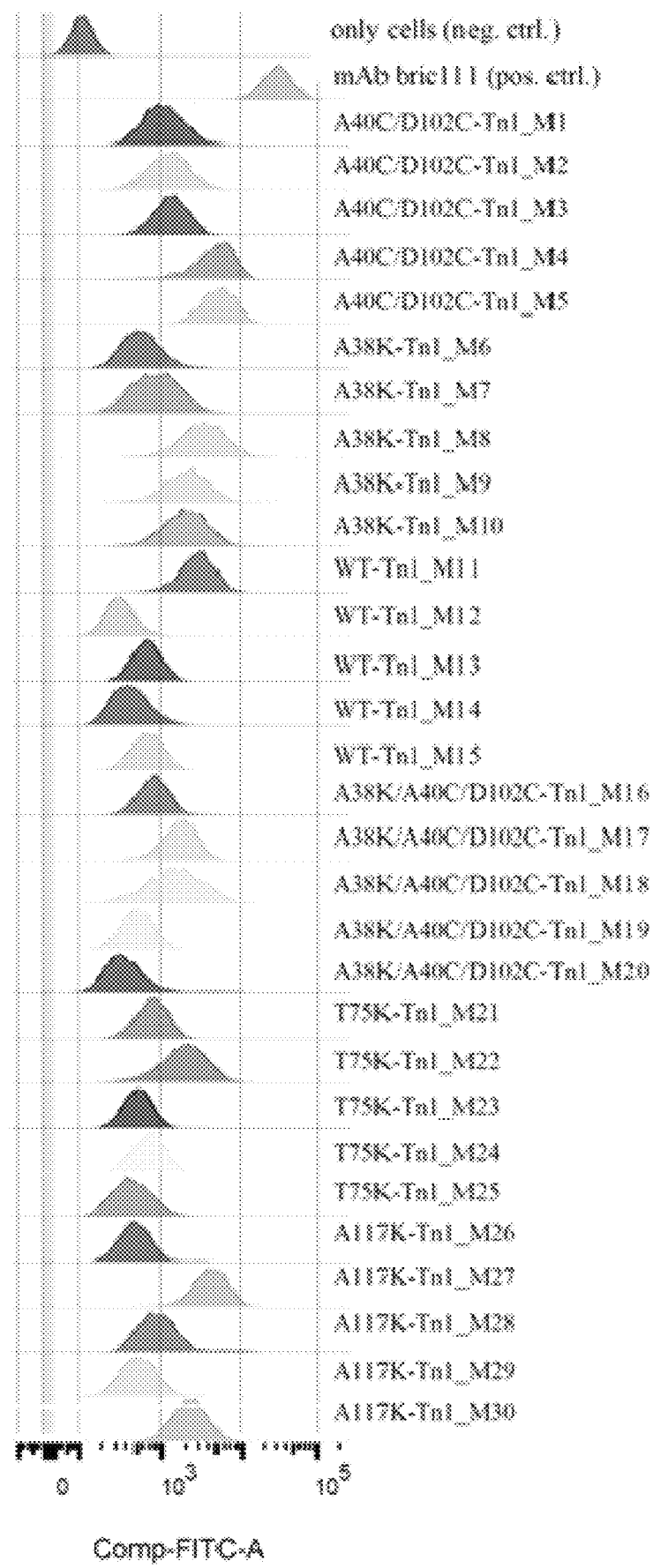
FIGS. 21A and 21B shows flow cytometry showing binding of elicited IgG antibodies by Qβ conjugates.
Figure 21B:
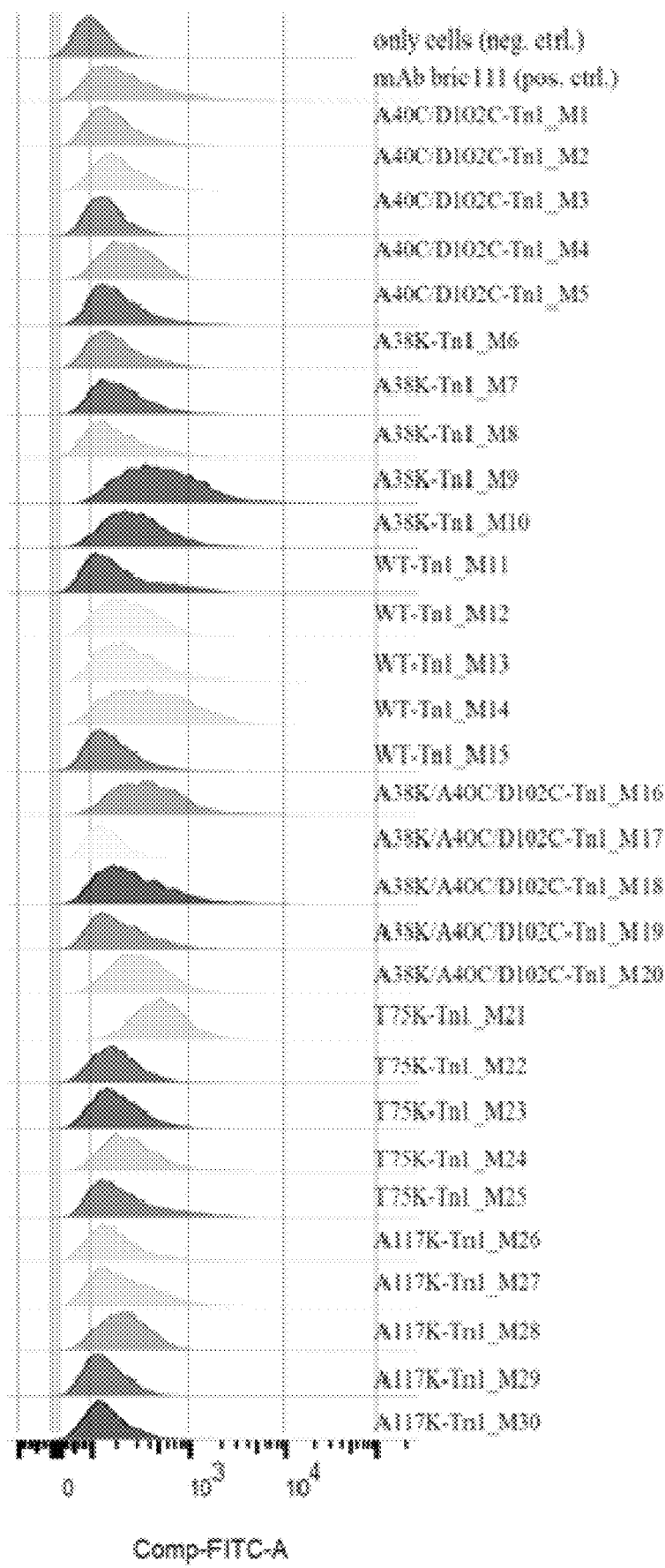
Figure 22A:
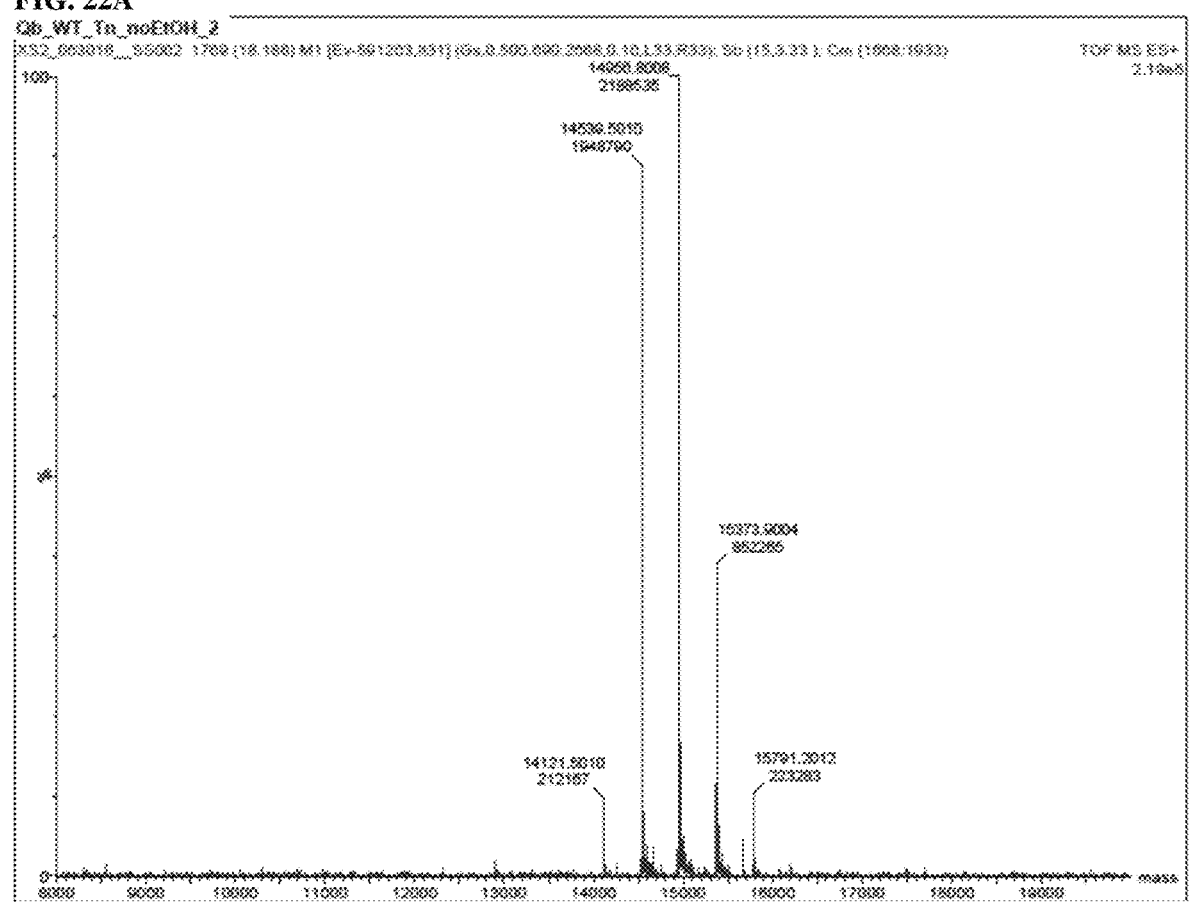
FIG. 22A-22M depict mass spectra of wild-type Qβ-Tn1 and varied Qβ mutant-Tn1 after applying MaxEnd1 algorithm.
Figure 22B:
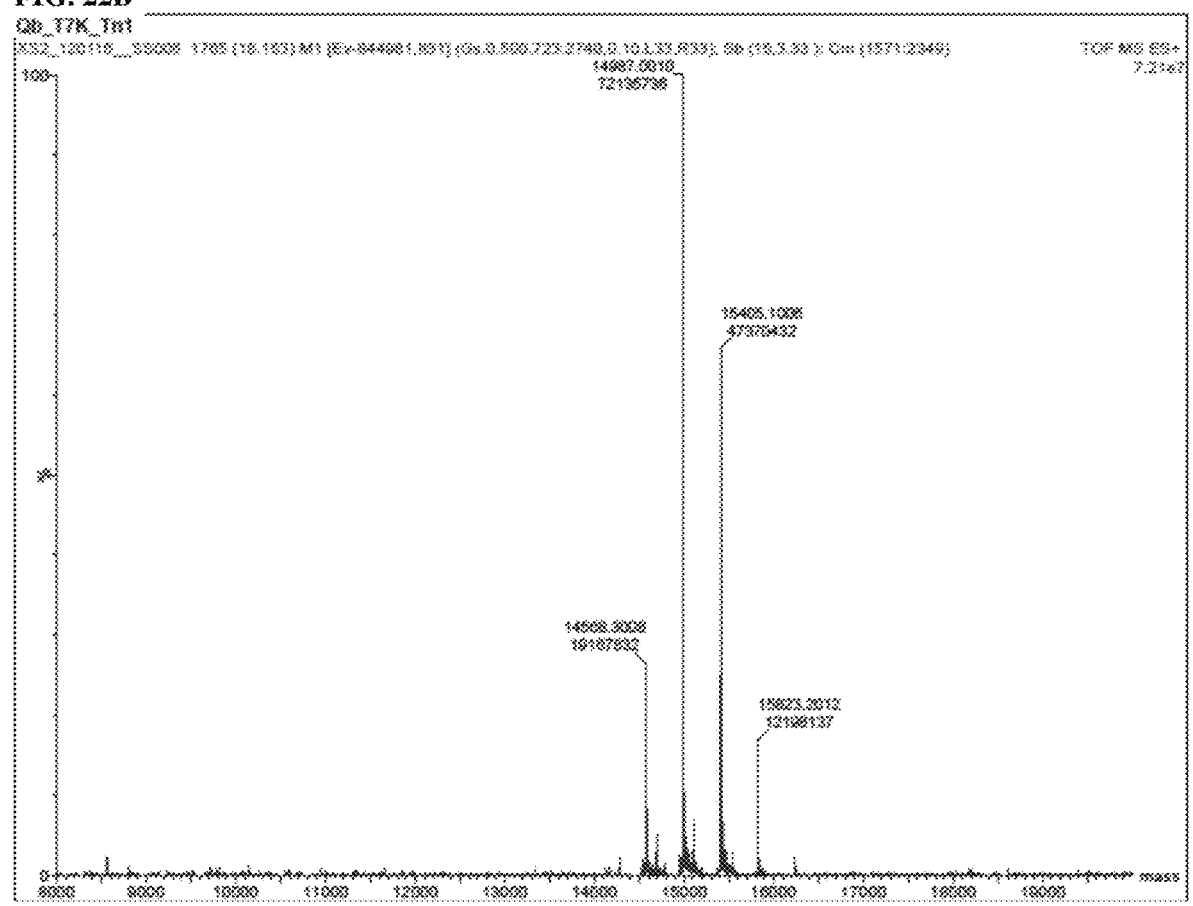
Figure 22C:
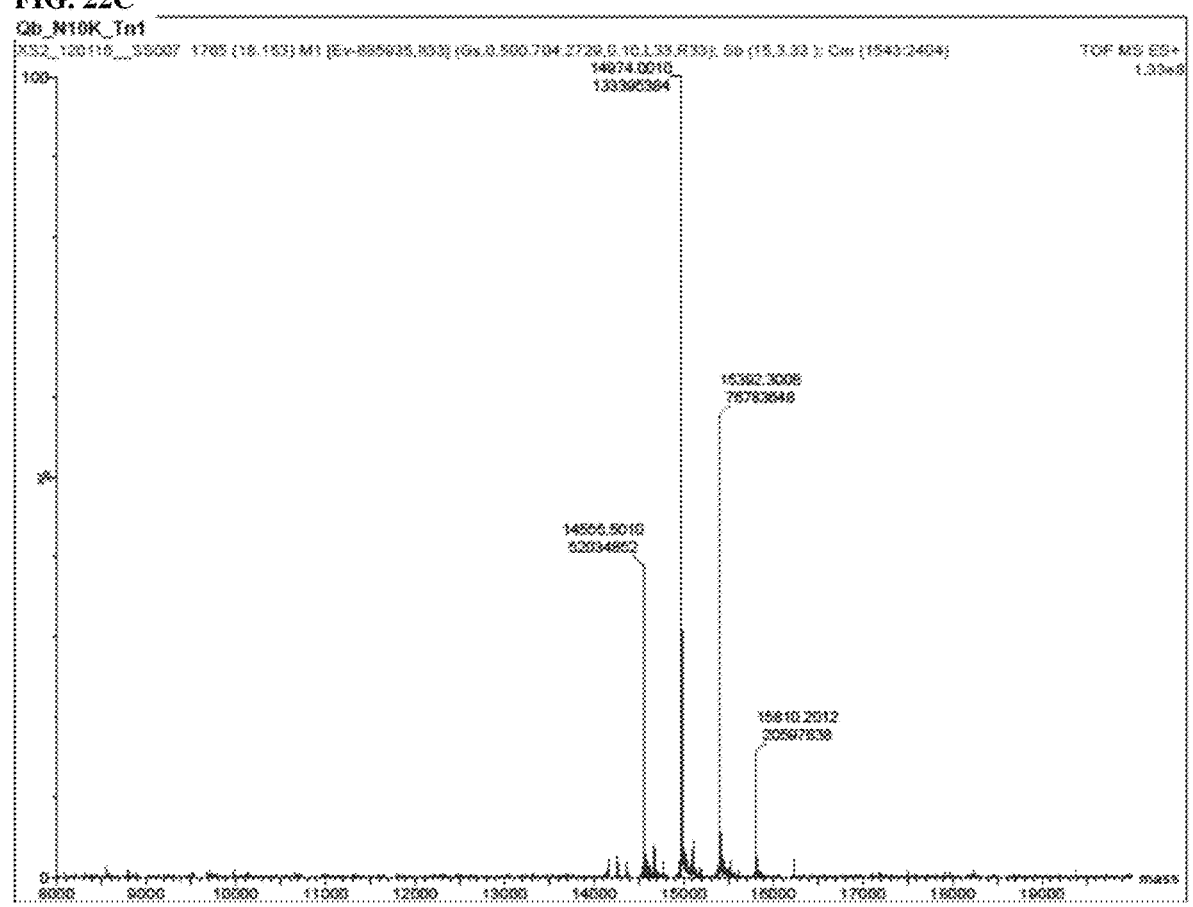
Figure 22D:
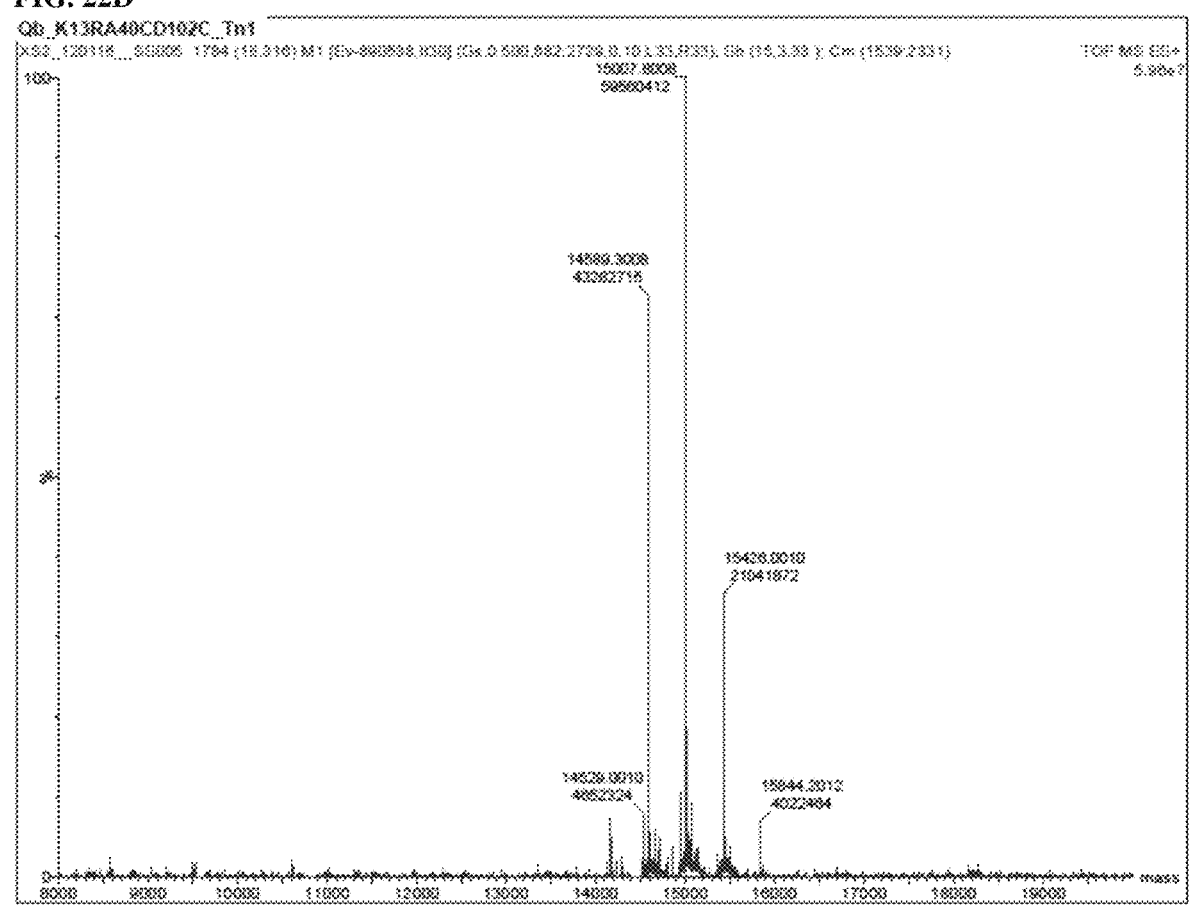
Figure 22E:
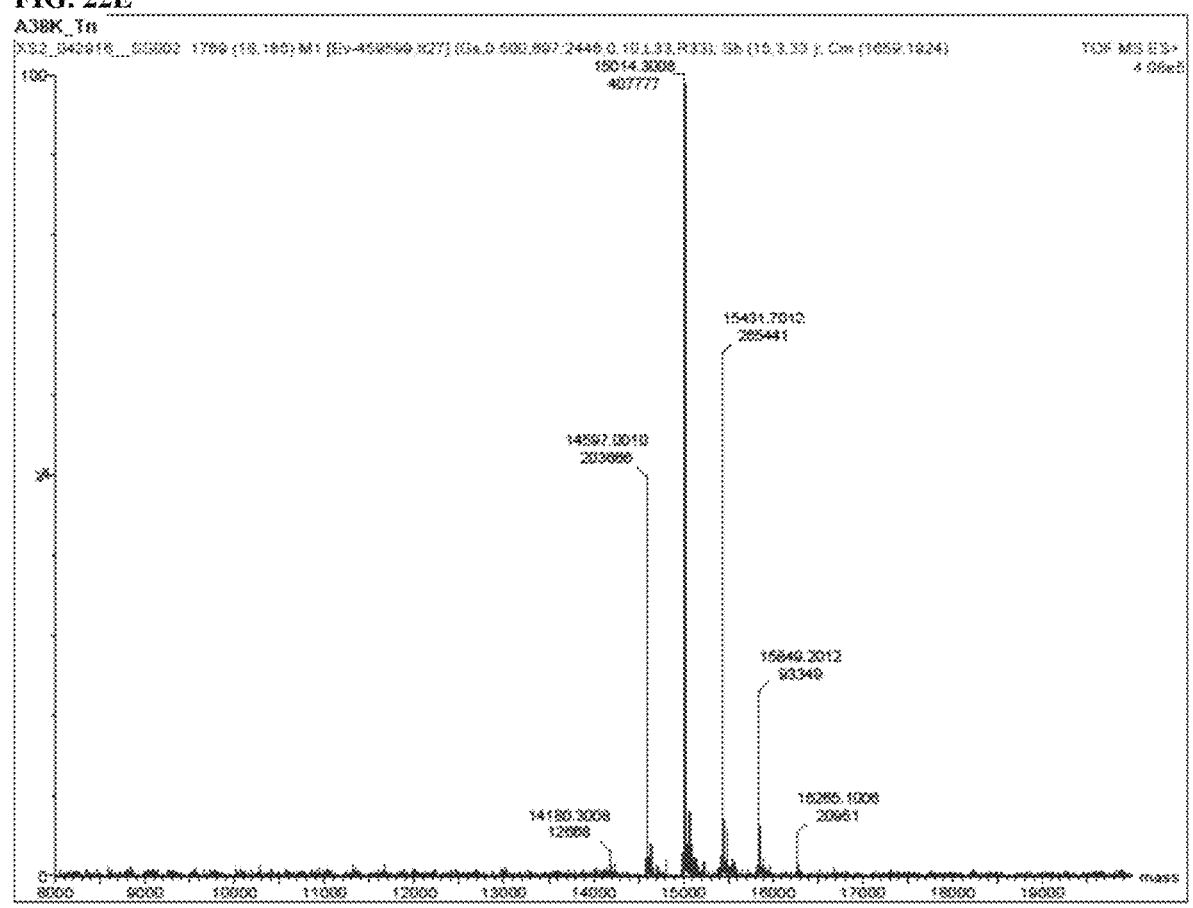
Figure 22F:
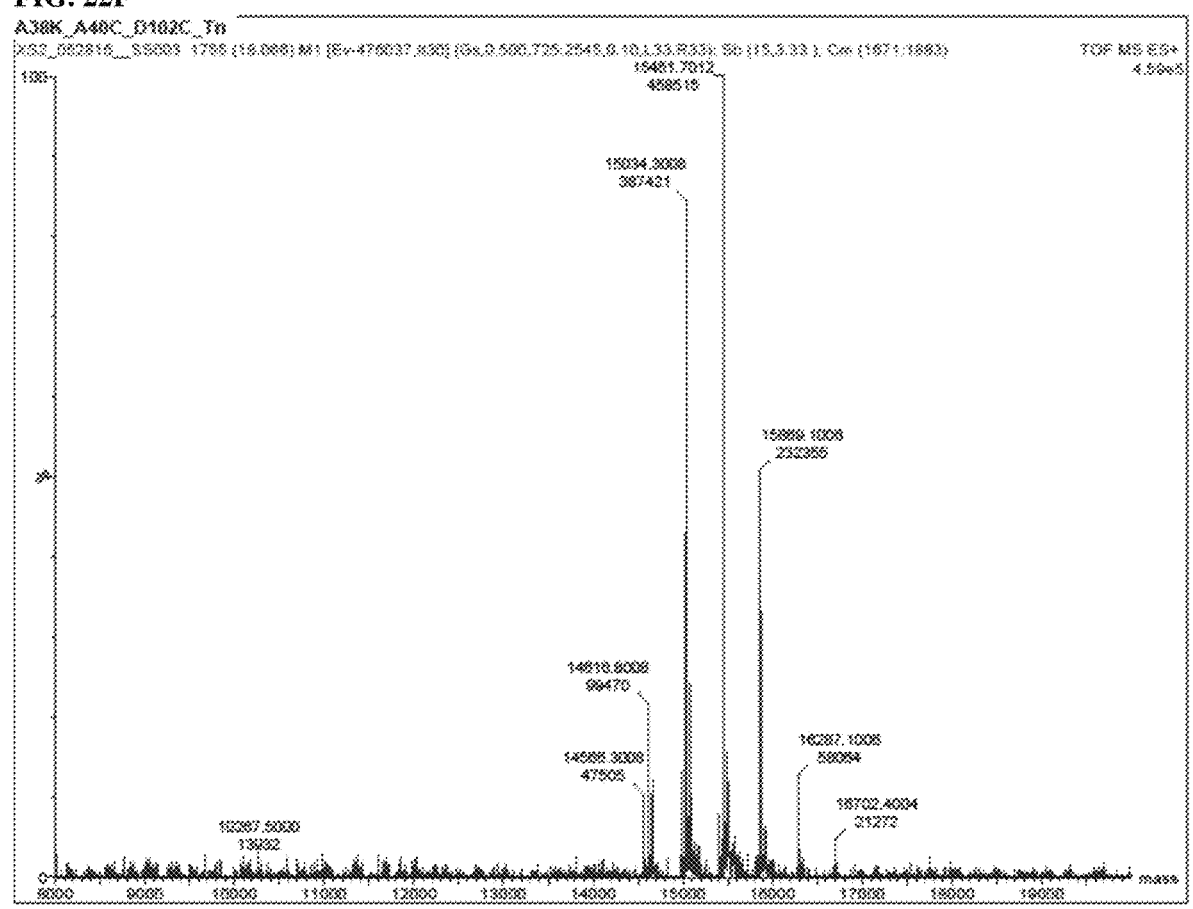
Figure 22G:
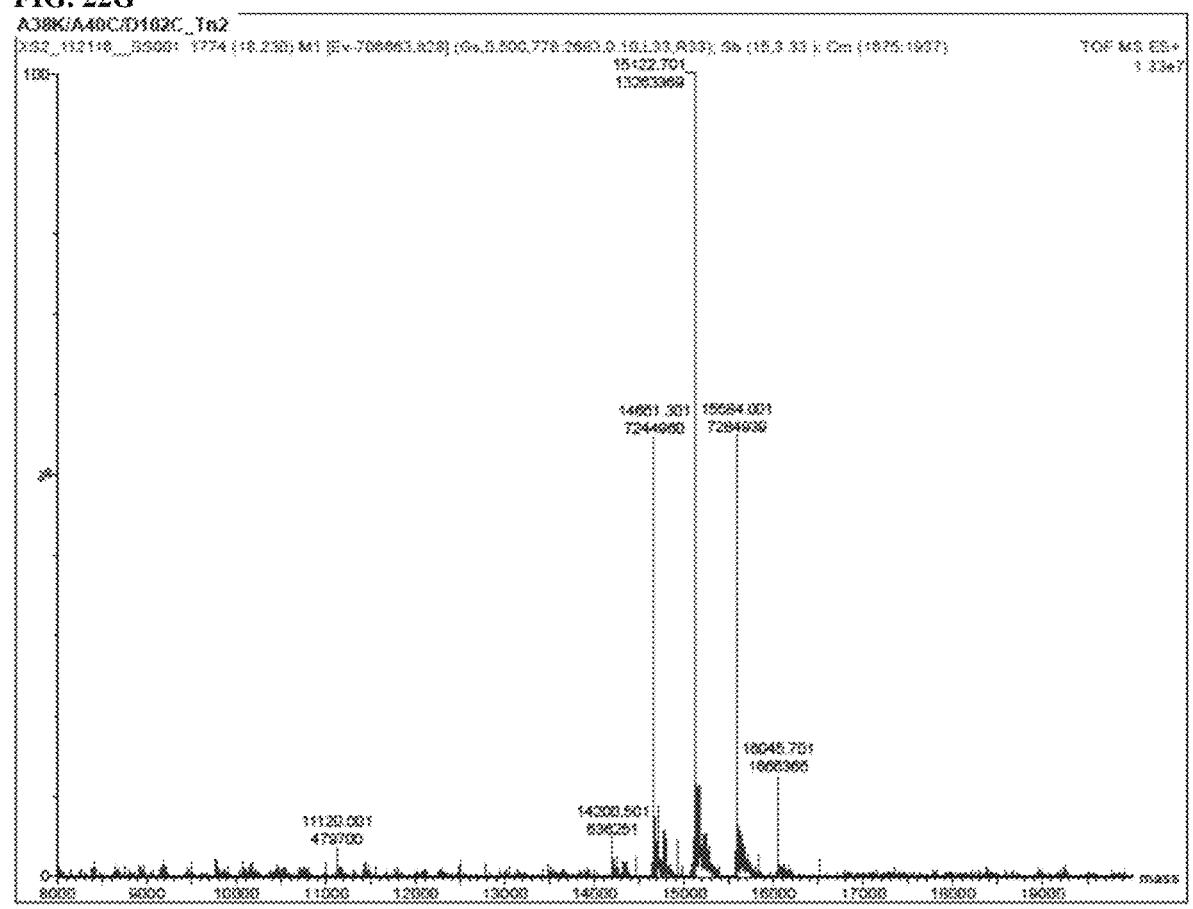
Figure 22H:
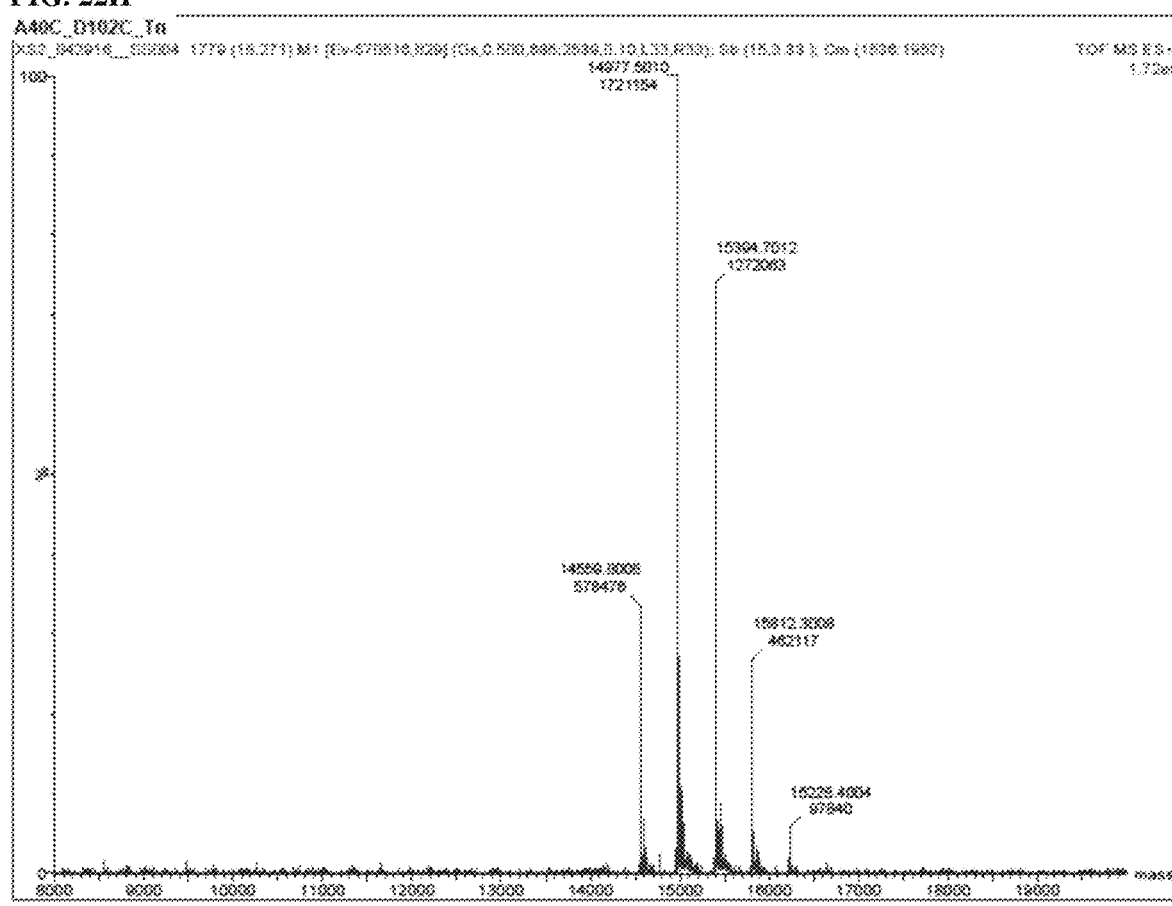
Figure 22I:
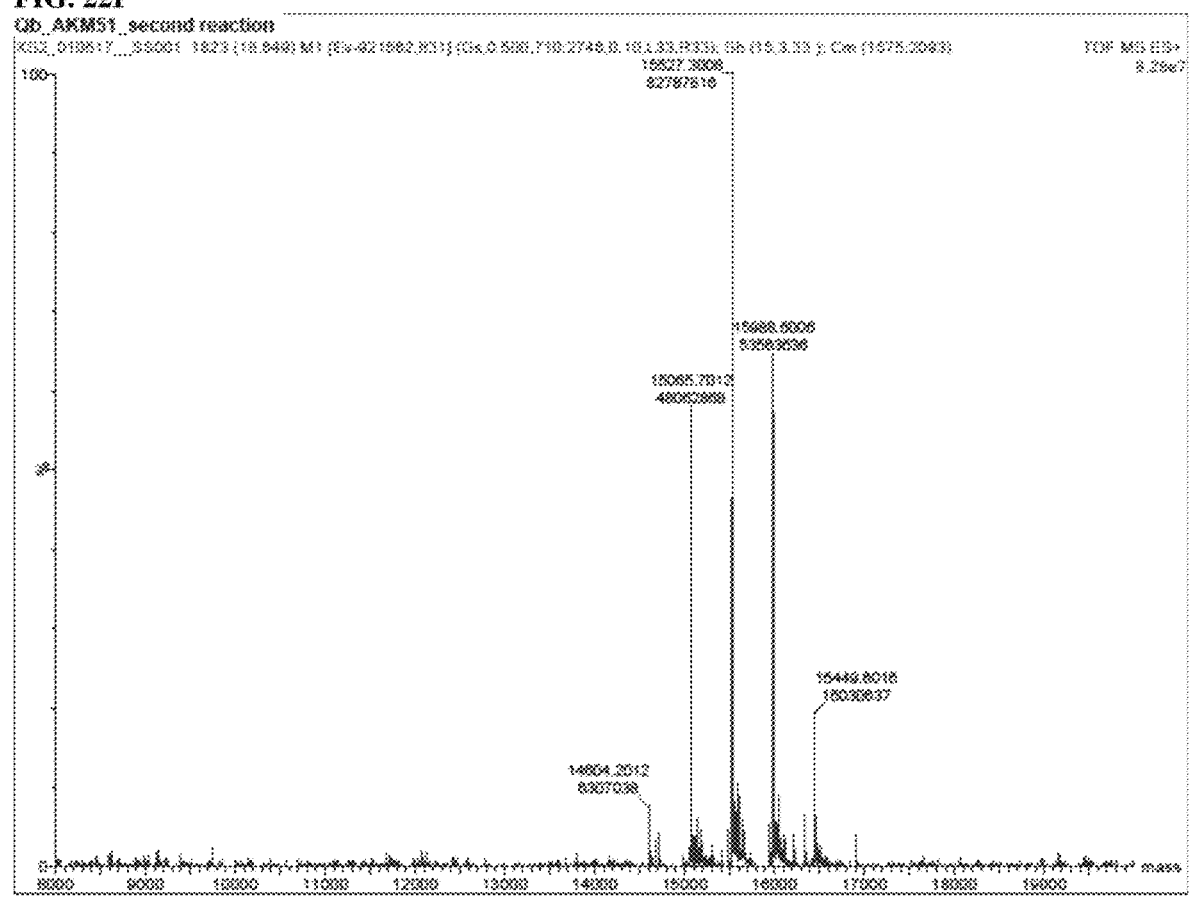
Figure 22J:
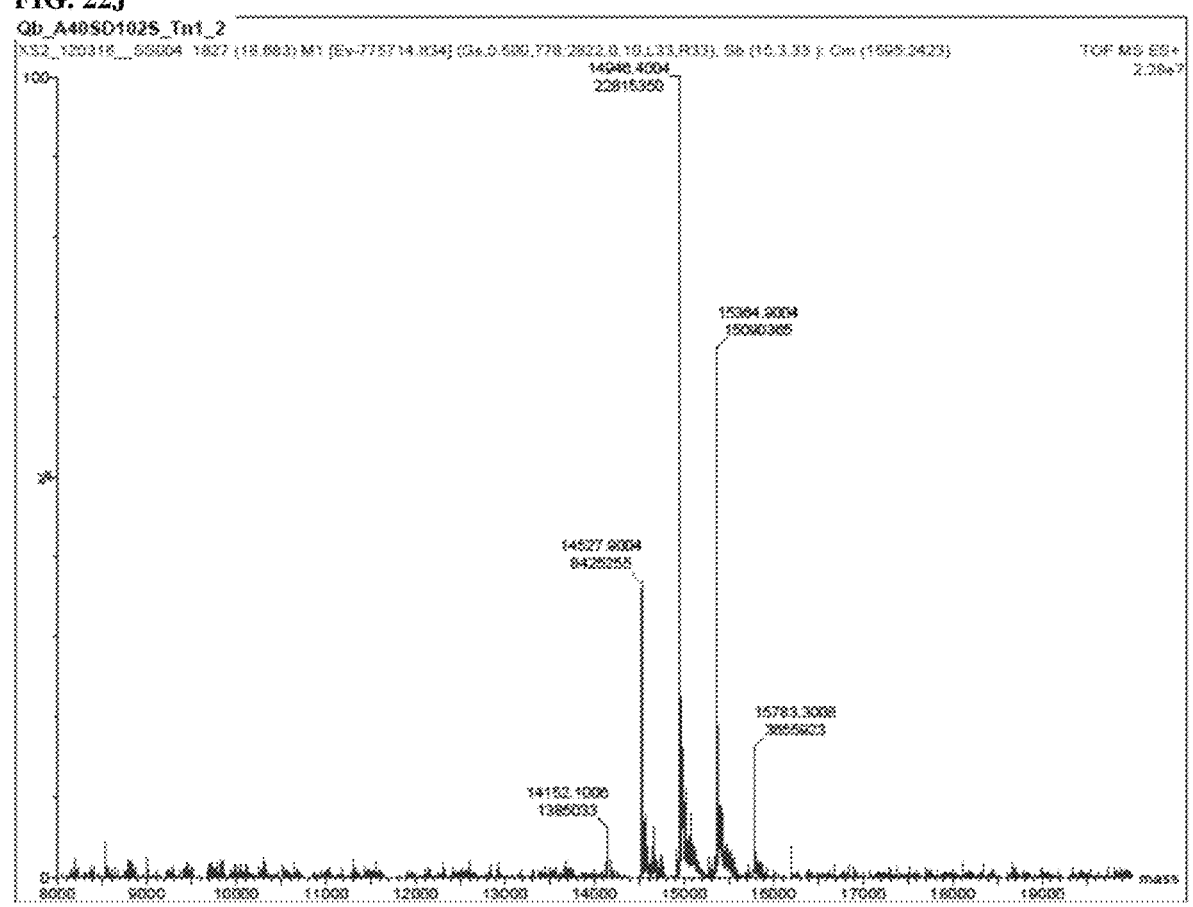
Figure 22K:
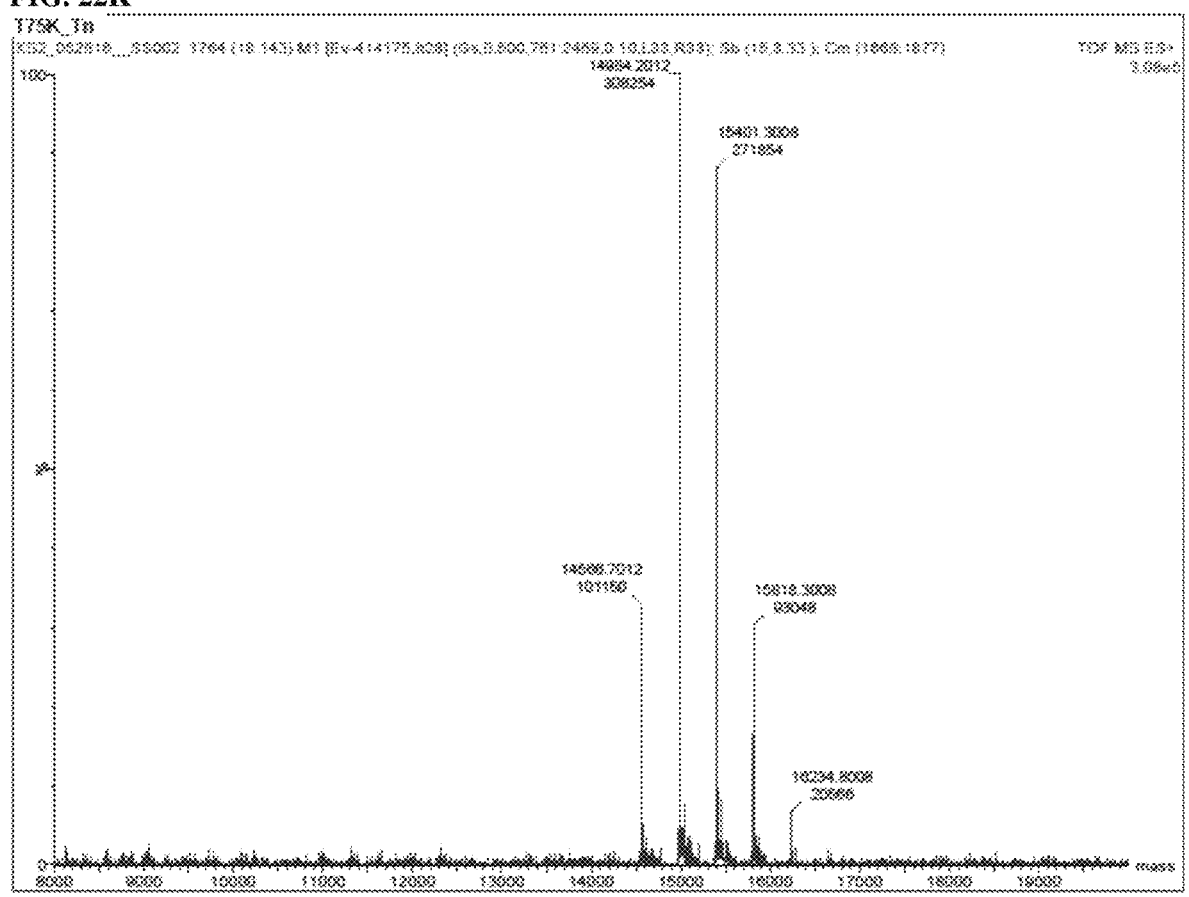
Figure 22L:
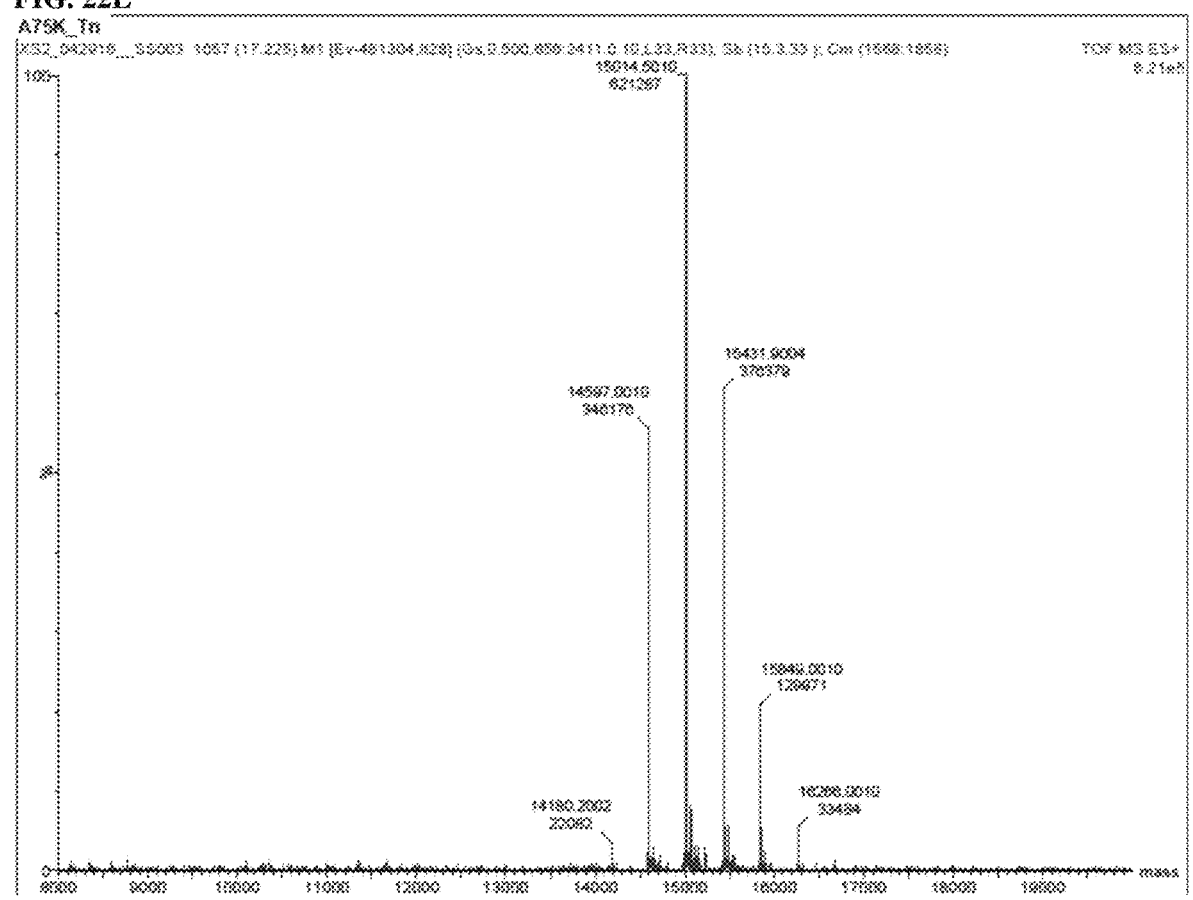
Figure 22M:
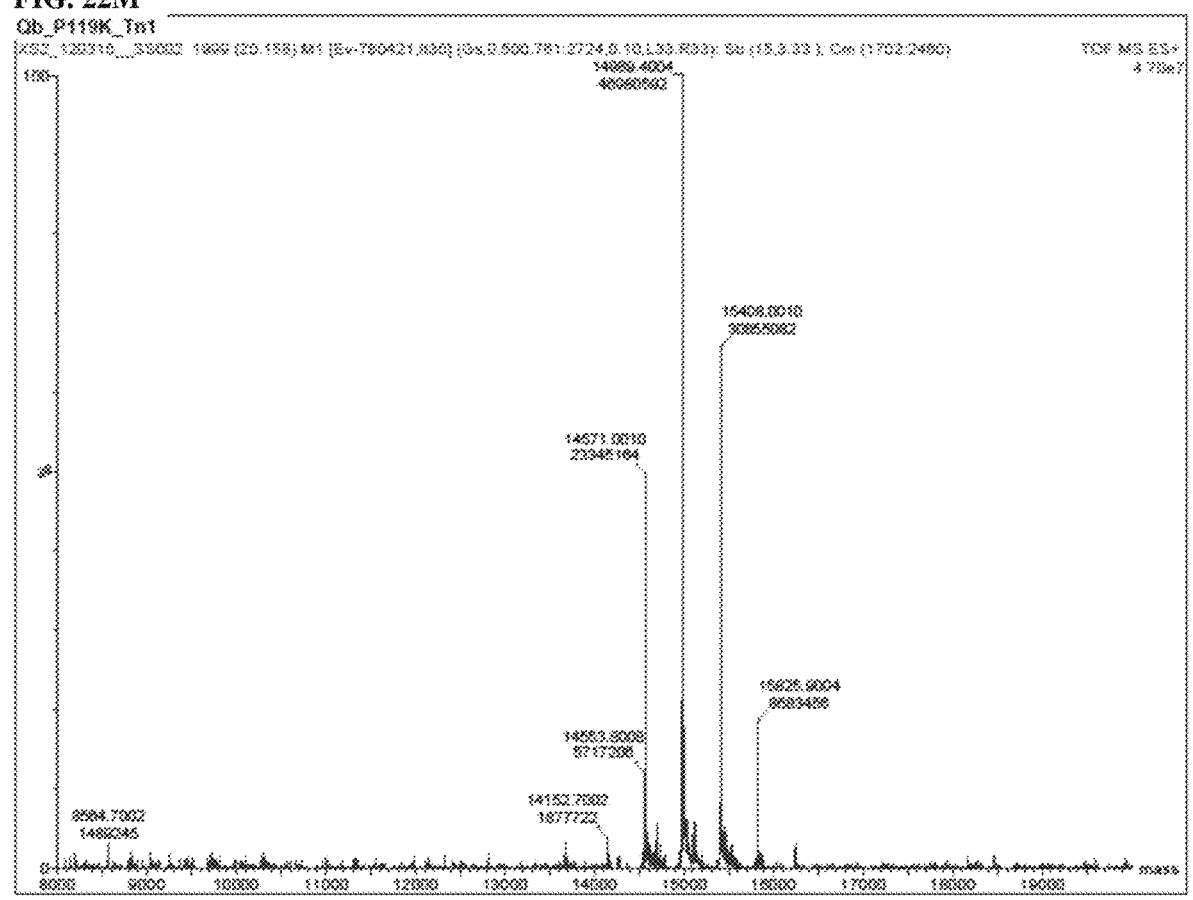
Figure 23A:
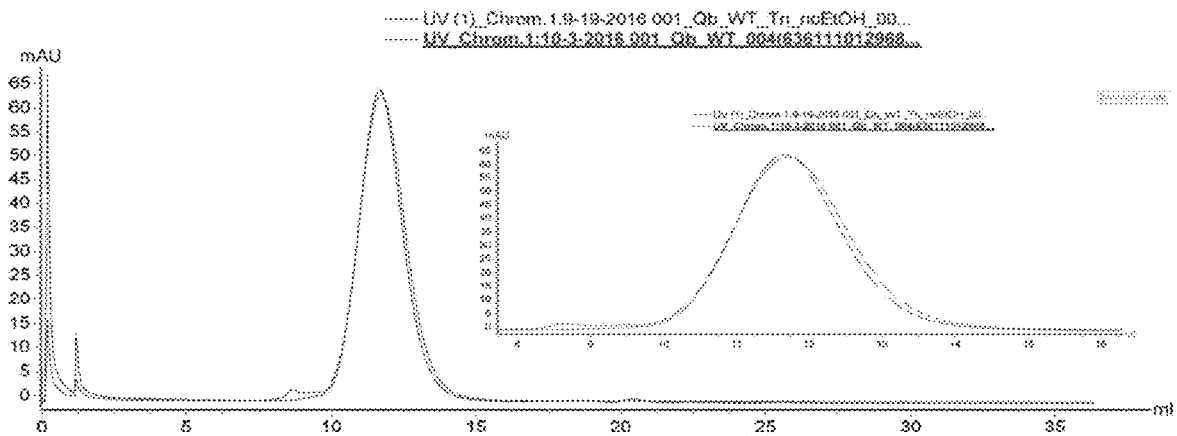
FIG. 23A-23I depict size-exclusion chromatography of wild-type Qβ, varied Qβ mutants and their Tn1 derivatives.
Figure 23B:
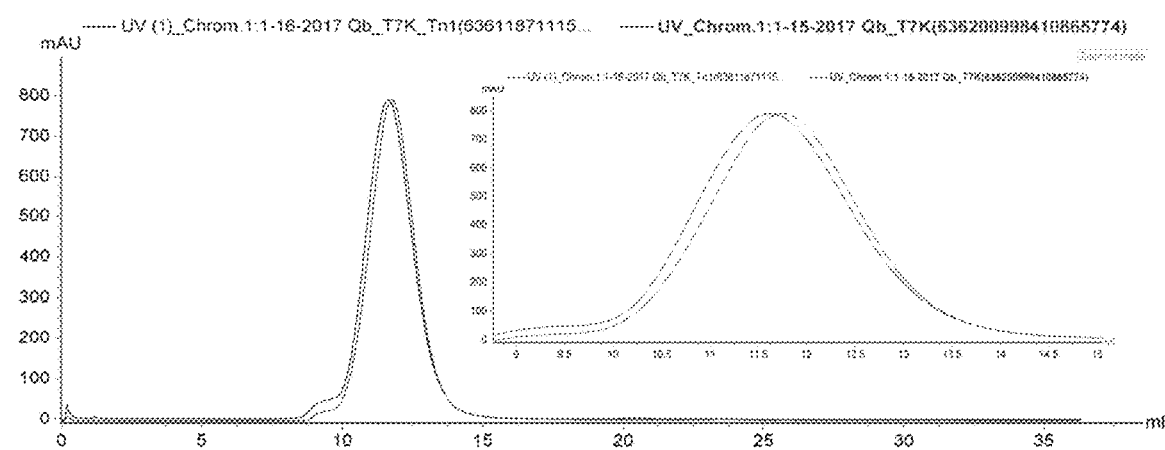
Figure 23C:
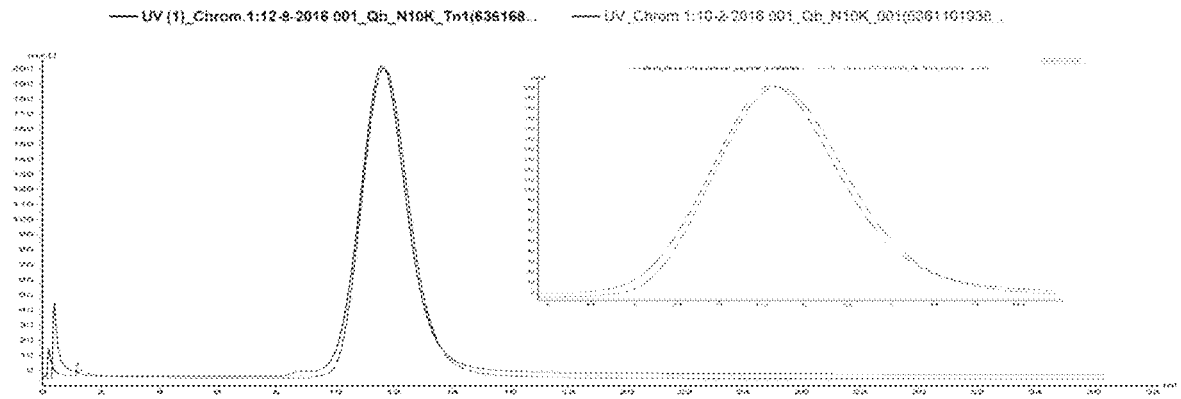
Figure 23D:
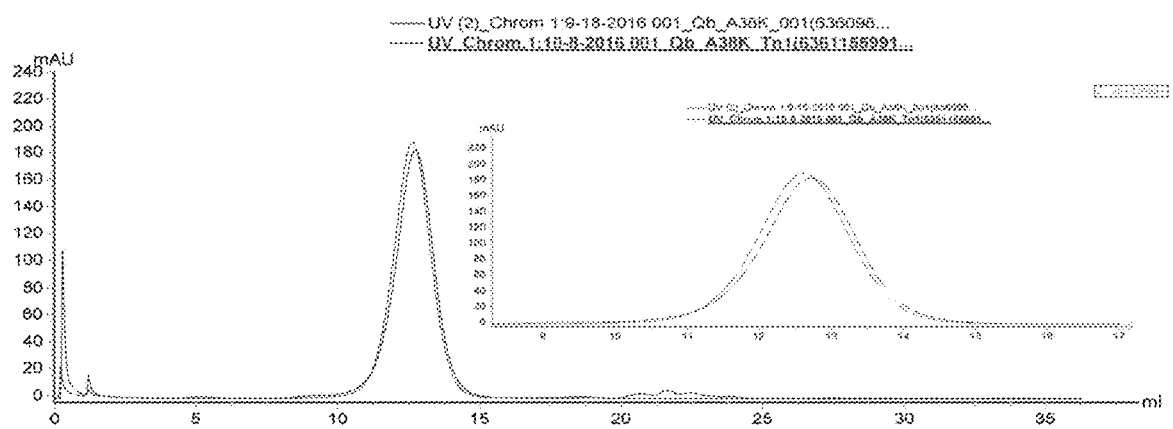
Figure 23E:
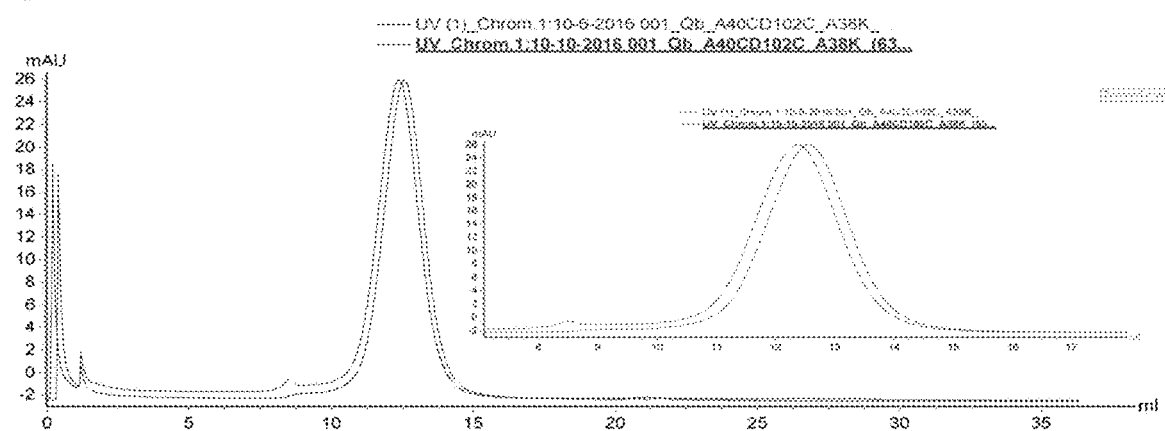
Figure 23F:
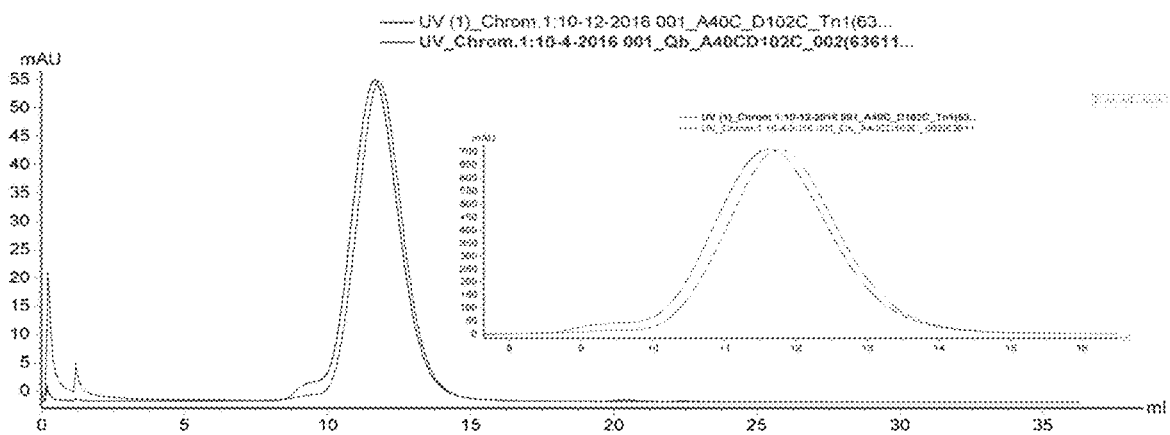
Figure 23G:
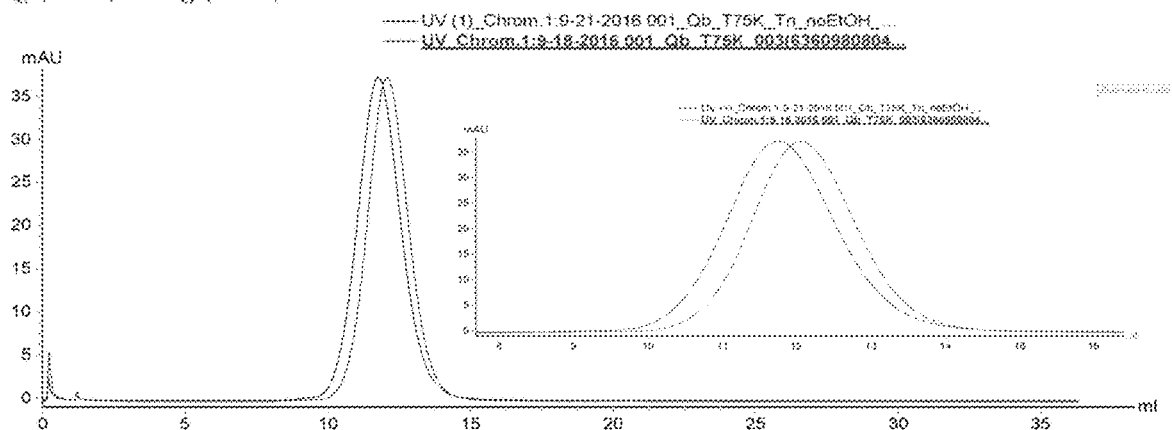
Figure 23H:
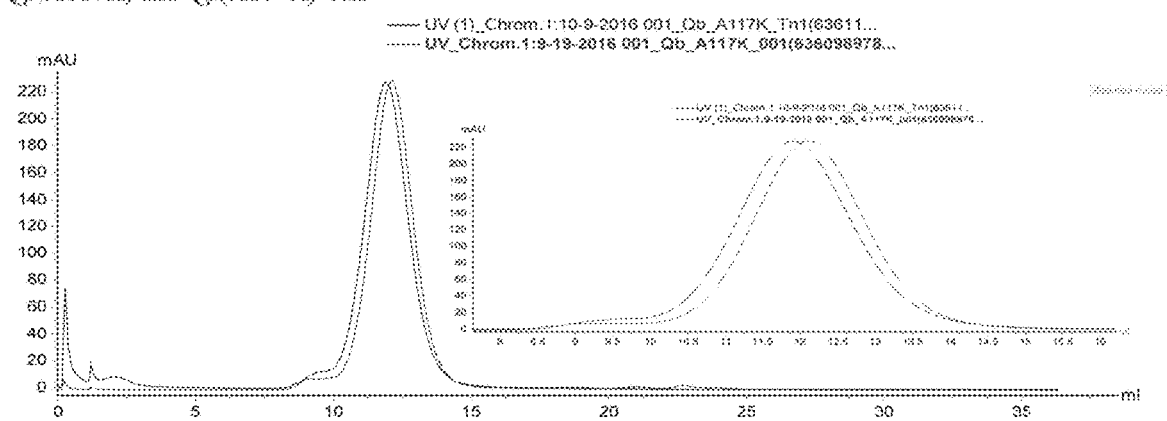
Figure 23I:
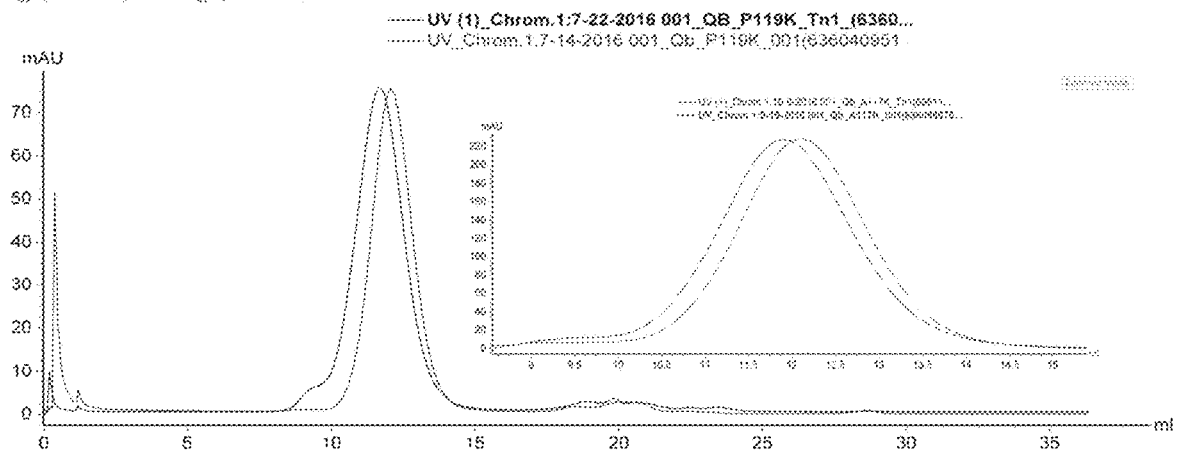

Example 7: mQb-Tn Induced Anti-Tn Antibodies Capable of Binding Strongly with Tn Expressing Tumor Cells To lay the groundwork for anti-cancer vaccine, the abilities of anti-Tn antibodies to recognize Tn on cancer cell surface were evaluated using two representative Tn expressing cell lines, i.e., human lymphoma Jurkat cells and mouse breast cancer cell TA3Ha. All mQb-Tn conjugates generated IgG antibodies capable of binding strongly with tumor cells. As shown in FIGS. 21A and 21B, compared to tumor cell binding by sera from wtQb-immunized Tn mice, A38K and A40C/D102C conjugates with Tn induced antibodies with much stronger recognition to Jurkat cells. The three mQb A38K, A38K/A40C/D102C and A40C/D102C Tn conjugates produced antibodies with higher binding to TA3Ha cells.

Due to the ease of its synthesis, Tn (FIG. 16A) was used as a representative Tn structure for immunogenecity evaluations. To optimize the immunogen construct, Tn2 was synthesized, which (FIG. 16A) was found to be superior to Tn as mQβ(A38K/A40C/D102C)-Tn2 and mQβ(A40C/

Figure 16B:
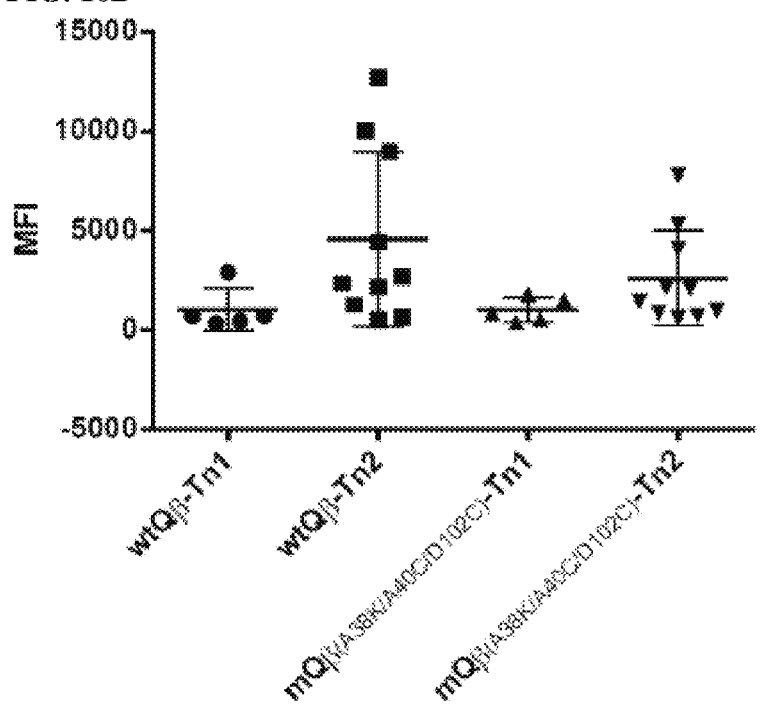
Figure 16C:
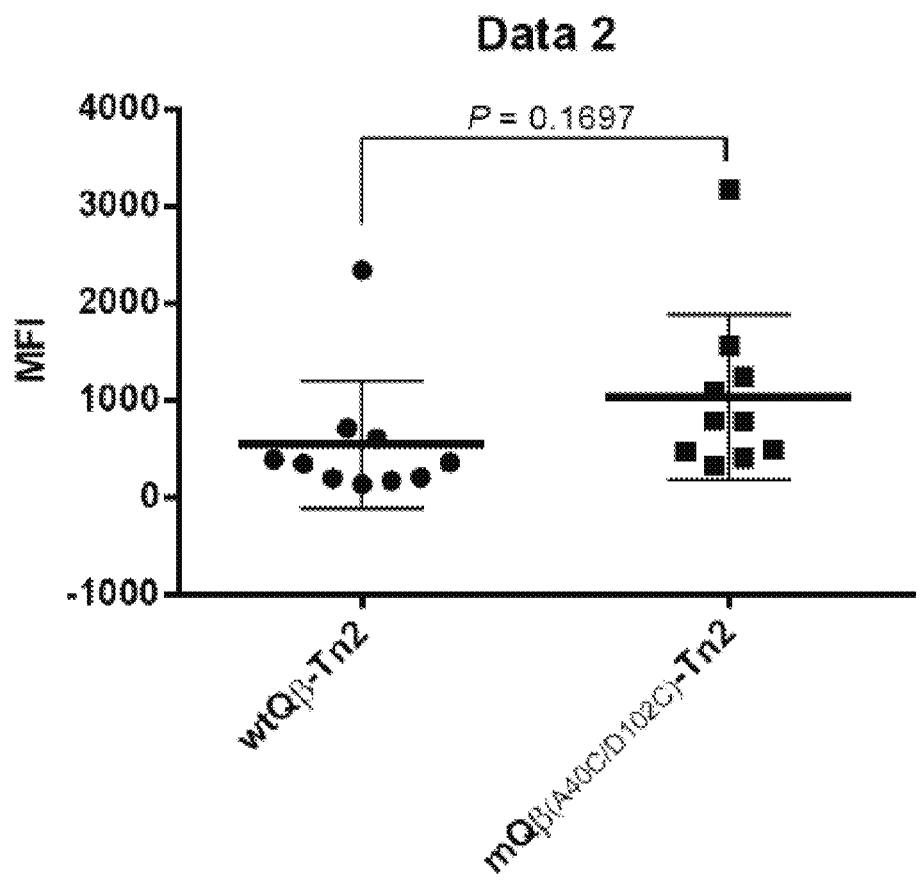
Figure 17A:
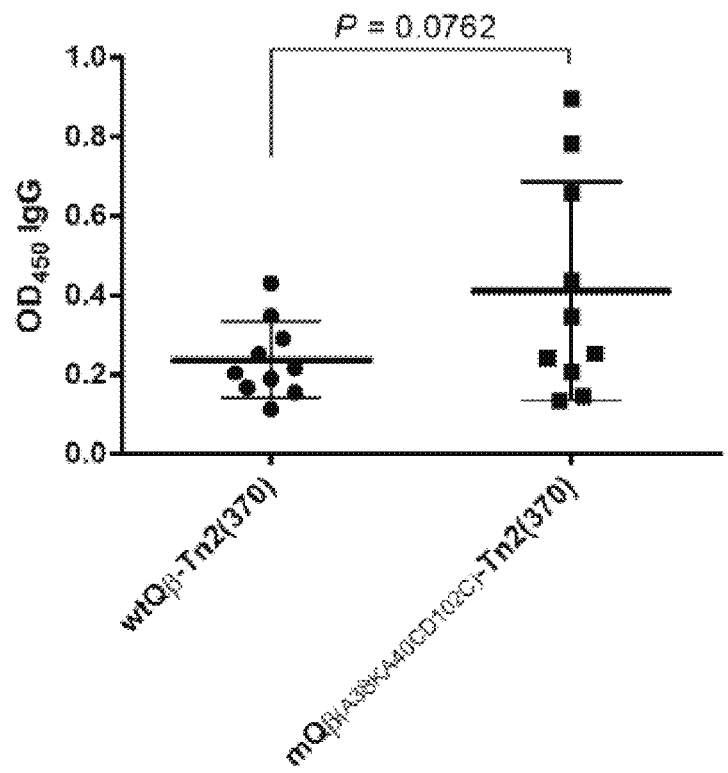
FIGS. 17A and 17B show flow cytometry showing binding of elicited IgG antibodies by wtQβ-Tn2 and mQβ (A38K/A40C/D102C)-Tn2.
Figure 17B:
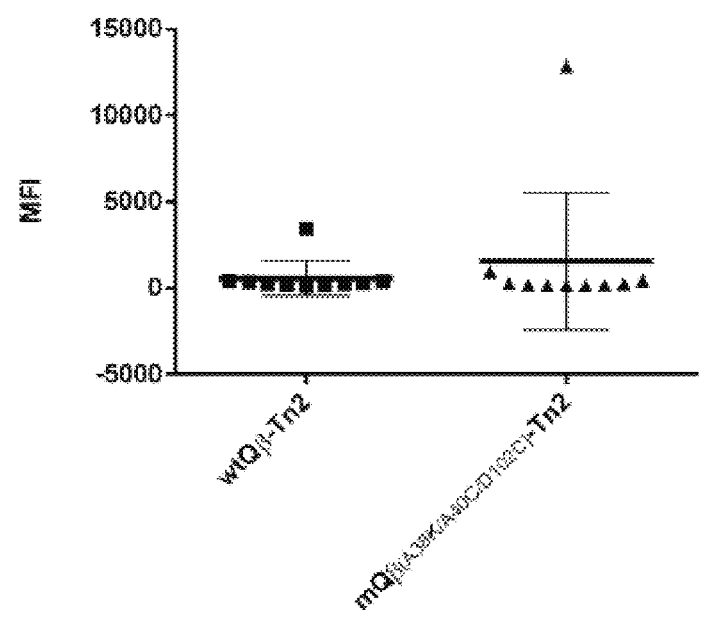

D102C)-Tn2 induced anti-Tn antibodies that bind tumor cells with higher affinity compared with sera from mice immunized with mQβ(A38K/A40C/D102C)-Tn1, mQβ (A40C/D102C)-Tn1 respectively (FIGS. 16B and 16C). mQb-Tn2 conjugate also generated antibodies trending towards stronger binding with tumor cells than those from wtQb-Tn2 immunized animals, demonstrating the enhancement effect of mQb is not restricted to Tn1.

Example 8: mQb-Tn Conjugate Provided Complete Protection of Mice from Tumor Challenge With the ability to elicit superior anti-Tn antibodies, mQb A40C/D102C was selected as the representative carrier for tumor challenge studies. Murine mammary adenocarcinoma cell TA3Ha is used as a highly aggressive tumor in C57/B16 mice, as only 5,000 tumor cells injected intraperitoneally were sufficient to kill all mice within 14 days due to tumor growth. Mice were immunized with wtQβ, wtQβ-Tn2 and mQβ(A40C/D102C)-Tn2 at equivalent dose of 1.9 μg of Tn respectively. The vaccine constructs were administered on day −36, −22 and −8 before the tumor challenge. On day 0, 5,000 cells of TA3Ha cells were injected into all mice. One day later, a group of wtQβ-Tn2 and a group of mQβ(A40C/D102C)-Tn2 immunized mice received cyclophosphamide (CP) at a dose of 50 mg/kg, which is a clinically applied therapeutics for breast cancer treatment.

Figure 18:
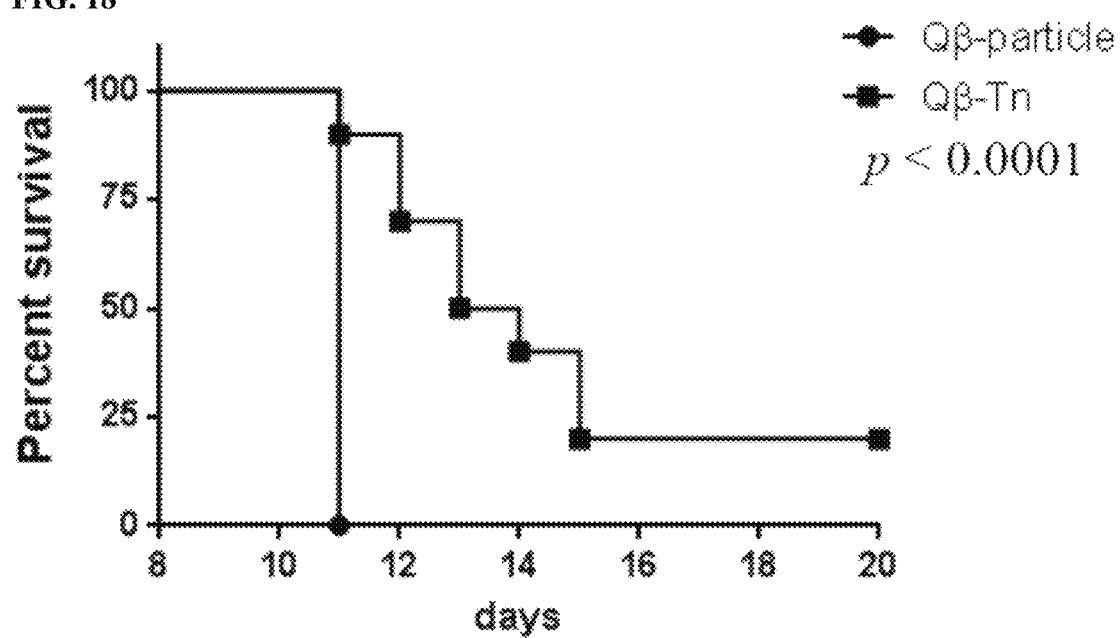
FIG. 18 shows Kaplan-Meier survival curves comparing the protective effect of wtQβ-Tn2 vs control group receiving wtQβ.
Figure 19A:
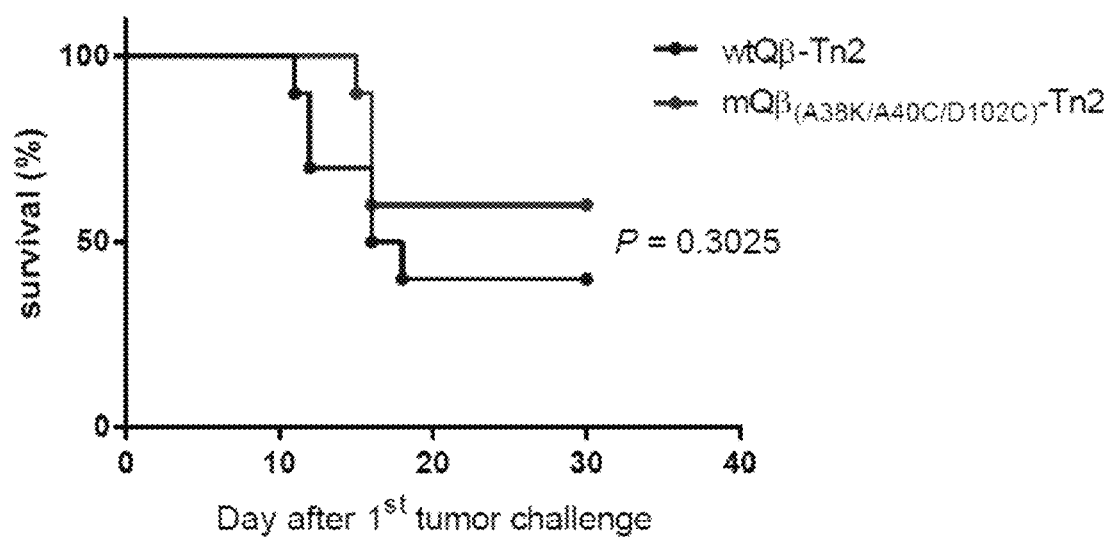
FIGS. 19A and 19B show Kaplan-Meier survival curves comparing the protective effect of wtQβ-Tn2 and mQβ (A38K/A40C/D102C)-Tn2.
Figure 19B:
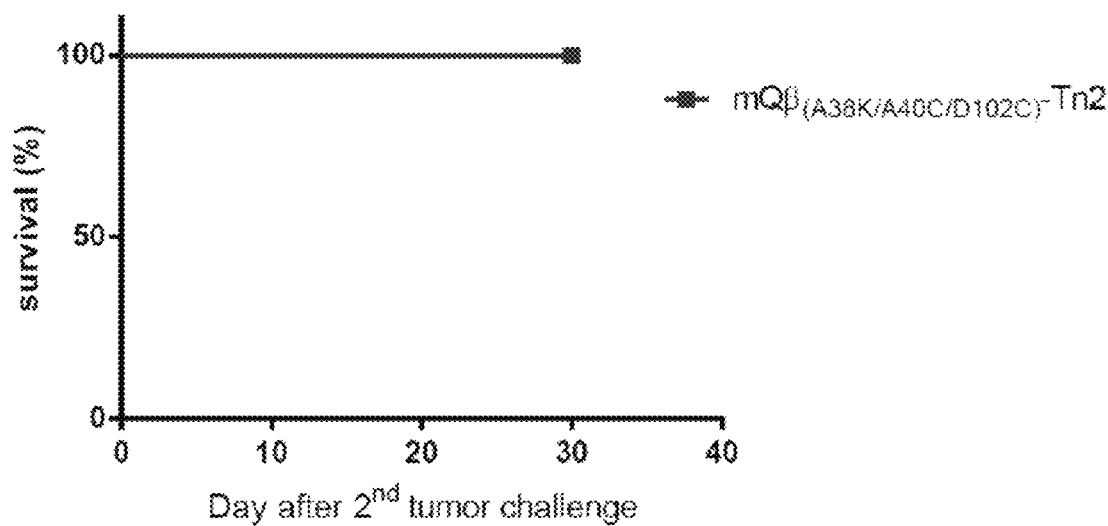
Figure 20:
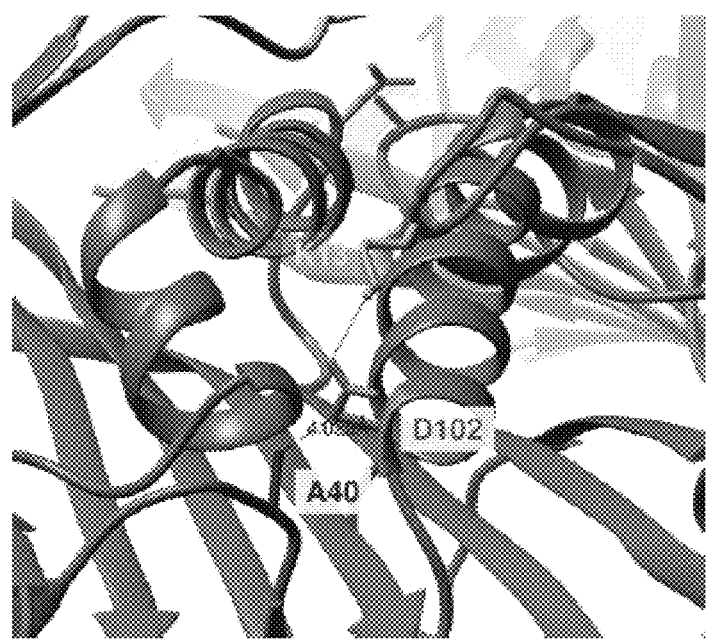
FIG. 20 depicts the X-ray crystal structure of Q3 showing the H-bond interaction between the carboxyl group on the side chain of D102 and the amino group on the side chain of K13

The survival of all mice was monitored. Mice immunized with wtQb suffered 100% mortality by day 11. Vaccination with wtQb-Tn protected 20% of mice from tumor challenge. The combination of CP with wtQb-Tn immunization improved the rate of survival to 40%. Excitingly, mice immunized with Qb (A40C/D102C)-Tn combined with CP were completely protected from tumor development with 100% survival and none of the mice exhibited any signs of tumor growth 30 days after tumor inoculation. (FIG. 18). Furthermore, 30 days after the first tumor challenge, mice in the Qb (A40C/D102C)-Tn group were re-challenged with 5,000 TA3Ha cells. Without any further vaccination or CP treatment, all mice survived the second tumor challenge with no tumor recurrence. (FIGS. 19A and 19B).

DISCUSSION

Multiple clinical studies have shown that cancer patient sera prognosis can be correlated with the levels of anti-TACA antibody generated following vaccination with a TACA construct. VLP Qb has shown great promises as TACA carriers by greatly enhancing anti-TACA antibody responses. There are several potential reasons for the superiority of Qb: 1) Qb has a highly organized 3D structure, capable of ordered display of carbohydrate antigens, leading to potent activation of glycan specific B cells; 2) Qb can activate helper T cells, boosting B cell responses. As shown in FIG. 18, 19A, 19B, the conjugate of wtQb and Tn can provide protection to 40% of the mice in combination with CP treatment, while mice without treatment or receiving CP alone had much lower survival rates. To provide better tumor protection efficiency, higher levels of anti-TACA antibodies are needed, which have been achieved through engineering of the carrier Qb.

While pre-existing immunity against carriers may enhance or suppress humoral responses against the conjugated hapten (Pobre et al. *Vaccine* 2014, 32, 1423) it has been reported that mice pre-immunized with Qb, thus having high titers of pre-existing anti-Qb IgG antibodies, produced much less anti-peptide antibodies upon immunization with the Qb-peptide conjugate. Our experience is consistent with this observation. A Qb-Tn construct containing antigenic triazoles gave much lower titers of anti-Tn antibodies compared to a similar Qb-Tn construct without triazoles, presumably due to the interference from anti-triazole antibodies. Qb can also generate high titers of anti-carrier antibodies. Kinetics studies showed that anti-Qb antibodies were produced sooner than those against glycans. Thus, anti-Qb antibodies may also interfere with the generation of desired anti-TACA antibodies.

There are multiple possible reasons for suppression of anti-glycan antibodies due to Qb: 1) As anti-Qb antibodies are generated earlier than those against the TACAs, during boost injection, the existing anti-Qb antibodies can bind with the vaccine construct, sterically hindering the recognition of glycan epitopes by glycan specific B cells; 2) anti-Qb antibodies can bind with the vaccine construct, sequestering the construct and reducing the availability of construct to interact with glycan specific B cells; 3) anti-Qb B cells can compete with anti-TACA B cells for limited helper T cells for T cell stimulation. Thus, reducing anti-Qb antibodies may enable the immune system to focus on the desired TACA glycan, thus enhancing anti-glycan responses.

Experimental identification of B cell epitopes can be challenging, especially when the epitopes are mainly conformational, not residing within a linear sequence as in the case of Qb. One major advantage of Qb compared to amorphous proteins such as KLH is that the crystal structure of Qb has been obtained in high resolution. This provides extremely valuable guidance for mutant design to reduce anti-carrier antibody responses. From structure based analysis, residues with high solvent exposure and potential to be B cell epitopes have been identified, which serve as targets for mutations to disrupt the inherent B cell epitopes. In addition, sites have been identified for introduction of cross-subunit disulfide bonds and to avoid disruption of capsid assembly. As a result, many Qb mutants designed have been expressed and form nanoparticle capsids in good yields in *E. coli*.

Upon conjugation with of Tn, multiple mQb including A38K, A40C/D102C and A38K/A40C/D102C are found to be superior in eliciting anti-Tn IgG antibodies than wtQb, with the highest mean anti-Tn titers reaching 30,000,000, five times higher than that by wtQb-Tn. Furthermore, sera from mice immunized with Tn conjugates with Qb mutants such as A38K and A40C/D102C were capable of stronger binding with both human and mouse cancer cells as compared to those from wtQb-Tn. This suggests the antibodies can recognize Tn in its native environment, i.e., on the surface of tumor cells, which bodes well as anti-cancer vaccines.

There can be multiple factors combined contributing to higher titers of anti-Tn IgG antibodies and lower anti-capsid antibodies induced by some of the mutants. Mutations such as A38K can directly remove the potential B cell epitopes of wtQb as A38 resides in a region predicted to be recognized by B cells. This is supported by the reduced abilities of mQb to compete with immobilized wtQb for binding anti-wtQb polyclonal antibodies (FIG. 13). Another factor is the enhanced thermal stability of mQbs containing A40C and D102C mutations. As new disulfide bonds are introduced into these capsids, these mutants are more stable compared to the corresponding ones without the mutations. Higher stability of the vaccine construct may increase the half-life of the vaccine in vivo, prolonging the stimulation of the immune system.

It is interesting to note that although mQb A40C/D102C does not contain an additional lysine vs wtQb, the average number of Tn that can be introduced into this mutant (436 copies of Tn) is much higher than that on wtQb (332 Tn), which corresponds to on average 0.6 more Tn molecule per monomeric coat protein on the mutant (there are 180 monomers for each capsid).

Crystal structure of wtQb showed that there are three lysines on the external surface of Qb (K2, K13 and K16) and the N-terminus available for amide formation. K2 residues are clustered tightly around the 3-fold symmetry axis, thus presumably less likely to react due to steric hindrance. The side chain carboxylic acid of D102 is close to the F-amino group of K13 (~4 Å). As a result, K13 can engage in ionic or hydrogen bonding with D102, thus would have lower reactivity towards amide formation with Tn1 and remain mostly unfunctionalized in wtQb-Tn conjugate. This is consistent with the observation that K13R mutant of Qb did not have lower number of conjugated molecules upon treatment with a NHS ester of fluorescein compared with wtQb. (Brown, S. D. Bacteriophage Qβ: A Versatile Platform for Nanoengineering The Scripps Research Institute, La Jolla, 2010 PhD thesis). When D102 was mutated to cysteine presumably leading to less interaction with K13, the amino group in the side chain of K13 can become available to react with NHS-Tn1. To confirm the derivatization of K13, triple mutant K13R/A40C/D102C was prepared and the capsid was treated under the identical reaction condition with NHS-Tn1. The number of Tn conjugated to the triple mutant K13R/A40C/D102C dropped to 328, close to the level on wtQb. K13 is located in a flexible and highly exposed loop with a high potential to be B cell epitopes. Conformational changes in this region can possibly reduce B cell recognition. In addition, functionalization of K13 by Tn can possibly block the binding of the epitope by anti-Qb antibodies, and further reduce anti-carrier antibody responses.

Another possible factor influencing anti-Tn antibodies is the number of Tn per capsid. We previously reported Qbs with low (78 Tn) and medium (150 Tn) density of Tn were much less efficient in inducing anti-Tn antibodies than that with high Tn (340 Tn) density. At the high loading level (>300), the number of Tn per capsid did not seem to play a critical role in determining anti-Tn antibody titers, as T75K mutant has a higher average number (447 Tn) of Tn1/capsid but induces lower titers of anti-Tn1 antibodies than A117K-Tn (390 Tn). Bachmann and coworker also showed that while increasing the number of copies of a peptide antigen per capsid from 13 to 94 significantly enhanced levels of anti-peptide antibodies, the titers of antibodies leveled out once the copy number was more than 142. (Jegerlehner, A et al. *Vaccine* 2010, 28 (33), 5503-5512)).

The efficacy of mQb A40C/D102C-Tn construct in protecting mice from tumor development was tested in TA3Ha tumor model, a highly aggressive tumor. Without any treatment, all mice died from tumor 11 days after inoculation of just 5,000 tumor cells. CP or wtQb-Tn vaccination alone was not very effective in tumor protection with 20% and 12.5% survival rates respectively. Combining CP and wtQb-Tn significantly enhanced the survival to 40%. While CP does not directly kill tumor cells at the dose administered (Hubert, P et al. (2011) *Cancer Res.* 71, 5134-5143), it can help boost the activities of natural killer cells, a type of effector cells that can kill tumor cells bound by antibodies. 45 Compared to wtQb-Tn, mQb-Tn was much more effective, which provided complete protection of mice from TA3Ha tumor when combined with CP. Furthermore, all vaccinated mice survived a second tumor challenge without any additional treatments, suggesting long term immunity was generated through vaccination.

Tn is an attractive target for the development of anti-cancer vaccines. Due to its weak immunogenecities, it has been challenging to elicit high titers of anti-Tn IgG antibodies, especially for the monomeric form of Tn. KLH conjugate with Tn failed to induce significant amounts of anti-Tn antibodies. To overcome this, two general approaches have been taken: 1) modifying the structure of Tn to render it more foreign to the immune system; 2) using dimeric or trimeric Tn as antigen. The power of the Qb platform enables the usage of the monomeric Tn as the antigen. To the best of our knowledge, the mean titers of anti-Tn IgG antibodies induced by mQb-Tn were the highest reported highlighting the power of the Qb platform.

Qb has been utilized as carriers of a range of antigens including nicotine (anti-smoking vaccine), interleukin (anti-inflammation) and amyloid b in multiple clinical trials with excellent safety profiles (Jegerlehner A et al. *Vaccine* 2010, 28, 5503). While we focus TACAs in the current study, the reduced anti-carrier responses associated with mQb suggest the carrier interference will be less a problem for mQb if it is widely used as vaccine carriers. This coupled with the powerful antibody potentiation abilities renders mQb a highly attractive platform for subunit based vaccine development.

Example 9: Rational Design of MUC1 Based Anti-Cancer Vaccines

Figure 29:
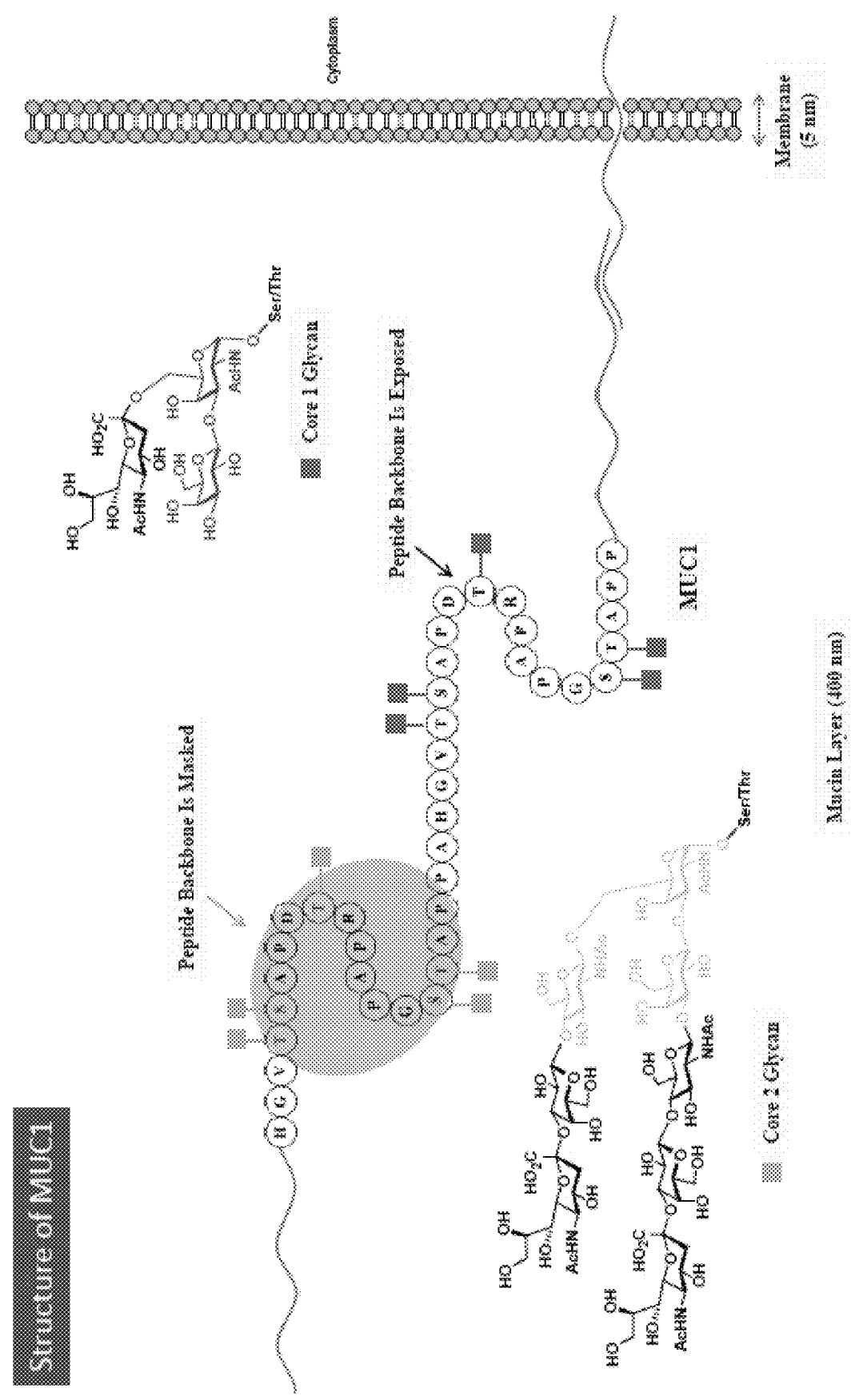
FIG. 29 shows the structure of MUC1. Figure discloses "HGVTSAPDTRPAPG" and "AHGVTSAPDTRPAPG-STAPP" as SEQ ID NOS 69 and 70, respectively.

Aberrant glycosylation in MUC1 is a hallmark in many types of cancer. On normal endothelial cells, the major O-glycans on MUC1 are based on core-2 type structures. MUC1 O-glycans on cancer cells are truncated, less branched, with heavily sialylated core-1 glycans as dominant structures, which render peptide backbone accessible for immune recognition. (FIG. 29)

Due to its importance, MUC1 was ranked as one of the top cancer vaccine targets by the NCI Translational Research Working Group.

Several MUC1 conjugate vaccines (MUC1-mannan or MUC1-KLH) have been evaluated in clinical trials. Significant antibodies have been induced but failed to recognize breast cancer cells, which is completely different from preclinical studies in wild type mice.

In order to develop MUC1 based anti-cancer vaccines, we have explored virus-like particles as powerful carriers to deliver MUC1 glycopeptides.

Figure 30:
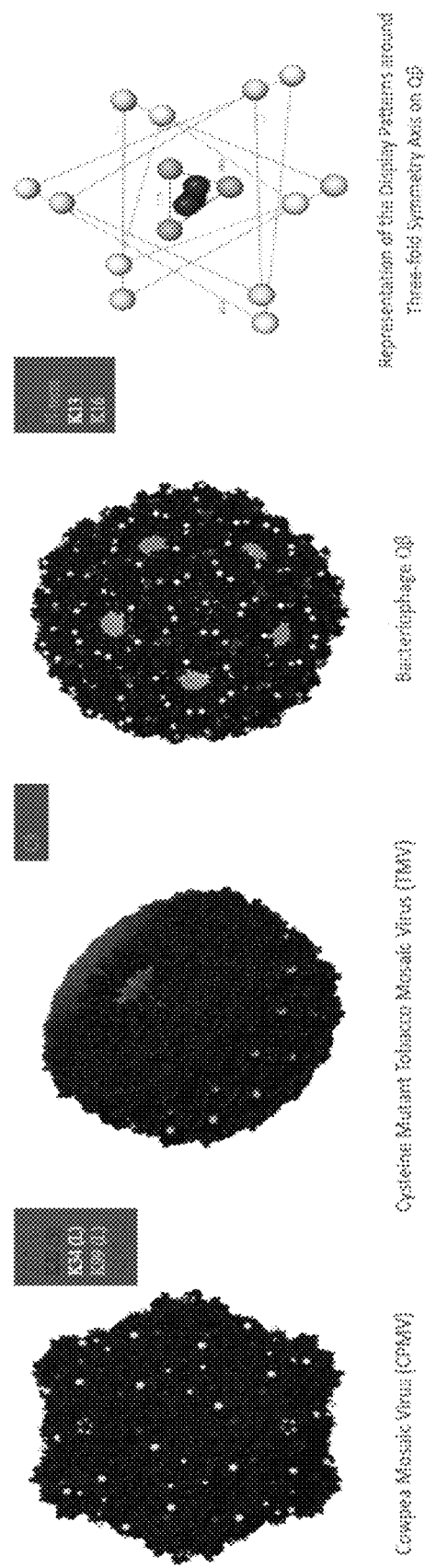
FIG. 30 shows the structures of virus-like particles and their available conjugation site.
Figure 31:
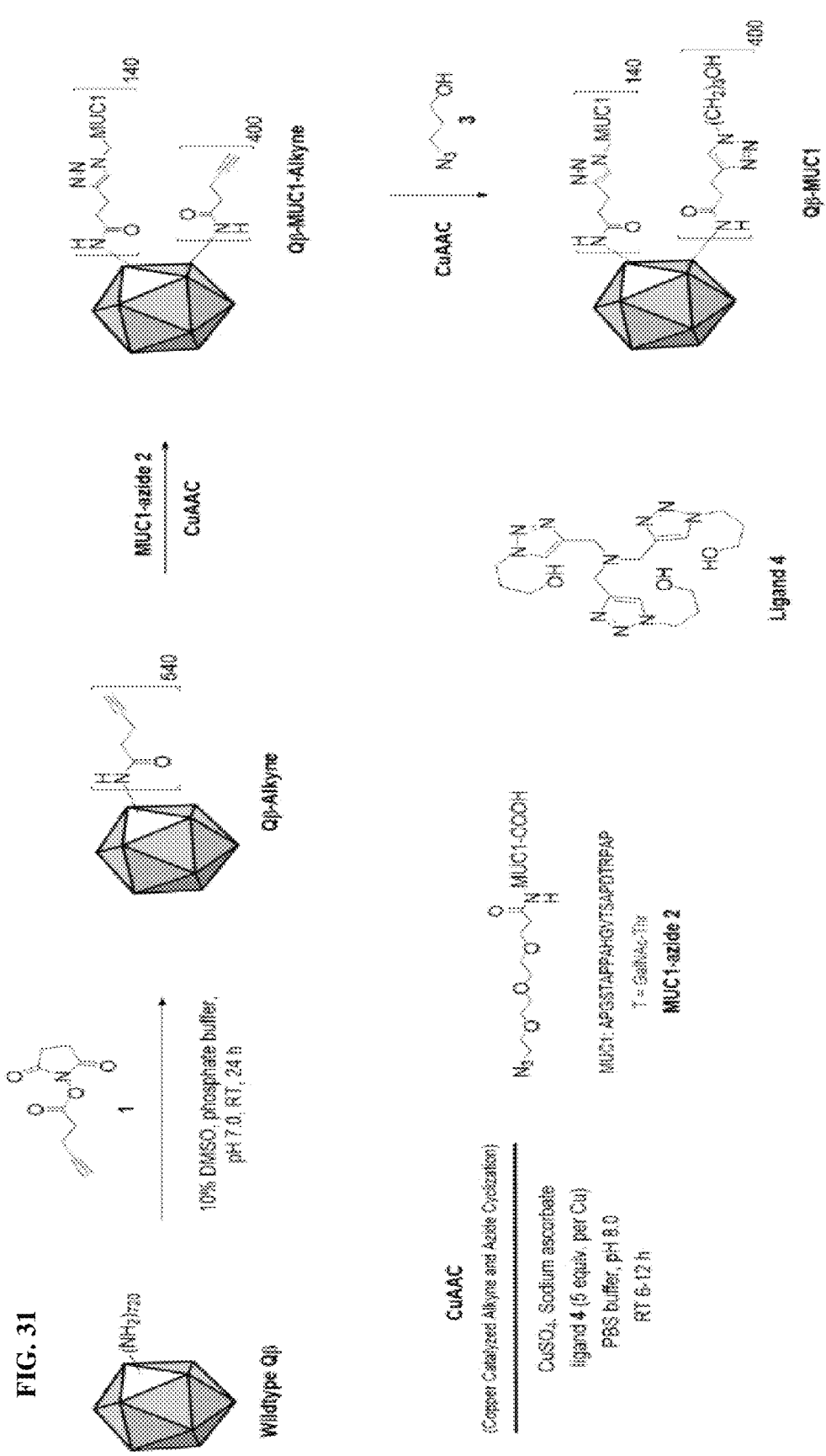
FIG. 31 shows the synthesis of first generation Qβ-MUC1 conjugates. Figure discloses SEQ ID NO: 71.

Virus-like particles have many potential advantages over traditional protein carriers, including homogenous and well-defined structures, possibility for organized high-density display of carbohydrate antigens, as well as stability towards a wide range of reaction conditions. Among several virus-like particles we have tested, bacteriophage Qβ is superior for eliciting anti-TACA IgG response. In addition, bacteriophage Qβ has been shown to be well tolerated in clinical studies. (FIG. 30). A scheme for the synthesis of Qβ-MUC1 conjugates is depicted in FIG. 31.

Figure 32:
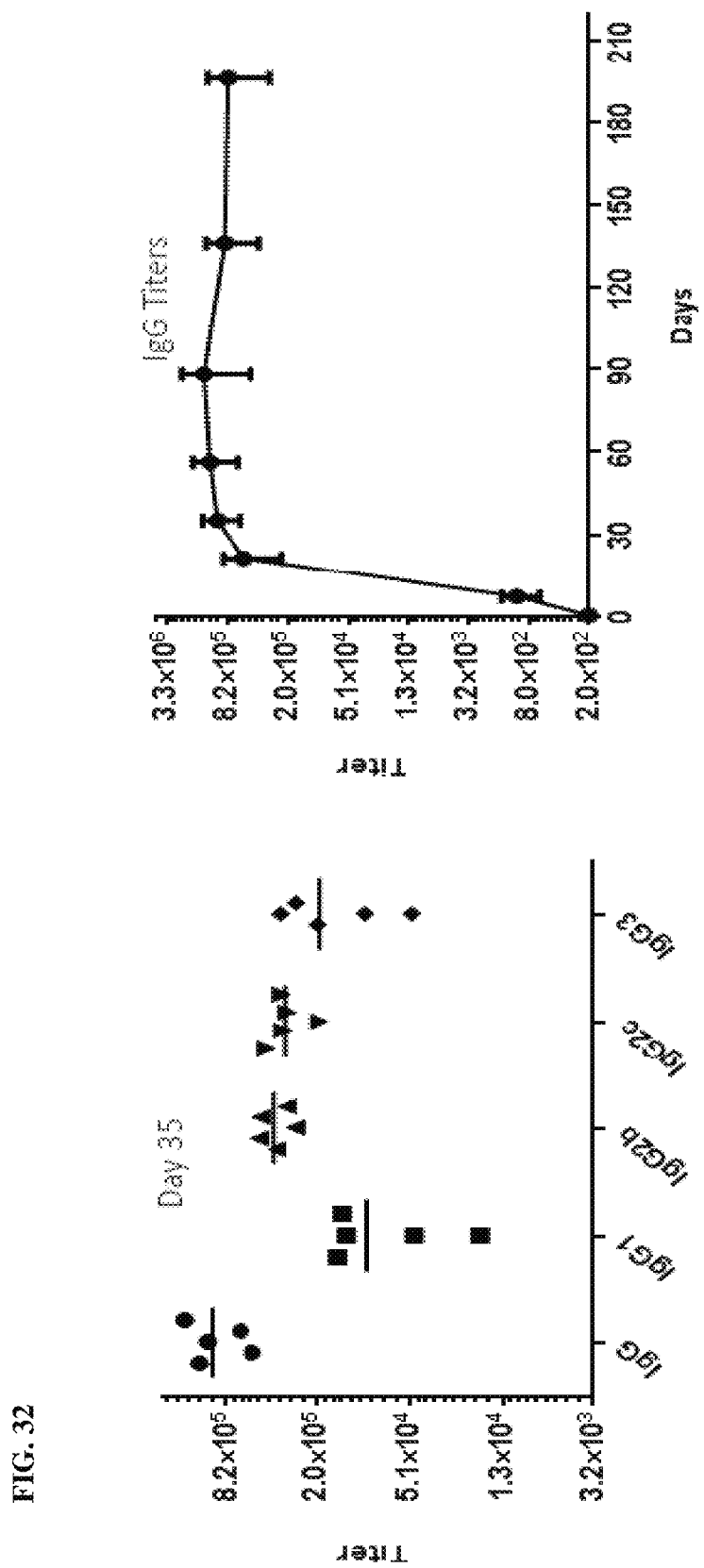
FIG. 32 shows that Qβ-MUC1 induced super high titers of IgG antibodies in WT Mice.

Immunization was performed in wild type (WT) C57B16 mice with Freund's adjuvant. Mice were vaccinated with Qβ-MUC1 three times two weeks apart. Super high titers and long lasting anti-MUC1 IgG antibody responses were obtained. (FIG. 32).

Figure 33A:
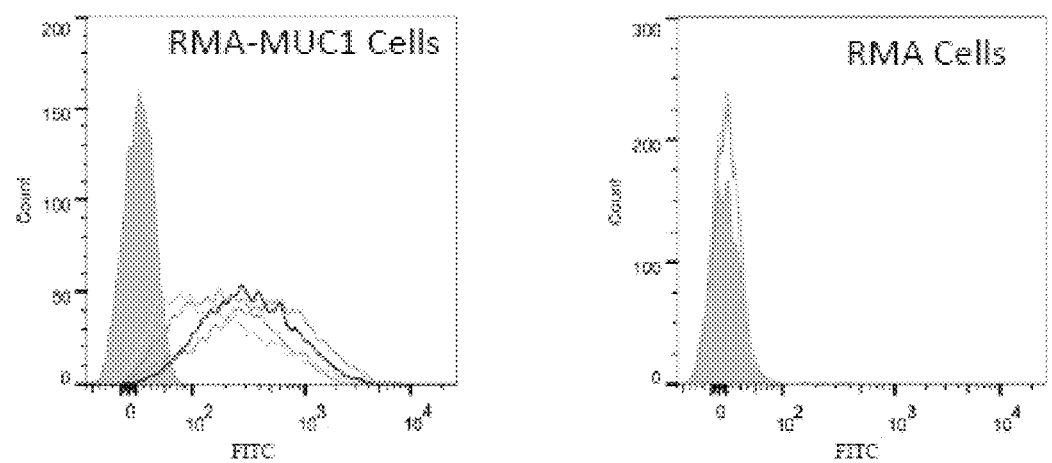
FIG. 33 shows vaccination of WT Mice with Qβ-MUC1 led to antibodies capable of binding MUC1 expressing tumor cells strongly as well as MUC1 specific cytotoxic T cell responses.
Figure 33B:
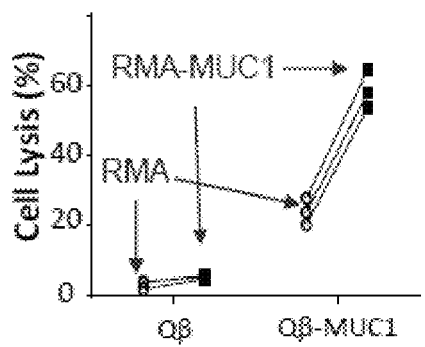
Figure 33B:
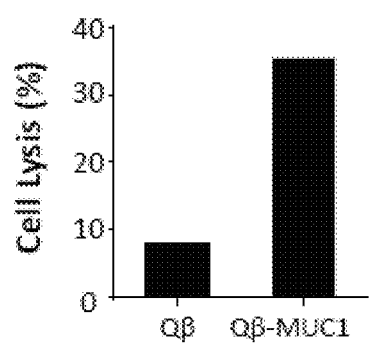

Vaccination of WT mice with Qβ-MUC1 led to antibodies capable of binding MUC1 expressing tumor cells strongly as well as MUC1 specific cytotoxic T cell responses. FIG. 33A shows binding of post-immune sera with tumor cells (1:50 dilution). The grey filled curve (sera from Qb immunized WT mice) and the colored curves (sera from Qb-MUC1 immunized WT mice). Strong binding to MUC1 expressing RMA-MUC1 cells was observed by sera from Qb-MUC1 immunized WT mice. Weak binding to RMA cells suggests the binding was MUC1 dependent. FIG. 33B shows cytotoxic T cell (CTL) assays. Mice immunized with Qβ-MUC1 exhibited significantly higher lytic abilities towards MUC1 expressing cells in vitro and in vivo.

Figure 34:
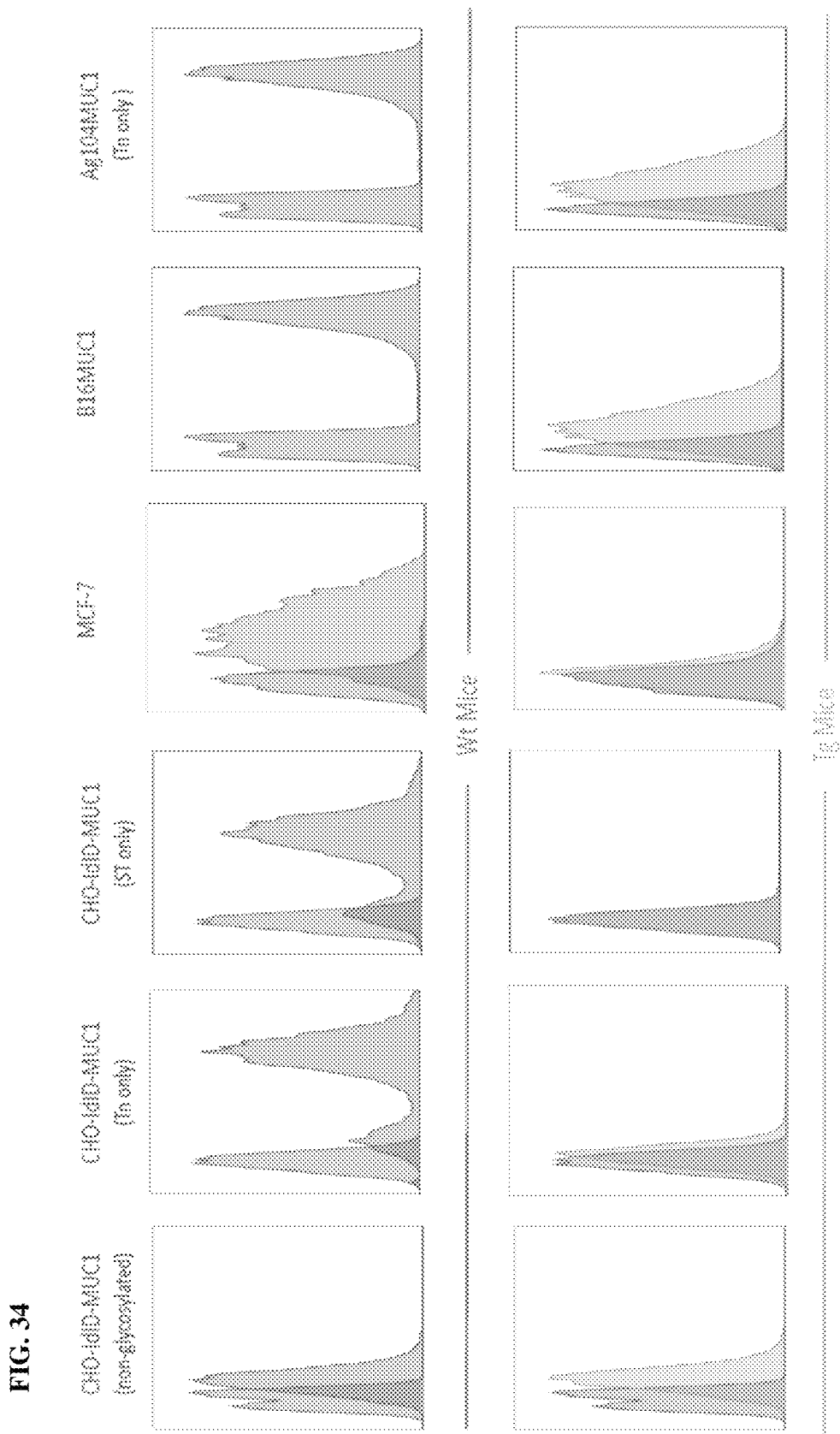
FIG. 34 shows first generation Qβ-MUC1 vaccine in tolerant human MUC1 transgenic (Tg) mice failed to elicit antibodies for strong binding with MUC1 expressing tumor cells.

First generation Qb-MUC1 vaccine in tolerant human MUC1 transgenic (Tg) mice failed to elicit antibodies for strong binding with MUC1 expressing tumor cells. (FIG. 34) Human MUC1 Tg mice mimic the immune tolerant environment towards MUC1 encountered in humans. While high anti-MUC1 IgG antibodies were elicited in Tg mice, the antibodies bound much weaker with MUC1 expressing tumor cells vs those from WT mice.

Figure 35:
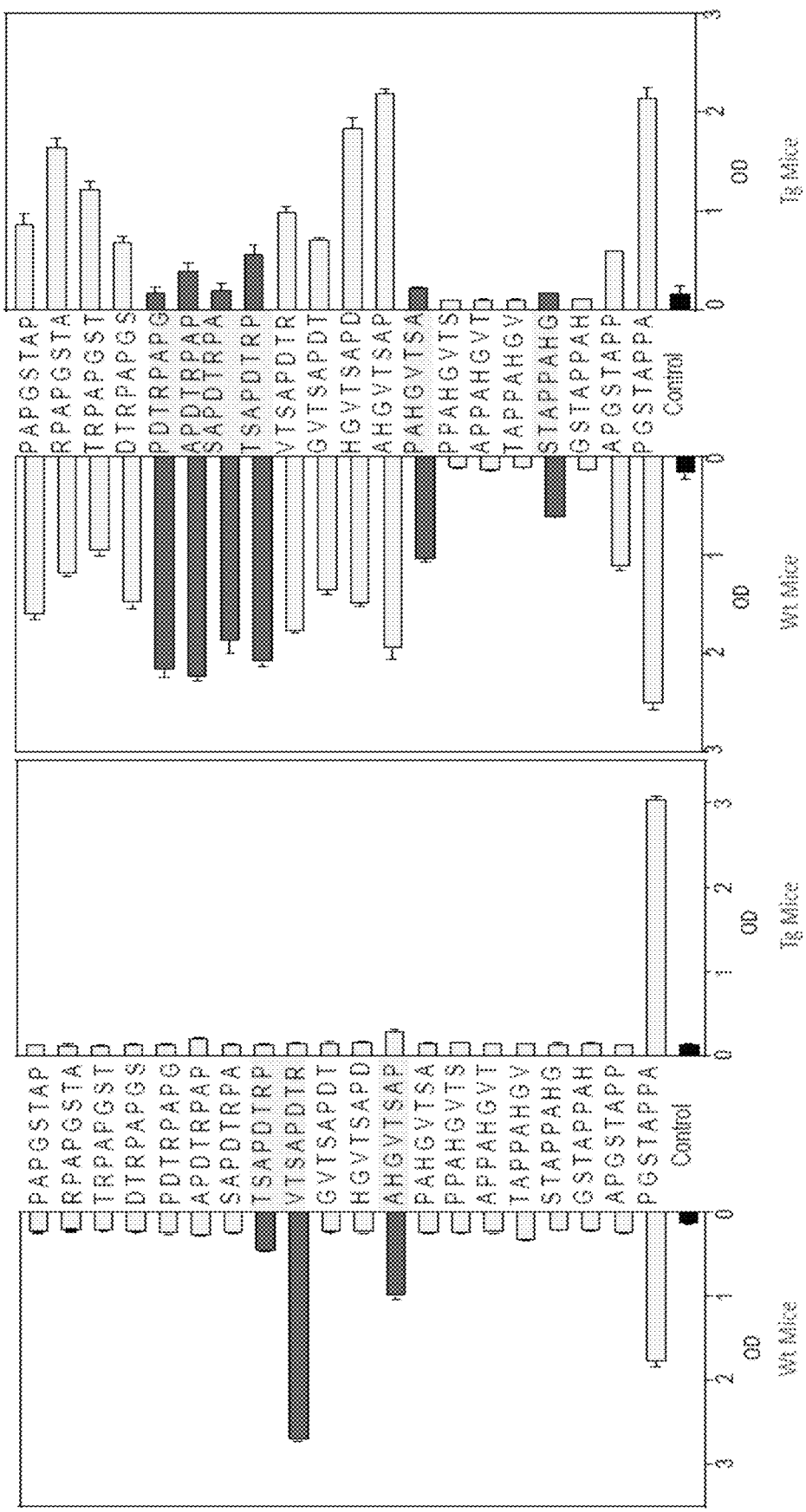
FIG. 35 shows analysis of epitope mapping. Figure discloses the Immunogen Sequence as SEQ ID NO: 72 and both columns of Mapping sequences as SEQ ID NOS 73-78, 58, 79-81, 54, 82-88, 57, and 55, all respectively, in order of appearance.

Epitope mapping showed that little antibody responses were generated against epitopes in TSAPDTRPAPG region (SEQ ID NO: 52) by Tg mice. (FIG. 35). The results also suggested that antibodies against epitopes out of TSAPDTRPAPG region (SEQ ID NO: 52) do not contribute much to tumor cells recognition.

Figure 36:
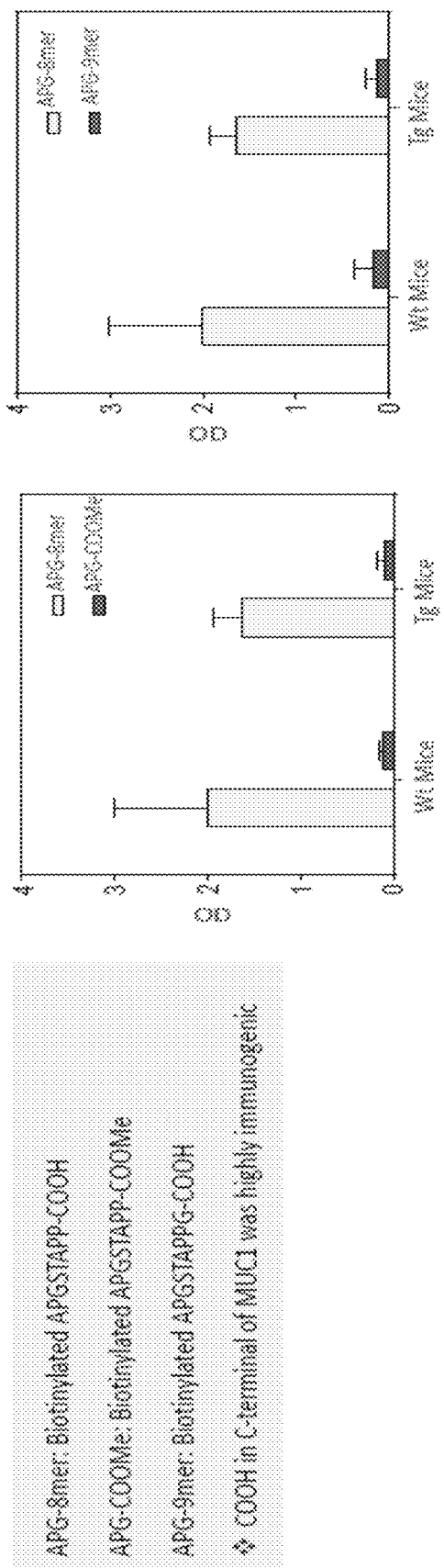
FIG. 36 shows that the C-terminal free carboxylic acid is involved in antibody binding. Figure discloses SEQ ID NOS 89-91, respectively, in order of appearance.
Figure 37:
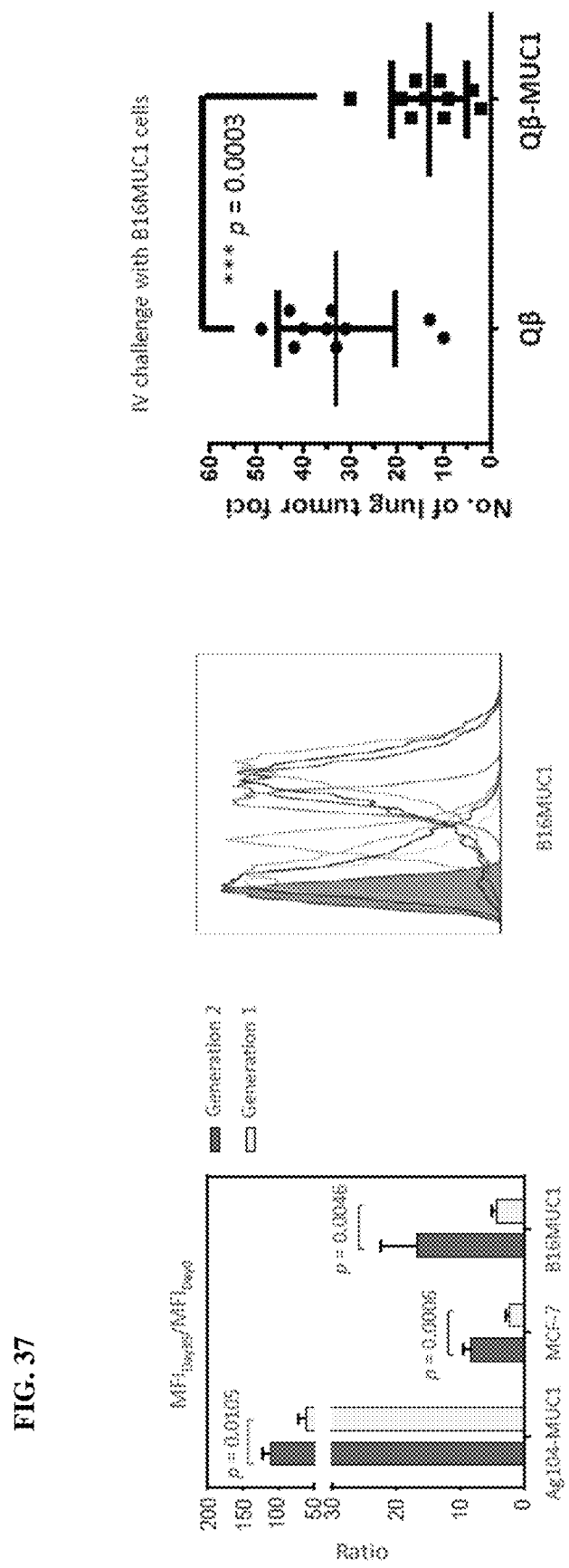
FIG. 37 shows a redesign of the Qβ-MUC1.
Figure 38:
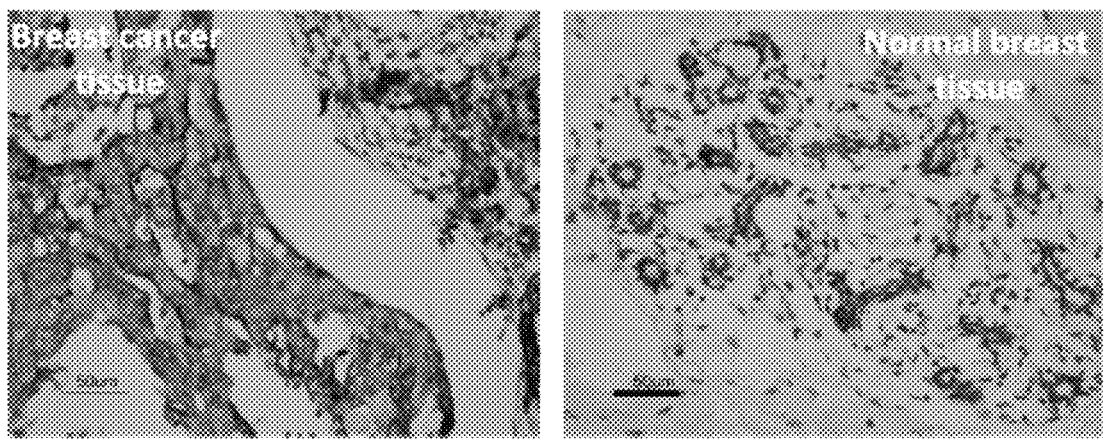
FIG. 38 shows that sera from MUC1.Tg mice immunized with second generation Qβ-MUC1 exhibited a) strong binding to human breast cancer tissues on a tissue microarray while having little reaction with b) normal breast tissues (1:1000 serum dilution). The images were representative out of 30 samples. The brown color in a) was due to antibody binding to tissues. The lack of brown staining in b) indicates little binding of antibodies to normal tissues. Scale bar is 50 μm.
Figure 39:
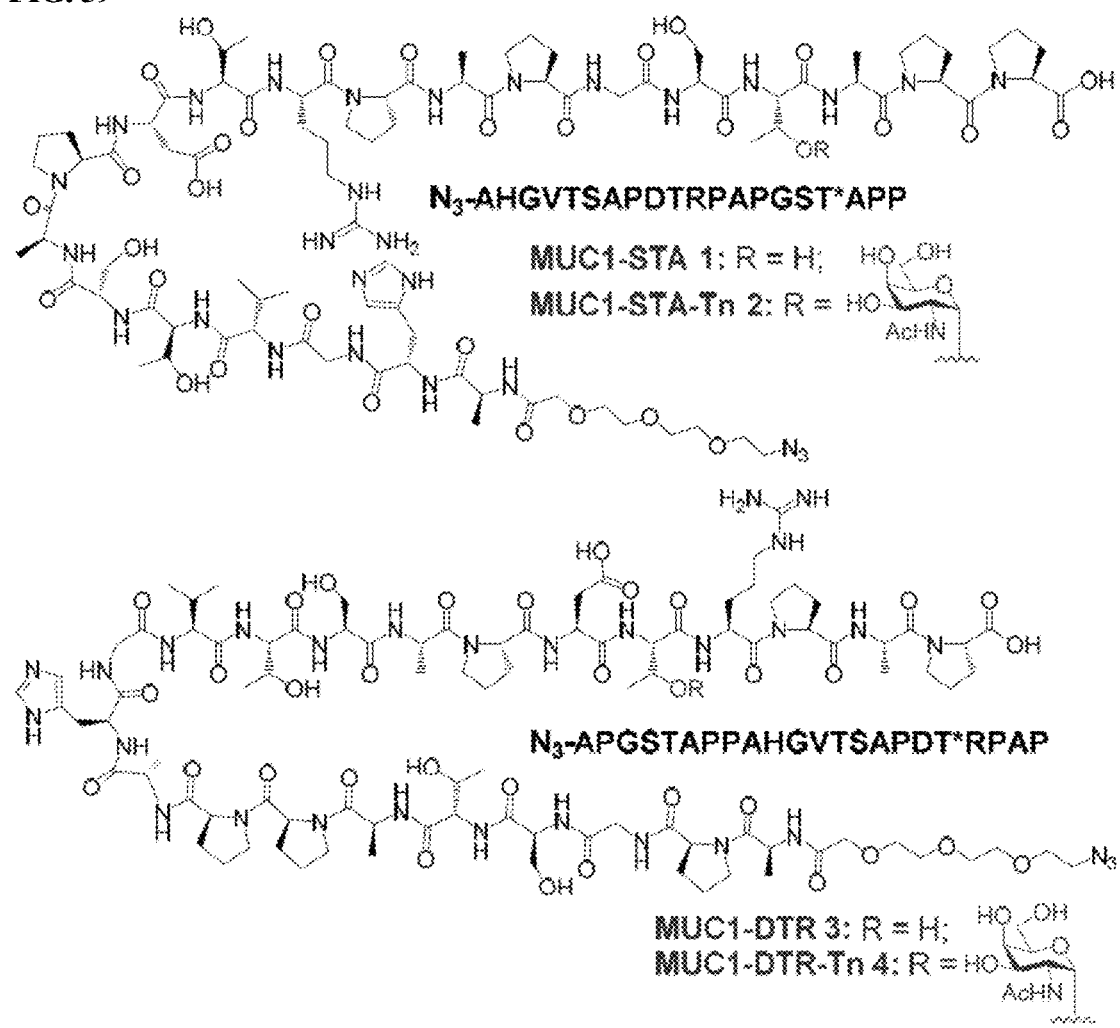
FIG. 39 depicts certain MUC1 (glycol)peptides (1-4). Figure discloses SEQ ID NOS 92 and 93, respectively, in order of appearance.
Figure 40:
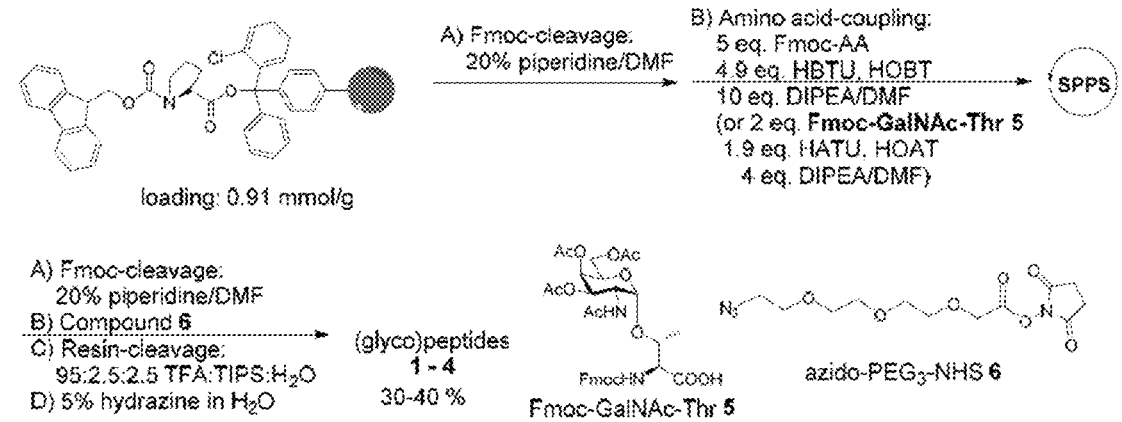
FIG. 40 depicts the solid phase synthesis of MUC1 (glycol)peptides was performed through solid-phase peptide synthesis (SPPS) using Fmoc chemistry (Scheme 1).
Figure 41:
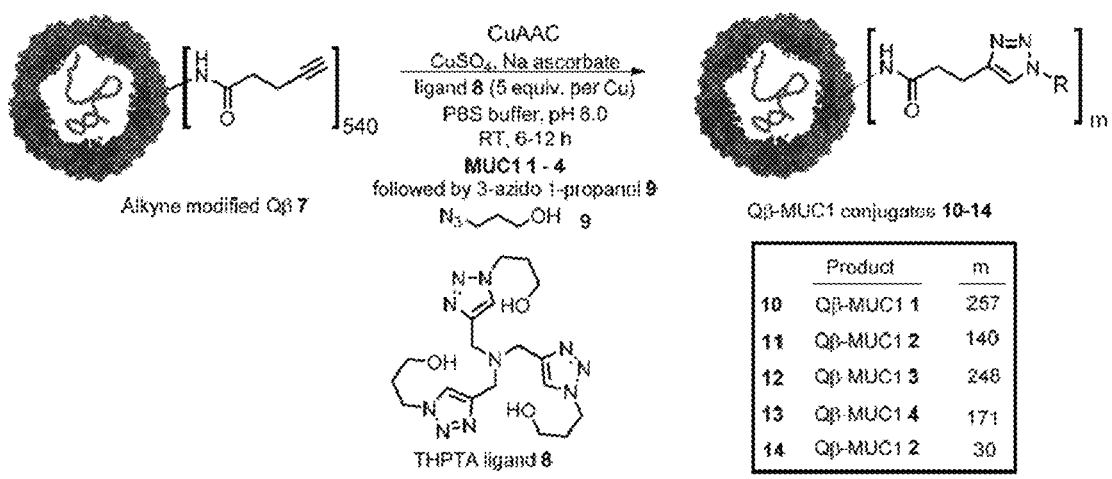
FIG. 41 depicts synthesis of Qβ-MUC1 conjugates (Scheme 2).

A second generation vaccine conjugate C-terminal of immunogen to virus-like particle and shorten MUC1 peptide was developed. (FIG. 36). Sera from MUC1.Tg mice immunized with second generation Qβ-MUC1 exhibited a) strong binding to human breast cancer tissues on a tissue microarray while having little reaction with b) normal breast tissues. (FIGS. 37 and 38).

With the help of epitope mapping to compare antibodies from WT mice and MUC1 Tg mice, we demonstrated the following. Not all epitopes in MUC1 are equally tolerated in MUC1 Tg mice. Antibody responses against non-TSAPDTRPAPG region (SEQ ID NO: 52) do not contribute much to binding with MUC1 on tumor cells. Antibody responses against TSAPDTRPAPG region (SEQ ID NO: 52) greatly improved recognition of various tumor cell lines. Rational MUC1 epitope design has significantly improved the quality of anti-MUC1 immune responses and increased mouse survival from tumor challenge.

Example 10: Materials and Methods for Examples 11-15

General Experimental Procedures and Methods for Synthesis

All chemicals were reagent grade and were used as received from the manufacturer, unless otherwise noted. Centrifugal filter units of 10,000 and 100,000 molecular weight cut-off (MWCO) were purchased from EMD Millipore. For protein liquid chromatography, GE ÄKTA Explorer (Amersham Pharmacia) on a Superose-6 column was used. Microfluidic capillary gel electrophoresis was performed with Bioanalyzer 2100 Protein 80 microfluidics chip (Agilent Technologies). For MALDI-TOF MS analysis, each viral sample (10 μL, 1 mg/mL) was denatured and cleaned using Cleanup C18 Pipette Tips (Agilent Technologies). The mixture (0.6 μL) and matrix solution (0.6 μL, saturated sinapic acid in 50% acetonitrile, 0.1% trifluoroacetic acid) was spotted on a MALDI plate, air-dried, and analyzed by MALDI-TOF mass spectrometry (AB SCIEX Voyager DE Pro MALDI-TOF). Protein concentration was measured using the Coomassie Plus Protein Reagent (Bradford Assay, Pierce) with bovine serum albumin (BSA) as the standard. RMA cells, RMA-MUC1 and MCF-7 cells were kindly provided by Prof. Olivera J. Finn (University of Pittsburgh). B16-MUC1 cells were kindly provided by Prof. Sandra J. Gendler (Mayo Clinic). RMA cells, RMA-MUC1 cells and B16-MUC1 cells were cultured in DMEM supplemented with 10% FBS, 100 U/mL/100 μg/mL Pen/Step, 2 mML-glutamine, 1 mM sodium pyruvate and 0.3 mg/mL G418. MCF-7 cells were cultured in Eagle's minimum essential medium with L-glutamine (2 mM), non-essential amino acids and sodium pyruvate, bovine insulin (10 μg/mL), and FBS (10%), 100 U/mL/100 μg/mL Pen/Step.

Synthesis of MUC1 (Glyco)Peptides

Figure 72:
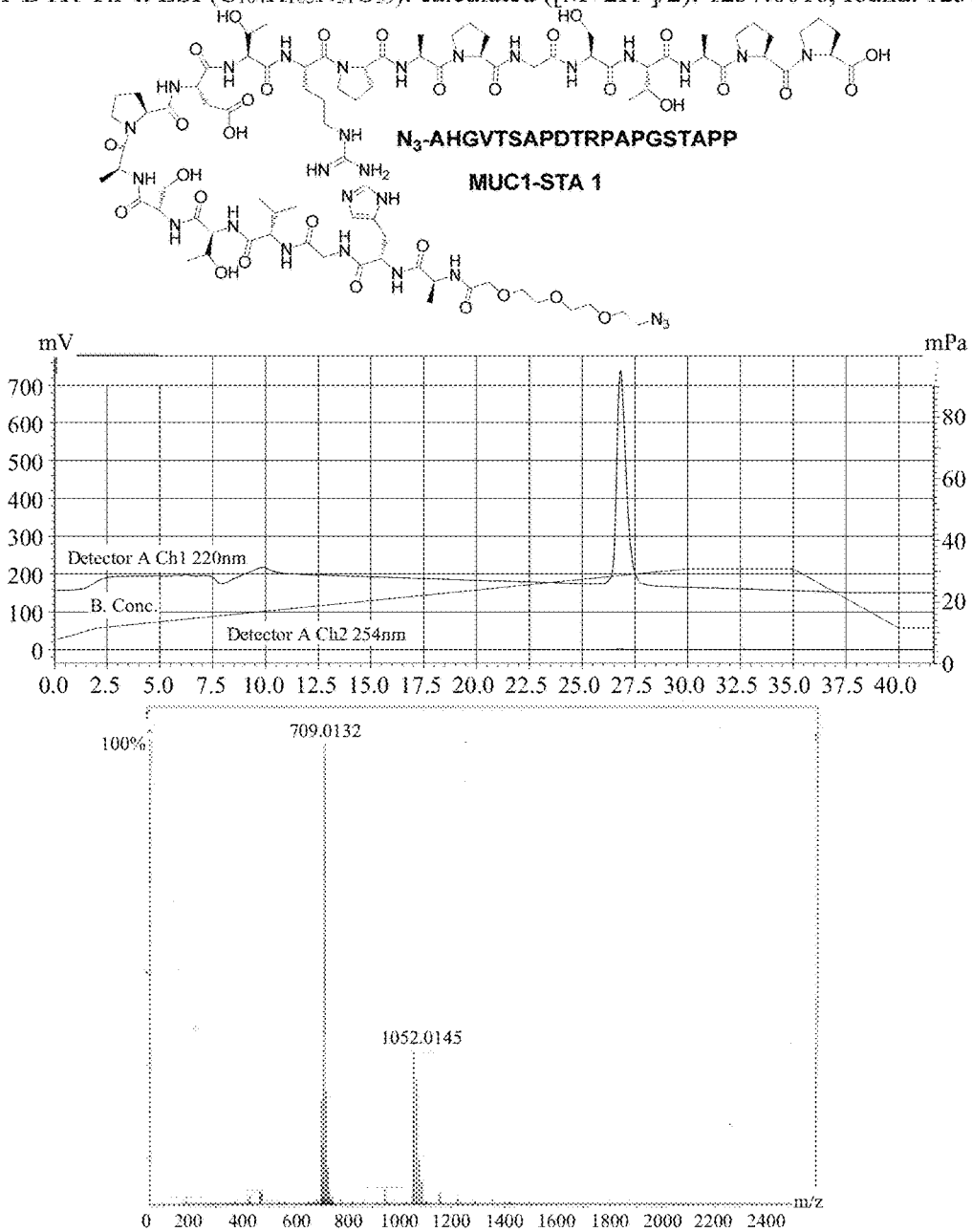
FIG. 72 shows HPLC and HRMS of MUC1 (glyco) peptides 1-4. Figure discloses SEQ ID NOS 96, 175, 98, and 97, respectively, in order of appearance.
Figure 72:
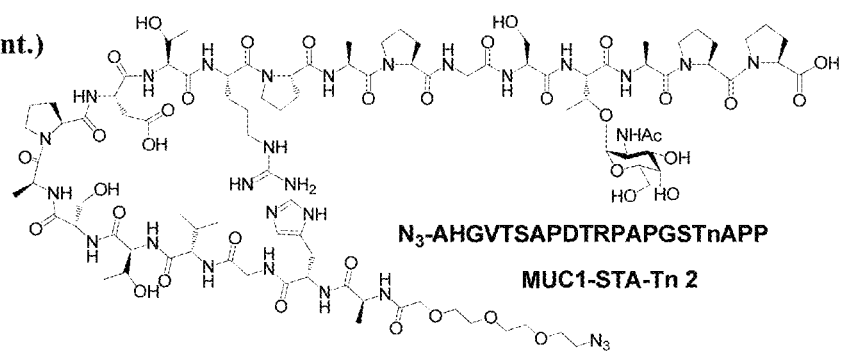
Figure 72:
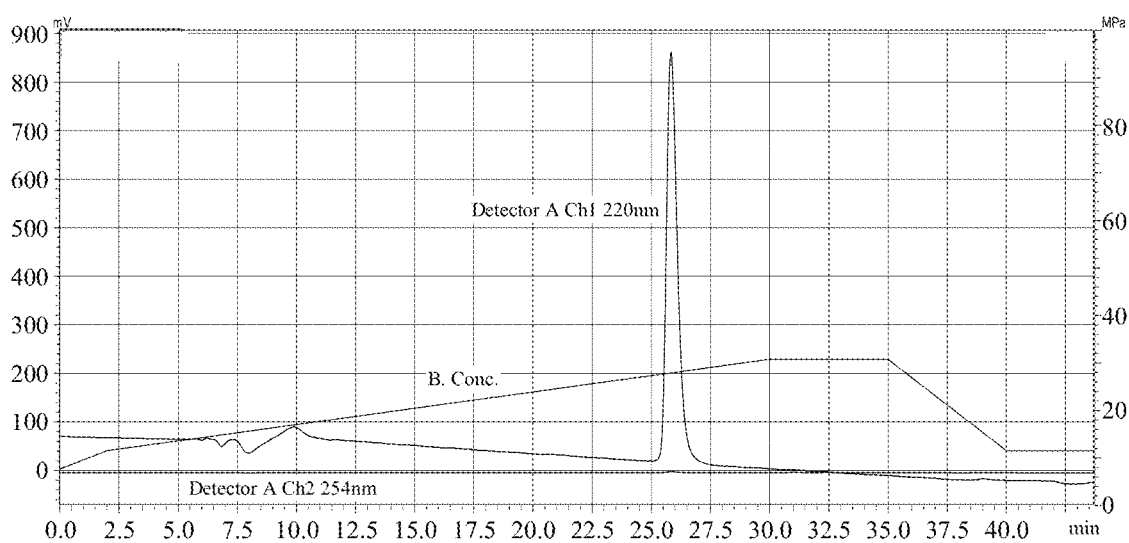
Figure 72:
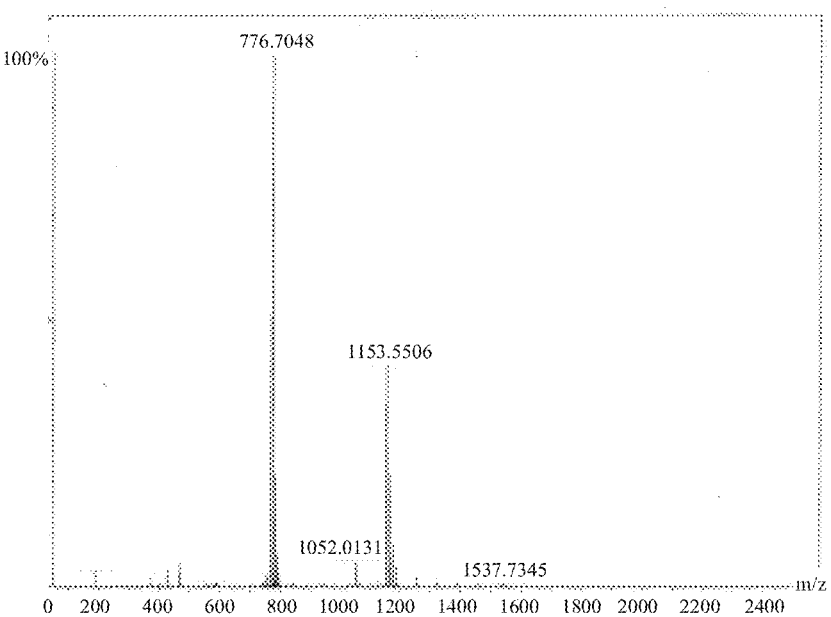
Figure 72:
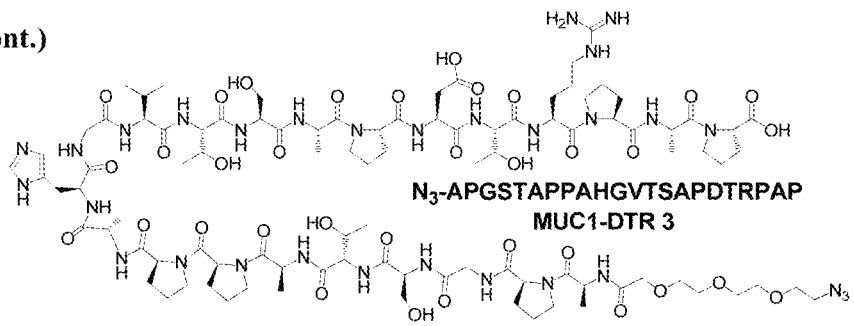
Figure 72:
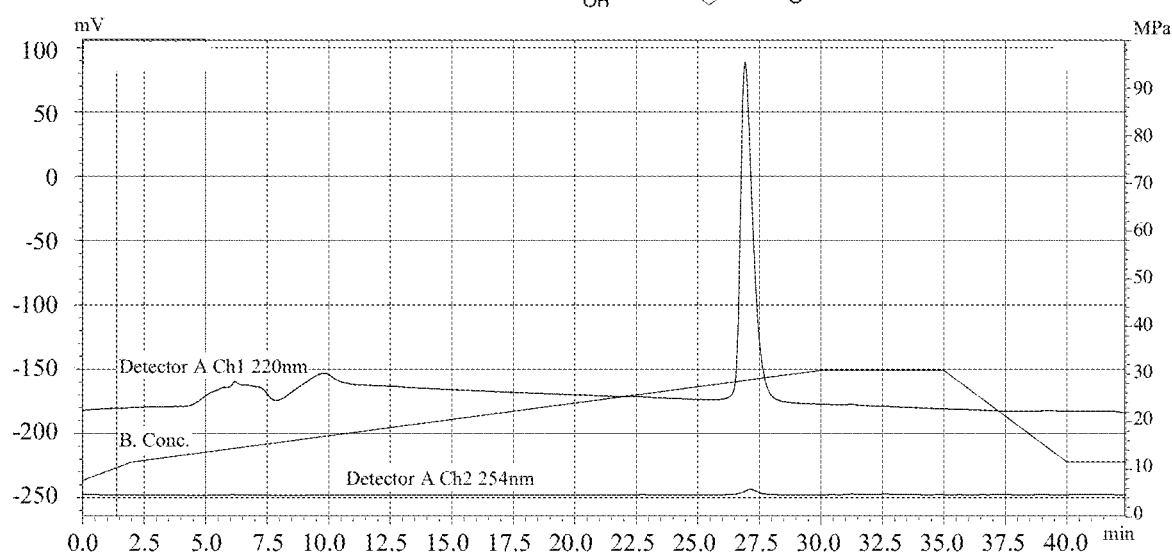
Figure 72:
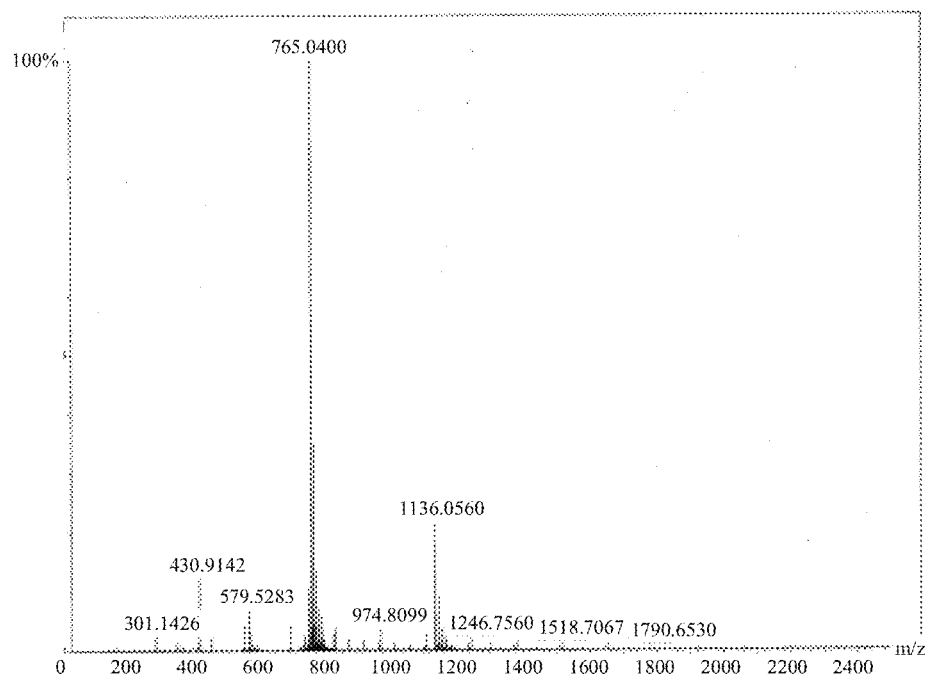
Figure 72:
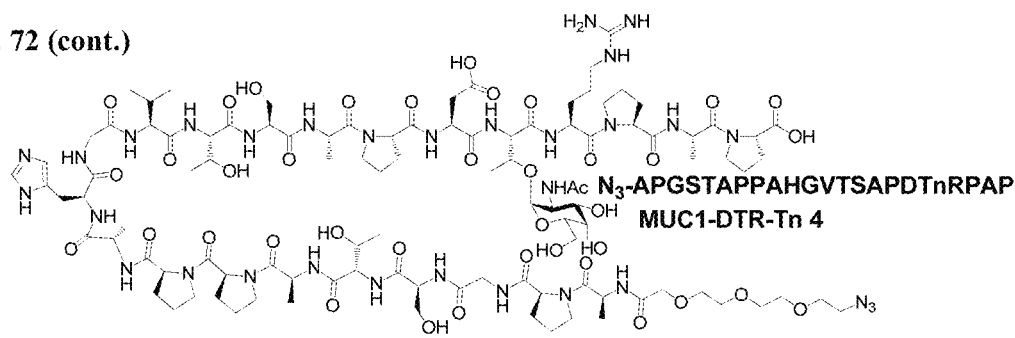
Figure 72:
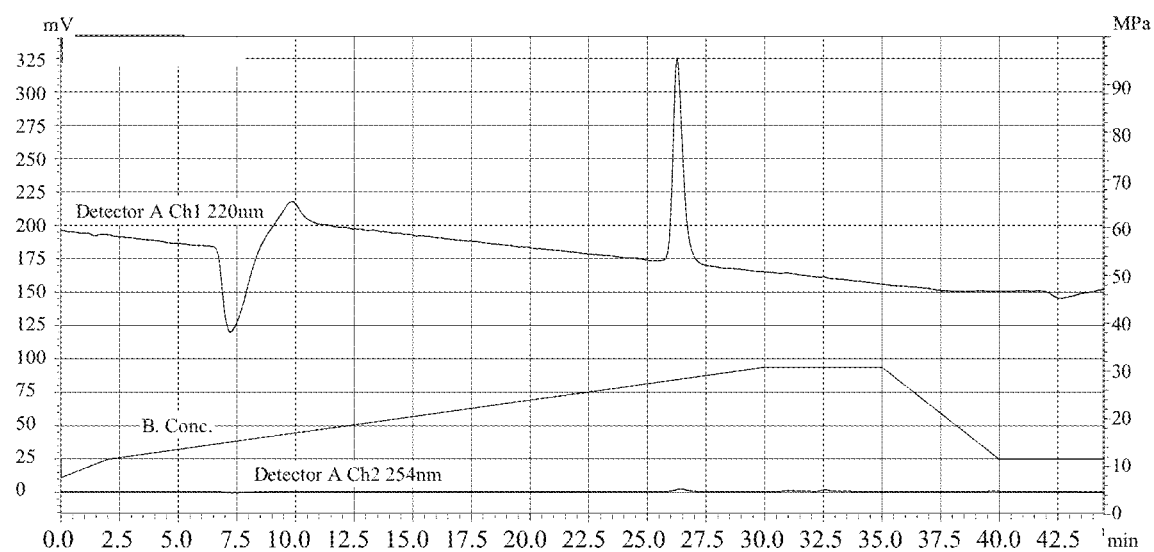
Figure 72:
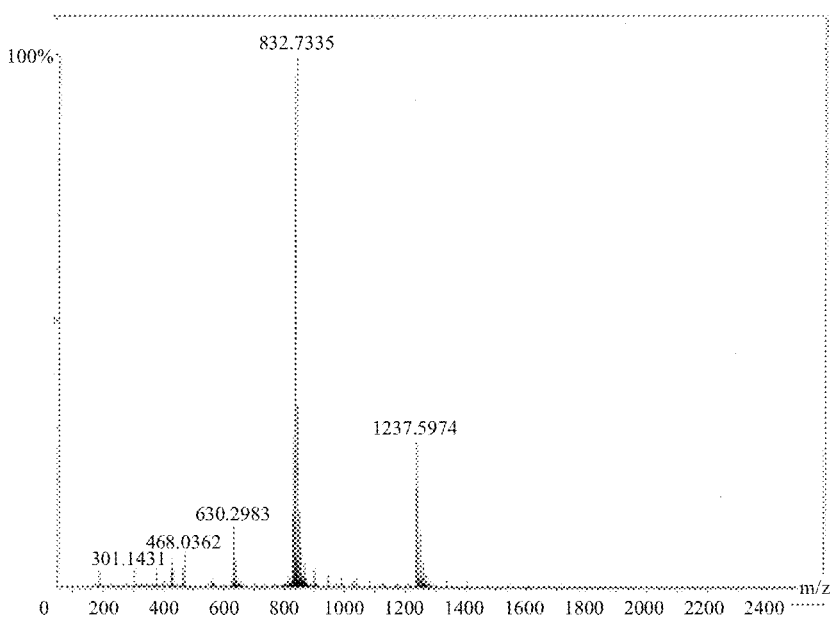

The MUC1 (glyco)peptides were synthesized using Fmoc based solid phase support peptide synthesis on 2-chlorotrityl resins. The N-terminal protecting group, Fmoc, was deprotected by 20% piperidine in DMF. The amino acid coupling was carried out with Fmoc amino acids (5 eq.) using HBTU/HOBt (4.9 eq.) and DIPEA (10 eq.), or Fmoc-Tn building block Fmoc-GalNAc-Thr 5 (2 eq.) using HATU/HOAt (1.9 eq.) and DIPEA (4 eq.). The peptide was cleaved from resins by TFA/TIPS/$H_2O$=95/2.5/2.5 for 2 hours. The excess TFA was evaporated. The peptide was precipitated by diethyl ether and centrifuged to pellet the solid. The peptide was further reprecipitated three times. To remove the acetyl protecting groups of the Tn, the crude glycopeptide was treated with 5% (v/v) hydrazine acetate for 2 hours. The crude reaction was neutralized to pH 7. The deprotected (glyco)peptides were purified on a Shimadzu HPLC (LC-8A Liquid Chromatograph Pump, DGU-14A, Degasser and SPD-10A UV-Vis Detector), using reverse phase column SUPERCOSIL LC18, 25 cm×10 mm 5 μm with gradient solvent $CH_3CN$ and $H_2O$ (0.1% TFA) gradient 0-5% in 2 min, 5-30% in 2-30 min and 30% in 30-35 min. The products were identified by MALDI-TOF. HPLC and HRMS spectra are shown in FIG. 72.

General Methods MUC5B Glycopeptide Synthesis

The MUC5B glycopeptides were synthesized in 13 μmol scale, according to the Fmoc-SPPS strategy (Pett, C. et al. (2017) Chem. Eur. J. 23, 3875). After resin cleavage (TFA/$H_2O$/TIPS 15:1:1), the crude peptides were passed through a C-18 column (Waters Sep-Pak, 1 g). All O-acetates on the glycans were carefully removed with NaOH in water/methanol at pH 11.5, which required intensive HPLC monitoring. All the glycopeptides were finally purified by preparative HPLC on a C-18 column. The HPLC eluents were composed of gradients of buffer A (water+0.1% TFA) and buffer B (84% acetonitrile+0.1% TFA).

Synthesis and Characterization of Qβ-MUC1 Conjugates

Figure 73:
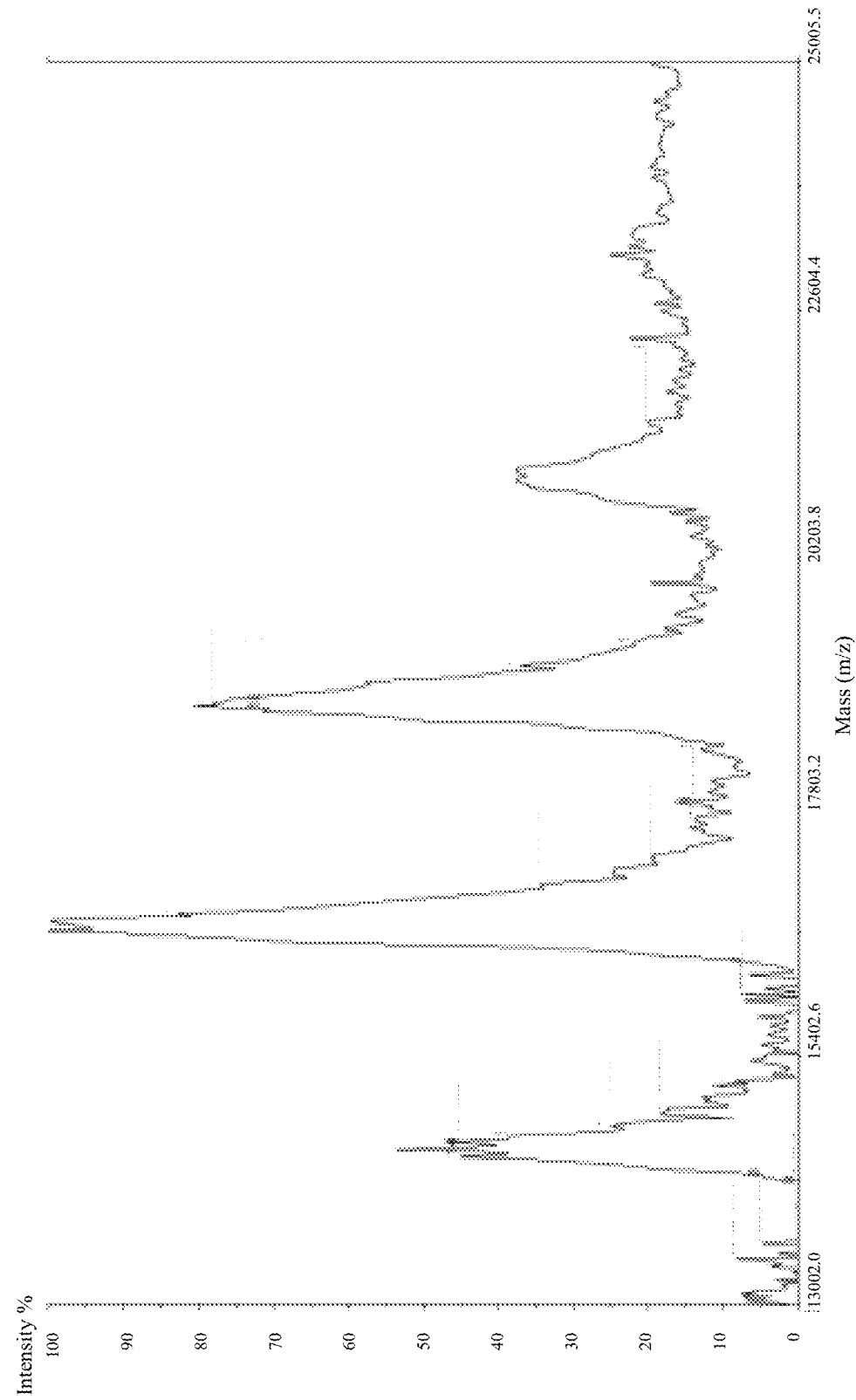
FIG. 73 shows MALDI mass spectrometry of Qβ-MUC1 conjugates 10-14.
Figure 73:
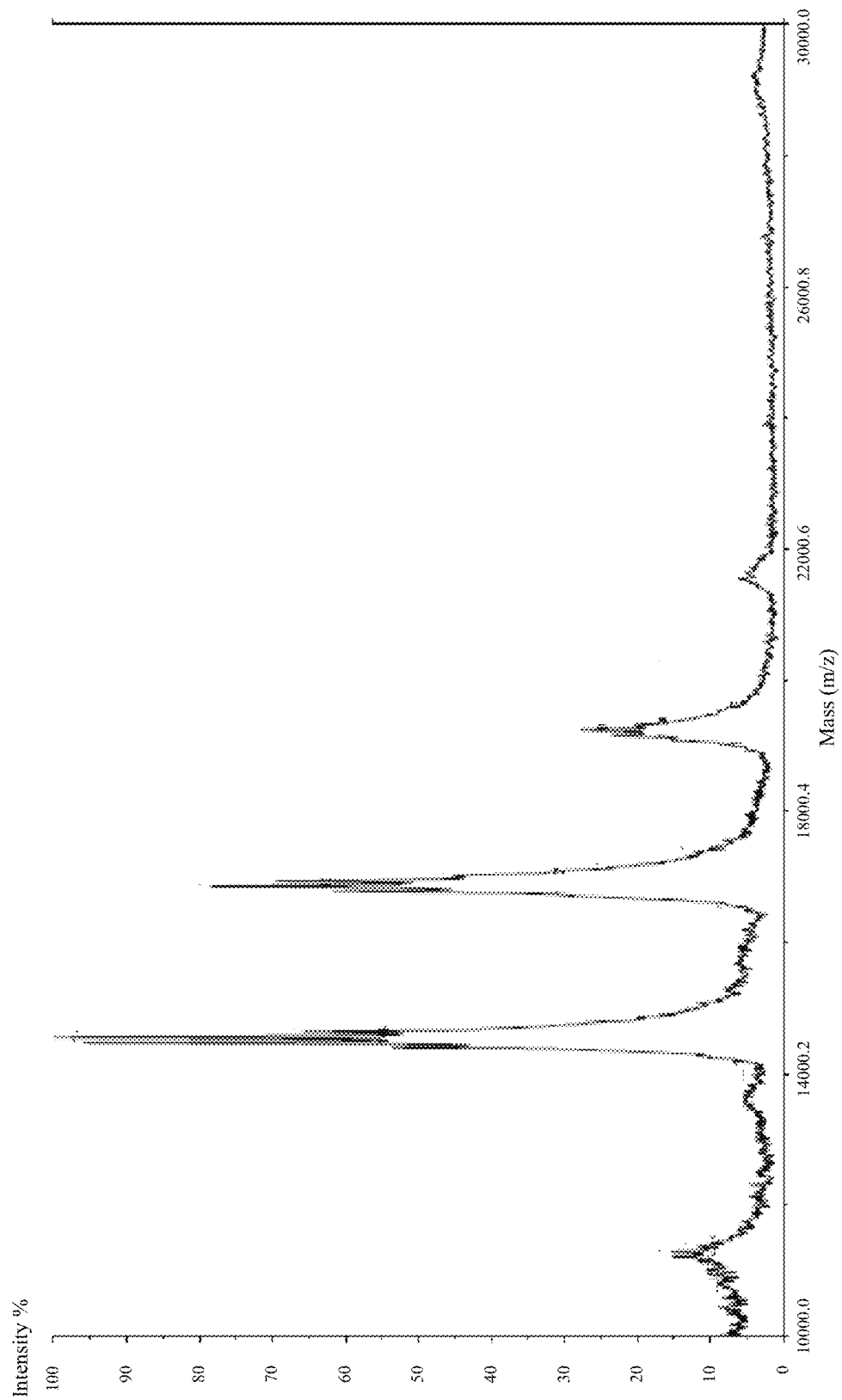
Figure 73:
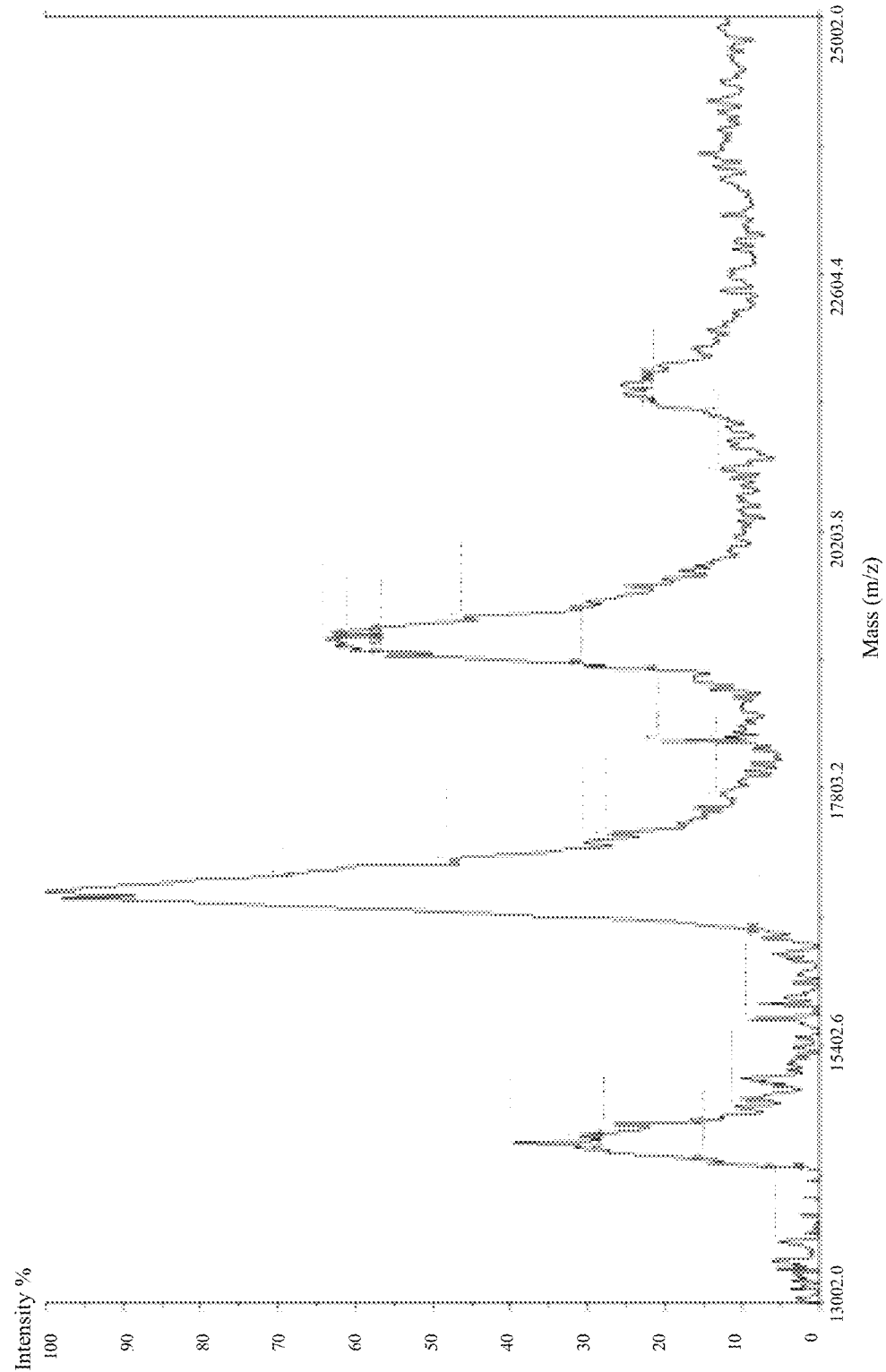
Figure 73:
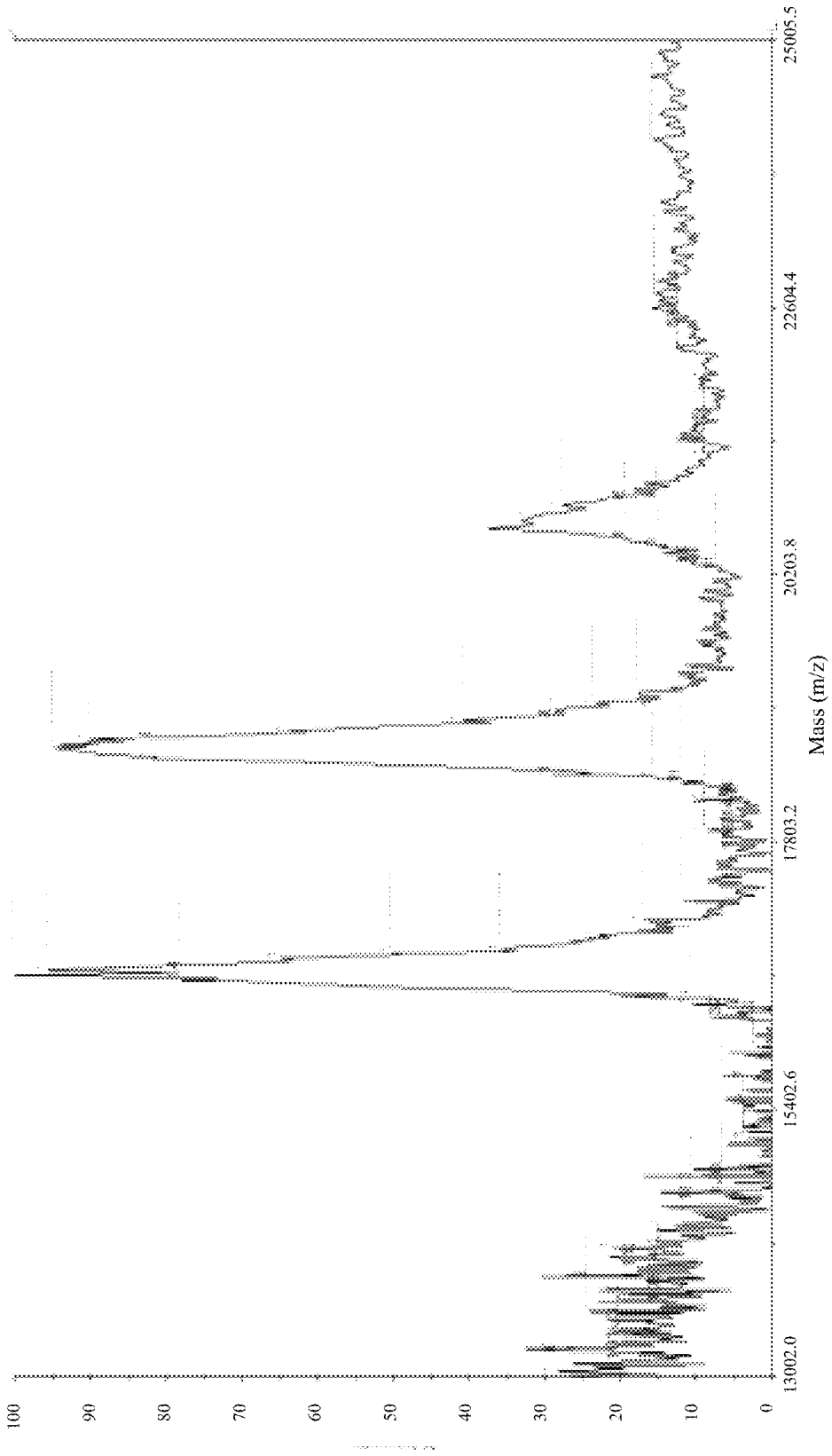
Figure 73:
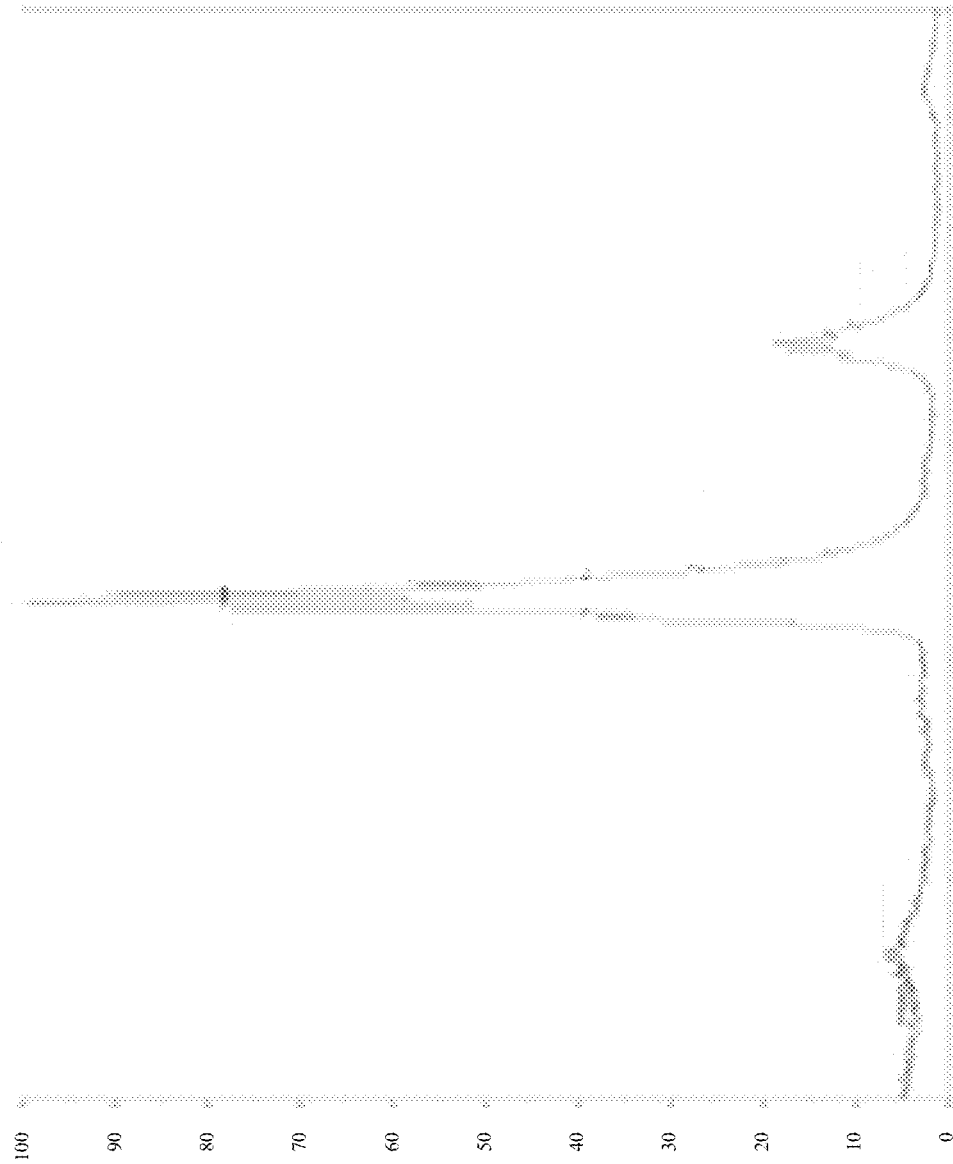
Figure 74:
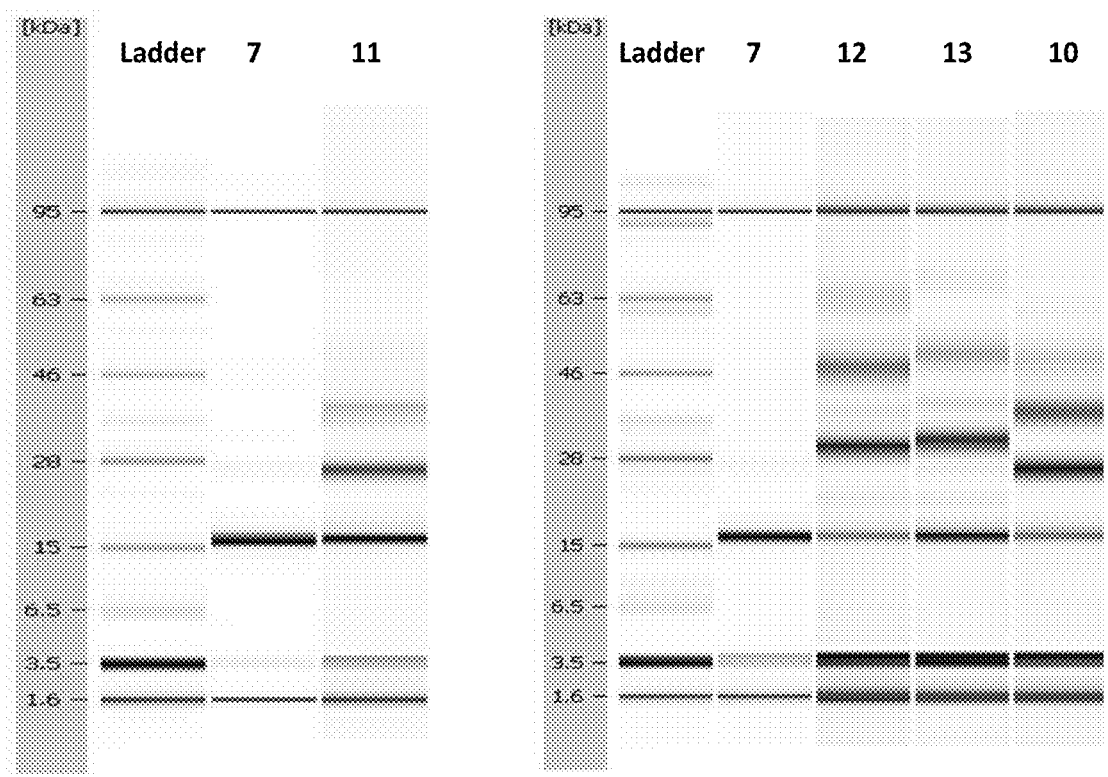
FIG. 74 shows electrophoretic analysis and Qβ-MUC1 conjugate loading determination.
Figure 74:
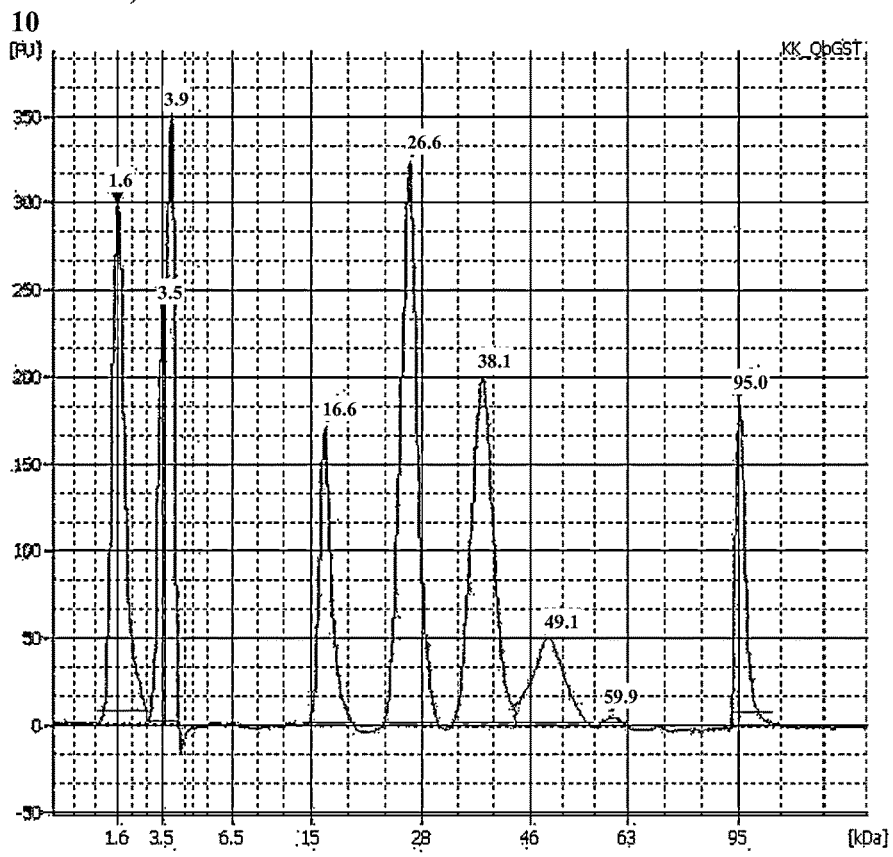
Figure 74:
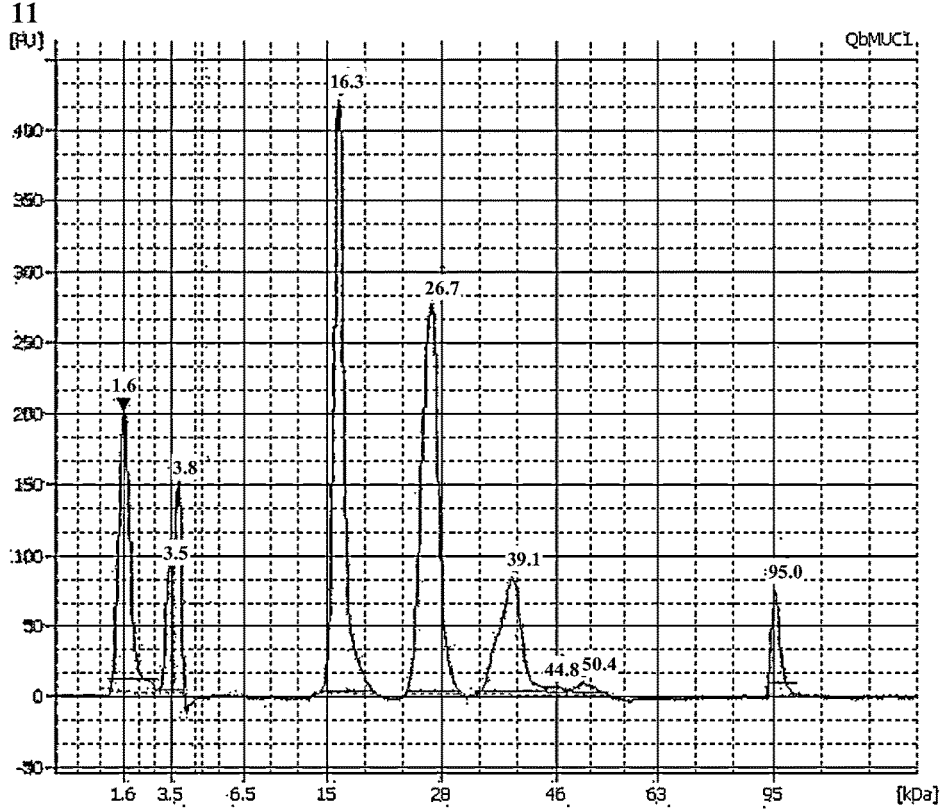
Figure 74:
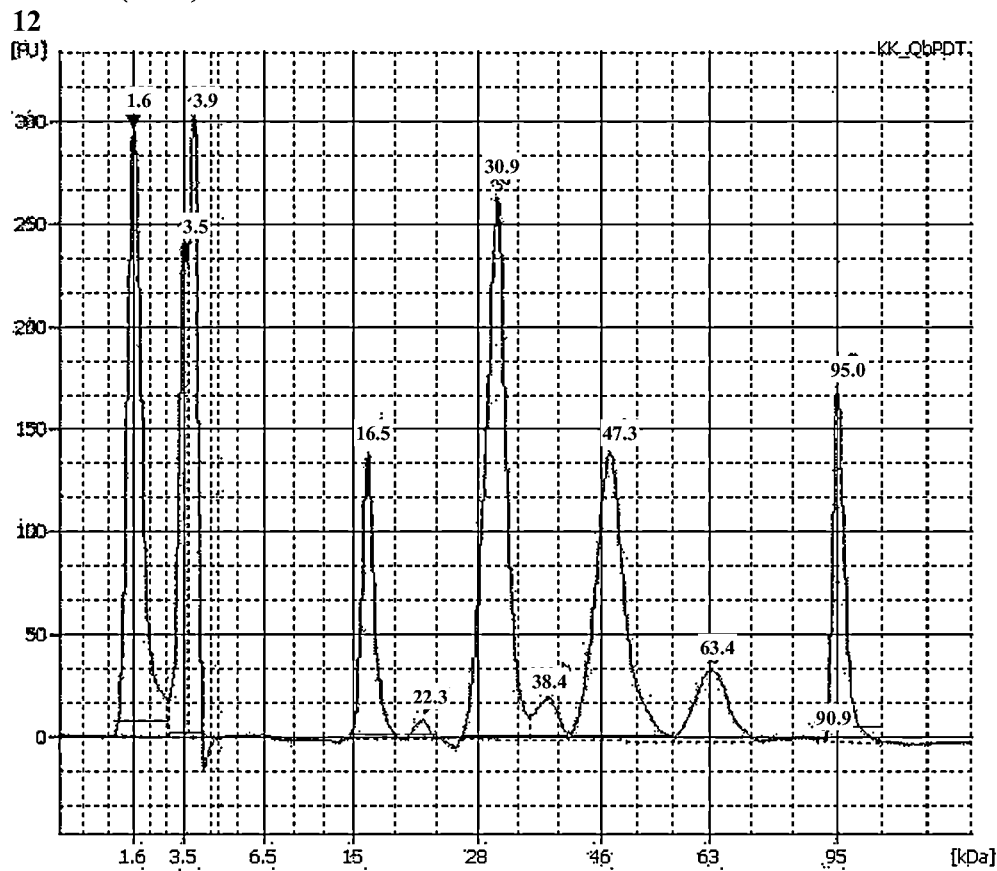
Figure 74:
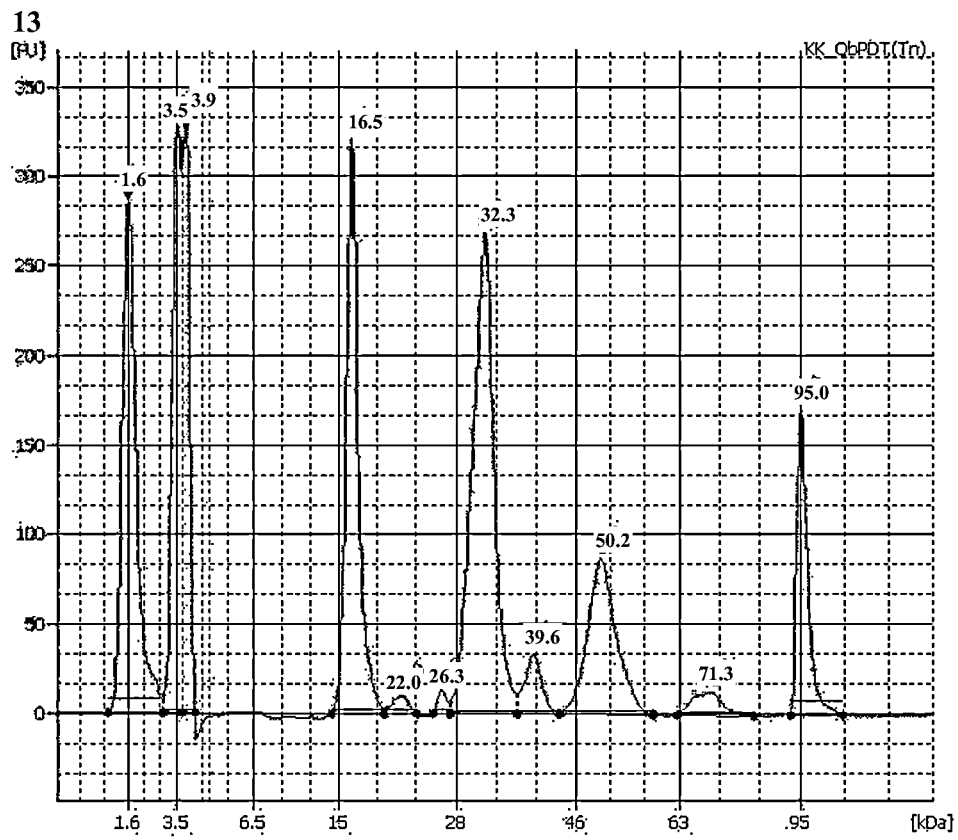
Figure 75:
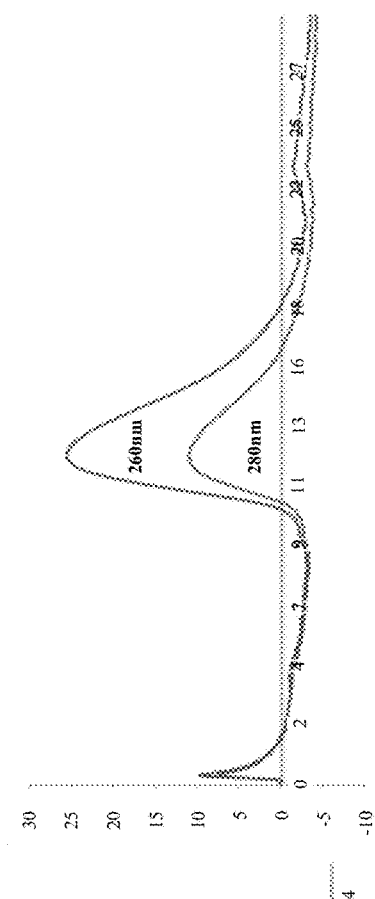
FIG. 75 shows FPLC chromatograms of Qβ-MUC1 conjugates 10-13.
Figure 75:
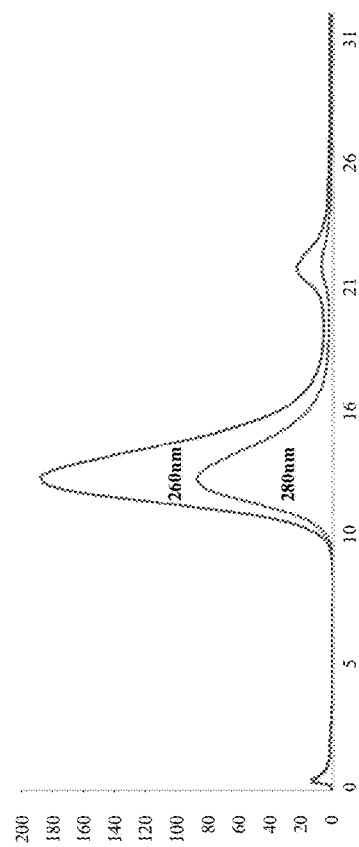
Figure 75:
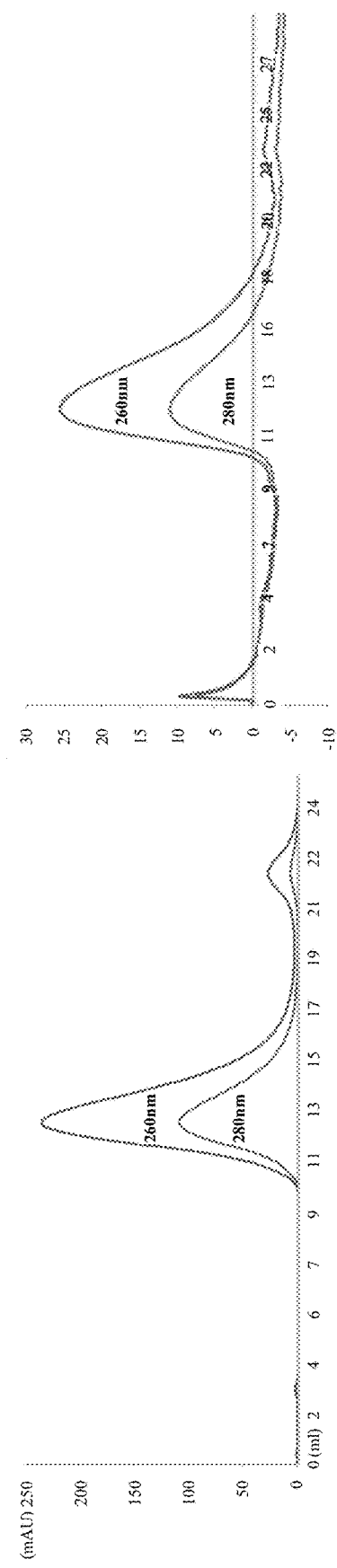
Figure 75:
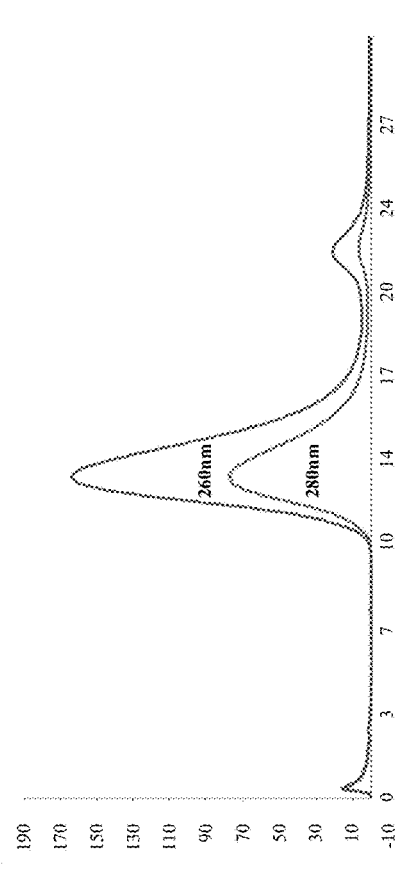

Alkyne modified Qβ 7 bearing 540 alkynes per Qβ was prepared with a reported procedure.[37] A solution of Qβ-alkyne 7 (2.20 mg/mL in 0.1 M pH=7.0 potassium phosphate buffer, 1.5 mL, 0.234 μmol in subunit, 0.707 μmol in reactive alkyne) was spiked with 10×PBS (0.074 mL). MUC1 (glyco)peptides (for 10-13: 10 mM in DMSO, 0.222 mL, 2.23 μmol, 9.5 equiv per protein monomer, which is approximately 3.15 equiv per alkyne; with low loading 14: 10 mM in DMSO, 0.058 mL, 0.58 μmol, 2.5 equiv per protein monomer, which is approximately 0.82 equiv per alkyne), premixed Cu-ligand solution ($CuSO_4$, 50 mM in water, 0.019 mL, 0.9 mol+THPTA ligand 8, 50 mM in water, 0.093 mL, 4.6 μmol), amino guanidine (100 mM in water, 0.231 mL, 0.023 mmol, 100 equiv per protein monomer), and sodium ascorbate (100 mM in water, 0.231 mL, 0.023 mmol, 100 equiv per protein monomer) were then added sequentially. The reaction vessel was inverted three times to ensure the reagents were mixed, and then incubated at room temperature for 16 h. The reaction progress was monitored by MALDI-MS. Upon completion, the remaining alkyne groups were capped as triazole propanol through another round of CuAAC conjugation with 3-azido propanol 9 as follows. To the crude golden colored solution was added 3-azido-propanol 9 (67.4 µL from 100 mM solution in DMSO, 6.74 µmol), THPTA (235 µL from 50 mM solution in H$_2$O, 11.8 µmol), CuSO$_4$ (47 L from 50 mM solution in H$_2$O, 2.35 µmol), amino guanidine (235 µL from 100 mM solution in H$_2$O, 23.5 µmol) and sodium ascorbate (235 µL from 100 mM solution in H$_2$O, 23.5 µmol). The reaction was inverted briefly, and was incubated at room temperature for 16 h. The product was purified by Amicon ultra 100,000 MW cut-off centrifugal filtration against 0.1 M potassium phosphate (3×15 mL). The total protein concentration was quantified by Bradford assay against BSA standards. An average loading of MUC1 per particle was determined by electrophoretic analysis and MALDI-TOF (FIGS. 73 and 74). Particle stability following CuAAC conjugation is shown by FPLC (FIG. 75).

Mouse Immunization.

Pathogen-free C57BL6 female mice aged 6-10 weeks were purchased from Charles River and maintained in the University Laboratory Animal Resources facility of Michigan State University. All animal experiments were performed in accordance with the guidelines of the Institutional Animal Care and Use Committee (IACUC) of Michigan State University. C57BL6 mice were injected subcutaneously under the scruff on day 0 with 0.1 mL various Qβ-MUC1 constructs as emulsions in Complete Freund's Adjuvant according to manufacturer's instructions. Boosters were given subcutaneously under the scruff on days 14 and 28 mixed with Incomplete Freund's Adjuvant. Sera samples were collected on days 0 (before immunization), 7 and 35.

Evaluation of antibody titers and subtypes by ELISA

A 96-well Nunc microtiter plate was first coated with a solution of the corresponding MUC1 (glyco)peptides (10 µg/mL, 100 µL/well) in NaHCO$_3$/Na$_2$CO$_3$ buffer (pH=9.5) and incubated at 4° C. overnight. The plate was washed with PBST (4×200 µL), blocked with 1% BSA/PBS (200 µL/well) for 1 h at room temperature, washed with PBST (4×200 µL), and incubated with serial dilutions of anti-sera from immunized mice in 0.1% BSA/PBS (100 µL/well, 4 wells for each dilution). The plate was incubated for 2 h at 37° C. and then washed with PBST (4×200 µL). A 1:2000 dilution of HRP-conjugated goat anti-mouse IgG, IgG+M, IgG1, IgG2b, IgG2c, or IgG3 (Jackson ImmunoResearch Laboratory) in 0.1% BSA/PBS (100 µL) was added to the wells respectively to determine the subtypes of antibodies generated. The plate was incubated for 1 h at 37° C. A solution of enzymatic substrate was prepared by dissolving TMB (5 mg) in a mixture of DMSO (2 mL) and citric acid buffer (18 mL) in a 50 mL centrifuge tube covered with aluminum foil. H$_2$O$_2$ (20 µL) was added and the mixture was homogenized by vortexing. The plate was washed with PBST (4×200 µL) and a solution of enzymatic substrate was added (200 µL). Color was allowed to develop for 15 min and 0.5 M H$_2$SO$_4$ (50 µL) was added to quench the reaction. The absorbance was measured at 450 nm using a microplate reader. The titer was determined by regression analysis with log 10 dilution plotted with optical density. The titer was reported as the highest fold of dilution that gives OD=0.3.

Microarray Spotting and Incubation

Glycopeptides (MUC1 synthesis previously described[1] and MUC5B synthesis described in FIG. 79) and glycoproteins (from Sigma-Aldrich) were dissolved and diluted to a spotting concentration of 50 mM in spotting buffer (150 mM NaH$_2$PO$_4$/Na$_2$HPO$_4$ buffer, pH 8.5). Microarrays were spotted with an iTwo 400 spotter (M2 Automation, Berlin, Germany). Droplets were produced by piezo-driven droplet generation. The spotter settings were adjusted to generate substrate spots from single droplets of 100 pL±3 pL onto the microarray slides. Amine-reactive, NHS-ester modified Nexterion® slide H (Schott, Mainz, Germany) microarray slides were used. During spotting, humidity in the spotting chamber was kept between 50-60%. After the spotting process, microarray slides were kept at 90-99% relative humidity overnight, to complete surface immobilization. Slides were stored below −20° C. until use.

Detection of Antibody Binding to Tumor Cells by Flow Cytometry

RMA cells, RMA-MUC1 cells, B16-MUC1 cells or MCF-7 cells were cultured at 37° C. under 5% C02 in cell growth medium respectively. The mixture of cells in cell growth medium was transferred to a conical centrifuge tube, and centrifuged at 1,600 rpm for 5 min at 4° C. The pellet was re-suspended in growth medium (10 mL). The number of cells was determined with a hemocytometer. Suspensions of 3.0×10$^5$ cells were added to each FACS tube, which were centrifuged at 1,600 rpm for 5 min to remove the supernatant. The cells were washed with FACS buffer (2% FBS in PBS with 0.1% sodium azide), and incubated with anti-sera at various dilutions in FACS buffer (100 µL) for 30 min on ice. The incubated cells are washed twice with FACS buffer, which was followed by incubation with FITC anti-mouse IgG (2 µL in 100 µL FACS buffer) for 30 min on ice. The cells were washed twice and re-suspended in FACS buffer before analysis by LSR II (BD Biosciences). Data is processed by FlowJo software.

Complement Dependent Cytotoxicity

Complement dependent cytotoxicity of B16-MUC1, RMA, RMA-MUC1 or MCF-7 cells was determined by MTS assay. B16-MUC1, RMA, RMA-MUC1 or MCF-7 tumor cells (7,000 cells/well) were cultured in DMEM (10% FBS) for 12-48 h (12 h for B16-MUC1, 24 h for RMA or RMA-MUC1, 48 h for MCF-7) incubated with a dilution of antisera (1/40 for B16-MUC1, 1/200 for RMA or RMA-MUC1, 1/40 for MCF-7) in 50 µL of culture medium at 37° C. for 30 min from different groups of immunized mice. Rabbit sera complement at a dilution (1/5 for B16MUC1, 1/15 for RMA or RMA-MUC1, 1/15 for MCF-7) in 50 µL of culture medium were added and then incubated at 37° C. for 4 h. MTS (CellTiter 96 Aqueous One Solution Cell Proliferation Assay; Promega, 20 µL) was added into each well and further incubated at 37° C. for 3 h. The optical absorption of each well was measured at 490 nm. Cells cultured in medium alone were used as a positive control (maximum OD), and culture medium was used as a negative control (minimum OD). All data were performed with four repeats. Cytotoxicity was calculated as follows: cytotoxicity (%)=(OD positive control−OD experimental)/(OD positive control−OD negative control)×100.

In Vitro CTL Assay

RMA or RMA-MUC1 cells (5-6×10$^6$) were harvested, washed with PBS and suspended in PBS (500 µL for RMA-MUC1 cells, 950 µL for RMA cells). 2 µL of a CFSE stock solution (5 mM) was added to 1 mL cold PBS to make 10 µM solution. 500 µL of the 10 µM CFSE solution was added to RMA-MUC1 cells (with final concentration of CFSE at 5 µM), 50 µL of the 10 µM CFSE solution was added to RMA cells (with final CFSE concentration of 0.5 µM) in the incubator for 10 min, and then 10 mL culture medium was added to each tube and incubated for 10 min at rt. The cells were centrifuged and washed once with culture medium and adjusted to 0.1×10$^6$ cells/mL. Spleen or lymph node cells were separated and suspended in RPMI medium, and the cell number was adjusted to $2.5 \times 10^6$/mL. 50 μL RMA and RMA-MUC1 cells, 100 μL spleen or lymph node cells were added respectively to 96-well plates and mixed thoroughly by pipetting up and down at least four times by multiple channel pipette, and then incubated for 6 h in the incubator. 4 μL 7-AAD was added to each tube before FACS analysis. The percentage of tumor cells lysis was calculated as follows: lysis of RMA %=(CFSE$^{lo}$7AAD$^+$/CFSE$^{lo}$)× 100%, Lysis of RMA-MUC1%=(CFSE$^{hi}$7AAD$^+$/CFSE$^{hi}$)× 100%.

In Vivo CTL Assay

Splenocytes from normal mice were harvested and half of cells were incubated with 10 μM of MUC1 (glyco)peptides 3 or 4 for 1 h respectively. The MUC1 peptide pulsed lymph node cells were labeled with a high concentration of CFSE (2.5 μM, CFSE$^{hi}$) and no MUC1 peptide pulsed Splenocytes were labeled with a low concentration of CFSE (0.25 μM, CFSE$^{lo}$). The resultant MUC1 peptide pulsed CFSE$^{hi}$ labeled cells were mixed with CFSE$^{lo}$ labeled cells (1:1) and then injected into Qβ-MUC1 immunized mice by tail vein (200 μL, total 2 million cells). 24 h later, lymph nodes were separated and 4 μL 7-AAD was added to the single suspension. The number of viable CFSE$^{hi}$ and CFSE$^{lo}$ cells were determined by FACS analysis.

Example 11: Synthesis of Qβ-MUC1 Conjugates

MUC1 has a large extracellular N-terminal domain, consisting of a variable number of tandem repeats of 20 amino acid residues with the sequence of PDTRPAPGSTAPPAHGVTSA (SEQ ID NO: 53) (Tang, C K et al. (2008) *Exp. Rev. Vaccines* 7: 951-962; Hattrup, C. L. et al. (2008) *Annu. Rev. Physiol.* 70, 431-457). The five serine and threonine residues within each tandem repeat can be potentially glycosylated. For the vaccine studies described herein, MUC1 (glyco)peptides 1-4, which contain 20-22 amino acid residues as the backbone covering one full length of the tandem repeat region, were designed. Peptides 1 and 3 represent two possible sequences of the repeat region designated MUC1-STA and MUC1-DTR (STA and DTR are the three amino acid sequence containing a threonine closest to the C-terminus). To establish possible influence of glycosylation on immune responses, GalNAc was installed on the threonine residue closest to the C-terminus producing MUC1 glycopeptides 2 and 4 designated MUC1-STA-Tn and MUC1-DTR-Tn. GalNAc modified MUC1 were focused on as they are widely expressed in cancer (Beatson, R. et al. (2015) *PLoS ONE* 10, e0125994) and can potentially function as CTL epitopes (Vlad, A. M. et al. (2002) *J. Exp. Med.* 196, 1435-1446; Apostolopoulos, V. et al. (2003) *Proc. Natd. Acad. Sci. U.S.A.* 100, 15029-1503440-41).

The synthesis of the MUC1 (glyco)peptides was performed through solid-phase peptide synthesis (SPPS) using Fmoc chemistry (Scheme 1). The coupling of Fmoc-protected amino acids to peptide chains was carried out with (2-(1H-benzotriazol-1-yl)-1,1,3,3-tetramethyluronium hexafluorophosphate (HBTU)/hydroxybenzotriazole (HOBt).

For glycopeptide synthesis, Fmoc protected GalNAc-threonine 5 (Fmoc-GalNAc-Thr) (Sungsuwan, S. et al. (2015) *ACS Appl. Mater. Interface* 7, 17535-17544) was used as a building block, which was introduced into the peptide chain mediated by 1-[bis(dimethylamino)methylene]-1H-1,2,3-triazolo[4,5-b]pyridinium 3-oxidhexafluorophosphate (HATU)/1-hydroxy-7-azabenzotriazole (HOAt). After assembly of (glyco)peptides, the N-terminal Fmoc group was removed and an azide terminated linker azido-PEG3-NHS 6 (Martin, A. L. et al. (2008) *Bioconjugate Chem.* 19, 2375-2384) was incorporated at the N-terminus. The resulting (glyco)peptides were cleaved from the resins by trifluoroacetic acid (TFA)/triisopropyl silane (TIPS)/H2O, and the O-acetates on the saccharide moiety were removed by 5% hydrazine in H2O. C18 reverse phase HPLC purification produced the desired MUC1 (glyco)peptides 1-4 in 30-40% yields.

The ligation of MUC1 onto Qβ-VLP was performed with the copper-catalyzed azide-alkyne cycloaddition (CuAAC) reaction optimized for bioconjugations (Hong, V. et al. (2009) *Angew. Chem. Int. Ed.* 48, 9879-9883). Azide modified MUC1 peptides 1-4 were coupled with alkyne functionalized Qβ7 (Yin, Z. et al. (2013) *ACS Chem. Biol.* 8, 1253-1262) promoted by Cu$^+$ catalyst with THPTA ligand 8 (Scheme 2). The average numbers of (glyco)peptides introduced onto Qβ were 257, 140, 248 and 171 (with an estimate distribution of ±15%) for conjugates 10-13 respectively (FIGS. 72-75). The unreacted alkyne groups on Qβ capsids were capped using a large excess of 3-azido 1-propanol 9 by a second CuAAC reaction. By reducing the reagent concentration and reaction time during conjugation of MUC1 glycopeptide 2 with Qβ-alkyne 7, Qβ-MUC1 14 was also synthesized bearing on average 30 copies of MUC1 glycopeptide 2 per capsid for analysis of antigen density effects.

Example 12: Qβ-MUC1 Conjugates can Generate Robust Titers of Anti-MUC1 IgG Antibodies and High Density of MUC1 is Critical for High Levels of IgG With Qβ-MUC1 conjugates in hand, their abilities to induce immune responses were investigated. Groups of C57BL6 mice were immunized with the conjugates three times biweekly (i.e., injections on days 0, 14, and 28) at equal total MUC1 concentrations per injection. Serum samples were taken one week after the final boost (day 35) and antibody titers and subtypes were determined by enzyme linked immunosorbent assay (ELISA) against the specific MUC1 glycopeptide structure used for immunization.

The first parameter we investigated is the effect of local antigen density on antibody responses by comparing Qβ-MUC1 constructs 11 and 14 (FIG. 42). The anti-MUC1 antibody responses elicited by Qβ-MUC1 11 were predominantly IgGs. The mean total IgG titers produced were 1,013,300, which was 500 times higher than titers from control mice immunized with Qβ only. Interestingly, despite receiving the same total amounts of MUC1, mice immunized with the Qβ-MUC1 14 gave average IgG antibody titers only 20% of those receiving Qβ-MUC1 11 with higher local density of MUC1. Furthermore, the intragroup variations of IgG titers by 11 were smaller than those induced by 14.

Figure 42A:
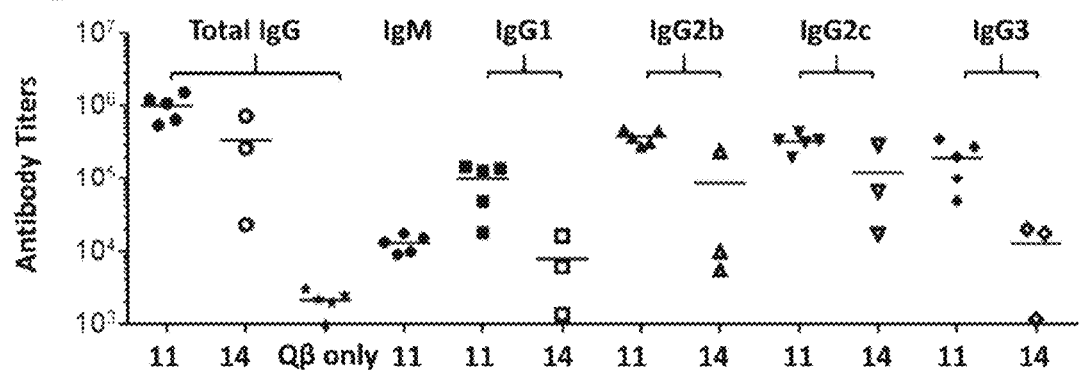
FIG. 42A depicts titers of anti-MUC1 total IgG and IgG subtypes from mice immunized wit Qβ-MUC1 construct 11 and 14 as well as Qβ only as the control. The average IgG titers induced by 11 were much higher than those by construct 14 containing low MUC1 density or Qβ only.
Figure 42B:
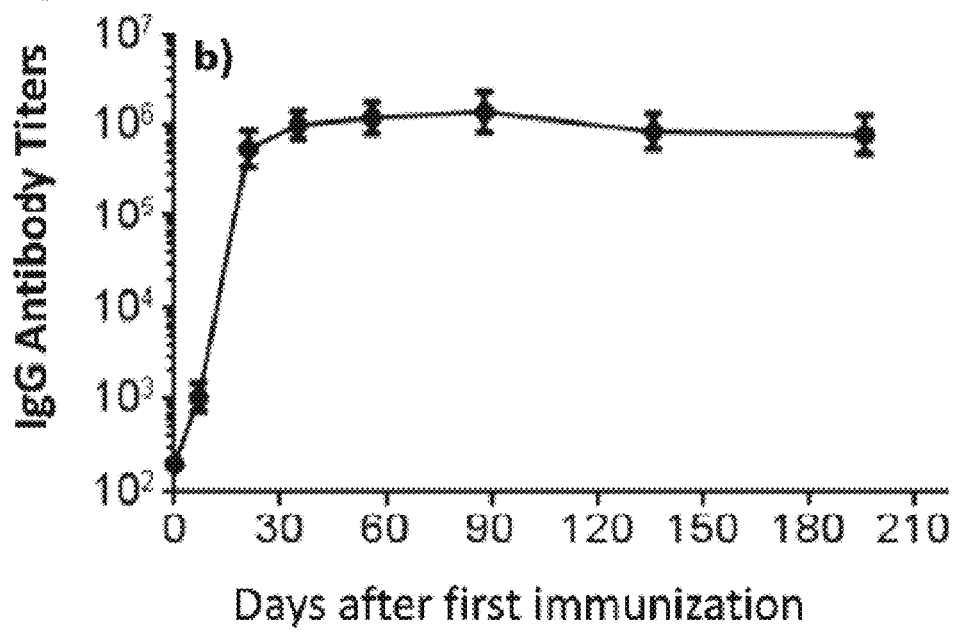
FIG. 42B depicts the high anti-MUC1 IgG antibody titers induced by 11 lasted more than 200 days.

Subtyping of IgG titers indicated that all major subtypes of IgGs including IgG1, IgG2b and IgG2c were elicited (FIG. 42A). Construct 11 also produced a large amount of IgG3 antibody, a subtype of IgG antibodies in mice that is traditionally induced by carbohydrate antigens (Klaus, T. et al. (2015) *Sci. Rep.* 6, 30938; Greenspan, N. S. et al. (1992) *Immunol. Today* 13, 164-168). The kinetics of MUC1 antibody generation as well as antibody persistence was next examined. IgG antibody responses to construct 11 approached the peak value 21 days after the first immunization. The super high IgG titers maintained for more than 6 months highlighting the power of Qβ as a carrier for glycopeptide for inducing long lasting immune responses (FIG. 42B).

Figure 42C:
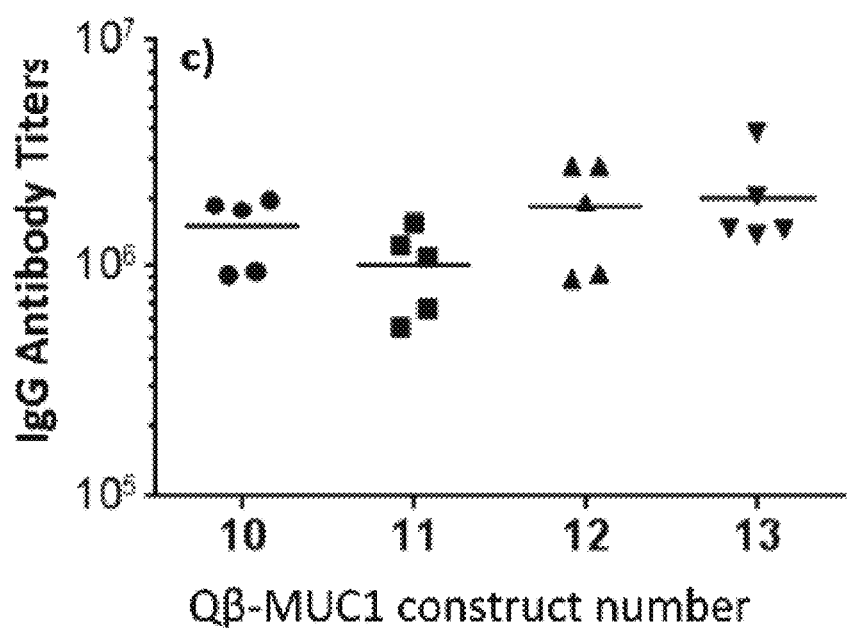
FIG. 42C depicts anti-MUC1 IgG titers from mice immunized with Qβ-MUC1 constructs 10-13 respectively. All ELISA measurements were performed against the plated specific MUC1 glycopeptide used for immunization.
Figure 77:
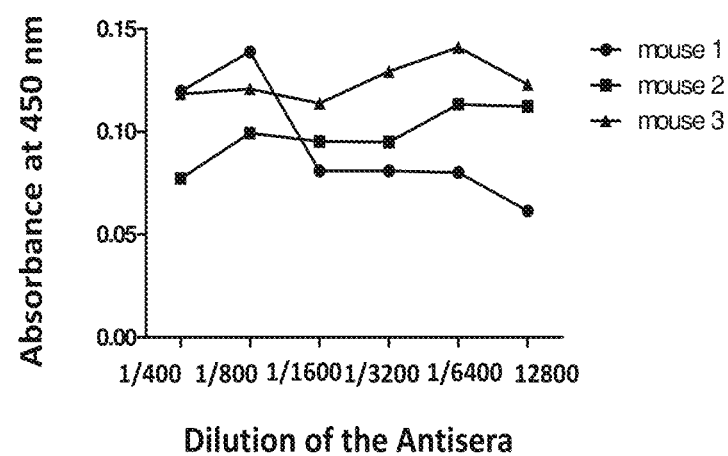
FIG. 77 shows ELISA results of sera from animals immunized with an admixture of Qβ and MUC1. Despite the relative low fold of dilution, there was no significant binding of antisera to MUC1. Based on these results, the anti-MUC1 IgG antibody titers induced were below 400, thus suggesting covalent conjugation of MUC1 glycopeptide with Qβ is critical for production of high antibody titers.

In order to establish the generality of Qβ as a MUC1 carrier, other Qβ-MUC1 constructs were tested following the same immunization protocol as for 11. As shown in FIG. 42C, all these Qβ-MUC1 vaccines elicited consistent and high anti-MUC1 IgG titers comparable to that of Qβ-MUC1 11 with the average IgG titers from mice immunized with Qβ-MUC1 13 exceeding 2,000,000. As a negative control, groups of WT C57BL6 mice were immunized with MUC1 glycopeptide admixed Qβ without the covalent conjugation. As shown in (FIG. 77), the anti-MUC1 IgG antibody titers induced were below 400, thus suggesting covalent conjugation of MUC1 glycopeptide with Qβ is critical for production of high antibody titers.

Example 13: Microarray Analysis of the Antibodies Induced by Qβ-MUC1 Conjugates 10-13

Figure 78:
FIG. 78 shows glycopeptide microarray screening results of antisera induced by Qβ-MUC1 conjugates 10-13. Glycopeptide microarray screening results of antisera induced by Qβ-MUC1 conjugates 10-13—Conjugate 10 induced antisera (SEQ ID NOS 99-174, respectively, in order of appearance); Conjugate 11 induced antisera (SEQ ID NOS 99-174, respectively, in order of appearance); Conjugate 12 induced antisera (SEQ ID NOS 99-174, respectively, in order of appearance); and Conjugate 13 induced antisera (SEQ ID NOS 99-174, respectively, in order of appearance). For each group, the results from four anti-sera were shown. The abbreviations for glycan structures are shown in the figure.
Figure 78:
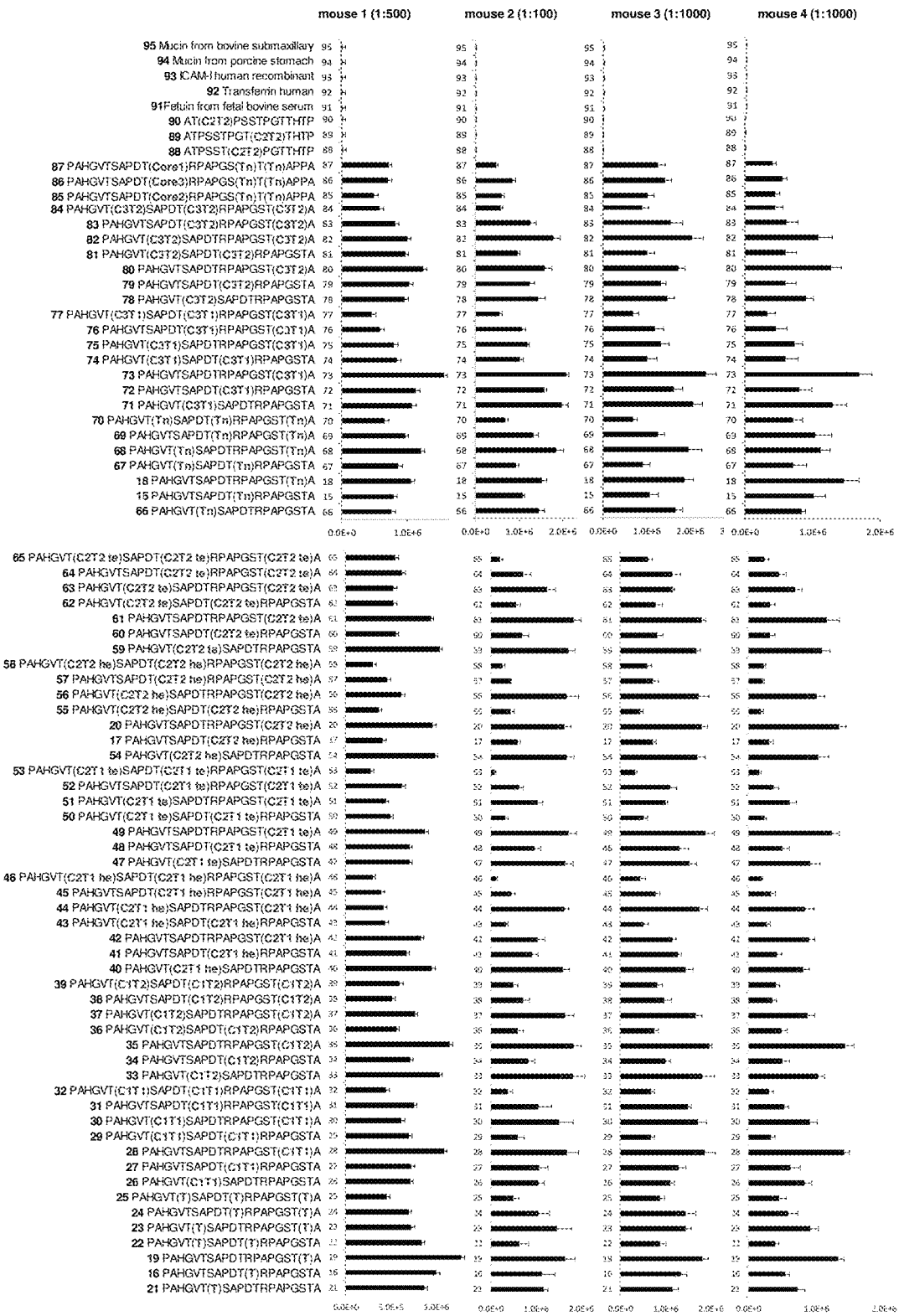
Figure 78:
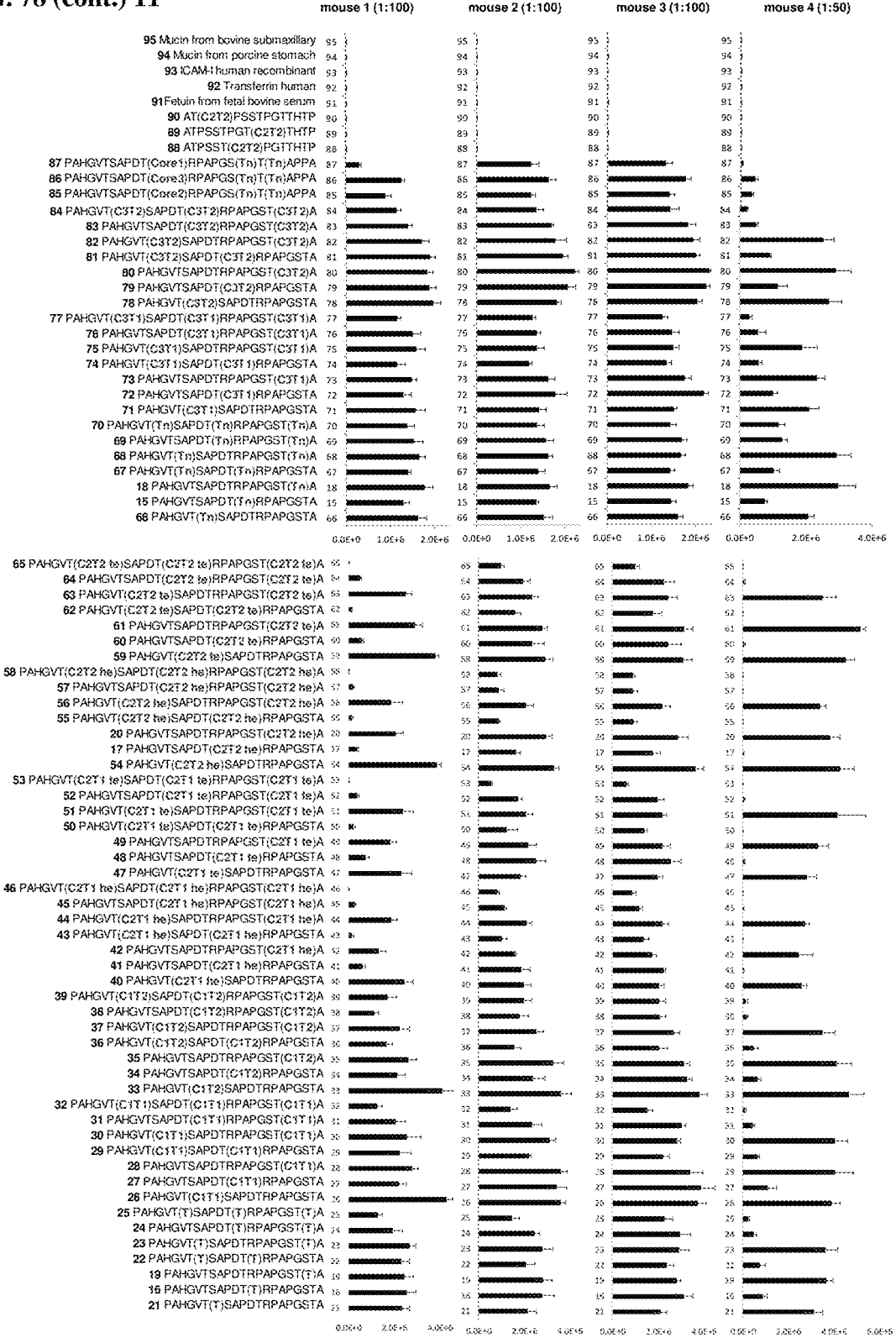
Figure 78:
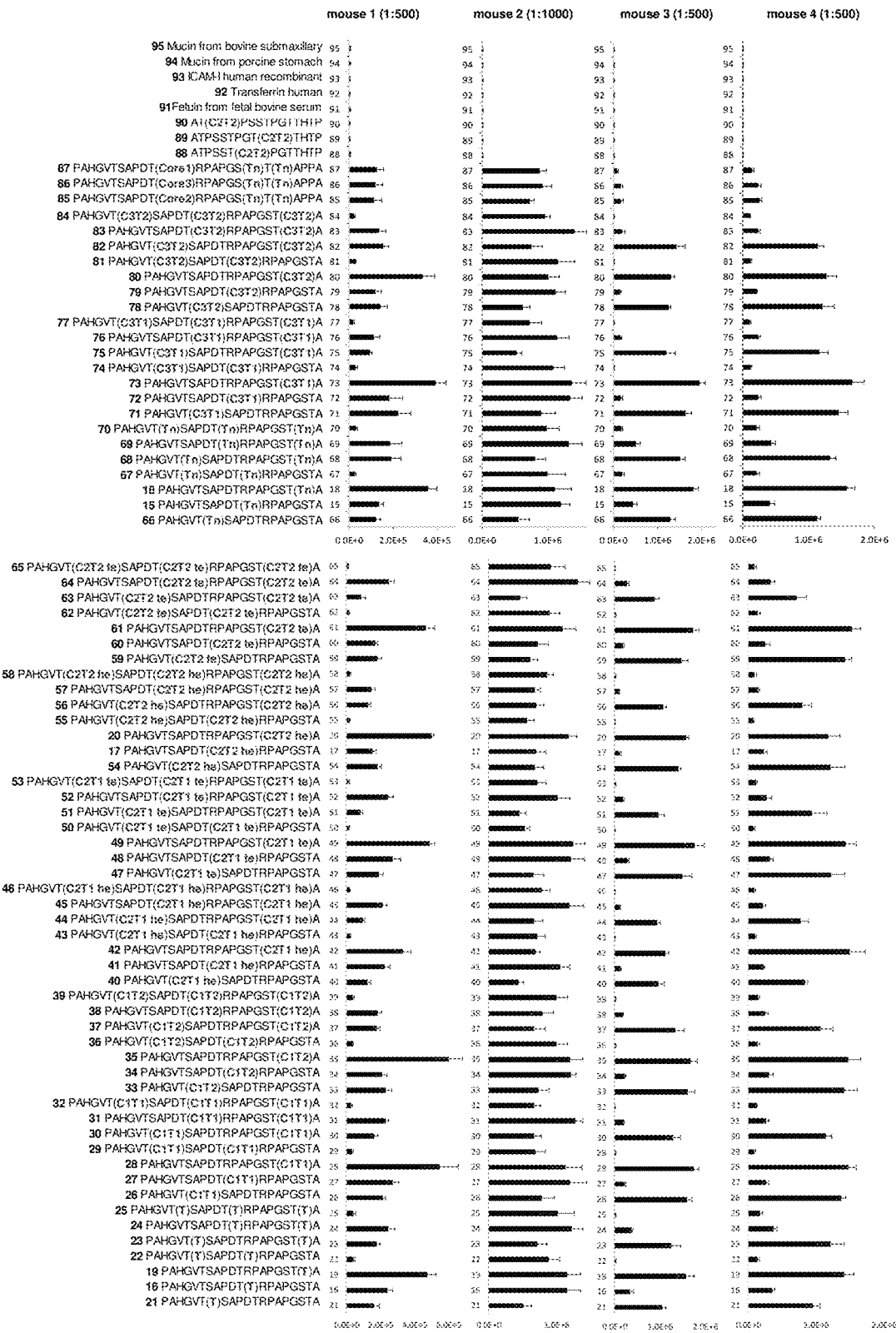
Figure 78:
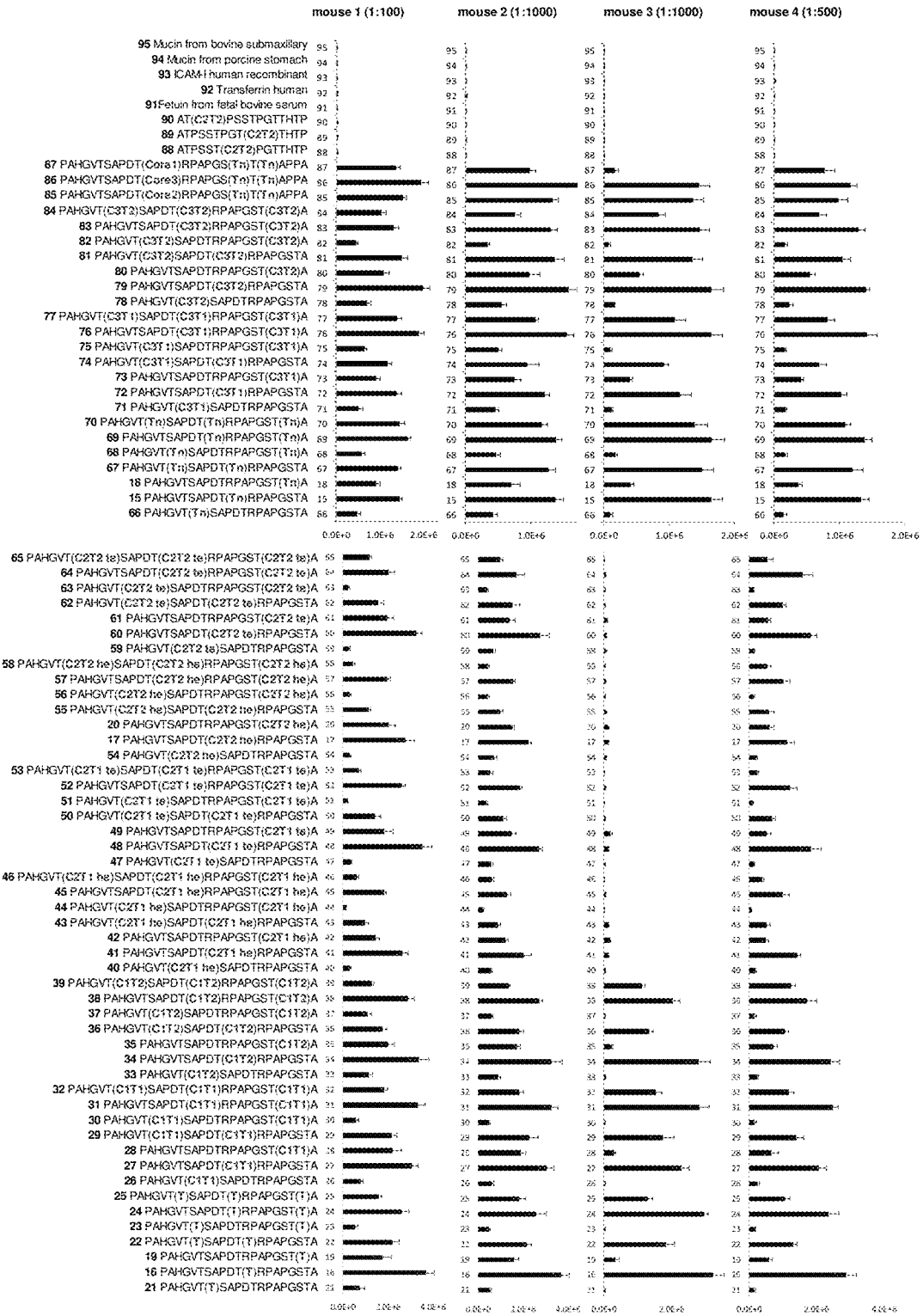

To better understand the binding specificity, the post-immune sera from Qβ-MUC1 10-13 vaccination were screened against a (glyco)peptide microarray with various MUC1 glycopeptides in addition to mucin-5 glycopeptides, mucins from porcine stomach and bovine submaxillary glands as well as several other glycoproteins (FIG. 78) (Pett, C. et al. (2017) Chem. Eur. J. 23, 3875-3884). On the microarray, there are 72 MUC1 glycopeptides each with one MUC1 tandem repeat PAHGVT*SAPDT*RPAPGST*A (SEQ ID NO: 25) (* denotes the potential glycosylation sites). The glycan structures are diverse, which include Tn, Thomsen-Friedenreich (T) antigen as well as a number of core 1, core 2 and core 3 oligosaccharides (FIG. 78). The microarray slides were incubated with individual mouse serum and unbound antibodies were removed by thorough washing. A fluorescently labeled secondary antibody was then added to the microarray to quantify the relative amounts of serum antibody bound to individual array components.

Figure 43A:
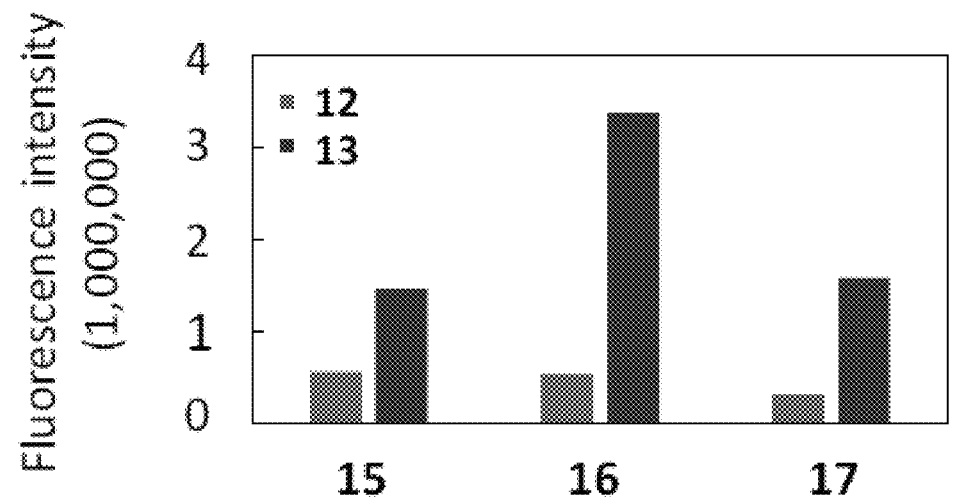
FIG. 43 contains two panels FIG. 43A and FIG. 43B, depicting MUC1 glycopeptide microarray screening showed that IgG antibodies generated could recognize MUC1 glycopeptides bearing a wide range of glycan structures suggesting a broad repertoire of antibodies was produced. Immunization with glycosylated MUC1 antigen (13 and 11) led to stronger binding to glycopeptides compared to the non-glycosylated counterparts (12 and 10).
Figure 43B:
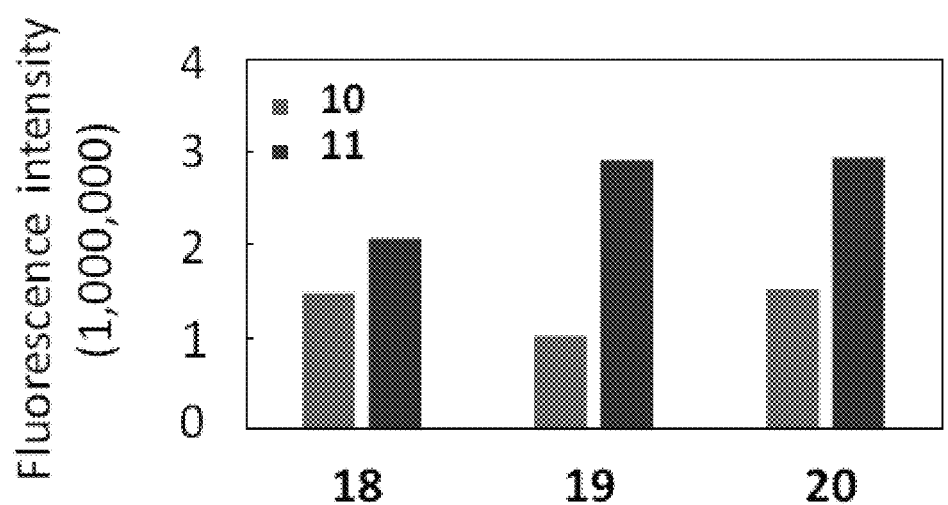

As shown in FIG. 78, the antibodies induced by Qβ-MUC1 conjugates 10-13 exhibited broad and strong recognition to almost all MUC1 glycopeptides carrying Tn, T, core1, core2, core3 or mix glycans. This suggests broad repertoire of anti-MUC1 IgG antibodies were elicited through vaccination, which bodes well for anti-cancer vaccine development as glycosylations of MUC1 proteins on tumor cell surface are generally heterogeneous. The antibodies were specific to MUC1 as there was little binding to mucin-5 glycopeptides or to any other proteins. Close examination of microarray binding profiles revealed interesting binding trend. MUC1 glycopeptides 15-17 PAHGVTSAPDT*RPAPGSTA (SEQ ID NO: 21) differed only in the glycan structure attached to the threonine in the middle of the peptide chain (* represents the location of glycosylation. Tn for 15, T for 16 and a core 2 hexasaccharide C2T2Hex for 17; for glycan structures, see figure S7). Despite the larger size of T antigen and the core 2 hexasaccharide compared to Tn, all three glycopeptides were recognized well (FIG. 43A). Immunogen Qβ-MUC1 13 contained Tn in the DTR region of its MUC1 and the antibodies induced by Qβ-MUC1 exhibited much stronger binding to the glycopeptides 15-17 compared to Qβ-MUC1 12 lacking any glycans. The same phenomena were observed of antibodies induced by 11 (glycosylation in the STA region) vs 10 against glycopeptides 18-20 PAHGVTSAPDTRPAPGST*A (SEQ ID NO: 22)(* represents the location of glycosylation. Tn for 18, T for 19 and a core 2 hexasaccharide for 20. FIG. 43B).

Figure 44A:
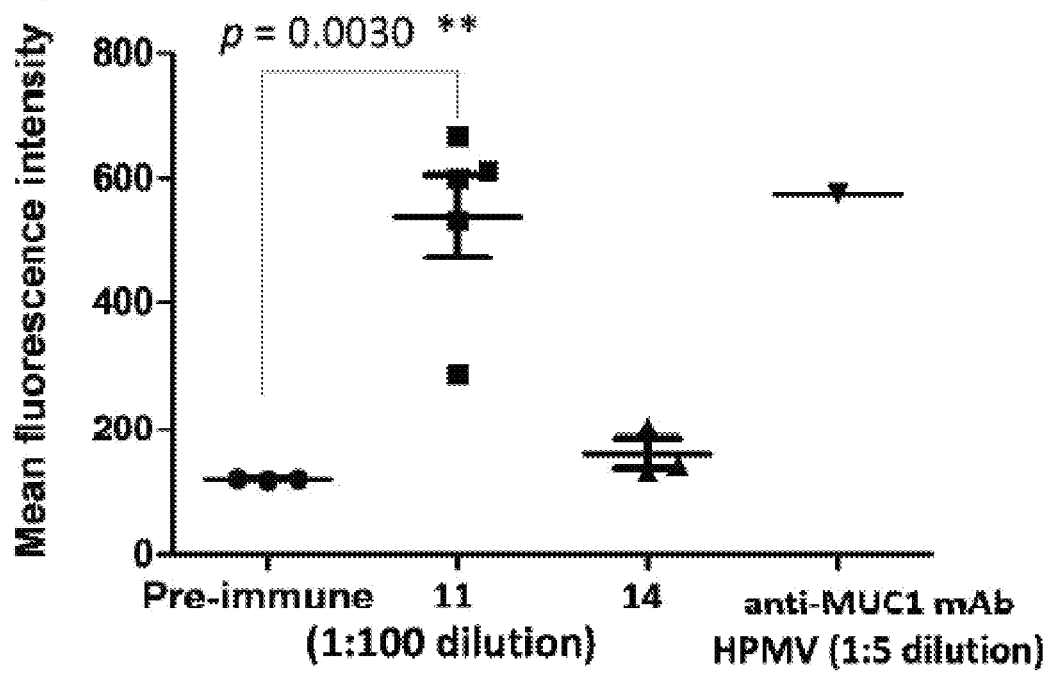
FIG. 44A shows the mean fluorescence intensities of binding of RMA-MUC1 cells by pre-immune sera and sera from mice immunized with vaccine constructs 11 and 14 respectively (1:100 dilution); MUC1 expression on RMA-MUC1 was confirmed by anti-MUC1 mAb HPMV (1:5 dilution). Immunization with 11 induced antibodies capable of binding RMA-MUC1 much stronger than those from 14 immunized mice.

Example 14: IgG Antibodies Induced by Qβ-MUC1 Conjugates are Capable of Binding MUC1 Expressing Tumor Cells and Selectively Kill Tumor Cells Through Complement Mediated Cytotoxicity For an effective vaccine, it is critical that antibodies generated can recognize the antigen expressed in its native environment, i.e., on tumor cells. To establish this, flow cytometry studies were performed using MUC1 transfected mouse lymphoma cell RMA-MUC1. RMA-MUC1 cells express human MUC1 on cell surface as confirmed by cellular binding with a commercially available anti-MUC1 mAb HPMV at 1:5 dilution (FIG. 44A).

Figure 44B:
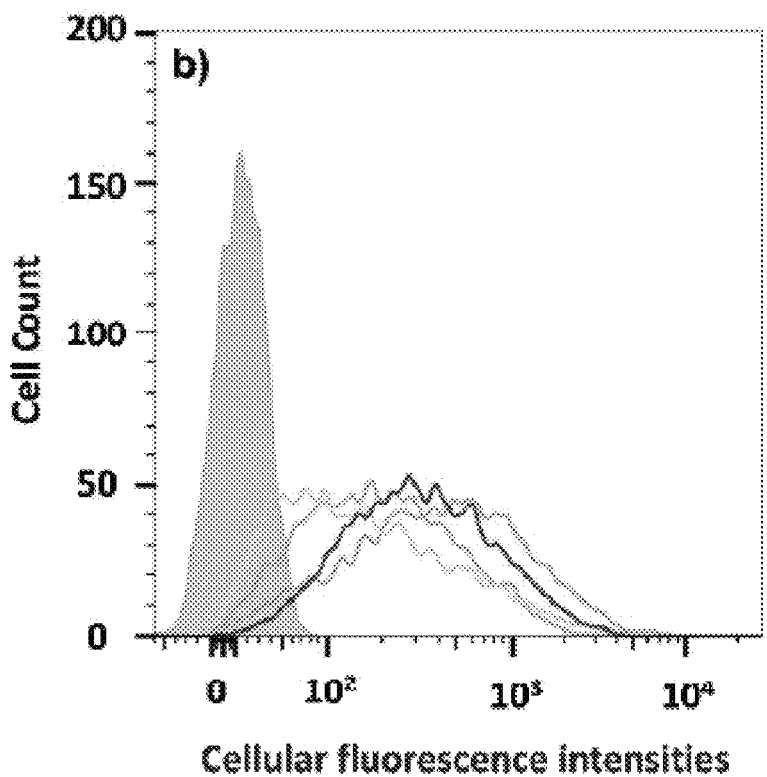
FIG. 44B depicts binding of RMA-MUC1 cells by sera from mice immunized with 10 (blue curve), 11 (orange curve), 12 (green curve) and 13 (red curve) at 1:50 dilution. The grey filled trace was from pre-immune serum. All post-immune sera showed strong binding to RMA-MUC1 cells.
Figure 44C:
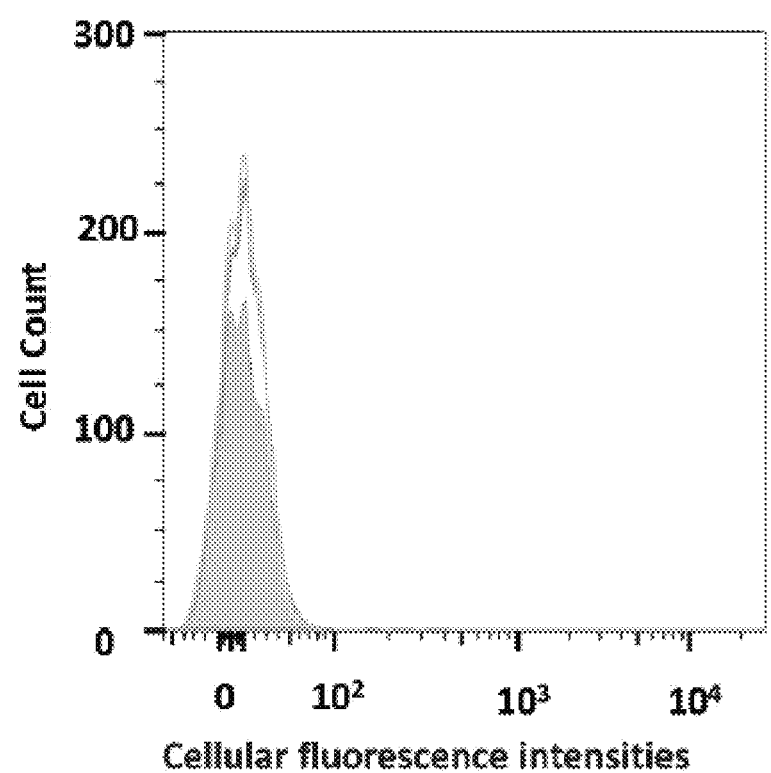
FIG. 44C shows little binding to RMA cells lacking MUC1 was observed with anti-MUC1 sera at 1:50 dilution.

To test the recognition of RMA-MUC1 cells by the post-immune sera, RMA-MUC1 cells were incubated with the sera. After washing off unbound antibodies, cells were treated with a fluorescently labeled anti-IgG secondary antibody. The sera from pre-immunized mice gave little binding to RMA-MUC1 cells (FIG. 44A). In contrast, the post-immune sera exhibited good recognition of RMA-MUC1 cells even at 1:100 dilution (FIG. 44A). Consistent with the ELISA results on the impact of MUC1 density on Qβ, stronger binding was observed from mouse sera following immunization with vaccine construct 11 vs 14 (low MUC1 density) (FIG. 44A). The binding of antibodies induced by 11 to tumor cells was MUC1 dependent, as the post-immune sera did not exhibit significant recognition of RMA cells lacking the MUC1 transgene demonstrating the specificities of the antibodies (FIGS. 44B and 44C).

Figure 45A:
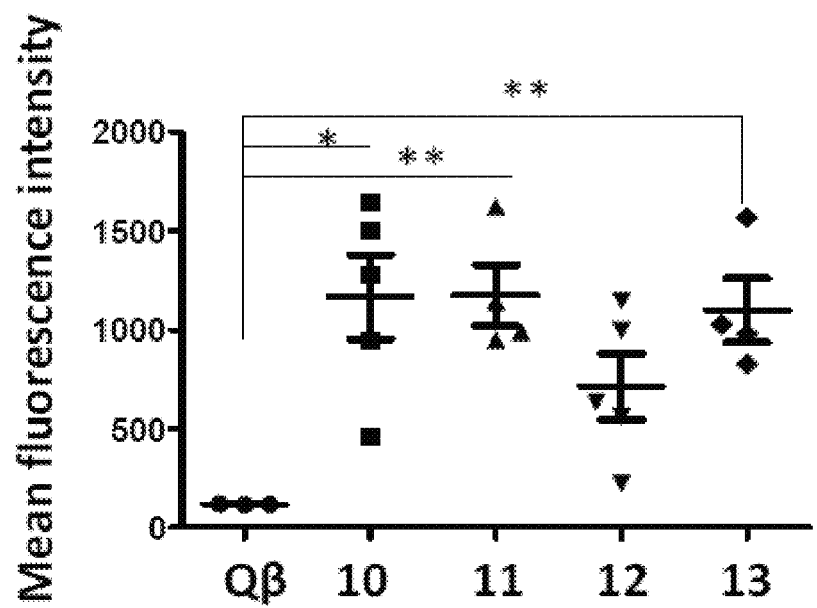
FIG. 45 contains three panels, FIGS. 45A-45C depicting flow cytometry analysis showed that immunization with Qβ-MUC1 conjugates 10-13 induced IgG antibodies capable of binding with a panel of MUC1 expressing tumor cells significantly stronger than sera from mice immunized with Qβ only. Mean fluorescence intensities of binding to (FIG. 45A) RMA-MUC1 cells.
(FIG. 45B) B16-MUC1 cells.
(FIG. 45C) MCF-7 cells. Binding was tested with 1:20 dilutions of the post-immune sera. *p<0.05, p<0.01, *p<0.001. The p values were determined through a two-tailed t-test using GraphPad Prism.
Figure 45B:
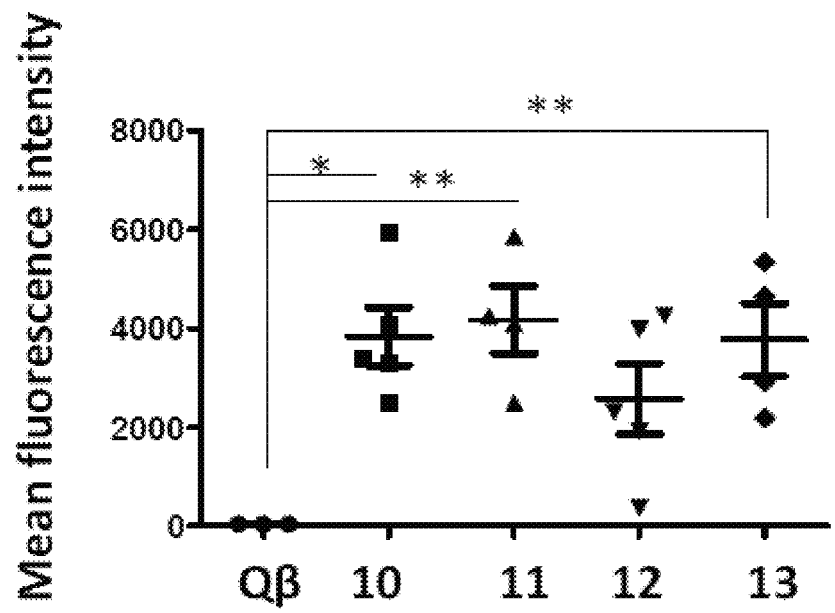
Figure 45C:
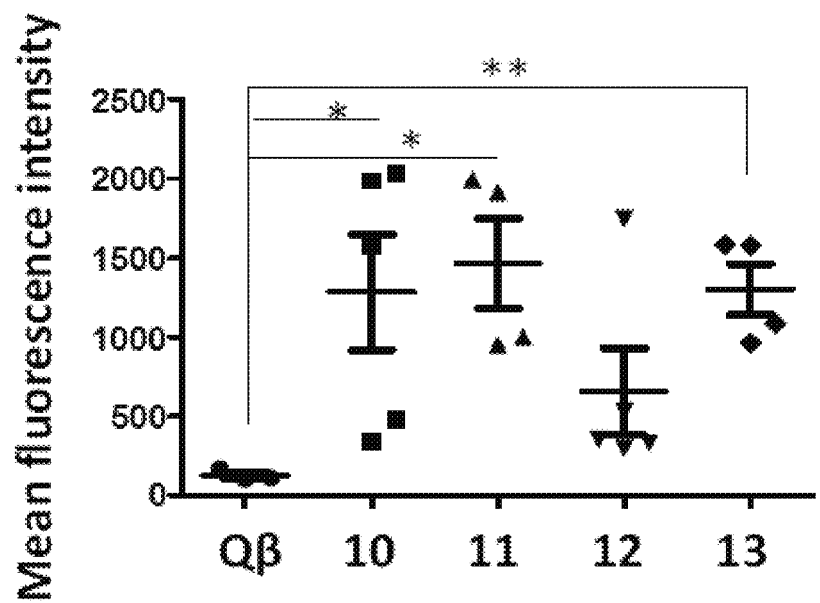

To test the generality of tumor cell recognition, besides RMA-MUC1 cells, binding to mouse melanoma B16-MUC1 cells as well as breast cancer MCF-7 cells were measured with the post-immune sera. Mice immunized with any of the four Qβ-MUC1 constructs 10-13 produced antibodies capable of strong recognition of all MUC1 expressing tumor cells tested (FIG. 45). Antibodies induced by construct 12 with non-glycosylated peptide 3 showed weaker binding to MUC1 expressing tumor cells, suggesting Tn glycosylation of MUC1 glycopeptide in PDT*R domain (SEQ ID NO: 19) contributes to the generation of antibodies for stronger tumor cell binding.

Figure 46:
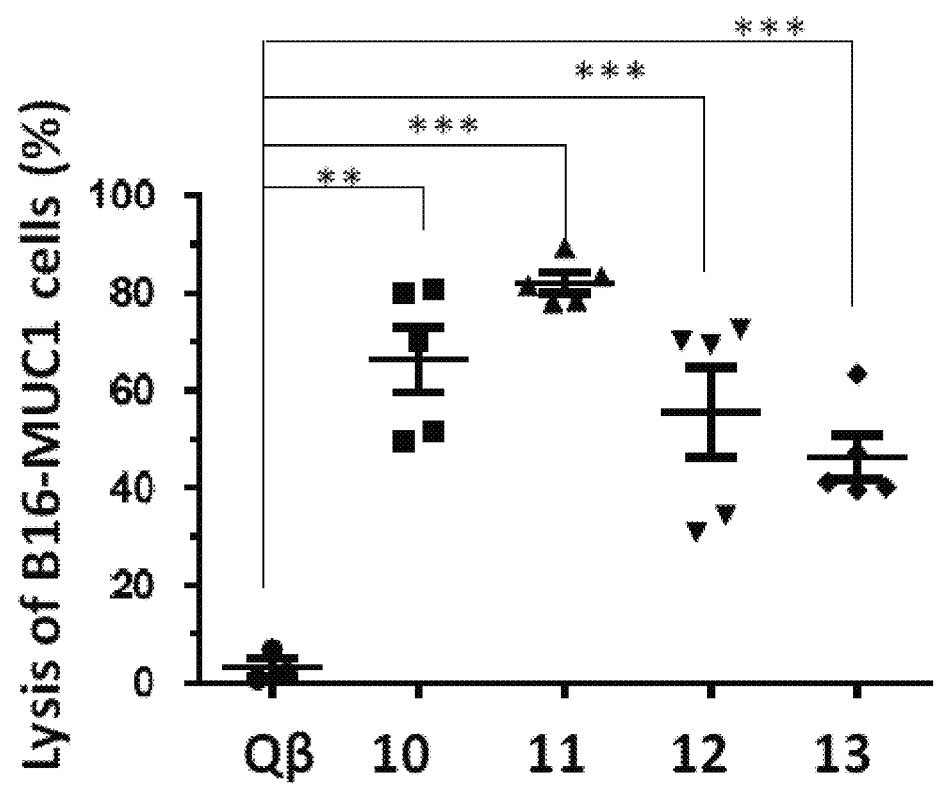
FIG. 46 depicts complement dependent cytotoxicity to B16-MUC1 cells induced by sera from mice immunized with Qβ control, Qβ-MUC1 10-13 respectively (p<0.01; *p<0.001). The p values were determined through a two-tailed t-test using GraphPad Prism.
Figure 76A:
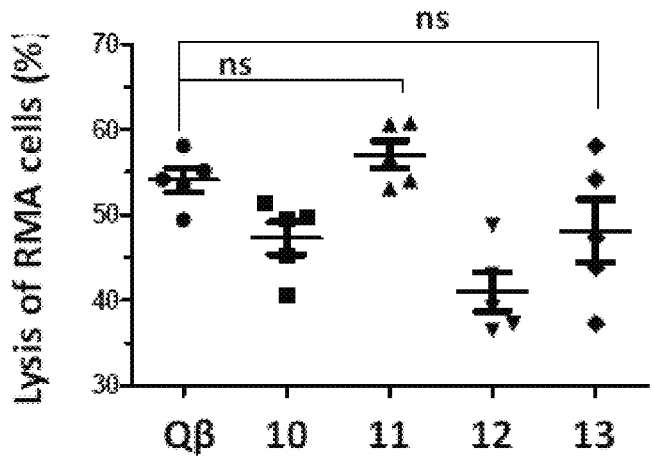
FIG. 76A RMA.
Figure 76B:
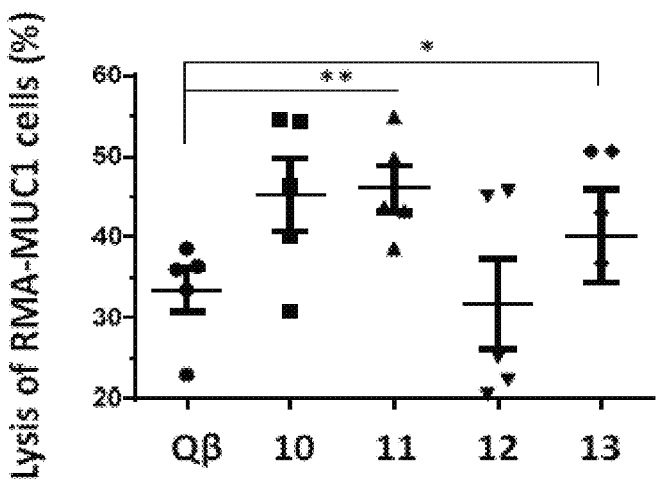
FIG. 76B RMA-MUC1.
Figure 76C:
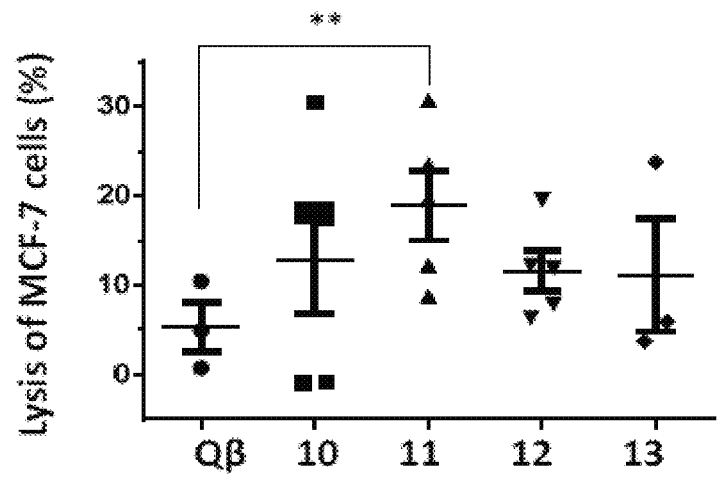
FIG. 76C depict MCF-7 cells induced by sera from mice immunized with Qβ control and Qβ-MUC1 10-13 respectively (p<0.01; *p<0.001). The p values were determined through a two tailed t test using GraphPad Prism. While post-immune sera did not exhibit much killing of RMA cells (panel a), significantly higher killings of MUC1 expressing RMA-MUC1 cells (FIG. 76B) and MCF-7 cells (FIG. 76C) were observed.

With the strong recognition of MUC1 expressing tumor cells, the abilities of the post-immune sera to kill the tumor cells were measured. Incubation of MUC1 expressing tumor cells with the post-immune sera and rabbit complement led to significantly higher percentages of tumor cell death compared to cells treated with control sera (FIG. 46 and FIG. 76. Post-immune sera could kill tumor cells efficiently and in a MUC1-dependent manner.

Example 15: Immunization with Qβ-MUC1 can Induce MUC1 Specific CTLs in Vitro and In Vivo MUC1 is known to contain several CTL epitopes within its tandem repeat regions (Vlad, A. M. et al. (2002) J. Exp. Med. 196, 1435-1446; Apostolopoulos, V. et al. (2003) Proc. Natl. Acad. Sci. U.S.A. 100, 15029-15034; Reddish, M. et al. (1998) Int. J. Cancer 76, 817-823). As one Qβ capsid can deliver hundreds of copies of MUC1, whether Qβ-MUC1 constructs can elicit MUC1 specific CTL responses in immunized mice was tested.

Figure 47A:
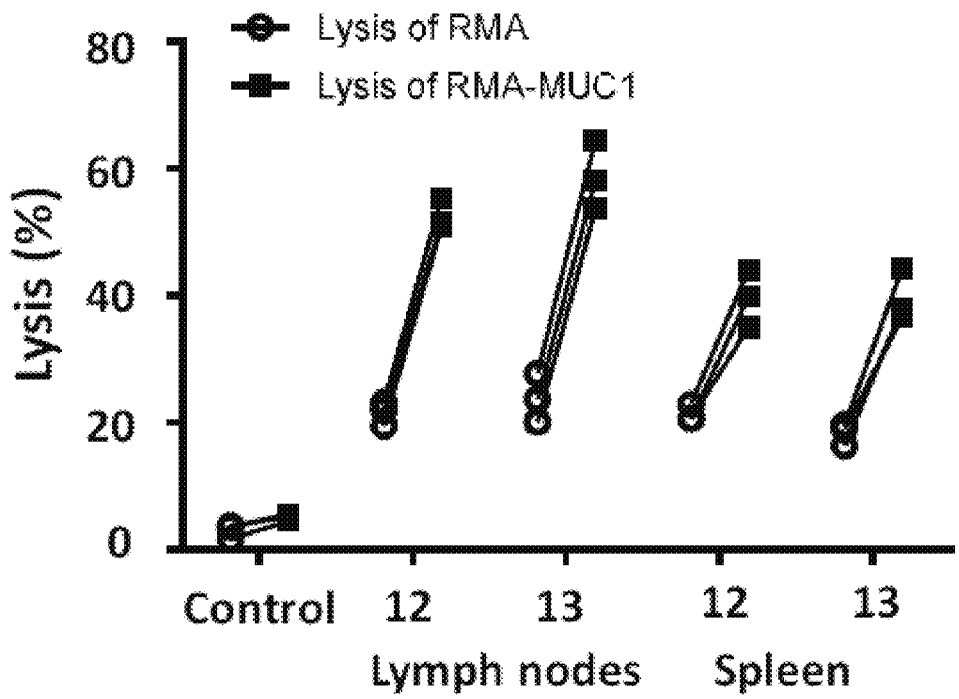
FIG. 47 contains two panels, FIG. 47A and FIG. 47B, depicting MUC1-specific CTL activities have been elicited through immunization with Qβ-MUC1 constructs. The CTL activities were analyzed (FIG. 47A) in vitro and (FIG. 47B) in vivo. Lymphocytes were harvested from lymph nodes and spleen of mice immunized with Qβ (control) or conjugates 12, 13, and analyzed for their cytotoxic activities against RMA and RMA-MUC1 cells by flow cytometry.
FIG. 47B shows CFSE labeled syngeneic splenocytes pulsed with MUC1 ($CFSE^{high}$) or not ($CFSE^{low}$) were injected intravenously into mice immunized with Qβ (control) or Qβ-MUC1 construct 12 or 13. After 24 hours, mice were sacrificed and lymph nodes were harvested. Analysis by flow cytometry showed significantly higher lysis of MUC1 pulsed target cells. Control groups for both panels were mice immunized with Qβ only.

MUC1 specific cytolytic activities were first measured using an in vitro CTL assay. The spleens and lymph nodes were harvested from mice immunized with constructs 12 and 13 as well as from control mice immunized with Qβ only. Splenocytes and lymph node cells were isolated and incubated with RMA-MUC1 and RMA cells respectively, and the viabilities of the tumor cells were measured. As shown in FIG. 46A, cells from mice receiving Qβ only did not lead to significant death of either RMA or RMA-MUC1 cells indicating Qβ by itself was not effective in generating anti-tumor CTL responses. In comparison, lymph node cells from Qβ-MUC1 immunized mice led to significantly higher lysis of RMA-MUC1 cells than RMA cells, suggesting MUC1 dependent CTL activities were generated by Qβ-MUC1 (FIG. 47A). Similar phenomena have been observed with spleen cells from the immunized mice.

Figure 47B:
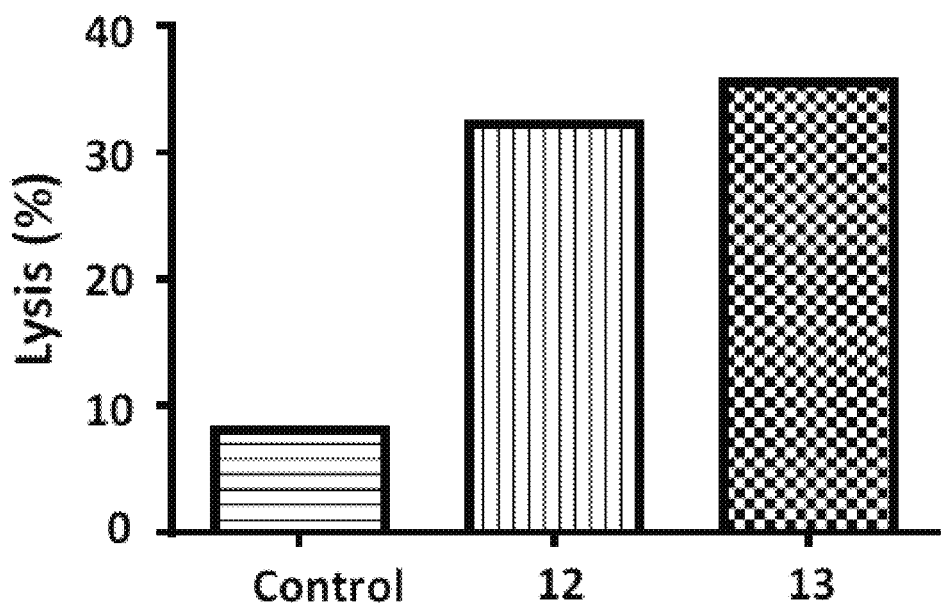
Figure 48:
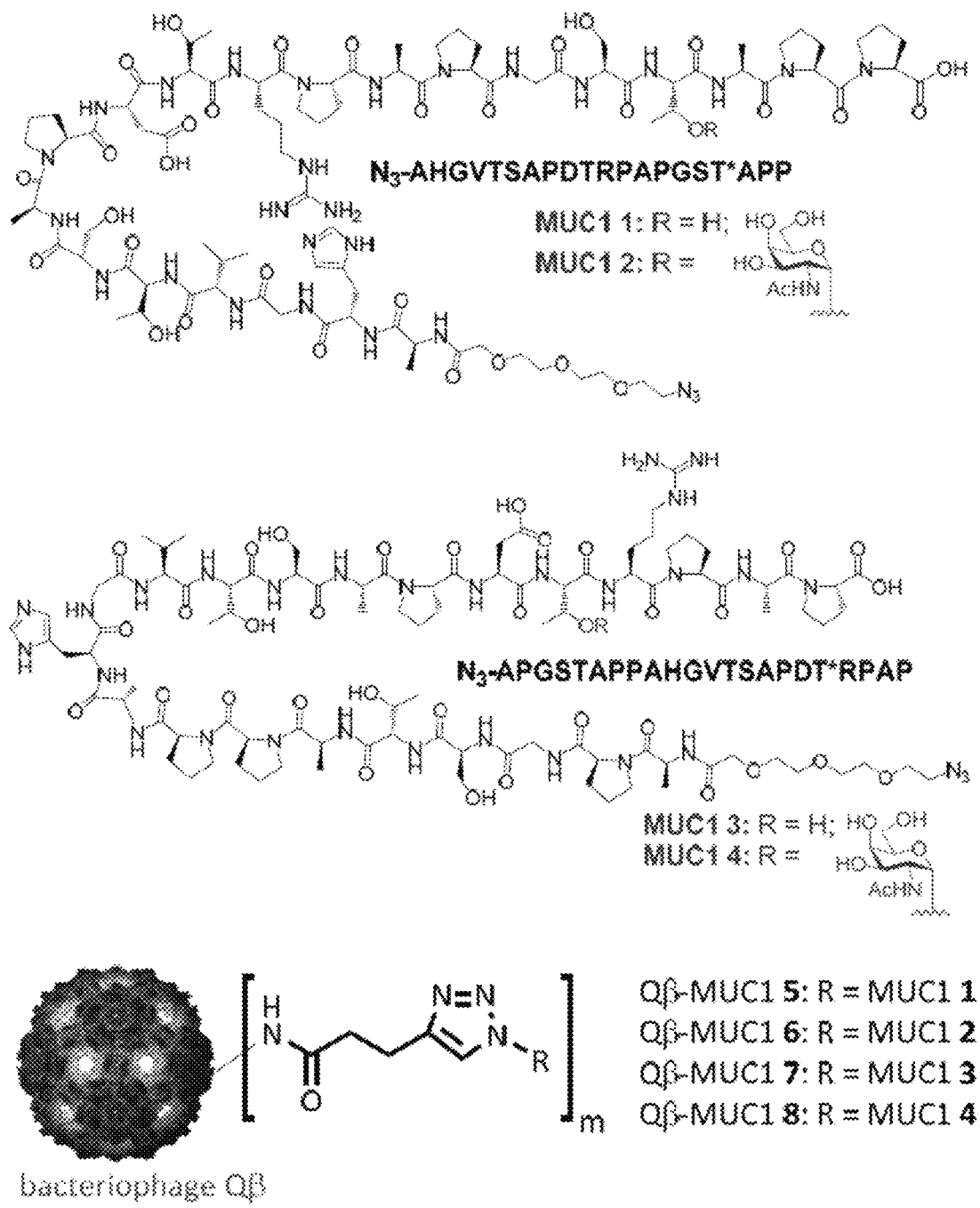
FIG. 48 depicts certain MUC1 (glycol)peptides (1-4) and Qβ-MUC1 conjugates (5-8). Figure discloses SEQ ID NOS 92 and 93, respectively, in order of appearance.

An in vivo cytotoxicity assay for CTLs was carried out. Splenocytes from naïve mice were harvested and labeled with two different concentrations of carboxyfluorescein succinimidyl ester (CFSE) (Jedema, I. et al. (2004) *Blood* 103, 2677-2682). The CFSE$^{high}$ cells were pulsed with a mixture of MUC1 (glyco)peptides 3 or 4, mixed with the same number of non-pulsed CFSE$^{low}$ cells and intravenously injected into mice immunized with Qβ-MUC1 constructs 12 and 13. As shown in FIG. 47B, CFSE$^{high}$ cells were lysed much more than the CFSE$^{low}$ cells that were not incubated with MUC1, suggesting Qβ-MUC1 vaccinations led to activation and expansion of CTLs specific against MUC1.

Example 16: Materials and Methods for Examples 17-26 {FH: This Corresponds to the Tg Manuscript}

Mouse Immunization. MUC1 Tg. mice with a 10.6 kb genomic SacII fragment of the human MUC1 gene, were generated by breeding a MUC1 Tg. male mice with a C57Bl/6 Wt female mice and identified by genotyping with approximately 50% yield. MUC1 Tg. female mice aged 6-10 weeks were maintained in the University Laboratory Animal Resources facility of Michigan State University and used for studies. All animal experiments were performed in accordance with the guidelines of the Institutional Animal Care and Use Committee (IACUC) of Michigan State University. MUC1 Tg. female mice were subcutaneously injected under the scruff on day 0 with 0.1 mL various Qβ-MUC1 vaccines as emulsions in Complete Freund's Adjuvant according to the manufacturer's instructions. Boosters were given subcutaneously under the scruff on days 14 and 28 mixed with Incomplete Freund's Adjuvant. All MUC1 vaccine conjugates administered have the same amounts of GalNAc (1.9 µg). Sera samples were collected on days 0 (before immunization), 7 and 35. The final bleeding was done by cardiac bleed.

Evaluation of antibody titers by ELISA. A Nunc MaxiSorp® flat-bottom 96 well plate was coated with a solution of the corresponding MUC1 (glyco)peptides (10 g/mL, 100 µL/well) in NaHCO$_3$/Na$_2$CO$_3$ buffer (0.05 M, pH 9.6) and incubated at 4° C. overnight. The coated plate was washed with PBS/0.5% Tween-20 (PBST) (4×200 µL) and blocked by 1% BSA/PBS (100 µL/well) at rt for 1 h. The plate was washed again with PBST (4×200 µL) and incubated with serial dilutions of mouse sera in 0.1% BSA/PBS (100 µL/well, 4 wells for each dilution). The plate was incubated for 2 h at 37° C. and then washed with PBST (4×200 µL). A 1:2000 dilution of HRP-conjugated goat anti-mouse IgG (Jackson ImmunoResearch Laboratory) in 0.1% BSA/PBS (100 µL) was added to the wells respectively to determine the titers of antibodies generated. The plate is incubated for 1 h at 37° C. A solution of enzymatic substrate was prepared by dissolving TMB (5 mg) in a mixture of DMSO (2 mL) and citric acid buffer (18 mL) in a 50 mL centrifuge tube covered with aluminum foil. H$_2$O$_2$ (20 µL) was added and the mixture was homogenized by vortexing. The plate was washed with PBST (4×200 µL) and a solution of enzymatic substrate was added (200 µL). Color was allowed to develop for 15 min and 0.5 M H$_2$SO$_4$ (50 µL) was added to quench the reaction. The absorbance was measured at 450 nm using a microplate reader. The titer was determined by regression analysis with log 10 dilution plotted with optical density. The titer was reported as the highest fold of dilution that gives OD=0.3.

Detection of antibody binding to tumor cells by flow cytometry. B16-MUC1 cells, Agl04-MUC1 cells, MCF-7 cells or MCF-10A cells were respectively cultured at 37° C. under 5% C02 in cell growth medium. The mixture of cells in cell growth medium was transferred to a conical centrifuge tube, and centrifuged at 1,600 rpm for 5 min at 4° C. The pellet was re-suspended in growth medium (10 mL). The number of cells was determined with a hemocytometer. Suspensions of 3.0×10$^5$ cells were added to each FACS tube, which were centrifuged at 1,600 rpm for 5 min to remove the supernatant. The cells were washed with FACS buffer (1% FBS in PBS with 0.1% NaN$_3$), and incubated with 1:20 dilution of mouse sera in PBS (100 µL) for 30 min on ice. The incubated cells are washed twice with FACS buffer, which was followed by incubation with FITC anti-mouse IgG (2 µL, 0.5 mg/mL) for 30 min on ice. The cells were washed twice and re-suspended in FACS buffer before analysis by LSR II (BD Biosciences). Data is processed by FlowJo software.

Complement dependent cytotoxicity. Complement dependent cytotoxicity of B16-MUC1 or MCF-7 cells were determined by MTS assay. B16-MUC1 or MCF-7 cells (7000 cells/well) were cultured for 12-48 h (12 h for B16-MUC1, 48 h for MCF-7), and incubated with a dilution of mouse sera (1/40 for B16-MUC1, 1/40 for MCF-7) in 50 µL of culture medium at 37° C. for 30 min from different groups of immunized MUC1 Tg. mice, rabbit sera complement at a dilution (1/5 for B16-MUC1, 1/15 for MCF-7) in 50 µL of culture medium were added and then incubated at 37° C. for 4 h. MTS (CellTiter 96 AQueous One Solution Cell Proliferation Assay; Promega, 20 µL) was added into each well and further incubated at 37° C. for 3 h. The optical absorption of the MTS assay was measured at 490 nm. Cells cultured in medium alone were used as a positive control (maximum OD), and culture medium was used as a negative control (minimum OD). All data were performed with four repeats. Cytotoxicity was calculated as follows: cytotoxicity (%)=(OD positive control−OD experimental)/(OD positive control−OD negative control)×100.

Antibody-dependent cell-mediated cytotoxicity. Primary NK cells and LAK cells were generated by a standard method. Briefly, splenocytes from C57BL/6 mice were processed and labeled directly with CD45R microbeads (Miltenyi Biotec, Auburn, Calif.). B220-splenocytes were then FACS-sorted using anti-NK1.1 and TCRP antibodies (Biolegend, San Diego, Calif.), isolating populations that were more than 95% NK1.1$^+$TCR$^-$. All monoclonal antibodies were from Biolegend. Purified NK cells were plated in complete IMDM (Gibco, Waltham, Mass.) with 500 U/mL rhIL-2 (Peprotech, Rocky Hill, N.J.) and maintained for 8 days to generate LAK cells. Freshly isolated and expanded LAK cells were used in the ADCC assay. B16-MUC1 cells were incubated with either control sera from Qβ immunized MUC1 Tg. mice or study sera from Qβ-MUC1 27 immunized MUC1 Tg. mice and 100 µCi $^{51}$Cr (Na$_2$CrO$_4$) (Perkin Elmer, Waltham, Mass.) for 2 h at 37° C. Cells were extensively washed and plated (2000 cells/well/100 μL) with varying numbers of NK or LAK cells. After 16 h, culture supernatant was harvested and analyzed for $^{51}$Cr counts per minute (cpm) on LumaPlates (Perkin Elmer) in a MicroBeta2 gamma counter (Perkin Elmer). Percent specific lysis was calculated as described (Das et al. (2013) *Blood* 121, 3386-3395).

Immunochemistry staining of a breast cancer tissue microarray. The breast carcinoma tissue array from US Biolab (BRE060-03) was performed antigen retrieval to unmask the antigenic epitope with 10 mM citrate buffer (pH 6.0) at 95-100° C. for 10 min. The slide was moved to rt to cool for 20 min, washed with PBS (2×, 5 min each) and incubated with blocking buffer (5% BSA in PBS) at rt for 1 h. The slide was then incubated with diluted mouse sera (1:1000) from Qβ-MUC1 43 immunized MUC1 Tg. mice at rt for 1 h, washed with PBS (2×, 5 min each) and stained with diluted goat-anti-mouse IgG secondary antibody conjugated to horseradish peroxidase (HRP) (1/1000) at rt for 30 min. The slide was washed with PBS (2×, 5 min each), incubated with DAB substrate solution for allowing the color development for <5 min until the desired color intensity is reached, followed by washing with PBS (3×, 2 min each) and staining with hematoxylin for 1-2 min. The brown color of the antibody staining in the tissue was observed under microscopy.

Cancer immunotherapy studies. For the lung metastasis model, pathogen-free MUC1 Tg. female mice aged 6-10 weeks were subcutaneously injected under the scruff on day 0 with 0.2 mL Qβ-MUC1 43, KLH-MUC1 44 or Qβ in PBS mixed with MPLA (20 μL, 1 mg/mL in DMSO). Boosters were given subcutaneously under the scruff on days 14 and 28 mixed with MPLA. On day 35, vaccinated mice were challenged by intravenous injection of 1×10$^5$ B16-MUC1 cells per mouse, followed by 4$^{th}$ immunization of conjugates mixed with MPLA. On day 45, the mice were given 5$^{th}$ immunization of vaccines mixed with MPLA. On day 56, pulmonary metastases were enumerated by intra-tracheal injection of black ink (50% in PBS). Black ink injected lungs were washed in Feket's solution (300 ml 70% EtOH, 30 ml 37% formaldehyde, 5 ml glacial acetic acid) and then placed in fresh Feket's solution overnight. White tumor nodules against a black lung background were then counted.

For combinatorial immunotherapy, pathogen-free MUC1 Tg. female mice aged 6-10 weeks were immunized with Qβ or Qβ-MUC1 43 on days 0, 14 and 28 plus MPLA as an adjuvant, challenged with 5×10$^5$ B16-MUC1 cells on day 35 by subcutaneous inoculation, followed by 4$^{th}$ immunization, and then given 5$^{th}$ immunization on day 42, followed by anti-PD1 (100 μg per mouse, clone: RMP1-14, BioXcell) treatment on day 43 and day 46 respectively via intraperitoneal injection. On day 49, the mice were given 6$^h$ immunization with MPLA, followed by anti-PD1 treatment on day 50 and day 53. Tumor volume was determined by the formula: Volume (mm$^3$)=(length×width×height) (Tomayko, M. M. et al. (1989) *Cancer chemotherapy and pharmacology* 24, 148-154). Mice were euthanized when the tumor volume was over 1600 mm$^3$ or ulceration of tumors was observed.

Example 17: Despite Producing High IgG Titers Against the Immunizing MUC1 Structures in Immunotolerant MUC1 Transgenic Mice, First Generation Qβ-MUC1 Constructs 5-8 Failed to Elicit IgG Antibodies for Strong Tumor Cell Binding For MUC1 based vaccine design, our first generation approach was based on MUC1 (glyco)peptides 1-4, which contain 20-22 amino acid residues as the backbone covering one full length of the tandem repeat region. MUC1 (glyco) peptides were conjugated to bacteriophage Qβ as the carrier through an N-terminal azide group by the copper-catalyzed azide-alkyne cycloaddition (CuAAc) reaction (Qβ-MUC1 conjugates 5-8). When administered in wild type (WT) C57BL/6 mice, these constructs elicited super strong antiMUC1 IgG responses, with average titers exceeding 2,000,000 evaluated by ELISA assays against the immunizing MUC1 structures. Furthermore, the antibodies produced could recognize multiple MUC1 expressing tumor cells when analyzed by fluorescence activated cell sorting (FACS) assays. With these promising results in hand, further studied these constructs in human MUC1 transgenic (MUC1.Tg) mice.

As discussed above, the sequences of mouse mucins are different from that of human MUC1, and human MUC1 is a foreign antigen with good immunogenicity in mice. As a result, human MUC1 expressing tumor cannot grow in wild type mice as they are rejected by the immune system. To mimic the tolerant condition towards MUC1 in humans, human MUC1 transgenic C57BL/6 mice (MUC1.Tg) were bred that endogenously express human MUC1 in a developmentally regulated and tissue-specific fashion. MUC1.Tg mouse is a suitable model for vaccine evaluation, since MUC1 expression levels and patterns as well as MUC1 tolerance by immune cells in MUC1.Tg mice are similar to those in humans. Unlike wildtype mice, untreated MUC1.Tg mice cannot reject MUC1-expressing tumor cells confirming the immune tolerance to human MUC1.

Figure 49A:
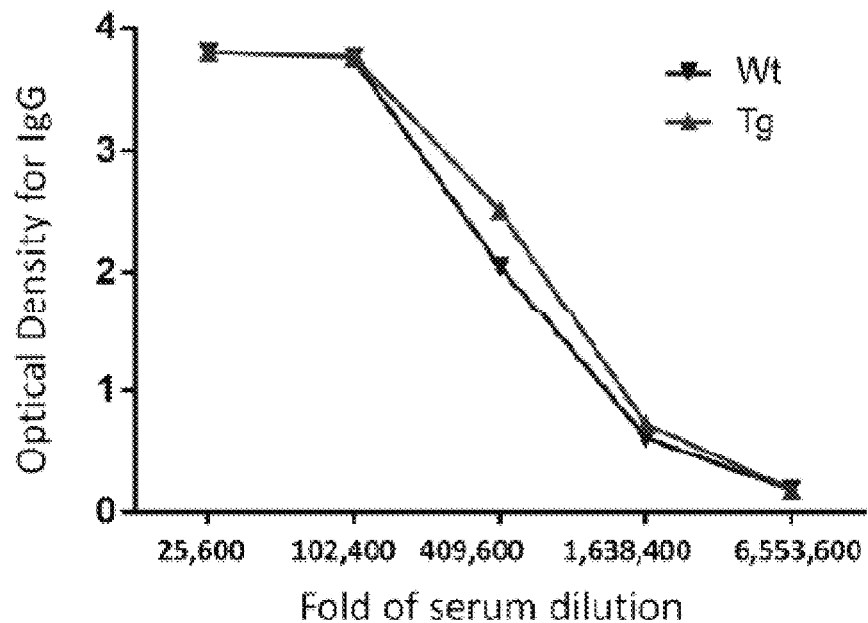
FIG. 49A depicts a comparison of post-immune sera from WT and MUC1.Tg mice immunized with Qβ-MUC1 5 showed that the IgG antibody titers were similar when assayed against the immunizing antigen MUC1 1. For clarity, only results from one representative mouse are shown.
Figure 49B:
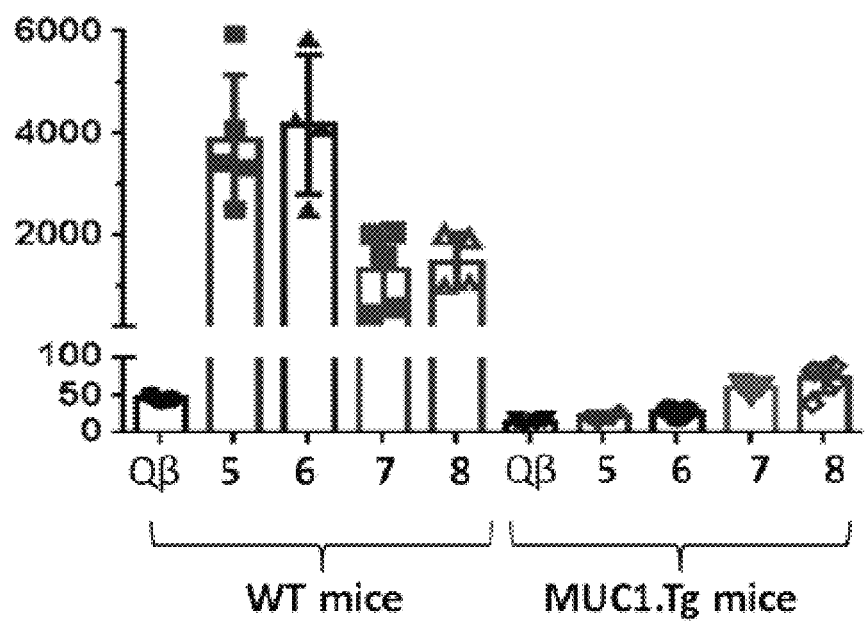
FIG. 49B shows mean fluorescence intensities of B16-MUC1 cells upon incubation with post-immune sera from immunized mice. Despite similar IgG titers, sera from Tg mice bound B16-MUC1 cells significantly weaker than those from the corresponding WT mice.

Following the same immunization protocol with one prime and two booster injections two weeks apart as in WT mouse studies, MUC1.Tg mice were vaccinated with the conjugates of Qβ-MUC1 5-8. On day 35 after the initial injection, sera were collected from mice and analyzed. ELISA showed that high levels of anti-MUC1 IgG were generated, similar to those from WT mice when assayed against the corresponding MUC1 (glyco)peptide 1-4 (FIG. 49A). FACS analysis was then carried out to test the binding of a panel of MUC1 expressing tumor cells including Ag104-MUC1 fibrosarcoma, B16-MUC1 melanoma and MCF-7 breast cancer cells. The tumor cells were incubated with the post-immune sera from Qβ-MUC1 5-8 immunized Tg. mice, followed by staining with FITC-labeled anti-mouse IgG secondary antibody. In spite of the good IgG titers, FACS results indicated that these sera exhibited much weaker binding to MUC1 expressing tumor cells (FIG. 49B) with the binding levels less than 3% of those from wild type mice. The observations of low reactivities against tumor cells induced in MUC1.Tg mice are similar to results from clinical studies of MUC1 based vaccines. Previously we reported that Qβ-MUC1 7 and 8 were able to generate MUC1 specific cytotoxic T cell (CTL) responses in WT mice. However, when evaluated in Tg mice, these constructs did not elicit significant CTL based cytotoxicities towards cancer cells (data not shown). The poor tumor cell binding by antibodies generated and low CTL activities suggest Qβ-MUC1 5-8 would not be effective in providing protections against tumor development in immunotolerant MUC1.Tg mice. While both CTL and antibody responses can be important for tumor protection, we chose to first focus on designing Qβ-MUC1 to elicit protective antibodies.

Example 18: Epitope Profiling of Induced Antibodies from WT and Tg Mice Provided Critical Insights into Epitope Design To better understand the weak tumor cell recognition by antibodies from Tg mice immunized with the first generation Qβ-MUC1 vaccines, we performed epitope scanning of these antibodies. A library of twenty MUC1 peptides was synthesized, each of which contained 8 amino acid residues with sequences overlapping by 7 amino acids covering the full length of one MUC1 tandem repeat. These peptides were then conjugated with bovine serum albumin (BSA) as a multivalent platform to afford twenty BSA-MUC1 conjugates 9-28.

For epitope mapping, ELISA wells coated with individual BSA-MUC1 conjugate were incubated with the post-immune sera from Qβ-MUC1 5 immunized MUC1.Tg mice. The relative levels of recognition of each MUC1 epitope were quantified through ELISA, which indicated that sera exhibited bindings to two main regions, i.e., HGVTSAPD (SEQ ID NO: 54) and PGSTAPPA (SEQ ID NO: 55) and adjacent amino acid residues (right panel FIG. 50). These results suggest that HGVTSAPD (SEQ ID NO: 54) and PGSTAPPA (SEQ ID NO: 55) are the epitopes within MUC1 peptide 1 dominating antibody responses in Tg mice. The lack of strong tumor cell binding by post-immune sera could be because levels of antibodies against HGVTSAPD (SEQ ID NO: 54) or PGSTAPPA (SEQ ID NO: 55) were not high enough. Alternatively, epitopes other than HGVTSAPD (SEQ ID NO: 54) and PGSTAPPA (SEQ ID NO: 55) may be critical for tumor cell binding.

Figure 50:
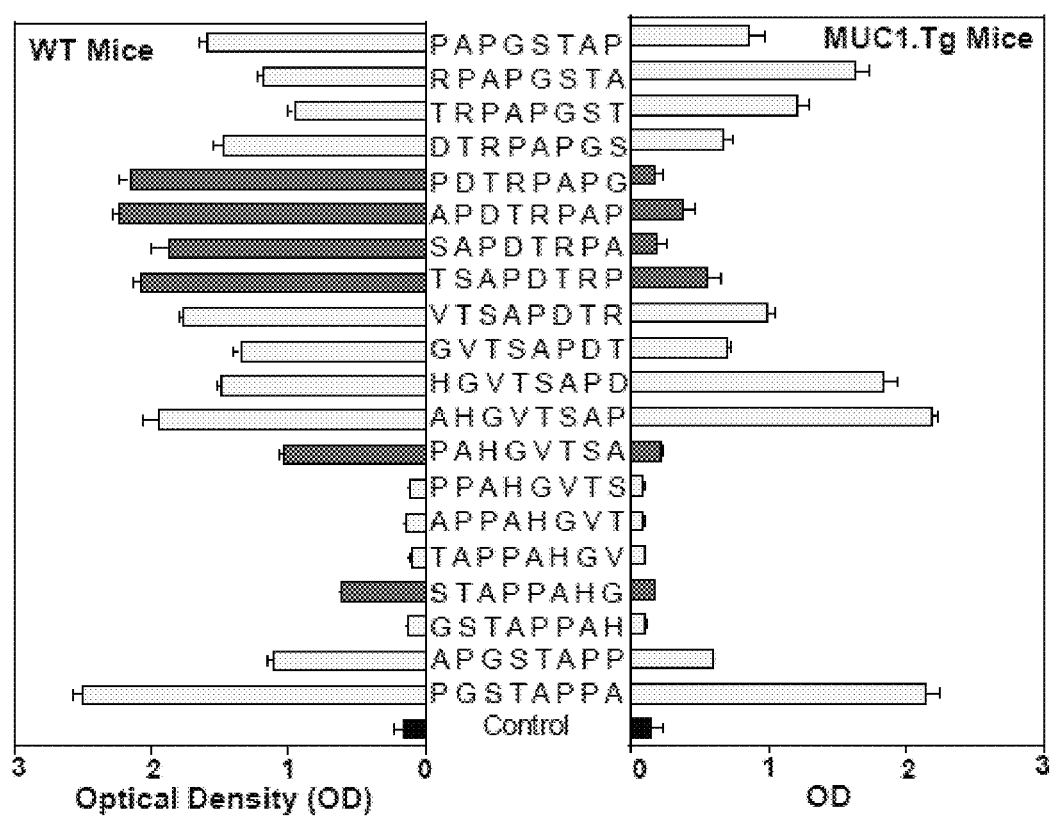
FIG. 50 shows epitope mapping of IgG antibody binding to BSA-MUC1 conjugates by sera from Qβ-MUC1 5 immunized WT and MUC1.Tg mice. Figure discloses SEQ ID NOS 73-78, 58, 79-81, 54, 82-88, 57, and 55, respectively, in order of appearance.

To gain insights on key epitopes of MUC1, epitope profiles of post-immune sera from WT mice were obtained from BSA-MUC1 peptide binding and compared with those from MUC1.Tg mice. It was interesting to note that the levels of antibody binding to HGVTSAPD (SEQ ID NO: 54) and PGSTAPPA (SEQ ID NO: 55) regions were comparable in WT vs Tg mice, which are consistent with the observations of similar IgG titers in ELISA (FIG. 49A). However, WT mouse sera exhibited much stronger binding to the SAPDTRPAP region (SEQ ID NO: 56) (FIG. 50, left panel). This suggests SAPDTRPAP (SEQ ID NO: 56) may be the key epitope required for strong tumor cell recognition with antibodies to other regions such as HGVTSAPD (SEQ ID NO: 54) and APGSTAPP (SEQ ID NO: 57) not contributing significantly.

Figure 51:
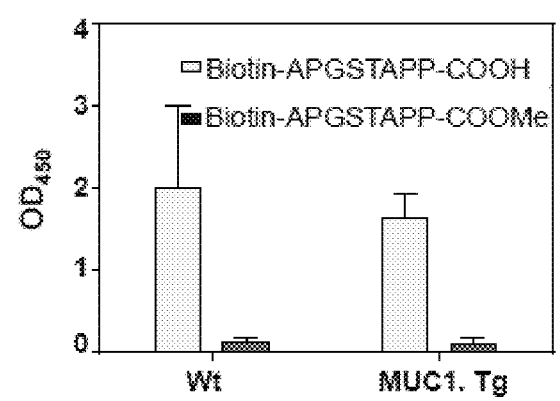
FIG. 51 shows the conversion of the C-terminus of MUC1 peptide to methyl ester significantly reduced antibody binding to MUC1 by sera from both WT and MUC1.Tg mice. Figure discloses SEQ ID NOS 89 and 90, respectively, in order of appearance.
Figure 52:
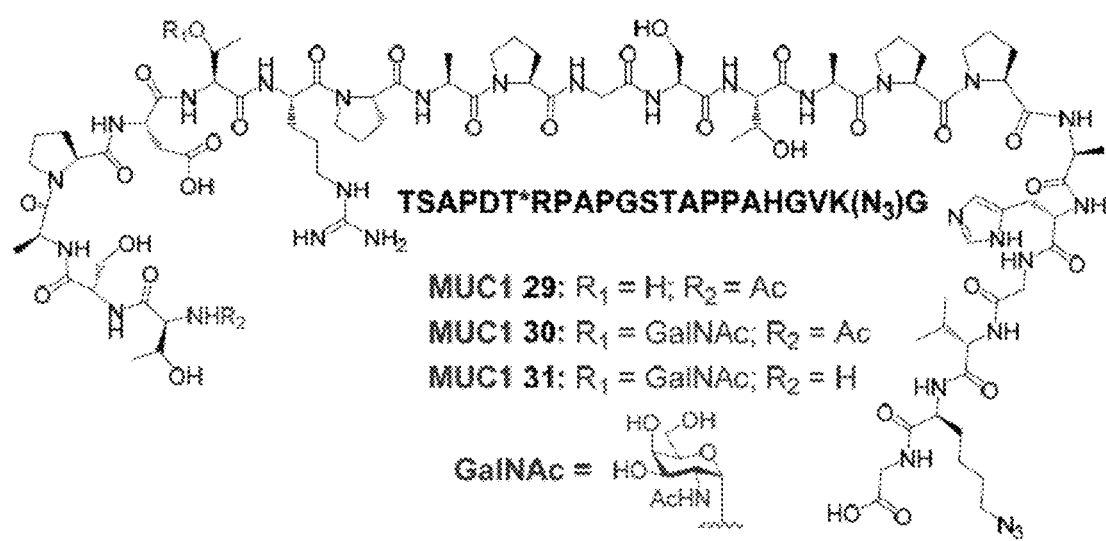
FIG. 52 shows synthesis of MUC1 (glycol)peptides 29-31. Figure discloses SEQ ID NO: 94.

Example 19: Antibodies were Elicited Against the Free C-Termini of MUC1 Peptides During epitope scanning of post-immune sera from immunized mice, free C-termini of MUC1 peptides were found to be important for antibody recognition. As shown in FIG. 51, sera from conjugate Qβ-MUC1 5 vaccinated WT and Tg mice exhibited similar strong recognition to the APGSTAPP region (SEQ ID NO: 57). However, when the C-terminus of this peptide was capped as a methyl ester, binding was much reduced (FIG. 51). Similar phenomena were observed for other regions of MUC1. This suggests that the free C-termini of MUC1 peptides 1-4 contributed significantly to epitope recognition. As the tandem repeat regions of MUC1 do not contain free C-termini in nature, antibody responses against the free C-terminus of the immunizing antigen would not contribute to binding of MUC1 expressing tumor cells.

Example 20: Synthesis and Evaluation of Second Generation of Qβ-MUC1 Conjugates 35-37 with MUC1 Linked from the C-Terminus To remove the interference of free C-terminus of MUC1, our second generation vaccines have the MUC1 (glyco) peptide conjugated to Qβ through its C-terminus. In addition, as antibodies against the SAPDTRPAP region (SEQ ID NO: 56) were thought to be important for tumor cell binding, MUC1 peptide sequence 29 was designed with SAPDTRPAP (SEQ ID NO: 56) moved closer to the N-terminus, which would be more accessible to B cell binding. Furthermore, a GalNAc moiety was introduced onto the threonine residue in the SAPDTRPAP region (SEQ ID NO: 56) leading to glycopeptide 30 to explore the effect of glycosylation Ryan, S. O. et al. (2010) *Cancer Res.* 70, 5788-5796; von Mensdorff-Pouilly, S. et al. (2011) *Cancers* 3, 3073-3103). Glycopeptide 31 was also designed, which had the same structure as 30 except for its free N-terminus.

Figure 53:
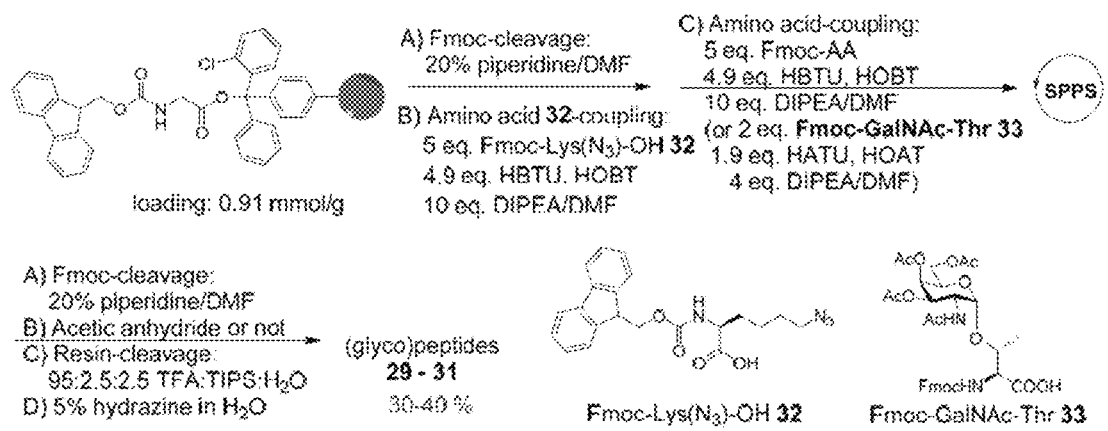
FIG. 53 shows solid phase synthesis of MUC1 (glycol) peptides 29-31 (Scheme 3).

The synthesis of the MUC1 (glyco)peptides 29-31 was performed through solid-phase peptide synthesis (SPPS) using Fmoc chemistry (FIG. 53). To facilitate bioconjugation, azido lysine was introduced close to the C-terminus with the $N^α$-Fmoc-$N^ε$-azide-L-Lysine (Fmoc-Lys($N_3$)—OH building block 32). For glycopeptide synthesis, Fmoc protected GalNAc-threonine 33 (Fmoc-GalNAc-Thr) (Sungsuwan, S. et al. (2015) *ACS Appl. Mater. Interface* 7, 17535-17544) was used as a glycosyl amino acid cassette. After assembly of (glyco)peptides, the N-terminal Fmoc group was removed and was either left free (for glycopeptide 31) or capped with acetic anhydride (29-30). The resulting (glyco)peptides were cleaved from the resins by trifluoroacetic acid (TFA)/triisopropyl silane (TIPS)/$H_2O$. C18 reverse phase HPLC purification produced the desired MUC1 (glyco)peptides 29-31 in 30-40% yields.

Figure 54:
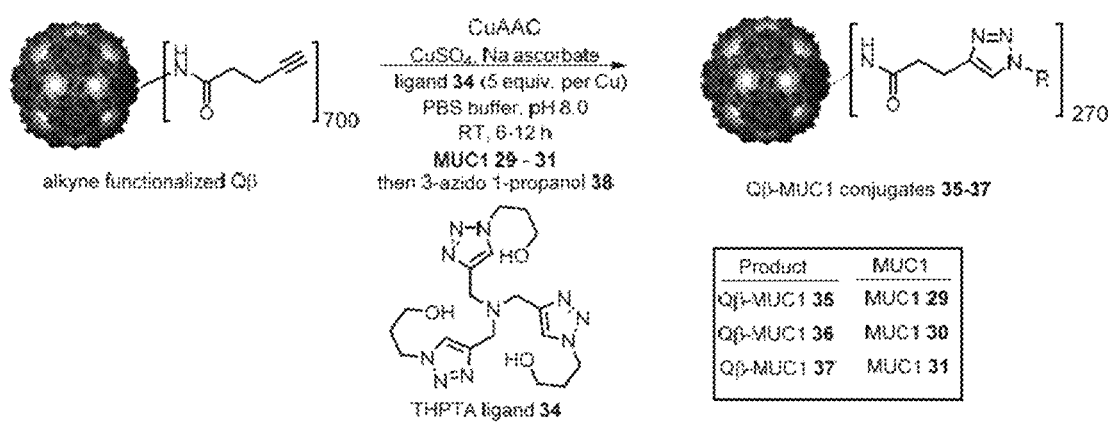
FIG. 54 shows synthesis of Qβ-MUC1 conjugates 35-37 (Scheme 4).

The ligation of MUC1 29-31 onto Qβ-VLP was performed with the CuAAC reaction (Hong, V. et al. (2009) *Angew. Chem. Int. Ed.* 48, 9879-9883). Azide modified MUC1 29-31 were coupled with the alkyne functionalized Qβ promoted by $Cu^{2+}$ catalyst and ligand 34 (FIG. 54). The numbers of (glyco)peptides introduced onto Qβ were 270 on average for conjugates 35-37. The unreacted alkyne groups on Qβ capsids were capped using an excess of 3-azido 1-propanol 38 by a second CuAAC reaction.

Figure 55A:
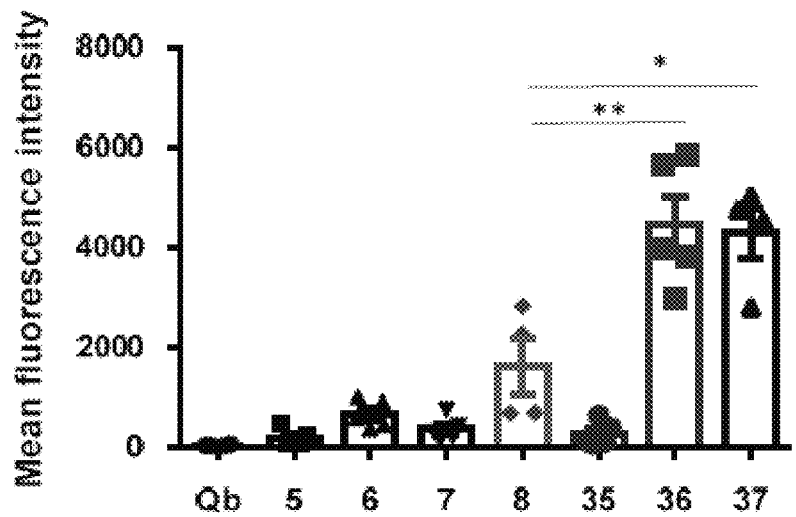
FIG. 55 contains two panels, FIG. 55A and FIG. 55B showing flow cytometry analysis of the specificity of anti-MUC1 IgG antibodies by various conjugates. Binding to (FIG. 55A) Ag104-MUC1 cells.
(FIG. 55B) B16-MUC1 cells; was tested with 1:20 dilution of the corresponding serum. *p<0.05, **p<0.01. The p values were determined through a two tailed t test using GraphPad Prism.
Figure 55B:
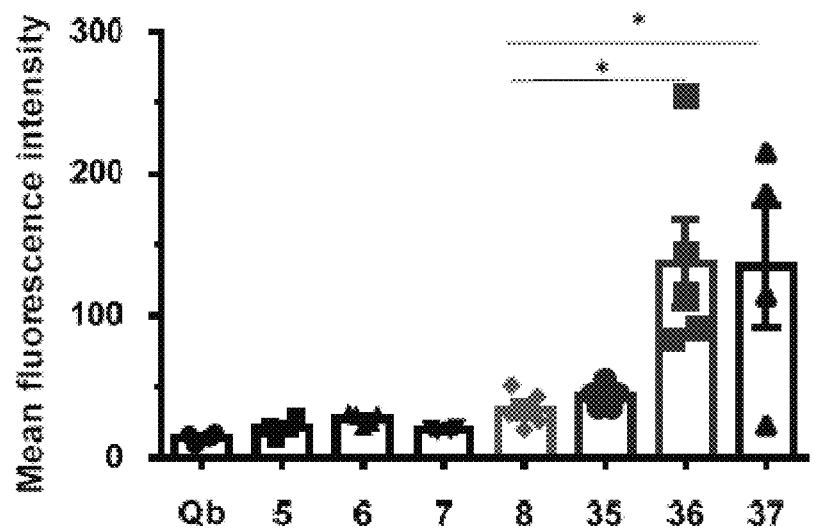

With Qβ-MUC1 conjugates 35-37 in hand, immunization of MUC1.Tg mice was performed. As ELISA titers only measure the levels of antibodies to the immunizing antigen, our analysis of post-immune sera primarily focused on tumor cell binding as a measure of the quality of immune responses. Similar bindings to tumor cells by sera from 36 and 37 immunization (FIG. 55) were observed, suggesting the amino group of N-terminus of MUC1 (glyco)peptides can be either free or protected as acetamide without affecting much the production of anti-MUC1 antibodies. Compared to the first generation vaccine, both Qβ-MUC1 36 and 37 elicited antibodies with higher binding to tumor cells (FIGS. 55A-55B). Thus, connecting MUC1 peptide through the C-terminus could significantly enhance tumor cell binding by the induced antibodies.

Figure 56:
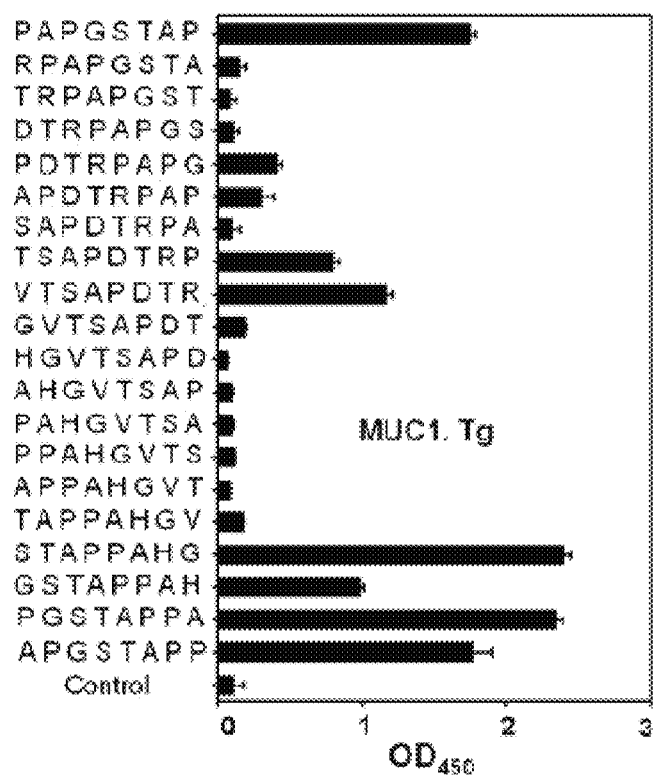
FIG. 56 shows epitope mapping of antibodies binding to BSA-MUC1 conjugates 9-28 coated in ELISA wells by the sera from Qβ-MUC1 37 immunized MUC1.Tg mice. Figure discloses SEQ ID NOS 73-78, 58, 79-81, 54, 82-88, 55, and 57, respectively, in order of appearance.
Figure 57:
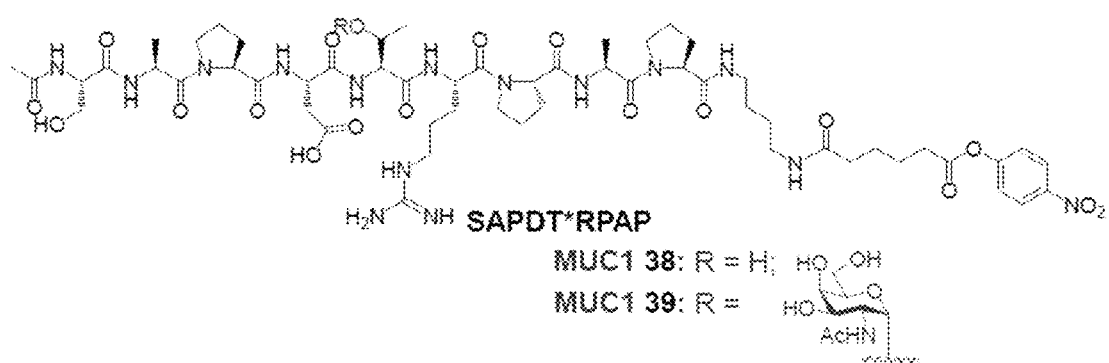
FIG. 57 shows synthesis of MUC1 peptide 38 and glycopeptide 39. Figure discloses SEQ ID NO: 95.

With enhanced tumor binding, the binding epitopes of mice immunized with the second generation vaccine were mapped with BSA-MUC1 conjugates 9-28. As shown in FIG. 56, significant binding to SAPDTRPA (SEQ ID NO: 58) region was observed (double check peptide scanning results). Interestingly, while antibody binding to HGVTSAPD (SEQ ID NO: 54) was much reduced, there were still significant levels of antibodies recognizing the APGSTAPP region (SEQ ID NO: 57) even though it was located at the C-terminus of the antigen, suggesting APGSTAPP (SEQ ID NO: 57) is immunodominant, which may compete with SAPDTRPA (SEQ ID NO: 58) for B cell recognition and subsequent antibody production.

Example 21: Synthesis of Third Generation Q-MUC1 Conjugates 42-43 and KLH-MUC1 Conjugate 44

To further focus the antibody responses on the desired region, for the third generation immunogen design, MUC1 peptide was shortened to remove both HGVTSAPD (SEQ ID NO: 54) and APGSTAPP (SEQ ID NO: 57) regions. In addition, in our prior studies of other carbohydrate based vaccines, we discovered that the triazole moiety in the linker formed through the CuAAC reaction was detrimental to antibody generation against the desired carbohydrate antigen. Thus, a flexible alkyl amide linker was selected to link MUC1 (glyco)peptides to Qβ carrier.

Figure 58A:
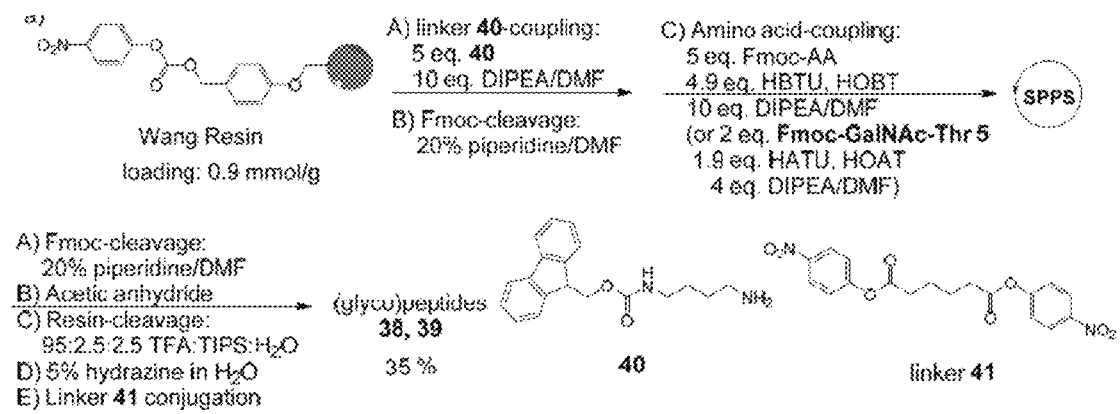
FIG. 58A-58C.
Figure 58B:
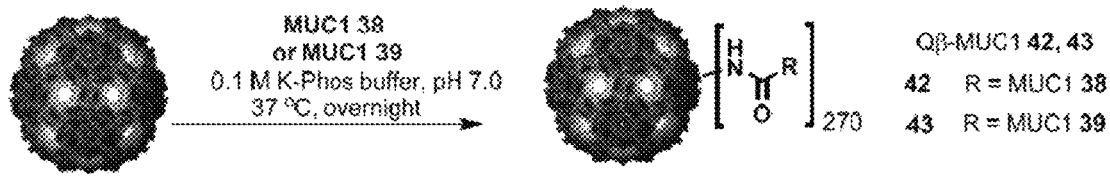
Figure 58C:
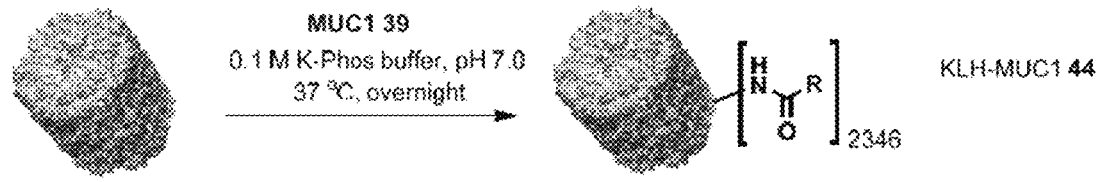

MUC1 peptide 38 and glycopeptide 39 were synthesized using SPPS starting from the p-nitrophenyl carbonate functionalized Wang resins, which were loaded with Fmoc-1,4-diaminobutane 40 first followed by peptide/glycopeptide elongation (FIG. 58A). After capping the N-terminus, deprotection and cleavage from the resin, the free (glyco)peptides were incubated with adipate bis(4-nitrophenyl) ester 41, producing MUC1 (glyco)peptides 38 and 39. MUC1 (glyco) peptides 38 and 39 were then ligated with Qβ through amide bonds to give Qβ-MUC1 42, 43 (FIG. 58B).

Example 22: Antibodies Induced by Qβ-MUC1 43 in MUC1.Tg Mice Showed the Strongest Binding to MUC1-Expressing Tumor Cells Compared to Second Generation Qβ-MUC1 37 and KLH-MUC1 44

Figure 59A:
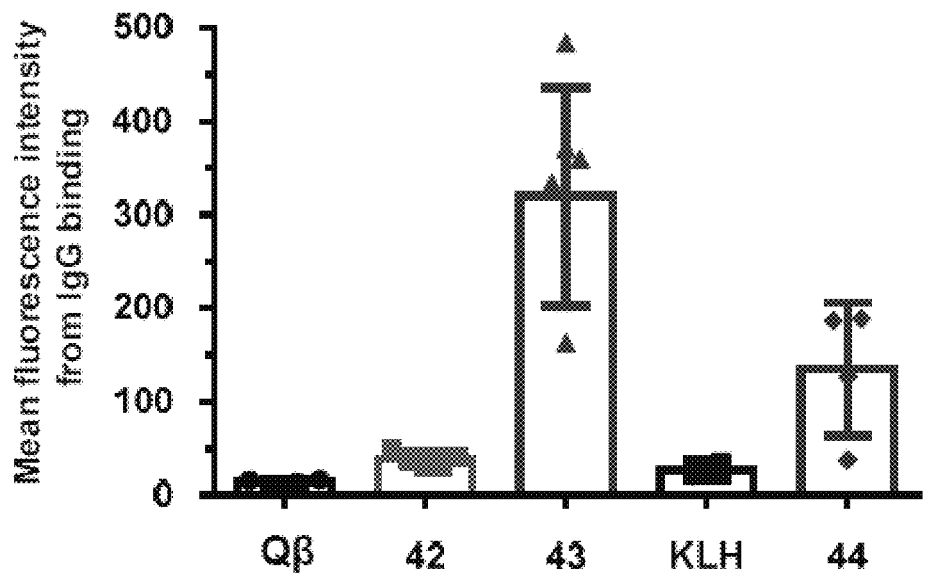
FIG. 59A-59C, showing flow cytometry analysis of cell binding by post-immune sera elicited by various conjugates. Mean fluorescence intensities of IgG antibody binding to (FIG. 59A) B16-MUC1 cells.
Figure 59B:
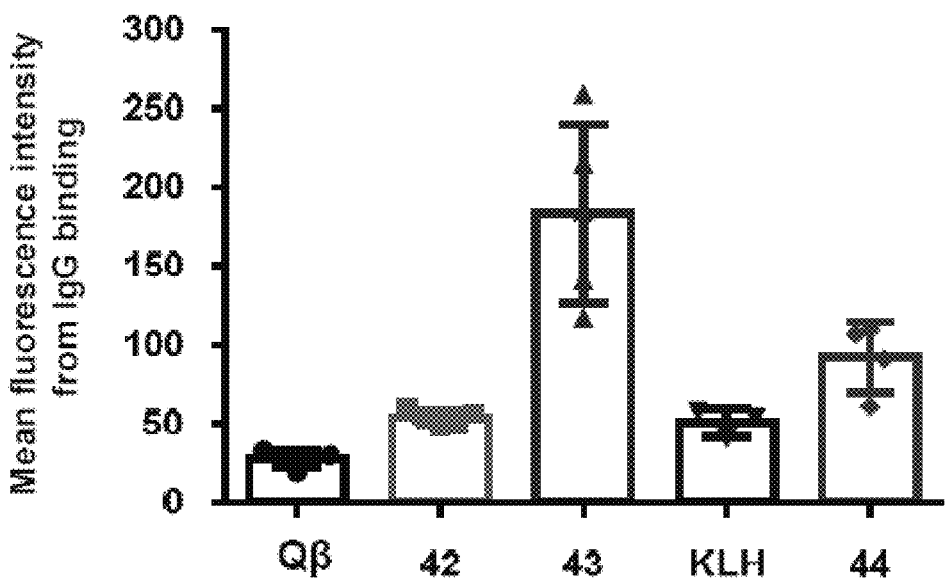
Figure 59C:
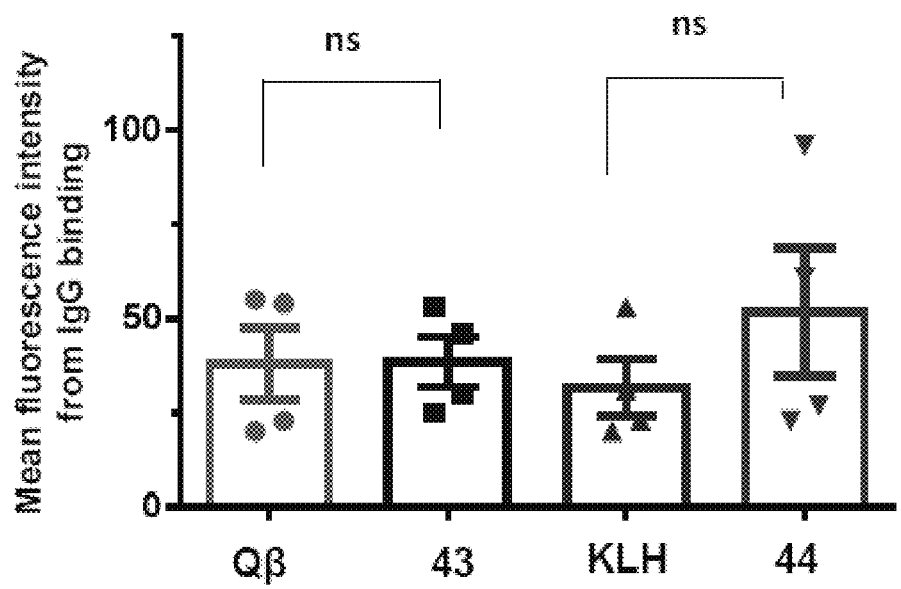
Figure 60:
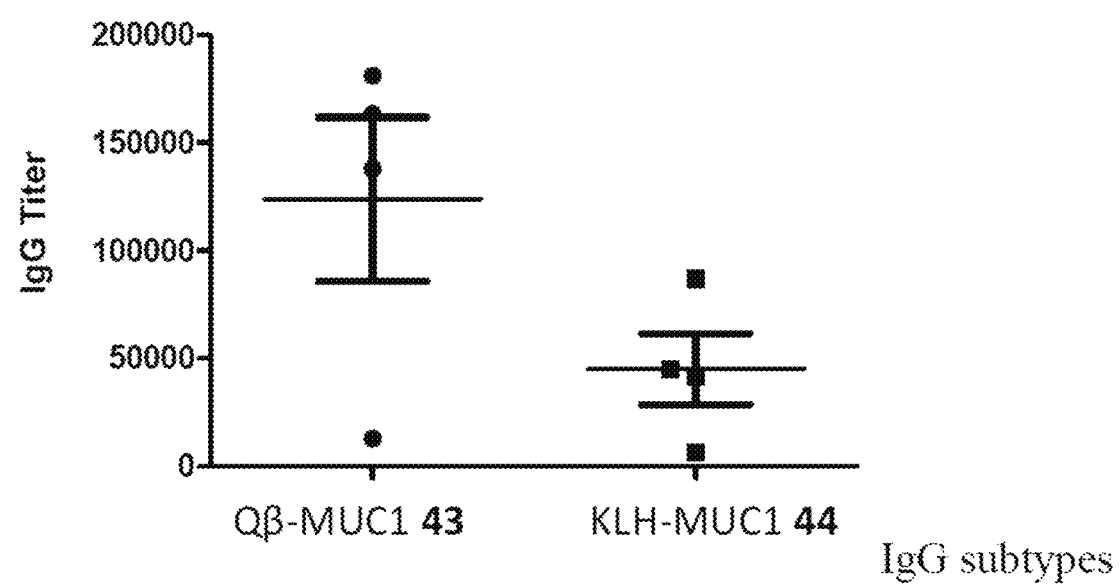
FIG. 60 shows IgG subtypes elicited by Qβ-MUC1 43 and KLH-MUC1 44.

MUC1 Tg. mice were immunized with Qβ-MUC1 42, 43 and KLH-MUC1 44. When analyzed against MUC1 expressing B16-MUC1 cells and MCF-7 cells through flow cytometry, Qβ-MUC1 43 was found to induce IgG antibodies in MUC1.Tg mice capable of binding much stronger with tumor cells than all other Qβ-MUC1 constructs including 37 (FIGS. 59A and 59B). This indicates removal of nonessential MUC1 epitopes from the immunogen could significantly improve the quality of antibody responses. Furthermore, post-immune antibodies did not exhibit much recognition of a normal cell line MCF-10A, suggesting good tumor selectivities by the antibodies (FIG. 59C). Compared to KLH-MUC1 44, Qβ-MUC1 43 immunization induced 3 times higher IgG antibody titers and 2 times higher tumor cell binding than those from KLH-MUC1 44 immunized MUC1 Tg. mice (FIGS. 59A and 59B). These results indicate Qβ is more superior than KLH for antibody production and Qβ-MUC1 43 is an excellent vaccine candidate for further evaluation.

Example 23: Glycopeptide Microarray Results Confirmed the MUC1-Tn Selectivity in Antibody Recognition To probe the binding profile of induced antibodies, pre-immune and post-immune sera from MUC1 Tg. mice immunized with Qβ-MUC1 43 or KLH-MUC1 44 or Qβ were screened against a MUC1 glycopeptide microarray. This glycopeptide array contained 72 MUC1 glycopeptides with the backbone sequence of one tandem repeat PAHGVTSAPDTRPAPGSTA (SEQ ID NO: 59). Glycans including Tn, T as well as cores 1-3 glycans were attached to various locations of the glycopeptides. In addition, mucin-5 (MUC5) glycopeptides as well as glycoproteins including fetuin, transferin, mucins from porcine stomach and bovine submaxillary glands have been immobilized on the array. The slides were incubated with individual mouse serum. Following removal of unbound antibodies by thorough washing, a fluorescently labeled anti-mouse IgG secondary antibody was added to semi-quantify the amounts of serum IgG antibodies bound to individual array components.

Consistent with higher anti-MUC1 titers from ELISA, Qβ-MUC1 conjugate gave rise to much stronger array component bindings on average compared to KLH-MUC1. A range of MUC1 glycopeptides were well recognized suggesting wide repertoire of antibodies were induced. No cross-reactivates were observed to MUC5 glycopeptides or other glycoproteins suggesting antibody responses were specific to MUC1 glycopeptides.

Close examination of microarray data reveals interesting structural dependence of binding. Glycopeptides bear Tn in its PDTR region (SEQ ID NO: 60) were bound much stronger than those lacking PDT*R structure (SEQ ID NO: 19). For example, glycopeptides 1-3 all contain the same protein backbone and one Tn, but the locations of Tn in these three sequences are different. Glycopeptide 2, which has Tn in its PDTR region (SEQ ID NO: 60), gives strongest binding to post-immune sera than 1 and 3 (FIG. 84A). Glycopeptides 4, 6 and 7 contain multiple Tns in the backbone, including Tn in its PDTR region (SEQ ID NO: 60). They were all recognized well by post-immune sera. These results suggest antibodies induced have excellent site selectivities with high preferences towards the PDT*R region (SEQ ID NO: 19) contained in the immunizing antigen MUC1 39.

Comparison of PAHGVTSAPDT*RPAPGSTA (SEQ ID NO: 21) with varying glycan structures showed that while the Tn bearing glycopeptide 2 was bound the strongest, glycopeptides with other glycans ranging from disaccharide T to core 3 pentasaccharide could be recognized as well (FIG. 84B). As glycosylation of tumor associated MUC1 can be heterogeneous, the abilities of Qβ-MUC1 39 induced antibodies to recognize multiple glycopeptides bode well for tumor recognition.

Figure 61A:
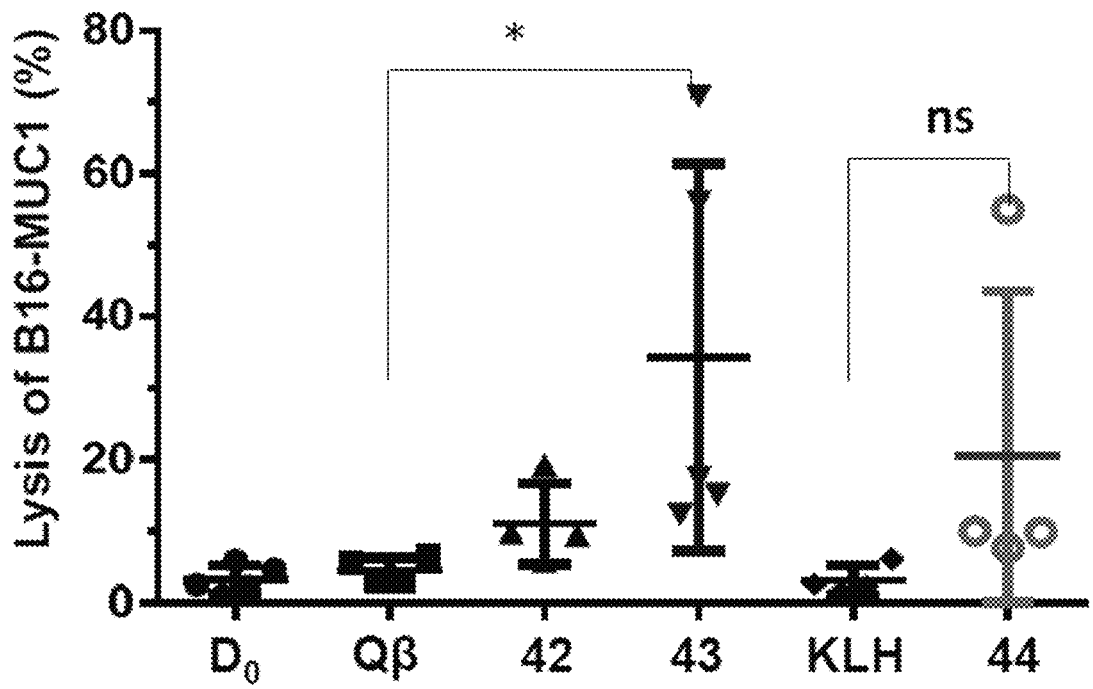
FIG. 61 contains two panels FIGS. 61A and 61B, showing that Qβ-MUC1 43 exhibited significantly higher CDC towards tumor cells. CDC towards (FIG. 61A) B16-MUC1 cells or (FIG. 61B) MCF-7 cells was determined by MTS assay. *p<0.05, p<0.01, *p<0.001. Do were the pre-immune sera. The p values were determined through a two tailed t test using GraphPad Prism. ns: not significant.
Figure 61B:
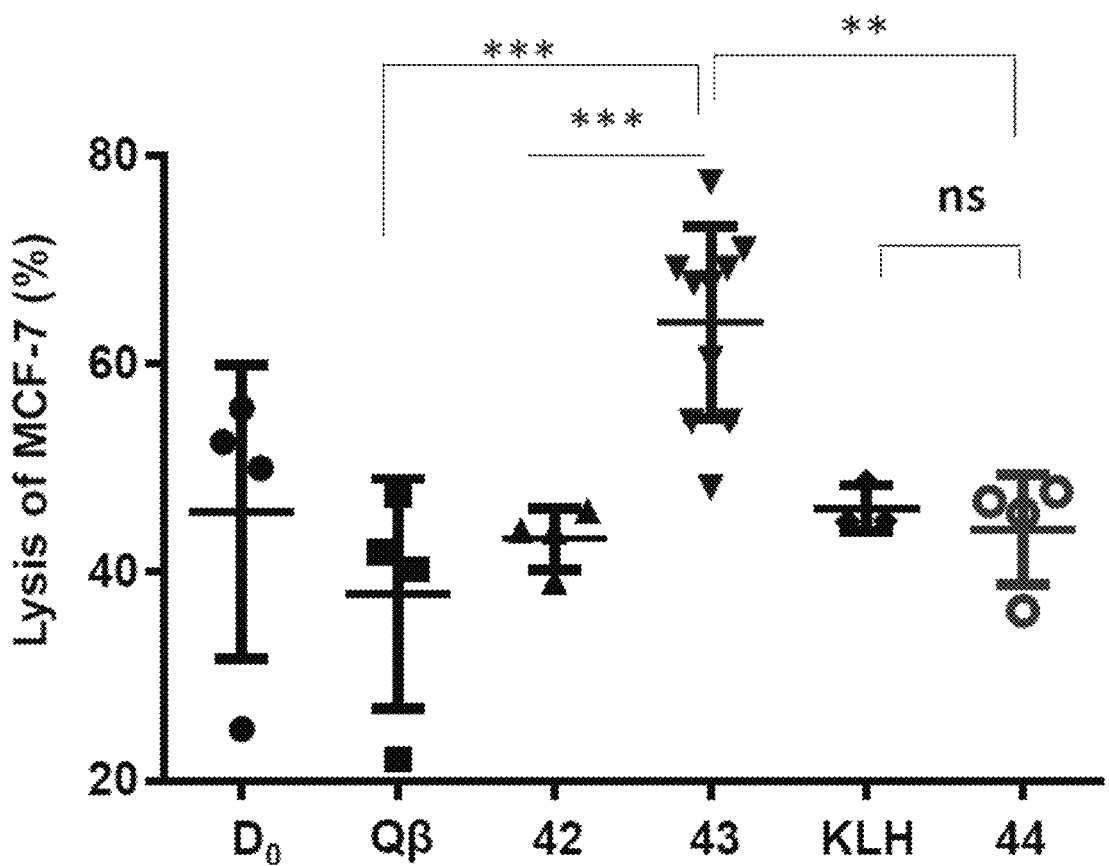

Example 23: Antibodies Induced by Qβ-MUC1 43 Exhibited Good Tumoricidal Activities Via Both Complement Mediated Cytotoxicity (CDC) and Antibody Dependent Cell Mediate Cytotoxicity (ADCC) Mechanisms With the strong tumor recognition by sera from Qβ-MUC1 43 immunized mice, their abilities to kill the tumor cells were measured in vitro. Upon incubation of B16-MUC1 cells (FIG. 61A) and MCF-7 cells (FIG. 61B) with post-immune sera and rabbit complement, significantly higher percentages of tumor cells were killed by Qβ-MUC1 43 immunized sera as compared to cells treated with other sera. Tn glycosylation of MUC1 significantly enhanced the CDC potency of the post-immune sera.

Figure 62A:
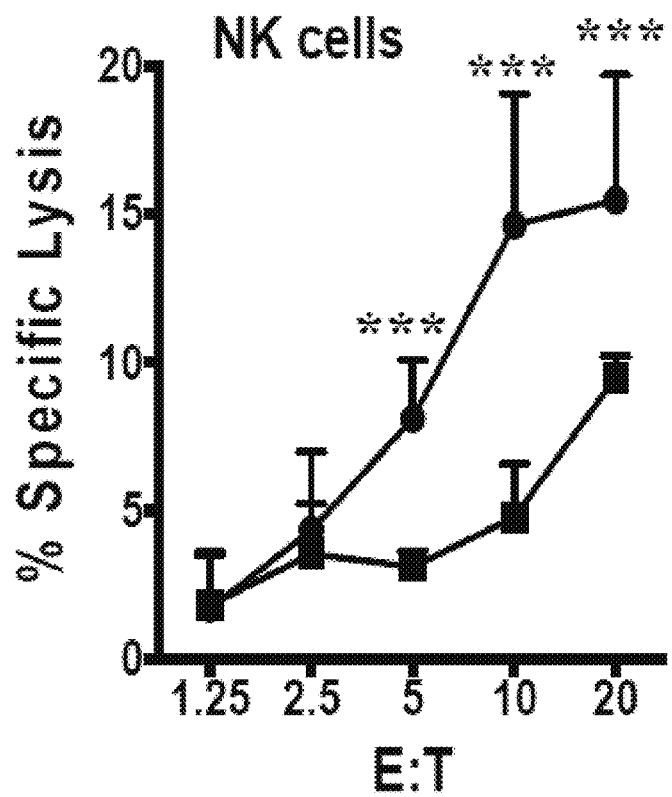
FIG. 62 contains two panels FIGS. 62A and 62B, showing the ADCC of B16-MUC1 target cells is increased in the presence of Qβ-MUC1 43 antisera. B16-MUC1 target cells (T) were radiolabeled with 100 µCi of $^{51}$Cr and pulsed with 40 µL of control or Qβ-MUC1 43 antisera simultaneously for 2 h at 37° C. Target cells were washed and plated either with freshly isolated (FIG. 62A) NK or (FIG. 62B) LAK cells (effectors, E) at various E:T ratios. After 16 h, the culture supernatant was harvested and the specific lysis was analyzed using a gamma counter. Significance was determined by two-way ANOVA with Tukey's post-hoc test. ***p<0.001.
Figure 62B:
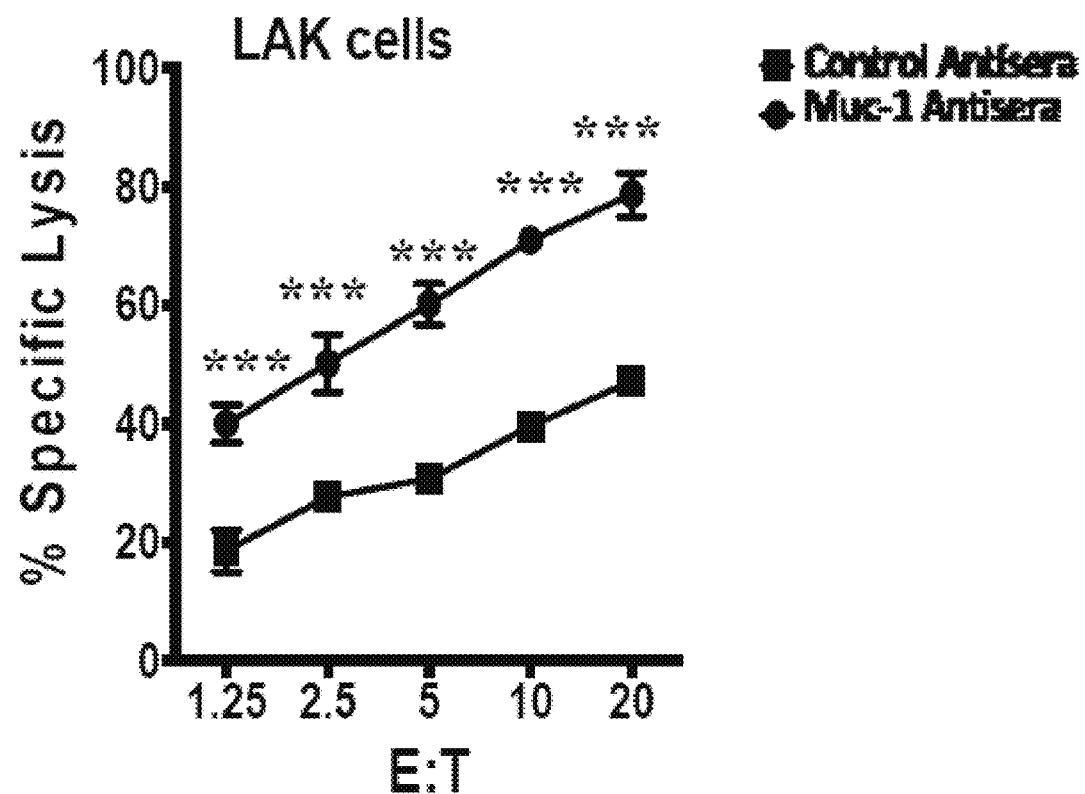

ADCC is another important mode of tumor cell killing bestowed by antibodies. An ADCC assay was set up using either natural killer (NK) cells or lymphokine-activated killer (LAK) cells as the effectors cells against MUC1 expressing B16-MUC1 targeted cells. As shown in FIG. 62, under a varity of ratios of targeted vs effector cells, stronger cytotixicities were observed from sera of Qβ-MUC1 43 immunized mice in contrast to control sera from Qβ immunized mice.

Figure 63:
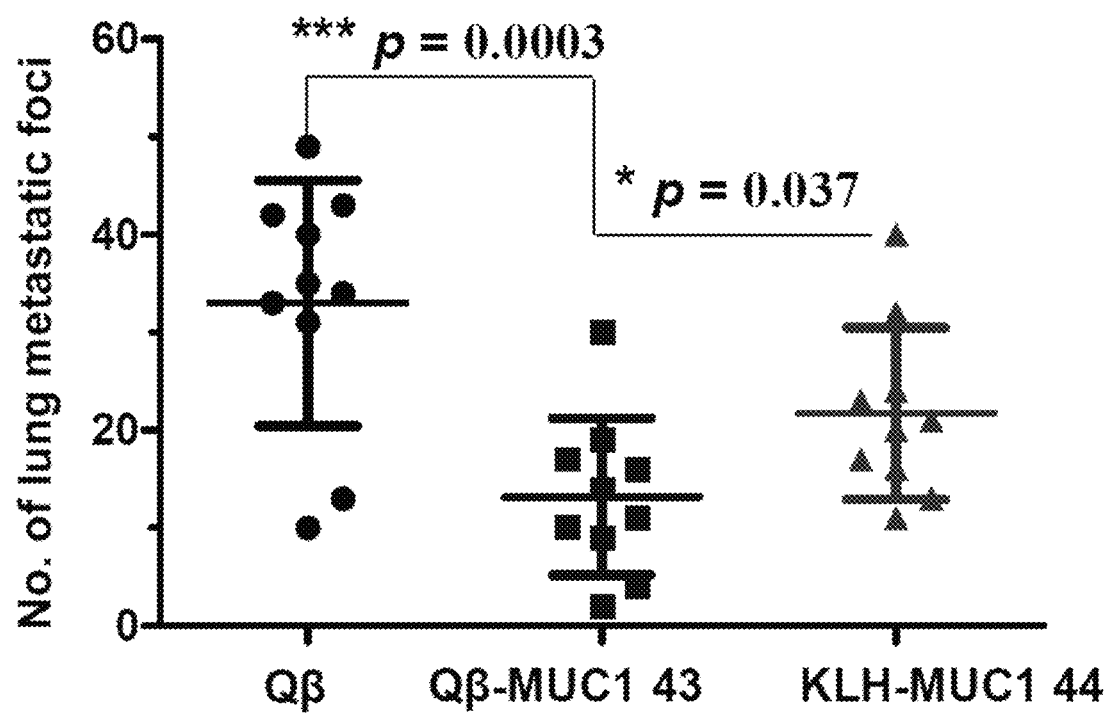
FIG. 63 shows immunization of Qβ-MUC1 43 significantly protected MUC1 Tg. mice from formation of metastatic-like lung tumors. MUC1 Tg. mice were respectively immunized with Qβ, Qβ-MUC1 43 or KLH-MUC1 44 on day 0, days 14 and days 28 plus MPLA as an adjuvant, challenged with 1×10⁵ B16-MUC1 cells on days 35 via tail vein injection, followed by 4$^{th}$ immunization, and then given 5$^{th}$ immunization on days 45. 21 days after tumor inoculation, mice were sacrificed and the number of tumor foci in the lungs were counted. Qβ-MUC1 43 vaccination significantly reduced the number of tumor compared to control animals receiving Qβ or KLH-MUC1 44 immunization. Each symbol represents one mouse. *p<0.05, p<0.01, *p<0.001. The p values were determined through a two tailed t test using GraphPad Prism.

Example 24: Vaccination of Qβ-MUC1 43 Exhibited Significant Tumor Protection in a Metastasis Model With high levels of IgG elicited by Qβ-MUC1 43 and strong tumor binding, we tested tumor protection in a metastasis model as tumor metastasis is a major hurdle to patient survival. MUC1.Tg mice were immunized with Qβ-MUC1 43 or Qβ (the control) with FDA approved MPLA as the adjuvant. B16-MUC1 melanoma cells were injected via tail vein and the numbers of tumor foci in lungs were determined 21 days after tumor inoculation. Excitingly, Qβ-MUC1 43 brought a notable reduction in tumor load (p=0.0003) vs. Qβ control (FIG. 63). The efficacy of KLH-MUC1 44 was also evaluated in this model. Immunization with KLH-MUC1 44 exhibited some tumor protection in this metastasis model, but was significnatly less effectively than Qβ-MUC1 43 in reducing tumor load (p=0.037) (FIG. 63), confirming that Qβ is superior as a carrier to induce anti-MUC1 IgG antibodies and tumor protection compared to KLH.

Figure 64:
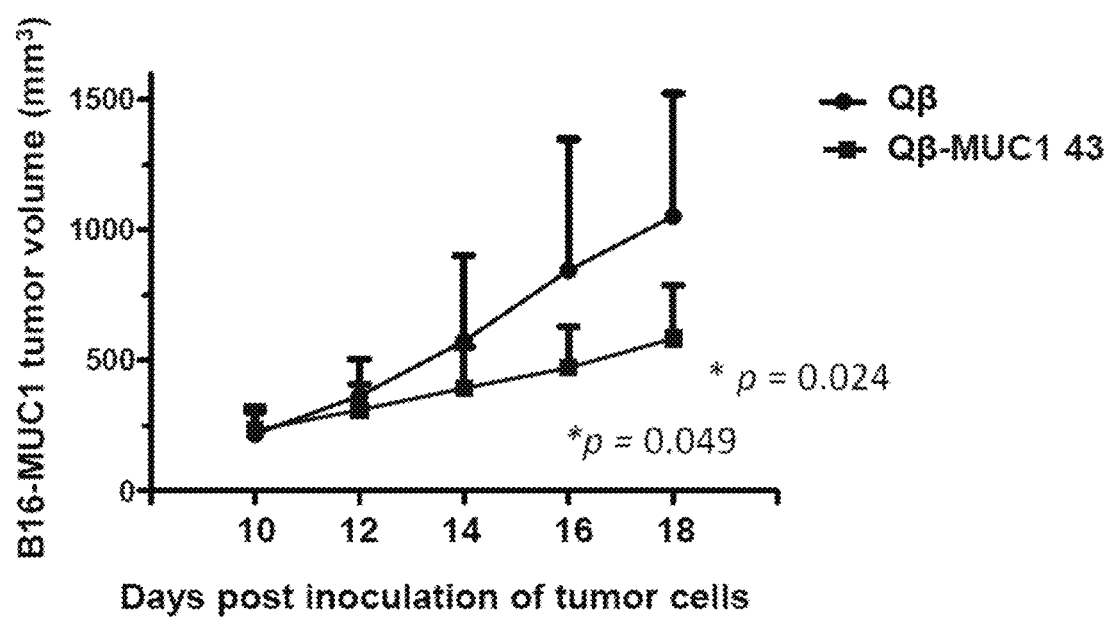
FIG. 64 shows that Qβ-MUC1 43 immunization plus anti-PD1 blockade treatment effectively regress the solid tumor growth. MUC1 Tg mice were immunized with Qβ or Qβ-MUC1 43 on days 0, 14 and 28 plus MPLA as an adjuvant, challenged with 5×10⁵ B16-MUC1 cells on days 35 by subcutaneous inoculation, followed by 4$^{th}$ immunization, and then given 5$^{th}$ immunization on days 42, followed by anti-PD1 injection on days 43 and days 46 respectively via intraperitoneal injection. On days 49, the mice were given another immunization with MPLA, followed by anti-PD1 treatment on days 50 and 53. *p<0.05. The p values were determined through a two tailed t test using GraphPad Prism.

Example 25: Vaccination of Qβ-MUC1 43 Provided Significant Tumor Protection in a Solid Tumor Model With the successful protection of MUC1.Tg mice from metastatic tumors with Qβ-MUC1 43, a solid tumor model was tested. Solid tumor is known to be difficult to treat, as there can be significant immunosuppression within the tumor microenvironment. Programmed cell death 1 (PD-1) and its ligand (PD-L1) are important inhibitory checkpoint molecules (Pardoll, D. M. (2012) *Nat. Rev. Cancer* 12, 252-264). Recently, we showed that PD-1 plays a major role in suppressing anti-TACA antibody responses. (Leyva, M. A. et al. (2016) *Cancer Immunol. Res.* 4, 1027-1037). As it is known that anti-PD-1 mAbs can neutralize the functions of PD-1, we tested the combination of anti-PD-1 mAbs with Qβ-MUC1 43 immunization for protection against solid tumor. MUC1.Tg mice were immunized with Qβ-MUC1 43 or Qβ (the control) and MPLA adjuvant. B16-MUC1 melanoma cells were then grafted subcutaneously, which was followed by further immunization and anti-PD-1 mAb administrations. Excitingly, the group receiving Qβ-MUC1 43 immunization had much reduced tumor growth (FIG. 64).

Figure 65A:
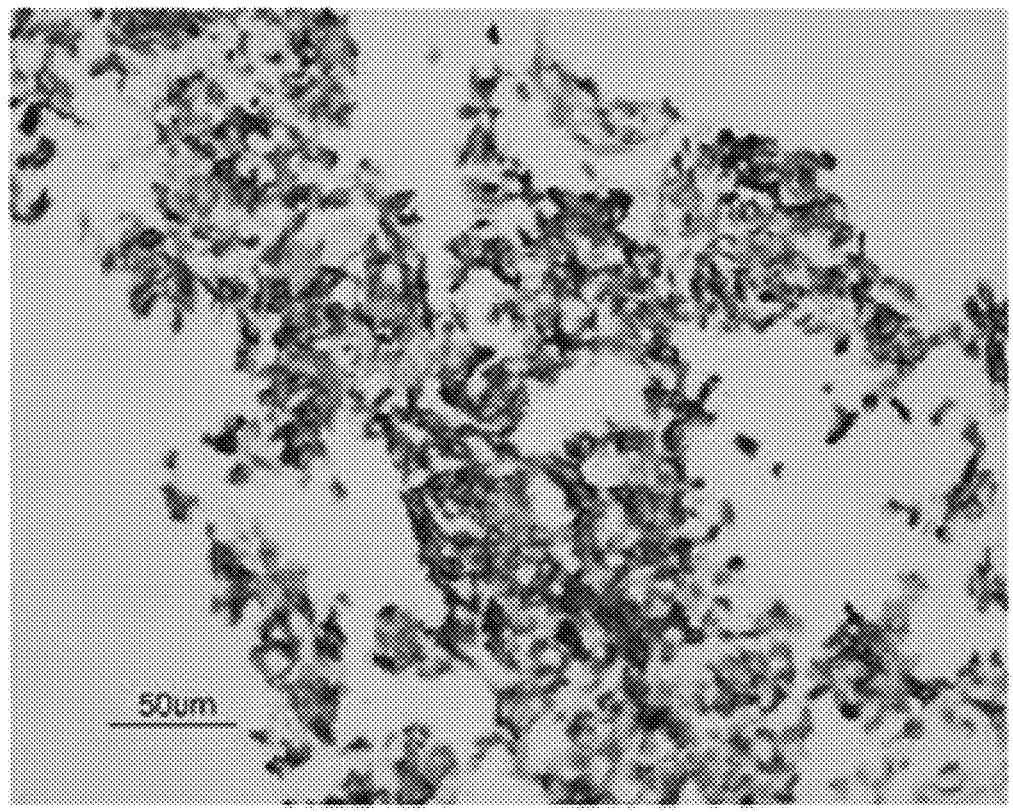
FIG. 65 contains two panels, FIG. 65A-65B, showing that sera from MUC1 Tg. mice immunized with Qβ-MUC1 43 exhibited (FIG. 65A) strong binding to human breast cancer tissues on a tissue microarray while having litter reaction with (FIG. 65B) normal breast tissues (1:1000 serum dilution). The images were representative out of 30 samples. The brown color in (FIG. 65A) was due to antibody binding to tissues. The lack of brown staining in (FIG. 65B) indicates little binding of antibodies to normal tissues. Scale bar is 50 m.
Figure 65B:
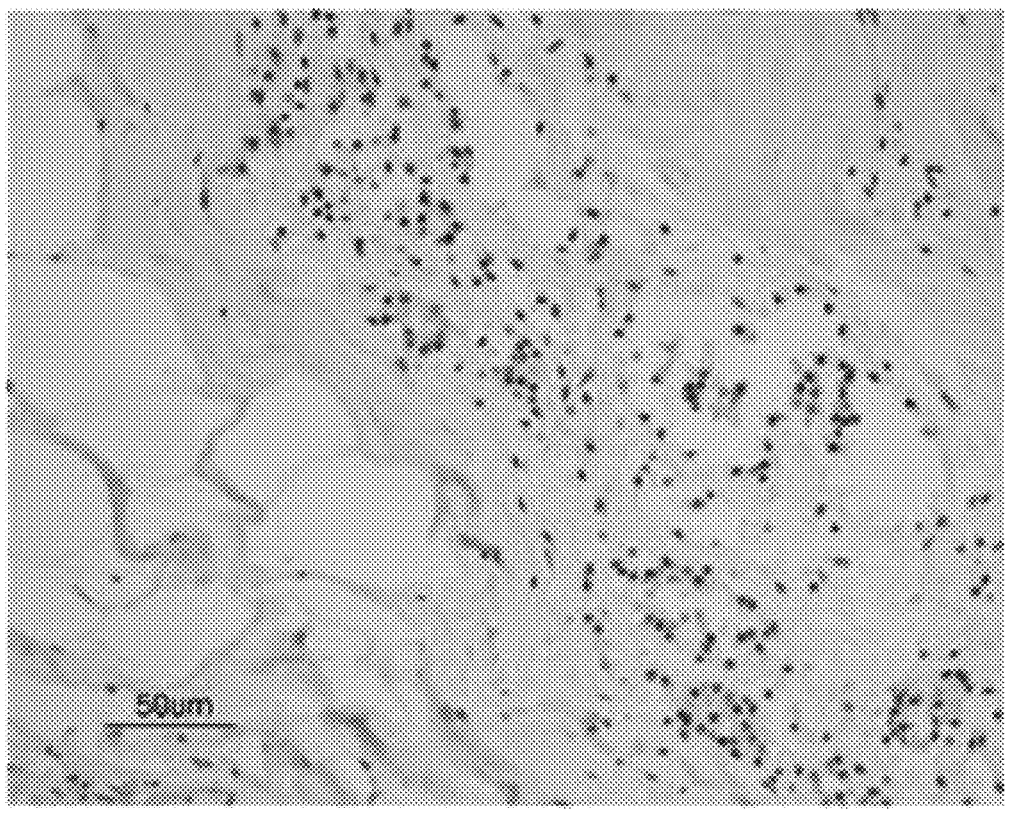
Figure 66A:
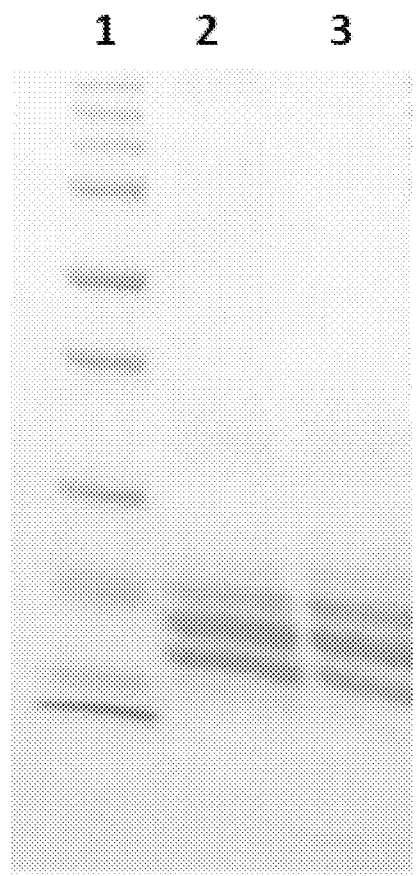
FIG. 66 contains two panels, FIG. 66A and FIG. 66B, showing immunization of MUC1 Tg. mice with Qβ-mutants-MUC1-Tn. The immunization protocol used for mouse immunization with the Qβ mutant-MUC1 conjugates. This is the same protocol as wild type Qβ-MUC1 conjugate.
Figure 66B:
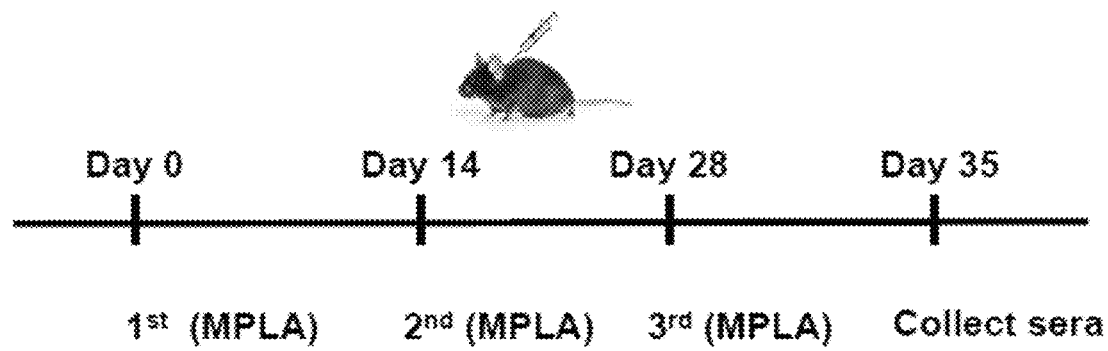
Figure 67:
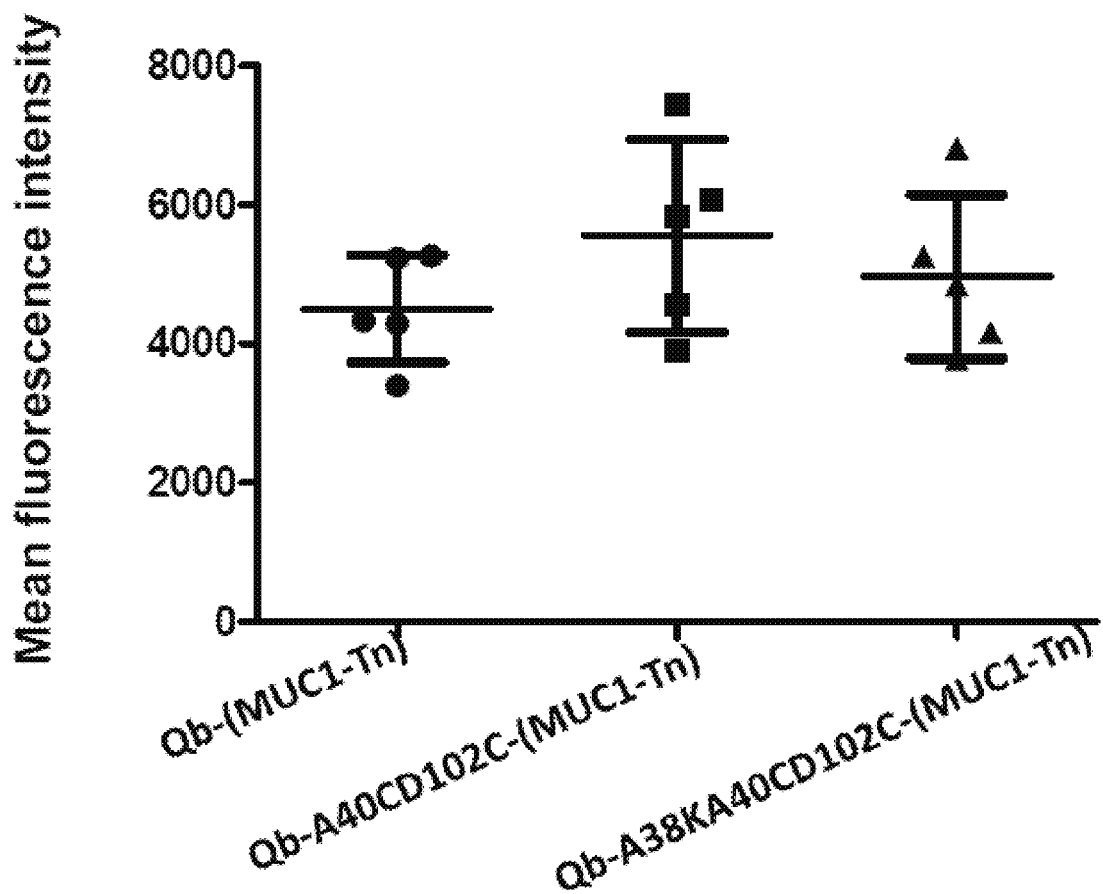
FIG. 67 shows Ag104 MUC1 binding with the sera from Qβ-mutants-MUC1-Tn. Head to head comparison of binding of mouse fibrosarcoma Ag104MUC1 cells by Qβ wild type-MUC1 conjugate vs Qβ mutant-MUC1 conjugates. The two mutants studied are Qβ-A40CD102C; and Qβ-A38KA40CD102C.
Figure 68:
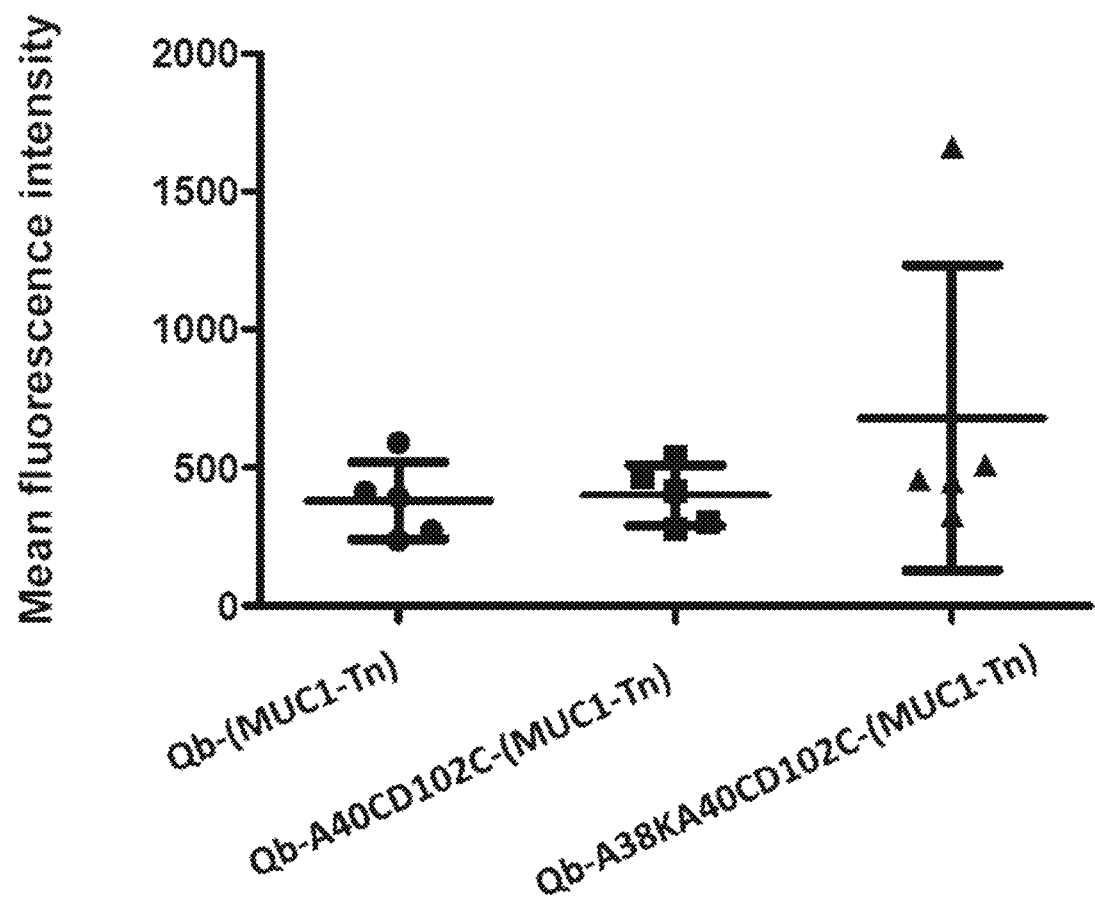
FIG. 68 shows B16MUC1 binding with the sera from Qβ-mutants-MUC1-Tn. Head to head comparison of binding of mouse melanoma cell B16MUC1 by Qβ wild type-MUC1 conjugate vs Qβ mutant-MUC1 conjugates. The two mutants studied are Qβ-A40CD102C; and Qβ-A38KA40CD102C.
Figure 69:
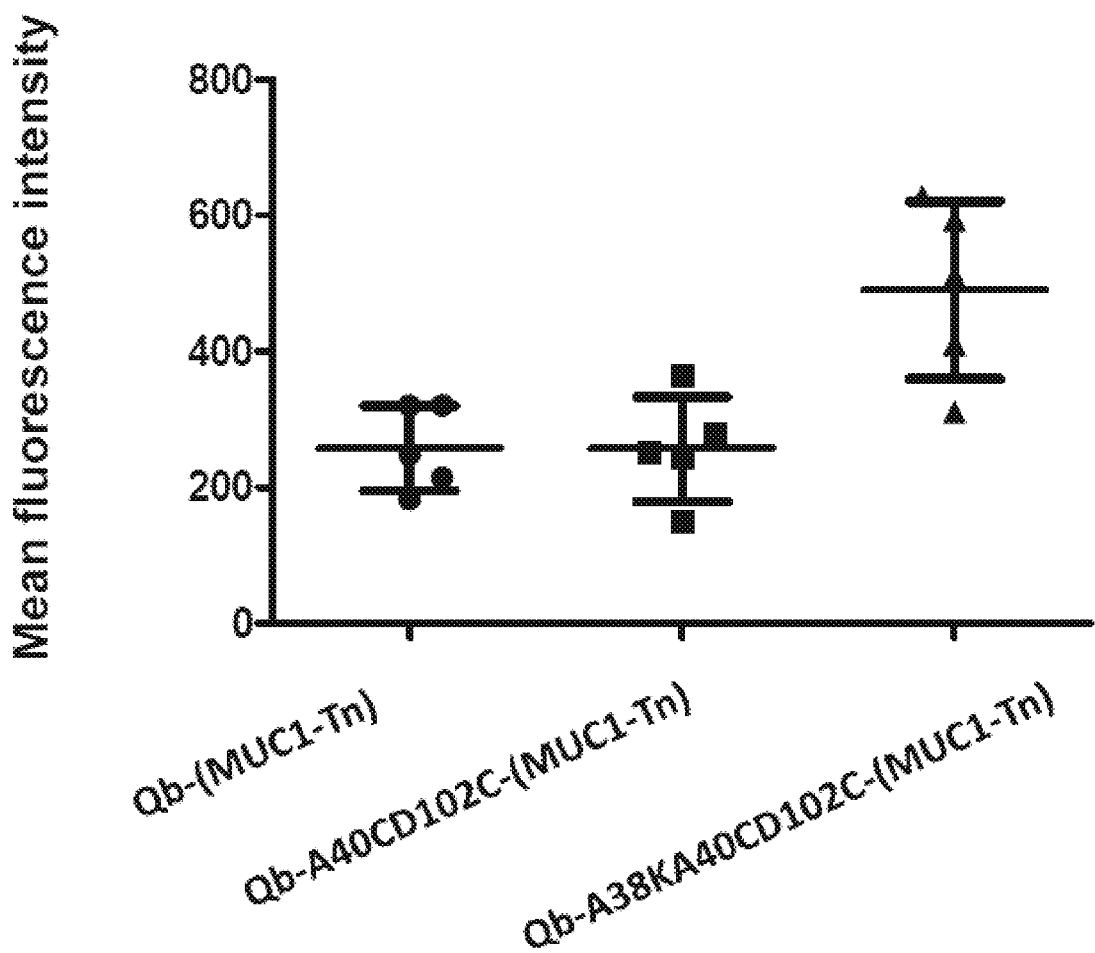
FIG. 69 shows MCF-7 binding with the sera from Qβ-mutants-MUC1-Tn. Head to head comparison of binding of human breast cancer cell MCF-7 by Qβ wild type-MUC1 conjugate vs Qβ mutant-MUC1 conjugates. The two mutants studied are Qβ-A40CD102C; and Qβ-A38KA40CD102C. The triple mutant led to significantly higher binding.
Figure 70:
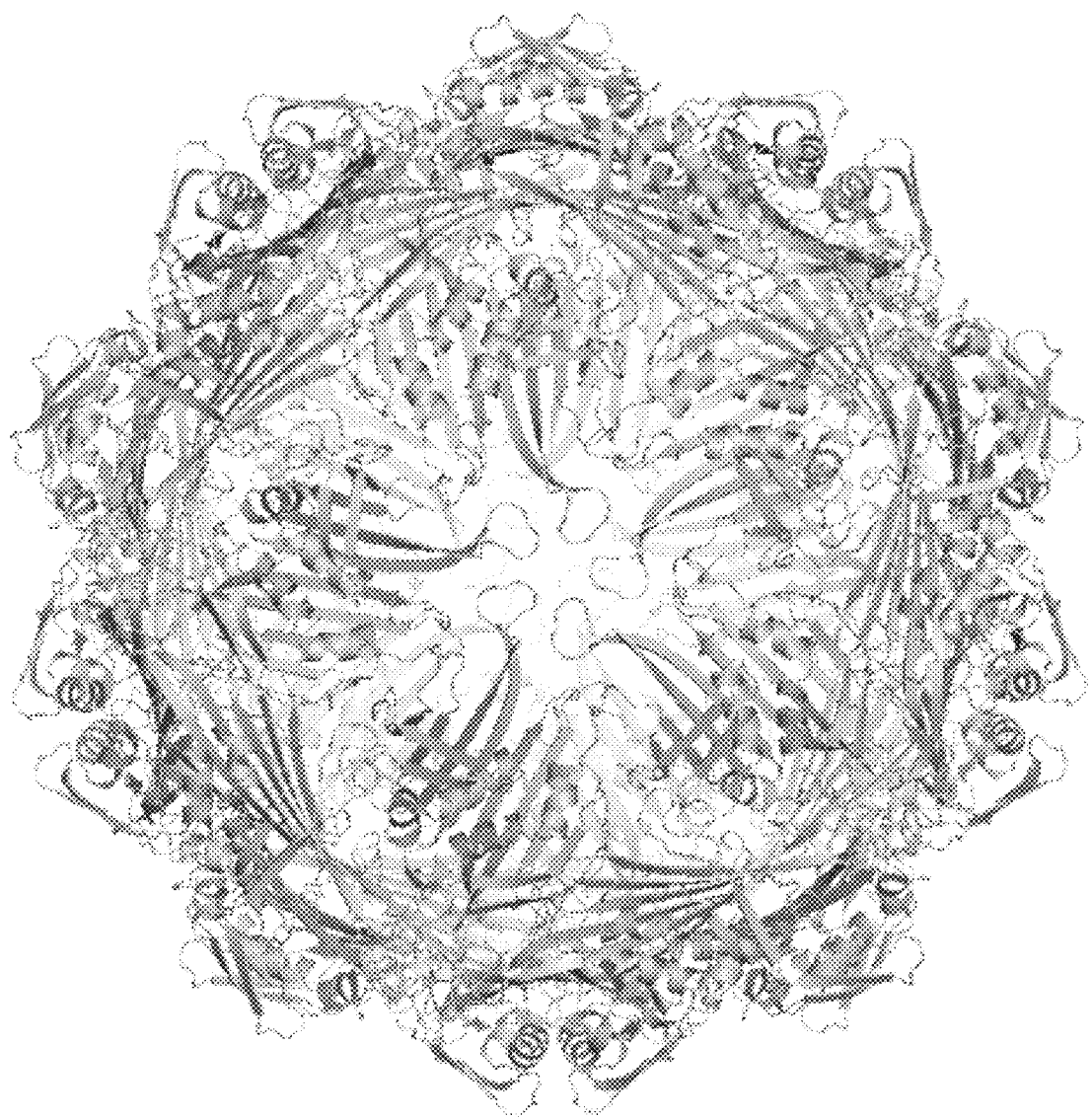
FIG. 70 shows the structure of Qβ WT assembled in a T=1 capsid.
Figure 71:
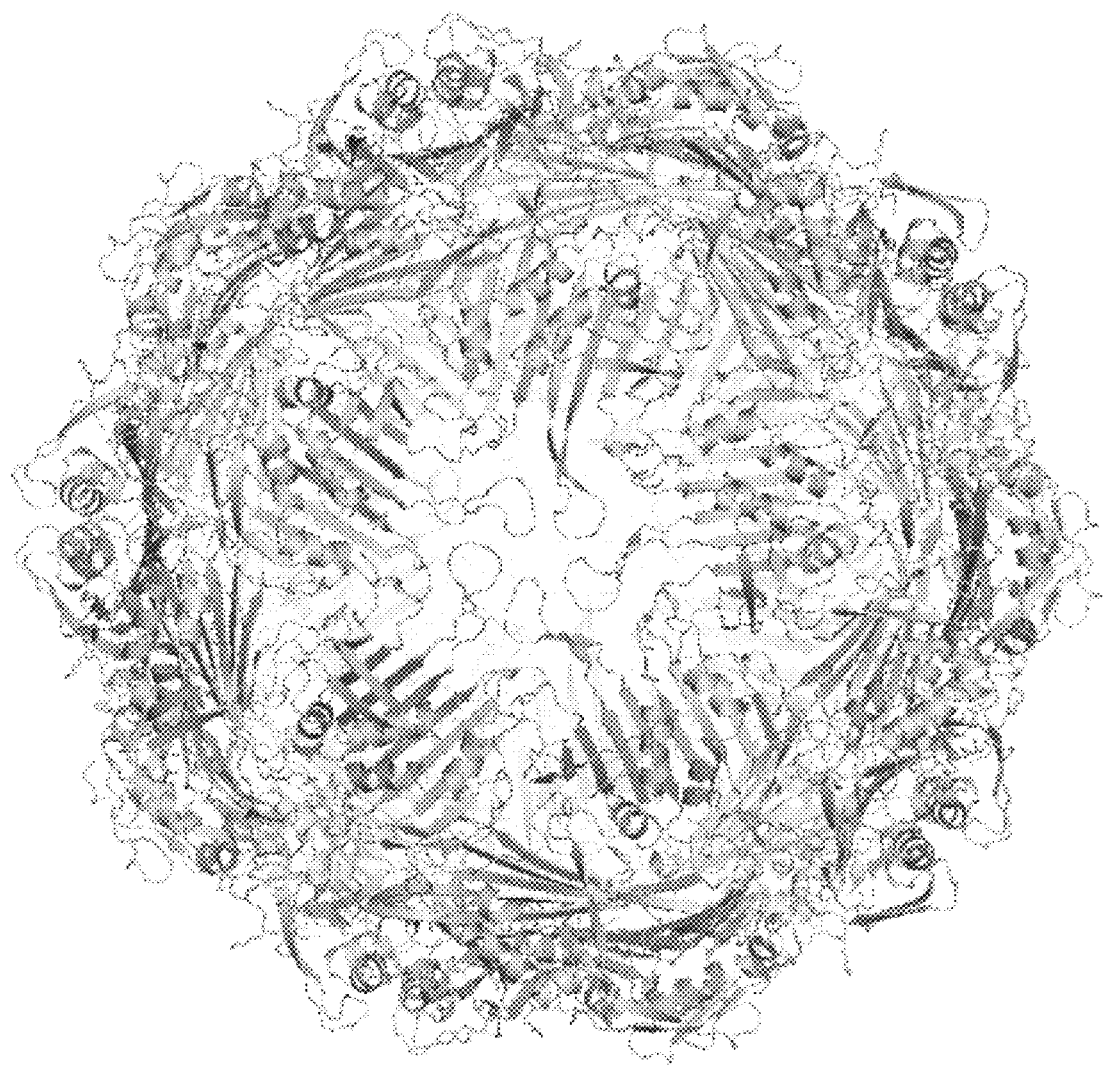
FIG. 71 shows the structure of Qβ A38KA40CD102C assembled capsid; inter-subunit disulfide bonds are in yellow sticks.

Example 26: High Selectivity in Binding to Human Breast Cancer Vs Normal Tissues by Qβ-MUC1 43 Induced Sera in MUC1.Tg Mice To test the translational potential of Qβ-MUC1 43 to human patients, we obtained breast cancer tissue microarrays with cancer tissues from breast cancer patients immobilized together with normal adjacent breast tissues from the same patient on the array. Sera from Qβ-MUC1 43 immunized MUC1.Tg mice were used to stain the tissues, which bound strongly with breast cancer tissues (FIG. 65A). In stark contrast, little normal breast tissues were stained under the same condition (FIG. 65B). This highlights the remarkable selectivity of the antibodies induced in recognition of MUC1 expressing human cancer tissues.

Example 27: Qβ Anti-Cancer Vaccine Candidate

In addition to MUC1, we have also investigated Qβ conjugates with GD2 and 9-NHAc-GD2. GD2 is known to be overexpressed on lymphoma, neuroblastoma cells as well as breast cancer stem cells. Qβ-GD2 and Qβb-9-NHAc-GD2 conjugates can be potential vaccines against lymphoma, neuroblastoma and breast cancer. The Qβ anti-cancer vaccine can also target cancer stem cells. Mice immunized with Qβ conjugates of GD2 and 9-NHAc-GD2 produced IgG antibodies capable of strong binding with EL4 lymphoma cells (FIG. 80). The levels of EL4 binding were much stronger than antibodies from Qβ-GM3 and Qβ-GM2 immunized mice (FIG. 80). Furthermore, sera from Qβ-GD2 and Qβb-9-NHAc-GD2 immunized mice exhibited strong killing of lymphoma cells EL4 via complement mediated cytotoxicities (FIG. 81).

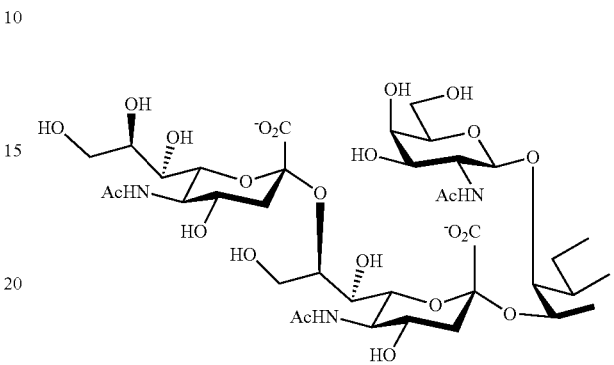

Example 28: Qβ *Salmonella* Glycan Conjugate as a Potential Anti-*Salmonella*

Vaccine

We have also investigated Qβ conjugates with glycans from *Salmonella* (FIG. 82A). Mice immunized with Qβ conjugates of *Salmonella* glycans produced high titer and long lasting IgG antibodies (FIG. 82B). The post-immune sera provided significant protection to mice against lethal *salmonella* infection (FIG. 83).

INCORPORATION BY REFERENCE

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

EQUIVALENTS

Although the foregoing subject matter has been described in some detail by way of illustration and example for purposes of clarity of understanding, it will be understood by those skilled in the art that certain changes and modifications can be practiced within the scope of the appended claims.

What is claimed:

1. A vaccine composition comprising an antigen conjugated to a carrier capsid, wherein said capsid comprises at least one non-natural mutation that induces a reduced anti-carrier immune response; wherein said capsid comprises the amino acid sequence set forth in SEQ ID NO: 3 and having the at least one non-natural mutation selected from N10K, K13R, A38K, A40C, A40S, T75K, D102C, D102S, or A117K, or any combination thereof.

2. The vaccine composition of claim 1, wherein the capsid further comprises at least two, three, four, five, six, seven, eight, or nine.

3. The vaccine composition of claim 1, wherein the at least one non-natural mutation is a disulfide bond mutation.

4. The vaccine composition of claim 1, wherein the antigen is a carbohydrate antigen.

5. The vaccine composition of claim 4, wherein the carbohydrate antigen is selected from the group consisting of (a) Mucin1 (MUC1), (b) Mucin4 (MUC4), (c) Ganglioside GD2 (GD2), (d) Fucosyl Ganglioside GM1 (GM1), (e) acetylated GD2, (f) Ganglioside GD3 (GD3), (g) acetylated GD3, (h) Fucosyl Ganglioside GM2 (GM2), (i) Globo-H, (j) Lewis A, (k) Lewis Y, (1) polysialic acid, (m) sialyl-Lewis A, (n) Tf, (o) Tn, (p) sTn, Tn1, and Tn2.

6. A vaccine composition comprising an antigen conjugated to a carrier capsid, wherein said capsid comprises at least two non-natural mutations that induce a reduced anti-carrier immune response; wherein said capsid comprises the amino acid sequence set forth in SEQ ID NO: 3 and having at least two non-natural mutations selected from A40C/D102C, A40S/D102S, A43C/Q98C, and any combination thereof.

7. The vaccine composition of claim 1, wherein said capsid comprises the amino acid sequence set forth in SEQ ID NO: 3, said sequence comprising at least three mutations selected from A40C/D102C/K13R or A38K/A40C/D102C.

8. A method for treating cancer associated with a carbohydrate antigen in a subject, the method comprising administering to the subject a vaccine composition of claim 1.

9. The method of claim 8, wherein the vaccine composition is administered systemically.

10. The method of claim 9, wherein the systemic administration is selected from the group consisting of oral, intravenous, intradermal, intraperitoneal, subcutaneous, and intramuscular administration.

11. The method of claim 8, wherein the composition is administered intratumorally or peritumorally.

12. The method of claim 8, wherein the cancer is a solid tumor.

13. The method of claim 8, wherein the cancer is selected from the group consisting of oral cancer, breast cancer, brain cancer, childhood cancer, ovarian cancer, prostate cancer, pancreatic cancer, lung cancer, liver cancer, throat cancer, stomach cancer, a neuroblastoma and kidney cancer.

* * * * *

SEQUENCE LISTING

<160> NUMBER OF SEQ ID NOS: 175

<210> SEQ ID NO 1
<211> LENGTH: 133
<212> TYPE: PRT
<213> ORGANISM: Bacteriophage Qbeta

<400> SEQUENCE: 1

```
Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
    130
```

<210> SEQ ID NO 2
<211> LENGTH: 133
<212> TYPE: PRT
<213> ORGANISM: Bacteriophage Qbeta

<400> SEQUENCE: 2

```
Met Ala Lys Leu Glu Thr Val Thr Leu Gly Lys Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
    130
```

<210> SEQ ID NO 3
<211> LENGTH: 132
<212> TYPE: PRT
<213> ORGANISM: Bacteriophage Qbeta

<400> SEQUENCE: 3

Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
        50                  55                  60

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
            115                 120                 125

Asn Pro Ala Tyr
        130

<210> SEQ ID NO 4
<211> LENGTH: 133
<212> TYPE: PRT
<213> ORGANISM: Bacteriophage Qbeta

<400> SEQUENCE: 4

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Lys Gly Ala Val Pro Ala Leu Glu Lys Arg
            35                  40                  45

Val Thr Val Ser Val Ser Gln Pro Ser Arg Asn Arg Lys Asn Tyr Lys
        50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
            115                 120                 125

Leu Asn Pro Ala Tyr
        130

<210> SEQ ID NO 5
<211> LENGTH: 133
<212> TYPE: PRT
<213> ORGANISM: Bacteriophage Qbeta

<400> SEQUENCE: 5

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Cys Val Pro Ala Leu Glu Lys Arg
            35                  40                  45

```
Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
                100                 105                 110

Leu Ala Ala Leu Leu Ala Ser Pro Leu Leu Ile Asp Ala Ile Asp Gln
        115                 120                 125

Leu Asn Pro Ala Tyr
    130

<210> SEQ ID NO 6
<211> LENGTH: 133
<212> TYPE: PRT
<213> ORGANISM: Bacteriophage Qbeta

<400> SEQUENCE: 6

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
                20                  25                  30

Val Ala Ser Leu Ser Gln Ala Gly Ser Val Pro Ala Leu Glu Lys Arg
            35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
                100                 105                 110

Leu Ala Ala Leu Leu Ala Ser Pro Leu Leu Ile Asp Ala Ile Asp Gln
        115                 120                 125

Leu Asn Pro Ala Tyr
    130

<210> SEQ ID NO 7
<211> LENGTH: 133
<212> TYPE: PRT
<213> ORGANISM: Bacteriophage Qbeta

<400> SEQUENCE: 7

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
                20                  25                  30

Val Ala Ser Leu Ser Gln Ala Gly Ala Val Pro Ala Leu Glu Lys Arg
            35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Lys Ala Asn Gly Ser
65                  70                  75                  80

Cys Asp Pro Ser Val Thr Arg Gln Ala Tyr Ala Asp Val Thr Phe Ser
                85                  90                  95
```

```
Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
        130

<210> SEQ ID NO 8
<211> LENGTH: 133
<212> TYPE: PRT
<213> ORGANISM: Bacteriophage Qbeta

<400> SEQUENCE: 8

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Cys Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
        130

<210> SEQ ID NO 9
<211> LENGTH: 133
<212> TYPE: PRT
<213> ORGANISM: Bacteriophage Qbeta

<400> SEQUENCE: 9

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Ser Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
        130
```

<210> SEQ ID NO 10
<211> LENGTH: 133
<212> TYPE: PRT
<213> ORGANISM: Bacteriophage Qbeta

<400> SEQUENCE: 10

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Lys Ser Pro Leu Leu Ile Asp Ala Ile Asp Gln
        115                 120                 125

Leu Asn Pro Ala Tyr
    130

<210> SEQ ID NO 11
<211> LENGTH: 133
<212> TYPE: PRT
<213> ORGANISM: Bacteriophage Qbeta

<400> SEQUENCE: 11

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Cys Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Cys Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
    130

<210> SEQ ID NO 12
<211> LENGTH: 133
<212> TYPE: PRT
<213> ORGANISM: Bacteriophage Qbeta -continued

```
<400> SEQUENCE: 12

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Cys Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Ser Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
    130

<210> SEQ ID NO 13
<211> LENGTH: 133
<212> TYPE: PRT
<213> ORGANISM: Bacteriophage Qbeta

<400> SEQUENCE: 13

Met Ala Lys Leu Glu Thr Val Thr Leu Gly Asn Ile Gly Arg Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Cys Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Cys Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
    130

<210> SEQ ID NO 14
<211> LENGTH: 133
<212> TYPE: PRT
<213> ORGANISM: Bacteriophage Qbeta

<400> SEQUENCE: 14

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30
```

Val Ala Ser Leu Ser Gln Ala Gly Ala Val Pro Cys Leu Glu Lys Arg
              35                  40                  45

Val Thr Val Ser Val Ser Gln Pro Ser Arg Asn Arg Lys Asn Tyr Lys
 50                  55                  60

Val Gln Val Lys Ile Gln Asn Pro Thr Ala Cys Thr Ala Asn Gly Ser
 65                  70                  75                  80

Cys Asp Pro Ser Val Thr Arg Gln Ala Tyr Ala Asp Val Thr Phe Ser
                  85                  90                  95

Phe Thr Cys Tyr Ser Thr Asp Glu Glu Arg Ala Phe Val Arg Thr Glu
                100                 105                 110

Leu Ala Ala Leu Leu Ala Ser Pro Leu Leu Ile Asp Ala Ile Asp Gln
                115                 120                 125

Leu Asn Pro Ala Tyr
            130

<210> SEQ ID NO 15
<211> LENGTH: 133
<212> TYPE: PRT
<213> ORGANISM: Bacteriophage Qbeta

<400> SEQUENCE: 15

Met Ala Lys Leu Glu Thr Val Thr Leu Gly Asn Ile Gly Lys Asp Gly
 1               5                  10                  15

Lys Gln Thr Leu Val Leu Asn Pro Arg Gly Val Asn Pro Thr Asn Gly
              20                  25                  30

Val Ala Ser Leu Ser Gln Lys Gly Cys Val Pro Ala Leu Glu Lys Arg
              35                  40                  45

Val Thr Val Ser Val Ser Gln Pro Ser Arg Asn Arg Lys Asn Tyr Lys
 50                  55                  60

Val Gln Val Lys Ile Gln Asn Pro Thr Ala Cys Thr Ala Asn Gly Ser
 65                  70                  75                  80

Cys Asp Pro Ser Val Thr Arg Gln Ala Tyr Ala Asp Val Thr Phe Ser
                  85                  90                  95

Phe Thr Gln Tyr Ser Thr Cys Glu Glu Arg Ala Phe Val Arg Thr Glu
                100                 105                 110

Leu Ala Ala Leu Leu Ala Ser Pro Leu Leu Ile Asp Ala Ile Asp Gln
                115                 120                 125

Leu Asn Pro Ala Tyr
            130

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Thr Pro Ser Ser Thr Pro Gly Thr Thr His Thr Pro
 1               5                  10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 17

Ala Thr Pro Ser Ser Thr Pro Gly Thr Thr His Thr Pro
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Thr Pro Ser Ser Thr Pro Gly Thr Thr His Thr Pro
1               5                   10

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Asp Thr Arg
1

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Pro Ala His Gly Val Thr Ser Ala Pro Asp Thr Arg Pro Ala Pro Gly
1               5                   10                  15

Ser Thr Ala

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Ala His Gly Val Thr Ser Ala Pro Asp Thr Arg Pro Ala Pro Gly
1               5                   10                  15

Ser Thr Ala

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 22

Pro Ala His Gly Val Thr Ser Ala Pro Asp Thr Arg Pro Ala Pro Gly
1               5                   10                  15

Ser Thr Ala

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Ala His Gly Val Thr Ser Ala Pro Asp Thr Arg Pro Ala Pro Gly
1               5                   10                  15

Ser Thr Ala

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Pro Ala His Gly Val Thr Ser Ala Pro Asp Thr Arg Pro Ala Pro Gly
1               5                   10                  15

Ser Thr Ala

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Pro Ala His Gly Val Thr Ser Ala Pro Asp Thr Arg Pro Ala Pro Gly
1               5                   10                  15

Ser Thr Ala

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
attagagact gttaagttag gtaacatcgg g                                    31

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cccgatgtta cctaacttaa cagtctctaa t                                       31

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctgttacttt aggtaagatc gggaaagatg g                                       31

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccatctttcc cgatcttacc taaagtaaca g                                       31

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggtaacatcg ggagagatgg aaaacaa                                            27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttgttttcca tctctcccga tgttacc                                            27

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcctcgcttt cacaaaaggg tgcagttcct gcg                                     33

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 33
cgcaggaact gcacccttttt gtgaaagcga ggc                                33

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cctcgctttc acaaagggt tgtgttcctg c                                    31

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcaggaacac aacccttttg tgaaagcgag g                                   31

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cacaagcggg ttgtgttcct gcgctgg                                        27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccagcgcagg aacacaaccc gcttgtg                                        27

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cacaagcggg ttcagttcct gcgctgg                                        27

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 39
ccagcgcagg aactgaaccc gcttgtg                                        27

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ccgaccgctt gcaaggcaaa cggttc                                         26

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gaaccgtttg ccttgcaagc ggtcgg                                         26

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gcagtatagt acctgtgagg aacgagc                                        27

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gctcgttcct cacaggtact atactgc                                        27

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gcagtatagt acctctgagg aacgagc                                        27

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 45
gctcgttcct cagaggtact atactgc                                          27

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gtatagtacc gataaggaac gagcttttg                                        29

<210> SEQ ID NO 47
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
caaaagctcg ttccttatcg gtactatac                                        29

<210> SEQ ID NO 48
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcttgctgct ctgctcaaga gtcctctgct gatcg                                 35

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cgatcagcag aggactcttg agcagagcag caagc                                 35

<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gctctgctcg ctagtaagct gctgatcgat gc                                    32

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 51
gcatcgatca gcagcttact agcgagcaga gc                                    32

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Ser Ala Pro Asp Thr Arg Pro Ala Pro Gly
1               5                   10

<210> SEQ ID NO 53
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Asp Thr Arg Pro Ala Pro Gly Ser Thr Ala Pro Pro Ala His Gly
1               5                   10                  15

Val Thr Ser Ala
            20

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

His Gly Val Thr Ser Ala Pro Asp
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Pro Gly Ser Thr Ala Pro Pro Ala
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Ala Pro Asp Thr Arg Pro Ala Pro
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Pro Gly Ser Thr Ala Pro Pro
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Ala Pro Asp Thr Arg Pro Ala
1               5

<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Pro Ala His Gly Val Thr Ser Ala Pro Asp Thr Arg Pro Ala Pro Gly
1               5                   10                  15

Ser Thr Ala

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Pro Asp Thr Arg
1

<210> SEQ ID NO 61
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr
                20                  25                  30

<210> SEQ ID NO 62
<211> LENGTH: 30
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 62

Gly Lys Gln Thr Leu Val Leu Asn Pro Arg Gly Val Asn Pro Thr Asn
1               5                   10                  15

Gly Val Ala Ser Leu Ser Gln Ala Gly Ala Val Pro Ala Leu
            20                  25                  30

<210> SEQ ID NO 63
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asn Gly Val Ala Ser Leu Ser Gln Ala Gly Ala Val Pro Ala Leu Glu
1               5                   10                  15

Lys Arg Val Thr Val Ser Val Ser Gln Pro Ser Arg Asn Arg
            20                  25                  30

<210> SEQ ID NO 64
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Lys Arg Val Thr Val Ser Val Ser Gln Pro Ser Arg Asn Arg Lys
1               5                   10                  15

Asn Tyr Lys Val Gln Val Lys Ile Gln Asn Pro Thr Ala Cys
            20                  25                  30

<210> SEQ ID NO 65
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Lys Asn Tyr Lys Val Gln Val Lys Ile Gln Asn Pro Thr Ala Cys Thr
1               5                   10                  15

Ala Asn Gly Ser Cys Asp Pro Ser Val Thr Arg Gln Ala Tyr
            20                  25                  30

<210> SEQ ID NO 66
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Ala Asn Gly Ser Cys Asp Pro Ser Val Thr Arg Gln Ala Tyr Ala
1               5                   10                  15

Asp Val Thr Phe Ser Phe Thr Gln Tyr Ser Thr Asp
            20                  25
```

```
<210> SEQ ID NO 67
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ala Asp Val Thr Phe Ser Phe Thr Gln Tyr Ser Thr Asp Glu Glu Arg
1               5                   10                  15

Ala Phe Val Arg Thr Glu Leu Ala Ala Leu Leu Ala Ser Pro
            20                  25                  30

<210> SEQ ID NO 68
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Glu Arg Ala Phe Val Arg Thr Glu Leu Ala Ala Leu Leu Ala Ser
1               5                   10                  15

Pro Leu Leu Ile Asp Ala Ile Asp Gln Leu Asn Pro Ala Tyr
            20                  25                  30

<210> SEQ ID NO 69
<211> LENGTH: 14
<212> TYPE: PRT
<213> ORGANISM: Unknown
<220> FEATURE:
<223> OTHER INFORMATION: Description of Unknown:
      MUC1 sequence

<400> SEQUENCE: 69

His Gly Val Thr Ser Ala Pro Asp Thr Arg Pro Ala Pro Gly
1               5                   10

<210> SEQ ID NO 70
<211> LENGTH: 20
<212> TYPE: PRT
<213> ORGANISM: Unknown
<220> FEATURE:
<223> OTHER INFORMATION: Description of Unknown:
      MUC1 sequence

<400> SEQUENCE: 70

Ala His Gly Val Thr Ser Ala Pro Asp Thr Arg Pro Ala Pro Gly Ser
1               5                   10                  15

Thr Ala Pro Pro
            20

<210> SEQ ID NO 71
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Pro Gly Ser Thr Ala Pro Pro Ala His Gly Val Thr Ser Ala Pro
1               5                   10                  15
```

Asp Thr Arg Pro Ala Pro
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala His Gly Val Thr Ser Ala Pro Asp Thr Arg Pro Ala Pro Gly Ser
1               5                   10                  15

Thr Ala Pro Pro
            20

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Ala Pro Gly Ser Thr Ala Pro
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Pro Ala Pro Gly Ser Thr Ala
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Thr Arg Pro Ala Pro Gly Ser Thr
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Thr Arg Pro Ala Pro Gly Ser
1               5

<210> SEQ ID NO 77

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Pro Asp Thr Arg Pro Ala Pro Gly
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Pro Asp Thr Arg Pro Ala Pro
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Ser Ala Pro Asp Thr Arg Pro
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Val Thr Ser Ala Pro Asp Thr Arg
1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Val Thr Ser Ala Pro Asp Thr
1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 82

Ala His Gly Val Thr Ser Ala Pro
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Pro Ala His Gly Val Thr Ser Ala
1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Pro Pro Ala His Gly Val Thr Ser
1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Pro Pro Ala His Gly Val Thr
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Ala Pro Pro Ala His Gly Val
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Thr Ala Pro Pro Ala His Gly
1               5

<210> SEQ ID NO 88
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Ser Thr Ala Pro Pro Ala His
1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Pro Gly Ser Thr Ala Pro Pro
1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Pro Gly Ser Thr Ala Pro Pro
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Pro Gly Ser Thr Ala Pro Pro Gly
1               5

<210> SEQ ID NO 92
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala His Gly Val Thr Ser Ala Pro Asp Thr Arg Pro Ala Pro Gly Ser
1               5                   10                  15

Thr Ala Pro Pro
            20

<210> SEQ ID NO 93
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 93

Ala Pro Gly Ser Thr Ala Pro Pro Ala His Gly Val Thr Ser Ala Pro
1               5                   10                  15

Asp Thr Arg Pro Ala Pro
            20

<210> SEQ ID NO 94
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Ser Ala Pro Asp Thr Arg Pro Ala Pro Gly Ser Thr Ala Pro Pro
1               5                   10                  15

Ala His Gly Val Lys Gly
            20

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Ala Pro Asp Thr Arg Pro Ala Pro
1               5

<210> SEQ ID NO 96
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala His Gly Val Thr Ser Ala Pro Asp Thr Arg Pro Ala Pro Gly Ser
1               5                   10                  15

Thr Ala Pro Pro
            20

<210> SEQ ID NO 97
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Pro Gly Ser Thr Ala Pro Pro Ala His Gly Val Thr Ser Ala Pro
1               5                   10                  15

Asp Thr Asn Arg Pro Ala Pro
            20

<210> SEQ ID NO 98
<211> LENGTH: 22
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 98

Ala Pro Gly Ser Thr Ala Pro Pro Ala His Gly Val Thr Ser Ala Pro
1               5                   10                  15

Asp Thr Arg Pro Ala Pro
            20

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Thr Pro Ser Ser Thr Pro Gly Thr Thr His Thr Pro
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Thr Pro Ser Ser Thr Pro Gly Thr Thr His Thr Pro
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Thr Pro Ser Ser Thr Pro Gly Thr Thr His Thr Pro
1               5                   10

<210> SEQ ID NO 102
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Pro Ala His Gly Val Thr Ser Ala Pro Asp Thr Arg Pro Ala Pro Gly
1               5                   10                  15

Ser Thr Ala Pro Pro Ala
            20

<210> SEQ ID NO 103
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 103

Pro Ala His Gly Val Thr Ser Ala Pro Asp Thr Arg Pro Ala Pro Gly
1               5                   10                  15

Ser Thr Ala Pro Pro Ala
            20

<210> SEQ ID NO 104
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Pro Ala His Gly Val Thr Ser Ala Pro Asp Thr Arg Pro Ala Pro Gly
1               5                   10                  15

Ser Thr Ala Pro Pro Ala
            20

<210> SEQ ID NO 105
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Pro Ala His Gly Val Thr Ser Ala Pro Asp Thr Arg Pro Ala Pro Gly
1               5                   10                  15

Ser Thr Ala

<210> SEQ ID NO 106
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Pro Ala His Gly Val Thr Ser Ala Pro Asp Thr Arg Pro Ala Pro Gly
1               5                   10                  15

Ser Thr Ala

<210> SEQ ID NO 107
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Pro Ala His Gly Val Thr Ser Ala Pro Asp Thr Arg Pro Ala Pro Gly
1               5                   10                  15

Ser Thr Ala

<210> SEQ ID NO 108
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 108

Pro Ala His Gly Val Thr Ser Ala Pro Asp Thr Arg Pro Ala Pro Gly
1               5                   10                  15

Ser Thr Ala

<210> SEQ ID NO 109
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Pro Ala His Gly Val Thr Ser Ala Pro Asp Thr Arg Pro Ala Pro Gly
1               5                   10                  15

Ser Thr Ala

<210> SEQ ID NO 110
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Pro Ala His Gly Val Thr Ser Ala Pro Asp Thr Arg Pro Ala Pro Gly
1               5                   10                  15

Ser Thr Ala

<210> SEQ ID NO 111
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Pro Ala His Gly Val Thr Ser Ala Pro Asp Thr Arg Pro Ala Pro Gly
1               5                   10                  15

Ser Thr Ala

<210> SEQ ID NO 112
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Pro Ala His Gly Val Thr Ser Ala Pro Asp Thr Arg Pro Ala Pro Gly
1               5                   10                  15

Ser Thr Ala

<210> SEQ ID NO 113
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 113

Pro Ala His Gly Val Thr Ser Ala Pro Asp Thr Arg Pro Ala Pro Gly
1               5                   10                  15

Ser Thr Ala

<210> SEQ ID NO 114
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Pro Ala His Gly Val Thr Ser Ala Pro Asp Thr Arg Pro Ala Pro Gly
1               5                   10                  15

Ser Thr Ala

<210> SEQ ID NO 115
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Pro Ala His Gly Val Thr Ser Ala Pro Asp Thr Arg Pro Ala Pro Gly
1               5                   10                  15

Ser Thr Ala

<210> SEQ ID NO 116
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Pro Ala His Gly Val Thr Ser Ala Pro Asp Thr Arg Pro Ala Pro Gly
1               5                   10                  15

Ser Thr Ala

<210> SEQ ID NO 117
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Pro Ala His Gly Val Thr Ser Ala Pro Asp Thr Arg Pro Ala Pro Gly
1               5                   10                  15

Ser Thr Ala

<210> SEQ ID NO 118
<211> LENGTH: 19
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 118

Pro Ala His Gly Val Thr Ser Ala Pro Asp Thr Arg Pro Ala Pro Gly
1               5                   10                  15

Ser Thr Ala

<210> SEQ ID NO 119
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Pro Ala His Gly Val Thr Ser Ala Pro Asp Thr Arg Pro Ala Pro Gly
1               5                   10                  15

Ser Thr Ala

<210> SEQ ID NO 120
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Pro Ala His Gly Val Thr Ser Ala Pro Asp Thr Arg Pro Ala Pro Gly
1               5                   10                  15

Ser Thr Ala

<210> SEQ ID NO 121
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Pro Ala His Gly Val Thr Ser Ala Pro Asp Thr Arg Pro Ala Pro Gly
1               5                   10                  15

Ser Thr Ala

<210> SEQ ID NO 122
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Pro Ala His Gly Val Thr Ser Ala Pro Asp Thr Arg Pro Ala Pro Gly
1               5                   10                  15

Ser Thr Ala

<210> SEQ ID NO 123
<211> LENGTH: 19

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Pro Ala His Gly Val Thr Ser Ala Pro Asp Thr Arg Pro Ala Pro Gly
1               5                   10                  15

Ser Thr Ala

<210> SEQ ID NO 124
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Pro Ala His Gly Val Thr Ser Ala Pro Asp Thr Arg Pro Ala Pro Gly
1               5                   10                  15

Ser Thr Ala

<210> SEQ ID NO 125
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Pro Ala His Gly Val Thr Ser Ala Pro Asp Thr Arg Pro Ala Pro Gly
1               5                   10                  15

Ser Thr Ala

<210> SEQ ID NO 126
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Pro Ala His Gly Val Thr Ser Ala Pro Asp Thr Arg Pro Ala Pro Gly
1               5                   10                  15

Ser Thr Ala

<210> SEQ ID NO 127
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Pro Ala His Gly Val Thr Ser Ala Pro Asp Thr Arg Pro Ala Pro Gly
1               5                   10                  15

Ser Thr Ala

<210> SEQ ID NO 128
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Pro Ala His Gly Val Thr Ser Ala Pro Asp Thr Arg Pro Ala Pro Gly
1               5                   10                  15

Ser Thr Ala

<210> SEQ ID NO 129
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Pro Ala His Gly Val Thr Ser Ala Pro Asp Thr Arg Pro Ala Pro Gly
1               5                   10                  15

Ser Thr Ala

<210> SEQ ID NO 130
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Pro Ala His Gly Val Thr Ser Ala Pro Asp Thr Arg Pro Ala Pro Gly
1               5                   10                  15

Ser Thr Ala

<210> SEQ ID NO 131
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Pro Ala His Gly Val Thr Ser Ala Pro Asp Thr Arg Pro Ala Pro Gly
1               5                   10                  15

Ser Thr Ala

<210> SEQ ID NO 132
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Pro Ala His Gly Val Thr Ser Ala Pro Asp Thr Arg Pro Ala Pro Gly
1               5                   10                  15

Ser Thr Ala
```

```
<210> SEQ ID NO 133
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Pro Ala His Gly Val Thr Ser Ala Pro Asp Thr Arg Pro Ala Pro Gly
1               5                   10                  15

Ser Thr Ala

<210> SEQ ID NO 134
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Pro Ala His Gly Val Thr Ser Ala Pro Asp Thr Arg Pro Ala Pro Gly
1               5                   10                  15

Ser Thr Ala

<210> SEQ ID NO 135
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Pro Ala His Gly Val Thr Ser Ala Pro Asp Thr Arg Pro Ala Pro Gly
1               5                   10                  15

Ser Thr Ala

<210> SEQ ID NO 136
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Pro Ala His Gly Val Thr Ser Ala Pro Asp Thr Arg Pro Ala Pro Gly
1               5                   10                  15

Ser Thr Ala

<210> SEQ ID NO 137
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Pro Ala His Gly Val Thr Ser Ala Pro Asp Thr Arg Pro Ala Pro Gly
1               5                   10                  15

Ser Thr Ala
```

<210> SEQ ID NO 138
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Pro Ala His Gly Val Thr Ser Ala Pro Asp Thr Arg Pro Ala Pro Gly
1               5                   10                  15

Ser Thr Ala

<210> SEQ ID NO 139
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Pro Ala His Gly Val Thr Ser Ala Pro Asp Thr Arg Pro Ala Pro Gly
1               5                   10                  15

Ser Thr Ala

<210> SEQ ID NO 140
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Pro Ala His Gly Val Thr Ser Ala Pro Asp Thr Arg Pro Ala Pro Gly
1               5                   10                  15

Ser Thr Ala

<210> SEQ ID NO 141
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Pro Ala His Gly Val Thr Ser Ala Pro Asp Thr Arg Pro Ala Pro Gly
1               5                   10                  15

Ser Thr Ala

<210> SEQ ID NO 142
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Pro Ala His Gly Val Thr Ser Ala Pro Asp Thr Arg Pro Ala Pro Gly
1               5                   10                  15

Ser Thr Ala

<210> SEQ ID NO 143
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Pro Ala His Gly Val Thr Ser Ala Pro Asp Thr Arg Pro Ala Pro Gly
1               5                   10                  15

Ser Thr Ala

<210> SEQ ID NO 144
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Pro Ala His Gly Val Thr Ser Ala Pro Asp Thr Arg Pro Ala Pro Gly
1               5                   10                  15

Ser Thr Ala

<210> SEQ ID NO 145
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Pro Ala His Gly Val Thr Ser Ala Pro Asp Thr Arg Pro Ala Pro Gly
1               5                   10                  15

Ser Thr Ala

<210> SEQ ID NO 146
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Pro Ala His Gly Val Thr Ser Ala Pro Asp Thr Arg Pro Ala Pro Gly
1               5                   10                  15

Ser Thr Ala

<210> SEQ ID NO 147
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Pro Ala His Gly Val Thr Ser Ala Pro Asp Thr Arg Pro Ala Pro Gly
1               5                   10                  15

Ser Thr Ala

<210> SEQ ID NO 148
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Pro Ala His Gly Val Thr Ser Ala Pro Asp Thr Arg Pro Ala Pro Gly
1               5                   10                  15

Ser Thr Ala

<210> SEQ ID NO 149
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Pro Ala His Gly Val Thr Ser Ala Pro Asp Thr Arg Pro Ala Pro Gly
1               5                   10                  15

Ser Thr Ala

<210> SEQ ID NO 150
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Pro Ala His Gly Val Thr Ser Ala Pro Asp Thr Arg Pro Ala Pro Gly
1               5                   10                  15

Ser Thr Ala

<210> SEQ ID NO 151
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Pro Ala His Gly Val Thr Ser Ala Pro Asp Thr Arg Pro Ala Pro Gly
1               5                   10                  15

Ser Thr Ala

<210> SEQ ID NO 152
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 152

Pro Ala His Gly Val Thr Ser Ala Pro Asp Thr Arg Pro Ala Pro Gly
1               5                   10                  15

Ser Thr Ala

<210> SEQ ID NO 153
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Pro Ala His Gly Val Thr Ser Ala Pro Asp Thr Arg Pro Ala Pro Gly
1               5                   10                  15

Ser Thr Ala

<210> SEQ ID NO 154
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Pro Ala His Gly Val Thr Ser Ala Pro Asp Thr Arg Pro Ala Pro Gly
1               5                   10                  15

Ser Thr Ala

<210> SEQ ID NO 155
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Pro Ala His Gly Val Thr Ser Ala Pro Asp Thr Arg Pro Ala Pro Gly
1               5                   10                  15

Ser Thr Ala

<210> SEQ ID NO 156
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Pro Ala His Gly Val Thr Ser Ala Pro Asp Thr Arg Pro Ala Pro Gly
1               5                   10                  15

Ser Thr Ala

<210> SEQ ID NO 157
<211> LENGTH: 19
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 157

Pro Ala His Gly Val Thr Ser Ala Pro Asp Thr Arg Pro Ala Pro Gly
1               5                   10                  15

Ser Thr Ala

<210> SEQ ID NO 158
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Pro Ala His Gly Val Thr Ser Ala Pro Asp Thr Arg Pro Ala Pro Gly
1               5                   10                  15

Ser Thr Ala

<210> SEQ ID NO 159
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Pro Ala His Gly Val Thr Ser Ala Pro Asp Thr Arg Pro Ala Pro Gly
1               5                   10                  15

Ser Thr Ala

<210> SEQ ID NO 160
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Pro Ala His Gly Val Thr Ser Ala Pro Asp Thr Arg Pro Ala Pro Gly
1               5                   10                  15

Ser Thr Ala

<210> SEQ ID NO 161
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Pro Ala His Gly Val Thr Ser Ala Pro Asp Thr Arg Pro Ala Pro Gly
1               5                   10                  15

Ser Thr Ala

<210> SEQ ID NO 162
<211> LENGTH: 19

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Pro Ala His Gly Val Thr Ser Ala Pro Asp Thr Arg Pro Ala Pro Gly
1               5                   10                  15

Ser Thr Ala

<210> SEQ ID NO 163
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Pro Ala His Gly Val Thr Ser Ala Pro Asp Thr Arg Pro Ala Pro Gly
1               5                   10                  15

Ser Thr Ala

<210> SEQ ID NO 164
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Pro Ala His Gly Val Thr Ser Ala Pro Asp Thr Arg Pro Ala Pro Gly
1               5                   10                  15

Ser Thr Ala

<210> SEQ ID NO 165
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Pro Ala His Gly Val Thr Ser Ala Pro Asp Thr Arg Pro Ala Pro Gly
1               5                   10                  15

Ser Thr Ala

<210> SEQ ID NO 166
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Pro Ala His Gly Val Thr Ser Ala Pro Asp Thr Arg Pro Ala Pro Gly
1               5                   10                  15

Ser Thr Ala

<210> SEQ ID NO 167

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Pro Ala His Gly Val Thr Ser Ala Pro Asp Thr Arg Pro Ala Pro Gly
1               5                   10                  15

Ser Thr Ala

<210> SEQ ID NO 168
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Pro Ala His Gly Val Thr Ser Ala Pro Asp Thr Arg Pro Ala Pro Gly
1               5                   10                  15

Ser Thr Ala

<210> SEQ ID NO 169
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Pro Ala His Gly Val Thr Ser Ala Pro Asp Thr Arg Pro Ala Pro Gly
1               5                   10                  15

Ser Thr Ala

<210> SEQ ID NO 170
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Pro Ala His Gly Val Thr Ser Ala Pro Asp Thr Arg Pro Ala Pro Gly
1               5                   10                  15

Ser Thr Ala

<210> SEQ ID NO 171
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Pro Ala His Gly Val Thr Ser Ala Pro Asp Thr Arg Pro Ala Pro Gly
1               5                   10                  15

Ser Thr Ala
```

```
<210> SEQ ID NO 172
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Pro Ala His Gly Val Thr Ser Ala Pro Asp Thr Arg Pro Ala Pro Gly
1               5                   10                  15

Ser Thr Ala

<210> SEQ ID NO 173
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Pro Ala His Gly Val Thr Ser Ala Pro Asp Thr Arg Pro Ala Pro Gly
1               5                   10                  15

Ser Thr Ala

<210> SEQ ID NO 174
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Pro Ala His Gly Val Thr Ser Ala Pro Asp Thr Arg Pro Ala Pro Gly
1               5                   10                  15

Ser Thr Ala

<210> SEQ ID NO 175
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ala His Gly Val Thr Ser Ala Pro Asp Thr Arg Pro Ala Pro Gly Ser
1               5                   10                  15

Thr Ala Pro Pro
            20
```